(12) United States Patent
Amodei et al.

US008734823B2

(10) Patent No.: US 8,734,823 B2
(45) Date of Patent: May 27, 2014

(54) DEVICE INCLUDING ALTERED MICROORGANISMS, AND METHODS AND SYSTEMS OF USE

(75) Inventors: Dario G. Amodei, Princeton, NJ (US); Mahalaxmi Gita Bangera, Renton, WA (US); Xiaoyan Robert Bao, Cambridge, MA (US); Anna Bershteyn, Somerville, MA (US); Brett Bethke, Arlington, MA (US); Philip A. Eckhoff, Bellevue, WA (US); Kevin Michael Esvelt, Cambridge, MA (US); Kyle B. Gustafson, Lausanne (CH); Edward K. Y. Jung, Bellevue, WA (US); William Michael Kaminsky, Alexandria, VA (US); Jordin T. Kare, Seattle, WA (US); Lily Yvonne Kim, Brookline, MA (US); Eric C. Leuthardt, St. Louis, MO (US); Erez Lieberman, Cambridge, MA (US); Ankur Moitra, Cambridge, MA (US); Christopher Somogyi, Woodinville, WA (US); Clarence T. Tegreene, Bellevue, WA (US); Lowell L. Wood, Jr., Bellevue, WA (US); Jeremiah James Zartman, Montgomery, AL (US)

(73) Assignee: The Invention Science Fund I, LLC, Bellevue, WA (US)

( * ) Notice: Subject to any disclaimer, the term of this patent is extended or adjusted under 35 U.S.C. 154(b) by 490 days.

(21) Appl. No.: 12/802,148

(22) Filed: May 28, 2010

(65) Prior Publication Data
US 2011/0027181 A1 Feb. 3, 2011

Related U.S. Application Data

(63) Continuation-in-part of application No. 12/802,149, filed on May 28, 2010, now Pat. No. 8,682,619, and a continuation-in-part of application No. 12/806,637, filed on May 28, 2010, and a continuation-in-part of application No. 12/657,604, filed on Jan. 22, 2010, and a continuation-in-part of application No. 12/657,605, filed on Jan. 22, 2010, and a continuation-in-part of application No. 12/657,606, filed on Jan. 22, 2010, and a continuation-in-part of application No. 12/657,607, filed on Jan. 22, 2010, and a continuation-in-part of application No. 12/657,608, filed on Jan. 22, 2010, and a continuation-in-part of application No. 12/657,609, filed on Jan. 22, 2010, and a continuation-in-part of application No. 12/462,114, filed on Jul. 28, 2009, now Pat. No. 8,551,750, and a continuation-in-part of application No. 11/975,605, filed on Oct. 18, 2007, now Pat. No. 8,114,647, and a continuation-in-part of application No. 11/974,750, filed on Oct. 15, 2007, now Pat. No. 8,304,220, and a continuation-in-part of application No. 11/974,852, filed on Oct. 15, 2007, now Pat. No. 8,367,384, and a continuation-in-part of application No. 11/974,798, filed on Oct. 15, 2007, and a continuation-in-part of application No. 11/906,664, filed on Oct. 2, 2007, and a continuation-in-part of application No. 11/906,581, filed on Oct. 2, 2007, and a continuation-in-part of application No. 11/906,580, filed on Oct. 2, 2007, and a continuation-in-part of application No. 11/900,870, filed on Sep. 12, 2007, and a continuation-in-part of application No. 11/900,776, filed on Sep. 12, 2007, and a continuation-in-part of application No. 11/900,773, filed on Sep. 12, 2007, now Pat. No. 8,252,570, and a continuation-in-part of application No. 11/701,163, filed on Jan. 31, 2007, now Pat. No. 8,354,258, and a continuation-in-part of application No. 11/452,019, filed on Jun. 12, 2006, and a continuation-in-part of application No. 11/451,994, filed on Jun. 12, 2006, and a continuation-in-part of application No. 11/451,986, filed on Jun. 12, 2006, now Pat. No. 8,053,220, and a continuation-in-part of application No. 11/389,268, filed on Mar. 24, 2006, and a continuation-in-part of application No. 11/304,499, filed on Dec. 14, 2005, now Pat. No. 8,278,094, and a continuation-in-part of application No. 11/304,492, filed on Dec. 14, 2005, now Pat. No. 7,855,062, and a continuation-in-part of application No. 11/304,486, filed on Dec. 14, 2005, now Pat. No. 8,198,080.

(51) Int. Cl.
*A61F 13/00* (2006.01)
*A61K 9/00* (2006.01)
*A01N 63/00* (2006.01)

(52) U.S. Cl.
USPC .......................... 424/422; 424/400; 424/93.1

(58) Field of Classification Search
None
See application file for complete search history.

(56) References Cited

U.S. PATENT DOCUMENTS 4,352,581 A  10/1982  Leuthold et al.
4,627,853 A  12/1986  Campbell et al.
(Continued)

FOREIGN PATENT DOCUMENTS

WO    WO 95/24929    9/1995
WO    WO 96/40947    12/1996
(Continued)

OTHER PUBLICATIONS

Haidinger et al. *Escherichia coli* Ghost Production by Expression of Lysis Gene E and Staphylococcal Nuclease. 2003. Applied and Environmental Microbiology. vol. 69, No. 10, pp. 6106-6113.*

(Continued)

*Primary Examiner* — Anne Gussow
*Assistant Examiner* — Channing S Mahatan

(57) ABSTRACT

Devices, methods, and systems are described for administration to at least one biological tissue of at least one device including at least one altered microorganism. In an embodiment, the altered microorganism includes at least one nucleic acid construct encoding at least one therapeutic agent.

49 Claims, 36 Drawing Sheets

(56) References Cited

U.S. PATENT DOCUMENTS

| | | | |
|---|---|---|---|
| 4,833,083 A | 5/1989 | Saxena | |
| 4,837,151 A | 6/1989 | Stocker | |
| 5,017,373 A | 5/1991 | Herrnstadt et al. | |
| 5,256,418 A | 10/1993 | Kemp et al. | |
| 5,316,940 A | 5/1994 | Georgiou et al. | |
| 5,324,294 A | 6/1994 | Elia et al. | |
| 5,578,485 A | 11/1996 | Naughton et al. | |
| 5,643,771 A | 7/1997 | Stocker | |
| 5,663,063 A | 9/1997 | Peoples et al. | |
| 5,762,965 A | 6/1998 | Burnett et al. | |
| 5,804,563 A | 9/1998 | Still et al. | |
| 5,820,873 A | 10/1998 | Choi et al. | |
| 5,823,993 A | 10/1998 | Lemelson | |
| 5,831,012 A | 11/1998 | Nilsson et al. | |
| 5,843,781 A | 12/1998 | Ballermann et al. | |
| 5,858,318 A | 1/1999 | Luo | |
| 5,876,452 A | 3/1999 | Athanasiou et al. | |
| 5,888,396 A | 3/1999 | Perriello | |
| 5,916,554 A | 6/1999 | Dionne et al. | |
| 5,916,870 A | 6/1999 | Lee et al. | |
| 5,928,635 A | 7/1999 | Schmidt | |
| 6,017,496 A | 1/2000 | Nova et al. | |
| 6,066,343 A | 5/2000 | Megeed et al. | |
| 6,100,388 A | 8/2000 | Casas et al. | |
| 6,126,936 A | 10/2000 | Lanza et al. | |
| 6,126,956 A | 10/2000 | Grossman et al. | |
| 6,200,347 B1 | 3/2001 | Anderson et al. | |
| 6,242,194 B1 | 6/2001 | Kullen et al. | |
| 6,254,832 B1 | 7/2001 | Rainin et al. | |
| 6,416,754 B1 | 7/2002 | Brown et al. | |
| 6,592,989 B1 | 7/2003 | Senna et al. | |
| 6,605,286 B2 | 8/2003 | Steidler et al. | |
| 6,610,529 B1 | 8/2003 | Curtiss, III et al. | |
| 6,646,867 B1 * | 11/2003 | Tuttle et al. | 361/679.6 |
| 6,652,849 B2 | 11/2003 | Brown et al. | |
| 6,670,427 B1 | 12/2003 | Ulbricht et al. | |
| 6,696,251 B1 | 2/2004 | Wittrup et al. | |
| 6,709,269 B1 | 3/2004 | Altshuler | |
| 6,767,928 B1 | 7/2004 | Murphy et al. | |
| 6,790,455 B2 | 9/2004 | Chu et al. | |
| 6,797,522 B1 | 9/2004 | Still et al. | |
| 6,852,511 B2 | 2/2005 | Romano et al. | |
| 6,875,356 B2 | 4/2005 | Perriello | |
| 7,001,359 B2 | 2/2006 | Rogers | |
| 7,220,418 B1 | 5/2007 | Hans et al. | |
| 7,226,612 B2 | 6/2007 | Sohier et al. | |
| 7,341,860 B2 | 3/2008 | Curtiss, III et al. | |
| 7,344,710 B2 | 3/2008 | Dang et al. | |
| 7,447,595 B1 | 11/2008 | Pohlschroder et al. | |
| 7,462,708 B2 | 12/2008 | Singh et al. | |
| 7,510,852 B2 | 3/2009 | Royer et al. | |
| 7,550,558 B2 | 6/2009 | Leite et al. | |
| 7,780,961 B2 | 8/2010 | Steidler | |
| 2001/0000802 A1 * | 5/2001 | Soykan et al. | 623/1.13 |
| 2001/0001817 A1 | 5/2001 | Humes | |
| 2002/0006437 A1 | 1/2002 | Grooms et al. | |
| 2002/0044948 A1 | 4/2002 | Khleif et al. | |
| 2002/0081732 A1 | 6/2002 | Bowlin et al. | |
| 2002/0090725 A1 | 7/2002 | Simpson et al. | |
| 2002/0156033 A1 | 10/2002 | Bratzler et al. | |
| 2003/0004403 A1 | 1/2003 | Drinan et al. | |
| 2003/0009235 A1 | 1/2003 | Manrique et al. | |
| 2003/0059461 A1 | 3/2003 | Backer et al. | |
| 2003/0064074 A1 | 4/2003 | Chang et al. | |
| 2003/0064095 A1 | 4/2003 | Martin et al. | |
| 2003/0068817 A1 | 4/2003 | Gazit et al. | |
| 2003/0185807 A1 | 10/2003 | Gazit et al. | |
| 2003/0229400 A1 | 12/2003 | Masuda et al. | |
| 2004/0005302 A1 | 1/2004 | Hortelano | |
| 2004/0018508 A1 | 1/2004 | Friedman | |
| 2004/0043481 A1 | 3/2004 | Wilson | |
| 2004/0078090 A1 | 4/2004 | Binette et al. | |
| 2004/0115132 A1 | 6/2004 | Young et al. | |
| 2004/0175407 A1 | 9/2004 | McDaniel | |
| 2004/0197375 A1 | 10/2004 | Rezania et al. | |
| 2004/0229333 A1 | 11/2004 | Bowlin et al. | |
| 2004/0241849 A1 * | 12/2004 | Kapat | 435/404 |
| 2005/0031643 A1 | 2/2005 | Szalay et al. | |
| 2005/0101005 A1 | 5/2005 | Steidler | |
| 2005/0112133 A1 | 5/2005 | Druilhe | |
| 2005/0124010 A1 | 6/2005 | Short et al. | |
| 2005/0131386 A1 | 6/2005 | Freeman et al. | |
| 2005/0137626 A1 | 6/2005 | Pastore et al. | |
| 2005/0226856 A1 | 10/2005 | Ahlfors | |
| 2005/0276788 A1 | 12/2005 | Steidler et al. | |
| 2006/0030948 A1 | 2/2006 | Manrique et al. | |
| 2006/0121054 A1 | 6/2006 | Sun et al. | |
| 2006/0177379 A1 | 8/2006 | Asgari | |
| 2006/0207168 A1 | 9/2006 | Harper | |
| 2007/0026005 A1 | 2/2007 | Sung et al. | |
| 2007/0073385 A1 | 3/2007 | Schaeffer et al. | |
| 2007/0110723 A1 | 5/2007 | Hans et al. | |
| 2007/0122427 A1 | 5/2007 | Hans et al. | |
| 2007/0134216 A1 | 6/2007 | Harlow et al. | |
| 2007/0134222 A1 | 6/2007 | Harlow et al. | |
| 2007/0134223 A1 | 6/2007 | Harlow et al. | |
| 2007/0134224 A1 | 6/2007 | Harlow et al. | |
| 2007/0134225 A1 | 6/2007 | Harlow et al. | |
| 2007/0134345 A1 | 6/2007 | Harlow et al. | |
| 2007/0134346 A1 | 6/2007 | Harlow et al. | |
| 2007/0184088 A1 | 8/2007 | Jung et al. | |
| 2007/0213659 A1 | 9/2007 | Trovato et al. | |
| 2007/0258901 A1 | 11/2007 | Boschert et al. | |
| 2008/0044448 A1 | 2/2008 | Harlow et al. | |
| 2008/0044900 A1 | 2/2008 | Mooney et al. | |
| 2008/0050416 A1 | 2/2008 | Harlow et al. | |
| 2008/0107686 A1 | 5/2008 | Mach | |
| 2008/0253990 A1 | 10/2008 | Steidler et al. | |
| 2008/0254014 A1 | 10/2008 | Rottiers et al. | |
| 2008/0311145 A1 | 12/2008 | Campion et al. | |
| 2009/0041836 A1 | 2/2009 | Boons et al. | |
| 2009/0115603 A1 | 5/2009 | Tabe | |
| 2009/0148408 A1 | 6/2009 | Chang et al. | |
| 2009/0202608 A1 | 8/2009 | Alessi et al. | |
| 2010/0152880 A1 | 6/2010 | Boyden et al. | |
| 2010/0272771 A1 | 10/2010 | Harlow et al. | |
| 2010/0292495 A1 | 11/2010 | Schüler et al. | |

FOREIGN PATENT DOCUMENTS

| | | |
|---|---|---|
| WO | WO 00/00177 | 6/1999 |
| WO | WO 99/38453 | 8/1999 |
| WO | WO 99/47080 | 9/1999 |
| WO | WO 00/66188 A3 | 11/2000 |
| WO | WO 01/68135 A2 | 3/2001 |
| WO | WO 01/24690 A2 | 4/2001 |
| WO | WO 02/09597 A2 | 2/2002 |
| WO | WO 2005/041848 A2 | 5/2005 |
| WO | WO 2007/011696 A2 | 1/2007 |

OTHER PUBLICATIONS

"Diatom"; The Columbia Encyclopedia; bearing a date of 2008; 2 pages; located at http://www.credoreference.com/topic/diatom.

"Eukaryotes"; Illustrated Dictionary of Science; bearing a date of 1988; 2 pages; located at: http://www.credoreference.com/topic/eukaryotic_cells.

"Prokaryotes"; Illustrated Dictionary of Science; bearing a date of 1988; 2 pages; located at: http://www.credoreference.com/topic/prokaryotes.

Hamilton, Kris; "Pseudomonas putida"; Microbe of the Week; Accessed Mar. 11, 2013 from http://web.mst.edu/~rnicrobio/bio221_2007/P_putida.htm; pp. 1-3 ; Missouri University of Science and Technology.

Hazan et al.; "*Escherichia coli mazEF*-Mediated Cell Death Is Triggered by Various Stressful Conditions"; Journal of Bacteriology; bearing a date of Jun. 2004, accepted Feb. 23, 2004; pp. 3663-3669; vol. 186, No. 11; American Society for Microbiology.

"Cell membrane"; definition from Answers.com; printed on Jun. 18, 2010; 18 pages; located at http://www.answers.com/topic/cell-membrane.

"Exhibit"; Definition from Merriam-Webster Online Dictionary; bearing a date of 2010; 2 pp.; located at http://www.merriam-webster.com/dictionary/exhibit.

(56) References Cited

OTHER PUBLICATIONS

Round, Frank Eric; "Diatoms"; bearing a date of 1990; pp. 38; Cambridge University Press; Cambridge, United Kingdom.
Abosereh et al.; "Mutation Induction for Genetic Improvement of *Saccharomyces boulardii* Which Used as Probiotic Yeast"; Research Journal of Agriculture and.Biological Sciences; bearing a date of 2006; pp. 478-482; vol. 2, No. 6; INSInet Publication.
Agarraberes et al.; "Review—Protein translocation across membranes"; Biochimica et Biophysica Acta; bearing a date of 2001; pp. 1-24; vol. 1513; Elsevier Science B.V.; located at: www.bba-direct.com.
Aggarwal et al.; "Human mesenchymal stem cells modulate allogenic immune cell responses"; Blood; bearing a date of Feb. 15, 2005; pp. 1815-1822; vol. 105, No. 4; The American Society of Hematology.
Alexander et al.; "Specific T cell recognition of peptides derived from prostate-specific antigen in patients with prostate cancer"; Abstract; one page; Urology; bearing a date of Jan. 1998; pp. 150-157; vol. 51, No. 1.
Allison et al.; "Synthesis and Secretion of Recombinant Tick-Borne Encephalitis Virus Protein E in Soluble and Particulate Form"; Journal of Virology; bearing a date of Sep. 1995; pp. 5816-5820; vol. 69, No. 9; American Society for Microbiology.
Alvarez et al.; "Fluorescence Analysis of Carrier Rat and Human Erythrocytes Loaded With FITC-Dextran"; Cytometry; bearing a date of 1996; pp. 181-189; vol. 24; Wiley-Liss, Inc.
Alverson et al.; "Research Article: Comments on Recent Progress Toward Reconstructing the Diatom Phylogeny"; Journal of Nanoscience and Nanotechnology; bearing a date of 2005; pp. 57-62; vol. 5, No. 1; American Scientific Publishers.
Amitai et al.; "MazF-Mediated Cell Death in *Escherichia coli*: a Point of No Return"; Journal of Bacteriology; bearing a date of Dec. 2004; pp. 8295-8300; vol. 186, No. 24; American Society for Microbiology.
Anal, Anil K.; "Time-Controlled Pulsatile Delivery Systems for Bioactive Compounds"; Recent Patents on Drug Delivery & Formulation; bearing a date of 2007; pp. 73-79; vol. 1; Bentham Science Publishers Ltd.
Anderson et al.; "Research Article: Zeolitisation of Diatoms"; Journal of Nanoscience and Nanotechnology; bearing a date of 2005; pp. 92-95; vol. 5, No. 1; American Scientific Publishers.
Andersson et al.; "Comparative Analysis of Human Gut Microbiota by Barcoded Pyrosequencing"; PLoS ONE; bearing a date of Jul. 2008; pp. 1-8; vol. 3, No. 7; plosone.org.
Angele et al.; "Engineering of Osteochondral Tissue with Bone Marrow Mesenchymal Progenitor Cells in a Derivatized Hyaluronan-Gelatin Composite.Sponge"; Tissue Engineering; bearing a date of 1999; pp. 545-553; vol. 5, No. 6, Mary Ann Liebert, Inc.
Angelow et al.; "Usefulness and limitation of primary cultured porcine choroid plexus epithelial cells as an in vitro model to study drug transport at the blood-CSF barrier"; Advanced Drug Delivery Reviews; bearing a date of 2004; pp. 1859-1873; vol. 56; Elsevier B.V.
Apt et al.; "Original Paper: Stable Nuclear Transformation of the Diatom Phaeodactylum Tricornutum"; Molecular Genetics and Genomics; bearing a date of 1996; pp. 572-579; vol. 252; Springer-Verlag.
Apt et al.; "Research Article: In Vivo Characterization of Diatom Multipartite Plastid Targeting Signals"; Journal of Cell Science; bearing a date of 2002; pp. 4061-4069; vol. 115, No. 21; The Company of Biologists Ltd.; located at: http://jcs.biologists.org/cgi/content/abstract/115/21/4061.
Bääth, E.; "Measurement of protein synthesis by soil bacterial assemblages with the.leucine incorporation technique"; Biol Fertil Soils; bearing a date of 1994; pp. 147-153; vol. 17; Abstract; 1 pg.; Springer-Verlag 1994.
Bakker et al.; "Melanocyte Lineage-specific Antigen gp100 Is Recognized by Melanoma-derived Tumor-infiltrating Lymphocytes"; The Journal of Experimental Medicine; bearing a date of Mar. 1994; pp. 1005-1009; vol. 179; The Journal of Experimental Medicine.

Balagadde et al.; "A synthetic *Escherichia coli* predator-prey ecosystem"; Molecular Systems Biology; bearing a date of 2008; pp. 1-8; vol. 4, No. 187; EMBO and Nature Publishing Group.
Balan et al.; "A conditional suicide system for *Saccharomyces cerevisiae* relying on the intracellular production of the *Serratia marcescens* nuclease"; Yeast; bearing a date of 2005; pp. 203-212; vol. 22; John Wiley & Sons, Ltd.
Barberi et al.; "Derivation of Multipotent Mesenchymal Precursors from Human.Embryonic Stem Cells"; PLoS Medicine; bearing a date of Jun. 2005; pp. 0554-0560; vol. 2, Issue 6; www.plosmedicine.com.
Baskin et al.; "Copper-free click chemistry for dynamic in vivo imaging"; PNAS; bearing a date of Oct. 23, 2007; pp. 16793-16797; vol. 104, No. 43; The National Academy of Sciences of the USA.
Bassler et al.; "Bacterially Speaking"; Cell; bearing a date of Apr. 21, 2006; pp. 237-246; vol. 125; Elsevier Inc.
Beers et al.; "Immunobiology of Rejection"; The Merck Manual of Diagnosis and Therapy: Section 12. Immunology; Allergic Disorders—Chapter 149. Transplantation; bearing a date of 1995-1996; pp. 1-5 plus cover pages (total of 7 pages); Merck & Co., Inc.; located at: http://www.merck.com/mrkshared/mmanual/section12/chanter149/149b.jsp.
Beers et al.; "Transplantation of Other Organs and Tissues"; The Merck Manual of.Diagnosis and Therapy: Section 12. Immunology; Allergic Disorders—Chapter 149. Transplantation; bearing date of 1999-2005; pp. 1-2; Merck & Co., Inc.; located at: http://www.merck.com/mrkshared/mmanual/section12/chapter149/149i.jsp.
Beno et al.; "Estimation of bone permeability using accurate microstructural measurements"; Journal of Biomechanics; bearing a date of 2006; pp. 2378-2387; vol. 39; Elsevier Ltd.
Benson et al.; "GenBank"; Nucleic Acids Research; bearing a date of 2008; pp. D25-D30; vol. 36, Database issue.
Ben-Yehuda et al.; "Immunogenicity and safety of a novel IL-2-supplemented liposomal influenza vaccine (INFLUSOME-VAC) in nursing-home residents"; Vaccine; bearing a date of 2003; pp. 3169-3178; vol. 21; Elsevier Science Ltd.
Berger et al.; "Phase I study with an autologous tumor cell vaccine for locally advanced or metastatic prostate cancer"; J Pharm Pharmaceut Sci; bearing a date of 2007; pp. 144-152; vol. 10, No. 2; can be located at www.cspsCanada.org.
Bermúdez-Humarán et al.; "Current prophylactic and therapeutic uses of a recombinant *Lactococcus lactis* strain secreting biologically active interleukin-12"; J Mol Microbiol Biotechnol; bearing a date of 2008; pp. 80-89; vol. 14; Nos. 1-3; Abstract; 1 pg.
Betz et al.; "Polarity of the Blood-Brain Barrier: Distribution of Enzymes Between the Luminal and Antiluminal Membranes of Brain Capillary Endothelial Cells"; Brain Research; bearing a date of 1980; pp. 17-28; vol. 192; Elsevier/North-Holland Biomedical Press.
Beyth et al.; "Human mesenchymal stem cells alter antigen-presenting cell maturation and induce T-cell unresponsiveness"; Blood; bearing a date of Mar. 1, 2005; pp. 2214-2219; vol. 105, No. 5; The American Society of Hematology.
Biggerstaff et al.; "Soluble fibrin augments platelet/tumor cell adherence in vitro and in vivo, and enhances experimental metastasis"; Clinical & Experimental Metastasis; bearing a date of 1999; pp. 723-730; vol. 17; Kluwer Academic Publishers.
Biswas et al.; "High-Efficiency Gene Inactivation and Replacement System for Gram-Positive Bacteria"; Journal of Bacteriology; bearing a date of Jun. 1993; pp. 3628-3635; vol. 175, No. 11; American Society for Microbiology.
Blanquet et al.; "Recombinant *Saccharomyces cerevisiae* Expressing P450 in Artificial Digestive Systems: a Model for Biodetoxication in the Human Digestive Environment"; Applied and Environmental Microbiology; bearing a date of May 2003; pp. 2884-2892; vol. 69, No. 5; American Society for Microbiology.
Blevins et al.; "Metabolism of Propane, n-Propylamine, and Propionate by Hydrocarbon-Utilizing Bacteria"; Journal of Bacteriology; bearing a date of Oct. 1972; pp. 513-518; vol. 112, No. 1; American Society for Microbiology.
Boix et al.; "Adsorption of recombinant human bone morphogenetic protein rhBMP-2m onto hydroxyapatite"; Journal of Inorganic Biochemistry; bearing a date of 2005; pp. 1043-1050; vol. 99; Elsevier Inc.

(56) References Cited

OTHER PUBLICATIONS

"Bone Anabolic Hormones, Their Receptors and Signal Transduction Pathways"; Office of Extramural Research; bearing a date of Oct. 10, 2002; pp. 1-10; National Institutes of Health; located at: located at: http://grants.nih.gov/grants/guide/search_results.htm?text_curr=PA-03-008&Search.x=24&Search.y=4&scope=all&year=all&sort=rel under Announcement No. PA-03-008.
Bone (anatomy), Microsoft® Encarta™ Online Encyclopedia 2003; http://encarta.msn.com © 1997-2003 Microsoft Corporation. All Rights Reserved; 1 page; available online Dec. 6, 2003; 1 page; obtained via WayBack, Internet Archive, http://web.archive.org accessed May 27, 2008.
Boron et al., "Medical Physiology: A Cellular and Molecular Approach"; bearing a date of 2004; synopsis; 1 pg.; Elsevier/Saunders.
Braat et al.; "A Phase 1 Trial With Transgenic Bacteria Expressing Interleukin-10 in Crohn's Disease"; Clinical Gastroenterology and Hepatology; bearing a date of 2006; pp. 754-759; vol. 4; American Gastroenterological Association Institute.
Bradbury, Jane; "Feature: Nature's Nanotechnologists: Unveiling the Secrets of Diatoms"; Public Library of Science—Biology; bearing a date of Oct. 2004; pp. 1512-1515; vol. 2, No. 10; Jane Bradbury; located at: www.plosbiology.org.
Bragança et al.; "Synergism between Multiple Virus-induced Factor-binding Elements Involved in the Differential Expression of Interferon A Genes"; The Journal of Biological Chemistry; bearing a date of Aug. 29, 1997; pp. 22154-22162; vol. 272, No. 35; The American Society for Biochemistry and Molecular Biology, Inc.
Brämswig et al.; "Immunization with Mimotypes Prevents Growth of Carcinoembryonic Antigen—Positive Tumors in BALB/c Mice"; Clin Cancer Res; bearing a date of Nov. 1, 2007; pp. 6501-6508; vol. 13, No. 21; American Association for Cancer Research.
Brannon-Peppas, Lisa; "Biomaterials: Polymers in Controlled Drug Delivery"; Medical Plastics and Biomaterials Magazine; bearing a date of Nov. 1997; pp. 1-10; Medical Plastics and Biomaterials; located at: http://www.devicelink.com/grabber.php3?URL=http://www.devicelink.com/mpb/archive/97/11/003.html.
Breguet et al.; "CHO immobilization in alginate/poly-L-lysine microcapsules: an understanding of potential and limitations"; Cytotechnology; bearing a date of 2007; pp. 81-93; vol. 53; Springer Science+Business Media B.V. 2007.
Brenner et al.; "Engineered bidirectional communication mediates a consensus in a microbial biofilm consortium"; PNAS; bearing a date of Oct. 30, 2007; pp. 17300-17304; vol. 104, No. 44; The National Academy of Sciences of the USA.
Brenner et al.; "Engineering microbial consortia: a new frontier in synthetic biology"; Trends in Biotechnology; bearing a date of 2008; pp. 483-489; vol. 26, No. 9; Elsevier Ltd.
Brichard et al.; "The Tyrosinase Gene Codes for an Antigen Recognized by Autologous Cytolytic T Lymphocytes on HLA-A2 Melanomas"; J. Exp. Med.; bearing a date of Aug. 1993; pp. 489-495; vol. 178; The Rockefeller University Press.
Brown, MJ; "Therapeutic potential of vaccines in the management of hypertension"; Drugs; Abstract; 1 pg.; bearing a date of 2008; pp. 2557-2560; vol. 68, No. 18.
Brown et al.; "Molecular Mechanisms of Cerebrospinal Fluid Production"; Neuroscience; bearing a date of 2004; pp. 957-970; vol. 129; Elsevier Ltd.
Brownlees et al.; "Short Review: Peptidases, Peptides, and the Mammalian Blood-Brain Barrier"; Journal of Neurochemistry; bearing a date of 1993; pp. 793-803; vol. 60, No. 3; International Society for Neurochemistry.
Brownson et al.; "Effect of Peptidases at the Blood Brain Barrier on the Permeability of Enkephalin"; The Journal of Pharmacology and Experimental Therapeutics; bearing dates of 1994 and Apr. 18, 1994; pp. 675-680; vol. 270, No. 2; The American Society for Pharmacology and Experimental Therapeutics.
Buesing et al.; "Incorporation of Radiolabeled Leucine into Protein to Estimate Bacterial Production in Plant Litter, Sediment, Epiphytic Biofilms, and Water Samples"; Microbial Ecology; bearing a date of 2003; pp. 291-301; vol. 45; Springer-Verlag New York Inc.
Butt et al.; "Electrical Resistance Across the Blood-Brain Barrier in Anaesthetized Rats: A Developmental Study"; Journal of Physiology; bearing a date of Oct. 1990; pp. 47-62; vol. 429; Printed in Great Britain.
Carinci et al.; "Genetic effects of anorganic bovine bone (Bio-Oss®) on osteoblast-like MG63 cells"; Archives of Oral Biology; bearing a date of 2006; pp. 154-163; vol. 51; Elssevier Ltd.; located at: www.intl.elsevierhealth.com/journals/arob and at: www.sciencedirect.com.
Carter et al.; "Identification and validation of cell surface antigens for antibody targeting in oncology"; Endocrine-Related Cancer; bearing a date of 2004; pp. 659-687; vol. 11; Society for Endocrinology.
Caspi et al.; "Tissue Engineering of Vascularized Cardiac Muscle From Human Embryonic Stem Cells"; Circulation Research; bearing a date of Feb. 2, 2007; pp. 1-11; American Heather Association, Inc.; located at: http://circres.ahajournals.org/cgi/reprint/01.RES.0000257776.05673.ffvl.
Casson et al.; "The POLARIS Gene of *Arabidopsis* Encodes a Predicted Peptide Required for Correct Root Growth and Leaf Vascular Patterning"; The Plant Cell; bearing a date of Aug. 2002; pp. 1705-1721; vol. 14; American Society of Plant Biologists.
Cecchelli et al.; "In vitro model for evaluating drug transport across the blood-brain barrier"; Advanced Drug Delivery Reviews; bearing a date of 1999; pp. 165-178; vol. 36; Elsevier Science B.V.
Celis, Esteban; "Toll-like Receptor Ligands Energize Peptide Vaccines through Multiple Paths"; Cancer Res; bearing a date of Sep. 1, 2007; pp. 7945-7947; American Association for Cancer Research.
Cervasi et al.; "Administration of Fludarabine-Loaded Autologous Red Blood Cells in Simian Immunodeficiency Virus-Infected Sooty Mangabeys Depletes Pstat-1—Expressing Macrophages and Delays the Rebound of Viremia after Suspension of Antiretroviral Therapy"; Journal of Virology; bearing a date of Nov. 2006; pp. 10335-10345; vol. 80, No. 21; American Society for Microbiology.
Charalambides et al.; "Poor results after augmenting autograft with xenograft (Surgibone) in hip revision surgery"; Acta Orthopaedica; bearing a date of 2005; pp. 544-549; vol. 76, No. 4; Taylor & Francis.
Chargelegue et al.; "A Peptide Mimic of a Protective Epitope of Respiratory Syncytial Virus Selected from a Combinatorial Library Induces Virus-Neutralizing Antibodies and Reduces Viral Load in Vivo"; Journal of Virology; bearing a date of Mar. 1998; pp. 2040-2046; vol. 72, No. 3; American Society for Microbiology.
Cohen et al.; "Phenotypic Characterization of Mononuclear Cells Following Anorganic Bovine Bone Implantation in Rats"; J Periodontol; bearing a date of Nov. 1994; pp. 1008-1015; vol. 65, No. 11.
Colleoni et al.; "Establishment, Differentiation, Electroporation, Viral Transduction, and Nuclear Transfer of Bovine and Porcine Mesenchymal Stem Cells"; Cloning and Stem Cells; bearing a date of Nov. 3, 2005; pp. 154-166; vol. 7, No. 3; Mary Ann Liebert, Inc.
Colton et al.; "Bioengineering in Development of the Hybrid Artificial Pancreas"; Journal of Biomechanical Engineering; bearing a date of May 1991; pp. 152-170; vol. 113.
Contreras et al.; "Conditional-Suicide Containment System for Bacteria Which Mineralize Aromatics"; Applied and Environmental Microbiology; bearing a date of May 1991; pp. 1504-1508; vol. 57, No. 5; American Society for Microbiology.
Coomber et al.; "Morphometric Analysis of CNS Microvascular Endothelium"; Microvascular Research; bearing a date of 1985; pp. 99-115; vol. 30; Academic Press.
Cornford et al.; "Localization of Brain Endothelial Luminal and Abluminal Transporters with Immunogold Electron Microsopy"; NeuroRx: The Journal of the American Society for Experimental NeuroTherapeutics; bearing a date of Jan. 2005; pp. 27-43; vol. 2; The American Society for Experimental NeuroTherapeutics, Inc.
Cotter et al.; "Surviving the Acid Test: Responses of Gram-Positive Bacteria to Low pH"; Microbiology and Molecular Biology Reviews; bearing a date of Sep. 2003; pp. 429-453; vol. 67, No. 3; American Society for Microbiology.
Cozzi et al.; "Review: Xenotransplantation, where do we stand?"; Journal of Nephrology; bearing a date of 2003; 9 pages; vol. 16,

(56) References Cited

OTHER PUBLICATIONS

Suppl. No. 7, S16-S21; Italian Society of Nephrology; located at: http://www.sin-italy.org/jnonline/vol16%20suppl%207n/s16.html; printed on Feb. 22, 2006.
Crawford et al.; "Effects of a Lignin Peroxidase-Expressing Recombinant, *Streptomyces lividans* TK23.1, on Biogeochemical Cycling and the Numbers and Activities of Microorganisms in Soil"; Applied and Environmental Microbiology; bearing a date of Feb. 1993; pp. 508-518; vol. 59, No. 2; American Society for Microbiology.
Crone et al.; "Electrical Resistance of a Capillary Endothelium"; The Journal of General Physiology; bearing a date of Apr. 1981; pp. 349-371; vol. 77, No. 4; The Rockefeller University Press.
D'Urso et al.; "Custom cranioplasty using stereolithography and acrylic"; British Journal of Plastic Surgery; bearing a date of 2000; pp. 200-204; vol. 53; The British Association of Plastic Surgeons.
Dalton et al.; "Phospholipid/Cell Membrane"; available as of 2003, via Wayback Machine; pp. 1-5; located at http://202.114.65.51/fzjx/wsw/newindex/website/cellb/chapter2/membrane.html.
De Boer et al.; "The Role of Drug Transporters at the Blood-Brain Barrier"; Annual Review of Pharmacology and Toxicology; bearing a date of 2003; pp. 629-656; vol. 43; Annual Reviews.
De Boer; Herman, MD; "The History of Bone Grafts"; Clinical Orthopedics and Related Research; bearing a date of Jan. 1988; pp. 292-298; No. 226; University Hospital Leiden; The Netherlands.
De Silva et al.; "Dietary Oleic Acid Protects Against the Development of Ulcerative Colitis—A UK Prospective Cohort Study Using Data From Food Diaries"; AGA Abstracts; p. S-18; printed on May 19, 2010.
De Stefano et al.; "Nanostructures in Diatom Frustules: Functional Morphology of Valvocopulae in Cocconeidacean Monoraphid Taxa"; Journal of Nanoscience and Nanotechnology; bearing a date of 2005; pp. 15-24; vol. 5, No. 1; American Scientific Publishers.
Deans et al.; "Mesenchymal stem cells: Biology and potential clinical uses"; International Society for Experimental Hematology; bearing a date of 2000; pp. 875-884; vol. 28; Elsevier Science Inc.
Deeba et al.; "Phospholipid diversity: Correlation with membrane-membrane fusion events"; Biochimica et Biophysica Acta 1669; bearing a date of 2005; pp. 170-181; Elsevier B.V.; located at: http://www.elsevier.com/locate/bba and at: www.sciencedirect.com.
Deli et al.; "Permeability Studies on In Vitro Blood-Brain Barrier Models: Physiology, Pathology, and Pharmacology"; Cellular and Molecular Neurobiology; bearing a date of Feb. 2005; pp. 59-127; vol. 25, No. 1; Springer Science + Business Media, Inc.
Delves et al.; Roitt's Essential Immunology, 11th Edition; bearing a date of Aug. 2006; Table of Contents; pp. 1-7; Wiley-Blackwell.
Dethlefsen et al.; "The Pervasive Effects of an Antibiotic on the Human Gut Microbiota, as Revealed by Deep 16S rRNA Sequencing"; PLoS Biology; bearing a date of Nov. 2008; pp. 2383-2400; vol. 6, No. 11; plosbiology.org.
Diggle et al.; "Quorum sensing"; Current Biology; bearing a date of Nov. 6, 2007; pp. R907-R910; vol. 17, No. 21.
Dueber et al.; "Synthetic protein scaffolds provide modular control over metabolic flux"; Nature Biotechnology; bearing a date of Aug. 2009; pp. 753-759; vol. 27, No. 8; Nature America, Inc.
Dunahay et al.; "Genetic Transformation of the Diatoms Cyclotella Cryptica and Navicula Saprophila"; Journal of Phycology; bearing a date of Dec. 1995; pp. 1004-1012; vol. 31, No. 6; Phycological Society of America; located at: http://www.blackwell-synergy.com.
Dunahay et al.; "Manipulation of Microalgal Lipid Production Using Genetic Engineering"; Appl. Biochem Biotechnol 57-58; bearing a date of 1996; pp. 223-231; Abstract; 1 page.
Duplomb et al.; "Embryonic stem cells: new tool to study osteoblast and osteoclast differentiation"; Stem Cells; published online Nov. 9, 2006; pp. 1-40; AlphaMed Press.
Duplomb et al.; "Concise Review: Embryonic Stem Cells: A New Tool to Study Osteoblast and Osteoclast Differentiation"; Stem Cells; bearing a date of 2007; pp. 544-552; vol. 25.
Duport et al.; "An in vitro blood-brain barrier model: Cocultures between endothelial cells and organotypic brain slice cultures"; Proc. Natl. Acad. Sci. USA; bearing a date of Feb. 1998; pp. 1840-1845; vol. 95; The National Academy of Sciences.
Ehrick et al.; "Ligand-Modified Aminobisphosphonate for Linking Proteins to Hydroxyapatite and Bone Surface"; Bioconjugate Chem.; bearing a date of 2008; pp. 315-321 plus cover page; vol. 19, No. 1; American Chemical Society.
Eiden-Plach et al.; "Viral Preprotoxin Signal Sequence Allows Efficient Secretion of Green Fluorescent Protein by *Candida glabrata, Pichia pastoris, Saccharomyces cerevisiae,* and *Schizosaccharomyces pombe*"; Applied and Environmental Microbiology; bearing a date of Feb. 2004; pp. 961-966; vol. 70, No. 2; American Society for Microbiology.
Emerich et al.; "Review: Update on Immunoisolation Cell Therapy for CNS Diseases"; Cell Transplantation; bearing a date of 2001; pp. 3-24; vol. 10; Cognizant Comm. Corp.
Engelberg-Kulka et al.; "Bacterial Programmed Cell Death and Multicellular Behavior in Bacteria"; PLoS Genetics; bearing a date of Oct. 2006; pp. 1518-1526; vol. 2, No. 10; plosgenetics.org.
Eschenfeldt et al.; "Transformation of Fatty Acids Catalyzed by Cytochrome P450 Monooxygenase Enzymes of *Candida tropicalis*"; Applied and Environmental Microbiology; bearing a date of Oct. 2003; pp. 5992-5999; vol. 69, No. 10; American Society for Microbiology.
Ewers et al.; "Histologic findings at augmented bone areas supplied with two different bone substitute materials combined with sinus floor lifting"; Clin. Oral Impl. Res.; bearing a date of 2004; pp. 96-100; vol. 15; Blackwell Munksgaard.
Falciatore et al.; "Transformation of Nonselectable Reporter Genes in Marine Diatoms"; Marine Biotechnology; bearing a date of May 1999; pp. 239-251; vol. 1, No. 3; Sprinter-Verlag New York, Inc.
Fanucci et al.; "Membrane mimetic environments alter the conformation of the outer membrane protein BtuB"; J Am Chem Soc; bearing a date of Nov. 19, 2003; pp. 13932-13933; Abstract; 1 pg.; vol. 125, No. 46.
Farrell et al.; "Neurobiology: Blood-brain Barrier Glucose Transporter is Asymmetrically Distributed on Brain Capillary Endothelial Lumenal and Abluminal Membranes: An Electron Microscopic Immunogold Study"; Proc. Natl. Acad. Sci. USA; bearing a date of Jul. 1991; pp. 5779-5783; vol. 88, No. 13.
Felfoul et al.; "Magnetic Resonance Imaging of Fe3O4 Nanoparticles Embedded in Living Magnetotactic Bacteria for Potential Use as Carriers for in Vivo Applications"; Engineering in Medicine and Biology Society, 2007, EMBS 2007—29th Annual International Conference of the IEEE; bearing dates of Aug. 22-26, 2007; pp. 1463-1466; Abstract, 1 page.
Fest et al.; "Characterization of GD2 Peptide Mimotope DNA Vaccines Effective against Spontaneous Neuroblastoma Metastases"; Cancer Res 2006; bearing a date of Nov. 1, 2006; pp. 10567-10575; vol. 66, No. 21; American Association for Cancer Research.
Fischer et al.; "Targeting and Covalent Modification of Cell Wall and Membrane Proteins Heterologously Expressed in the Diatom Cylindrotheca Fusiformis (Bacillariophyceae)"; Journal of Phycology; bearing a date of Feb. 1999; pp. 113-120; vol. 35, No. 1; located at http://www.blackwell-synergy.com/links/doi/10.1046/j.1529-8817.1999.3510113.x.
Florea et al.; "Epitope Prediction Algorithms for Peptide-based Vaccine Design"; Proceedings of the Computational Systems Bioinformatics; bearing a date of 2003; pp. 1-10; IEEE.
Folwarczna et al.; "Effects of standard heparin and low-molecular-weight heparins on the formation of murine osteoclasts in vitro"; Pharmacological Reports; bearing a date of 2005; pp. 635-645; vol. 57; Institute of Pharmacology Polish Academy of Sciences.
Frederiksen et'al.; "IL-21 induces in vivo immune activation of NK cells and CD8+ T cells in patients with metastatic melanoma and renal cell carcinoma"; Cancer Immunol Immunother; bearing a date of 2008; pp. 1439-1449; vol. 57; Springer.
Friedland et al.; "Synthetic Gene Networks That Count"; Science; bearing a date of May 29, 2009; pp. 1199-1202 plus cover page; vol. 324; sciencemag.org.
Frigeri et al.; "Research: Identification of Proteins from a Cell Wall Fraction of the Diatom *Thalassiosira pseudonana*"; Molecular & Cellular Proteomics 5.1; bearing a date of Jan. 2006; pp. 182-193;

(56) References Cited

OTHER PUBLICATIONS vol. 5, No. 1; The American Society for Biochemistry and Molecular Biology, Inc.; located at: www.mcponline.org.

Fulmer et al.; "Anorganic bovine bone and analogs of bone mineral as impl. for craniofacial surgery: a literature review."; J Long Term Eff Med Implants; bearing a date of 1998; pp. 69-78; vol. 8, No. 1; Abstract; 1 page.

Fulurija et al.; "Vaccination against GIP for the Treatment of Obesity"; PLoS ONE; bearing a date of Sep. 2008; pp. 1-11; vol. 3, No. 9.

Furuse et al.; "Manner of Interaction of Heterogeneous Claudin Species Within and Between Tight Junction Strands"; The Journal of Cell Biology; bearing a date of Nov. 15, 1999; pp. 891-903; vol. 147, No. 4; The Rockefeller University Press.

Gajewski et al.; "Immunization of HLA-A2+ Melanoma Patients with MAGE-3 or MelanA Peptide-pulsed Autologous Peripheral Blood Mononuclear Cells Plus Recombinant Human Interleukin 12"; Clinical Cancer Research; bearing a date of Mar. 2001 (Suppl.); pp. 895s-901s; vol. 7.

Gamradt et al.; "Genetic Modification of Stem Cells to Enhance Bone Repair"; Annals of Biomedical Engineering; bearing a date of Jan. 2004; pp. 136-147; vol. 32, No. 1; Biomedical Engineering Society.

Gao et al.; "Organic Anion Transport Across the Choroid Plexus"; Microscopy Research and Technique; bearing a date of 2001; pp. 60-64; vol. 52; Wiley-Liss, Inc.

Garmory et al.; "DNA vaccines: improving expression of antigens"; Genetic Vaccines and Therapy; bearing a date of 2003; pp. 1-5; vol. 1, No. 2; BioMed Central Ltd.

Garrait et al.; "Recombinant *Saccharomyces cerevisiae* Strain Expressing a Model Cytochrome P450 in the Rat Digestive Environment: Viability and Bioconversion Activity"; Applied and Environmental Microbiology; bearing a date of Jun. 2007; pp. 3566-3574; vol. 73, No. 11; American Society for Microbiology.

Gavin et al.; "Adjuvant-Enhanced Antibody Responses in the Absence of Toll-Like Receptor Signaling"; Science; bearing a date of Dec. 22, 2006; pp. 1936-1938; vol. 314.

Gebeshuber et al.; "Research Article: Diatom Bionanotribology—Biological Surfaces in Relative Motion: Their Design, Friction, Adhesion, Lubrication and Wear"; Journal of Nanoscience and Nanotechnology; bearing a date of 2005; pp. 79-87; vol. 5, No. 1; American Scientific Publishers.

"Genetically Engineered Materials and Micro/Nano Devices"; GEMS; bearing a date of 2006; pp. 1-16; School of Materials Science and Engineering Georgia Institute of Technology; located at: http://www.mls.gatech.edu.

Ghitescu et al.; "Diversity in Unity: The Biochemical Composition of the Endothelial Cell Surface Varies Between the Vascular Beds"; Microscopy Research and Technique; bearing a date of 2002; pp. 381-389; vol. 57; Wiley-Liss, Inc.; located at: www.interscience.wiley.com.

Glazer et al; "Microbial Biotechnology: Fundamentals of Applied Microbiology", bearing a date of Sep. 2007; $2^{nd}$ edition; Title pages and Table of Contents; total of 7 pgs.; Cambridge University Press.

Glowacki, Julie; "Review: A review of osteoinductive testing methods and sterilization processes for demineralized bone"; Cell and Tissue Banking; bearing a date of 2005; pp. 3-12; vol. 6; Springer.

Godeau et al.; "Lipid-Conjugated Oligonucleotides via 'Click Chemistry' Efficiently Inhibit Hepatitis C Virus Translation"; J. Med. Chem.; bearing a date of 2008; pp. 4374-4376 plus cover page; vol. 51, No. 15; American Chemical Society.

Gordon et al.; "Review: Potential Roles for Diatomists in Nanotechnology"; Journal of Nanoscience and Nanotechnology; bearing a date of 2005; pp. 35-40; vol. 5, No. 1; American Scientific Publishers.

Gordon et al.; "A Special Issue on Diatom Nanotechnology"; Journal of Nanoscience and Nanotechnology; bearing a date of 2005; pp. 1-4; vol. 5, No. 1; American Scientific Publishers.

Graham, Barney S.; "New Approaches to Vaccine Adjuvants: Inhibiting the Inhibitor"; PL$_o$S Medicine; bearing a date of Jan. 2006; pp. 0018-0020; vol. 3, Issue 1.

Graham, Sarah; "High-Res Images Expose Bone's 'Glue'"; Science News; bearing a date of Jul. 20, 2005, pp. 1-2.

Grangette et al.; "Enhanced Mucosal Delivery of Antigen with Cell Wall Mutants of Lactic Acid Bacteria"; Infection and Immunity; bearing a date of May 2004; pp. 2731-2737; vol. 72, No. 5; American Society for Microbiology.

Grant et al.; "Understanding the Physiology of the Blood-Brain Barrier: In Vitro Models"; News Physiol. Sci.; bearing a date of Dec. 1998; pp. 287-293; vol. 13; © 1998 Int. Union Physiol. Sci/Am. Physiol. Soc.; located at http://physiologyonline.physiology.org/cgi/content/full/13/6/287.

Griffith, Linda G.; "Emerging Design Principles in Biomaterials and Scaffolds for Tissue Engineering"; Ann. N.Y. Acad. Sci.; bearing a date of 2002; pp. 83-95; vol. 961; New York Academy of Sciences.

Hagenbeek et al.; "Trivalent Ions Activate Abscisic Acid-Inducible Promoters through an ABI1-Dependent Pathway in Rice Protoplasts"; Plant Physiology; bearing a date of Aug. 2000; pp. 1553-1560; vol. 123; American Society of Plant Physiologists.

Hakomori et al.; "Glycosylation defining cancer malignancy: New wine in an old bottle"; PNAS; bearing a date of Aug. 6, 2002; pp. 10231-10233; vol. 99, No. 16; Pacific Northwest Research Institute.

Hamm, Christian E.; "Research Article: The Evolution of Advanced Mechanical Defenses and Potential Technological Applications of Diatom Shells"; Journal of Nanoscience and Nanotechnology; bearing a date of 2005; pp. 108-119; vol. 5, No. 1; American Scientific Publishers.

Hanks et al.; "Comparison of cell viability on anorganic bone matrix with or without P-15 cell binding peptide"; Biomaterials; bearing a date of 2004; pp. 4831-4836; vol. 25; Elsevier Ltd.; located at: www.elsevier.com/locate/biomaterials and www.sciencedirect.com.

Hanniffy et al.; "Potential and Opportunities for Use of Recombinant Lactic Acid Bacteria in Human Health"; Advances in Applied Microbiology; bearing a date of 2004; pp. 1-64; vol. 56; Elsevier, Inc.

Hansen et al.; "Detection of Oxytetracycline Production by *Streptomyces rimosus* in Soil Microcosms by Combining Whole-Cell Biosensors and Flow Cytometry"; Applied and Environmental Microbiology; bearing a date of Jan. 2001; pp. 239-244; vol. 67, No. 1; American Society for Microbiology.

Harlow et al.; "Antibodies: A Laboratory Manual"; bearing a date of 1999; Abstract (3 pages); Cold Spring Harbor Laboratory Press.

Harrison, Leonard C.; "Vaccination against self to prevent autoimmune disease: the type 1 diabetes model"; Immunology and Cell Biology; Abstract; 2 pgs.; bearing a date of 2008; pp. 139-145; vol. 86.

Haskins et al.; "ZO-3, a Novel Member of the MAGUK Protein Family Found at the Tight Junction, Interacts with ZO-1 and Occludin"; The Journal of Cell Biology; bearing a date of Apr. 6, 1998; pp. 199-208; vol. 141, No. 1; The Rockefeller University Press.

Hasle et al.; Identifying Marine Phytoplankton; bearing a date of 1997; Chapter 2; Marine Diatoms; 2 pgs.; Academic Press. San Diego, CA.

Haynesworth et al.; "Characterization of Cells with Osteogenic Potential from Human Marrow"; Bone; bearing a date of 1992; pp. 81-88; vol. 13; Pergamon Press plc.

Hein et al.; "Click Chemistry, A Powerful Tool for Pharmaceutical Sciences"; Pharmaceutical Research; bearing a date of Oct. 2008; pp. 2216-2230; vol. 25, No. 10; Springer Science + Business Media, LLC.

Heit et al.; "Antigen co-encapsulated with adjuvants efficiently drive protective T cell immunity"; Eur J. Immunol.; bearing a date of 2007; pp. 2063-2074; vol. 37; WILEY-VCH Verlag GmbH & Co., KGaA, Weinheim.

Hernandez et al.; "Virus-Cell and Cell-Cell Fusion"; Annu. Rev. Cell Dev. Biol.; bearing a date of 1996; pp. 627-661; vol. 12; Annual Review.

Hildebrand, Mark; "Research Article: Prospects of Manipulating Diatom Silica Nanostructure"; Journal of Nanoscience and Nanotechnology; bearing a date of 2005; pp. 146-157; vol. 5, No. 1; American Scientific Publishers.

Hirschowitz et al.; "Autologous Dendritic Cell Vaccines for Non-Small-Cell Lung Cancer"; Journal of Clinical Oncology; bearing a date of Jul. 15, 2004; pp. 2808-2815; vol. 22, No. 14; American Society of Clinical Oncology.

(56) References Cited

OTHER PUBLICATIONS

Hoensch et al.; "Monooxygenase enzyme activity in alcoholics with varying degrees of liver damage"; Gut; bearing a date of 1979; pp. 666-672; vol. 20.

Hole et al.; "A study of biologically active peptide sequences (P-15) on the surface of an ABM scaffold (PepGen P-15™) using AFM and FTIR"; J Biomed Mater Res; bearing a date of Jul. 14, 2005; pp. 712-721; vol. 74A; Wiley Periodicals, Inc.; located at www.interscience.wiley.com.

Holy et al.; "Engineering three-dimensional bone tissue in vitro using biodegradable scaffolds: Investigating initial cell-seeding density and culture period"; J. Biomed Mater Res; bearing a date of 2000; pp. 376-382; vol. 51; John Wiley & Sons, Inc.

Horwitz et al.; "Isolated allogeneic bone marrow-derived mesenchymal cells engraft and stimulate growth in children with osteogenesis imperfecta: Implications for cell therapy of bone"; PNAS; bearing a date of Jun. 25, 2002; pp. 8932-8937; vol. 99, No. 13; located at: www.pnas.org/cgi/doi/10.1073/pnas.132252399.

Hosoya et al.; "A new in vitro model for blood-cerebrospinal fluid barrier transport studies: an immortalized choroid plexus epithelial cell line derived from the tsA58 SV40 large T-antigen gene transgenic rat"; Advanced Drug Delivery Reviews; bearing a date of 2004; pp. 1875-1885; vol. 56; Elsevier B.V.

Hou et al.; "Development of Peptide Mimotypes of Lipooligosaccharide from Nontypeable Haemophilus influenzae as Vaccine Candidates"; The Journal of Immunology; bearing a date of 2003; pp. 4373-4379; vol. 170; The American Association of Immunologists, Inc.

Hutmacher et al.; "Scaffold-based bone engineering by using genetically modified cells"; Gene: Section Functional Genomics; bearing a date of 2005; pp. 1-10; vol. 347; Elsevier B.V.; located at: www.elsevier.com/locate/gene and www.sciencedirect.com.

Ishaug-Riley et al.; "Three-dimensional culture of rat calvarial osteoblasts in porous biodegradable polymers"; Biomaterials; bearing a date of 1998; pp. 1405-1412; vol. 19; Elsevier Science Ltd.

Iwata et al; "Control of Complement Activities for Immunoisolation"; Annals New York Academy of Sciences; bearing a date of 1999; pp. 7-23.

Iwata et al.; "Agarose for a bioartificial pancreas"; Journal of Biomedical Materials Research; bearing a date of 1992; pp. 967-977; vol. 26; John Wiley & Sons, Inc.

Janáček et al.; "Minireview—Osmosis: Membranes Impermeable and Permeable for Solutes, Mechanism of Osmosis across Porous Membranes"; Physiological Research; bearing a date of 2000; pp. 191-195; vol. 49; Institute of Physiology, Academy of Sciences of the Czech Republic, Prague, Czech Republic.

Janigro et al.; "In vitro blood-brain barrier model for HIV-induced CNS disease"; NeuroAIDS; bearing a date of Aug. 1998; pp. 1-6; vol. 1, No. 4; The American Association for the Advancement of Science; located at: http://www.aidscience.org/neuroaids/Articles/Neurol(4).htm.

Jensen et al.; "A Substrate-Dependent Biological Containment System for *Pseudomonas putida* Based on the *Escherichia coli gef* Gene"; Applied and Environmental Microbiology; bearing a date of Nov. 1993; pp. 3713-3717; vol. 59, No. 11; American Society for Microbiology.

Jia et al.; "Gut microbiota: a potential new territory for drug targeting"; Nature Reviews; bearing a date of Feb. 2008; pp. 123-129; vol. 7; Nature Publishing Group.

Johanson et al.; "Enhanced Prospects for Drug Delivery and Brain Targeting by the Choroid Plexus-CSF Route"; Pharmaceutical Research; bearing a date of Jul. 2005; pp. 1011-1037; vol. 22, No. 7; Springer Science + Business Media, Inc.

Josserand et al.; "Evaluation of Drug Penetration into the Brain: A Double Study by in Vivo Imaging with Positron Emission Tomography and Using an in Vitro Model of the Human Blood-Brain Barrier"; The Journal of Pharmacology and Experimental Therapeutics; bearing a date of 2006; pp. 79-86; vol. 316, No. 1; The American Society for Pharmacology and Experimental Therapeutics.

Kambris et al.; "Immune Activation by Life-Shortening *Wolbachia* and Reduced Filarial Competence in Mosquitoes"; Science; bearing a date of Oct. 2, 2009; pp. 134-136 plus cover page; vol. 326.

Kamohara et al.; "Review Article—Artificial liver: Review and Cedars-Sinai experience"; Journal of Hepatobiliary Pancreat Surg; bearing a date of 1998; pp. 273-285; vol. 5; Springer-Verlag.

Kanzler et al.; "Therapeutic targeting of innate immunity with Toll-like receptor agonists and antagonists"; Nature Medicine; bearing a date of May 2007; pp. 552-559; vol. 13, No. 5.

Karageorgiou et al.; "Porosity of 3D biomaterial scaffolds and osteogenesis"; Biomaterials; bearing a date of 2005; pp. 5474-5491; vol. 26; Elsevier Ltd; located at: www.elseiver.com/locate/biomaterials and at: www.sciencedirect.com.

Kassem et al.; "MiniReview—Mesenchymal Stem Cells: Cell Biology and Potential Use in Therapy"; Pharmacology & Toxicology; bearing a date of 2004; pp. 209-214; vol. 95; Basic & Clinical Pharmacology & Toxicology.

Kawakami et al.; "Identification of the Immunodominant Peptides of the MART-1 Human Melanoma Antigen Recognized by the Majority of HLA-A2-restricted Tumor Infiltrating Lymphocytes"; The Journal of Experimental Medicine; bearing a date of Jul. 1994; pp. 347-352; vol. 180.

Kawakami et al.; "The Use of Melanosomal Proteins in the Immunotherapy of Melanoma"; Journal of Immunotherapy—Third Keystone Symposium on Cellular Immunology and the Immunotherapy of Cancer; bearing a date of 1998; pp. 237-246; vol. 21, No. 4; Lippincott-Raven Publishers, Philadelphia.

Kawamoto et al.; "A method for preparing 2- to 50-pm-thick fresh-frozen sections of large samples and undecalcified hard tissues"; Histochem Cell Biol; bearing a date of 2000; pp. 331-339; vol. 113; Springer-Verlag.

Kemp et al.; "Bone marrow-derived mesenchymal stem cells"; Leukemia & Lymphoma; bearing a date of 2005; pp. 1531-1544; vol. 46, No. 11; Taylor & Francis.

Keskar et al.; "In vitro evaluation of macroporous hydrogels to facilitate stem cell infiltration, growth, and mineralization"; Abstract; one page; Tissue Eng Part A; bearing a date of Jul. 2009; pp. 1695-1707; vol. 15, No. 7.

Khakbaznejad et al.; "Effects of titanium-coated micromachined grooved substrata on orienting layers of osteoblasts-like cells and collagen fibers in culture"; J Biomed Mater Res; bearing a date of 2004; pp. 206-218; vol. 70A; Wiley Periodicals, Inc.; located at: www.interscience.wiley.com.

Kilian et al.; "Identification and Characterization of a New Conserved Motif Within the Presequence of Proteins Targeted into Complex Diatom Plastids"; The Plant Journal; bearing a date of Jan. 2005; pp. 175-183; vol. 41, No. 2; Blackwell Publishing Ltd; located at: http://www.blackwell-synergy.com/doi/pdf/10.1111/j.1365-313X.2004.02294.x.

Knappik et al.; "Fully Synthetic Human Combinatorial Antibody Libraries (HuCAL) Based on Modular Consensus Frameworks and CDRs Randomized with Trinucleotides"; J. Mol. Biol.; bearing a date of 2000; pp. 57-86; vol. 296; Academic Press.

Knudsen et al.; "Development of Efficient Suicide Mechanisms for Biological Containment of Bacteria"; Applied and Environmental Microbiology; bearing a date of Jan. 1991; pp. 85-92; vol. 57, No. 1; American Society for Microbiology.

Koç et al.; "Mesenchymal stem cells: Allogeneic mesenchymal stem cell infusion for treatment of metachromatic leukodystrophy (MLD) and Hurler syndrome (MPS-IH)"; Bone Marrow Transplantation; bearing a date of 2002; pp. 215-222; vol. 30; Nature Publishing Group.

Kojima et al.; "Carbon source nutrition of rapamycin biosynthesis in *Streptomyces hygroscopicus*"; Journal of Industrial Microbiology; bearing a date of 1995; pp. 436-439; Abstract; 1 pg.; vol. 14; Society for Industrial Microbiology.

Koppenhagen et al.; "Sustained Cytokine Delivery for Anticancer Vaccination: Lipsomes as Alternative for Gene-transfected Tumor Cells"; Clinical Cancer Research; bearing a date of Aug. 1998; pp. 1881-1886; vol. 4.

Kumar et al.; "Determination of osteoprogenitor-specific promoter activity in mouse mesenchymal stem cells by recombinant adeno-associated virus transduction"; Biochimica et Biophysica Acta; bear-

(56) References Cited

OTHER PUBLICATIONS ing a date of 2005; pp. 95-103; vol. 1731; Elsevier B.V.; located at: http://www.elsevier.com/locate/bba and at: www.sciencedirect.com.
Kumar, Challa S. S. R.; "Nanoparticle for Drug Delivery"; Nanomaterials for Medical Diagnosis and Therapy; bearing a date of 2007; pp. 409-470; Wiley, John & Sons, Incorporated.
Kupper et al.; "Generation of human antibody fragments against *Streptococcus mutans* using a phase display chain shuffling approach"; BMC Biotechnology; bearing a date of 2005; pp. 1-12; vol. 5, No. 4; BioMed Central Ltd.
Lacy et al.; "Maintenance of Normoglycemia in Diabetic Mice by Subcutaneous Xenografts of Encapsulated Islets"; Science; bearing a date of Dec. 20, 1991; pp. 1782-1784; vol. 254.
Lai et al.; "The critical component to establish in vitro BBB model: Pericyte"; Brain Research Reviews; bearing a date of 2005; pp. 258-265; vol. 50; Elsevier B.V.
Lamprecht et al.; "Aberrant expression of the Th2 cytokine IL-21 in Hodgkin lymphoma cells regulates STAT3 signaling and attracts $t_{reg}$ cells via regulation of MIP-3α"; Blood; bearing a date of Oct. 15, 2008; pp. 3339-3347; vol. 112, No. 8.
Landers et al.; "Rapid prototyping of scaffolds derived from thermoreversible hydrogels and tailored for applications in tissue engineering"; Biomaterials; bearing a date of 2002; pp. 4437-4447; vol. 23; Elsevier Science Ltd.; located at: www.elsevier.com/locate/biomaterials.
Lanza et al.; "A Simple Method for Transplanting Discordant Islets Into Rats Using Alginate Gel Spheres"; Abstract; 2 pgs.; Transplantation; bearing a date of May 27, 1995; pp. 1485-1487; vol. 59, No. 10.
Larson et al.; "Development of a Reproducible Procedure for Plasmid DNA Encapsulation by Red Blood Cell Ghosts"; Biodrugs; bearing a date of 2004; pp. 189-198; vol. 18, No. 3; Adis Data Information.
Lau et al.; "Oligomerization of Fusogenic Peptides Promotes Membrane Fusion by Enhancing Membrane Destabilization"; Biophysical Journal; bearing a date of Jan. 2004; pp. 272-284; vol. 86, No. 1; Biophysical Society.
Laurencin et al.; "Bone Graft Substitute Materials"; eMedicine; bearing a date of Feb. 1, 2006; pp. 1-8; Sections 1-11; eMedicine.com, Inc.
Le Blanc et al.; "Research letters: Treatment of severe acute graft-versus-host disease with third party haploidentical mesenchymal stem cells"; The Lancet; bearing a date of May 1, 2004; pp. 1439-1441; vol. 363.
Le Blanc et al.; "HLA expression and immunologic properties of differentiated and undifferentiated mesenchymal stem cells"; Experimental Hematology; bearing a date of 2003; pp. 890-896; vol. 31; Elsevier, Inc.
Leary Swan et al.; "Fabrication and evaluation of nanoporous alumina membranes for osteoblast culture"; J. Biomed Mater Res; bearing a date of 2005; pp. 288-295; vol. 72A; Wiley Periodicals, Inc.
Lebeau et al.; "Mini-Review: Diatom Cultivation and Biotechnologically Relevant Products. Part II: Current and Putative Products"; Applied Microbiology and Biotechnology; bearing a date of Feb. 2003; pp. 624-632; vol. 60, No. 6; Springer-Verlag; located at: www.springerlink.com.
Lebeau et al.; "Mini-Review: Diatom Cultivation and Biotechnologically Relevant Products. Part I: Cultivation at Various Scales"; Applied Microbiology and Biotechnology; bearing a date of 2003; pp. 612-623; vol. 60, No. 6; Springer-Verlag; located at: www.springerlink.com.
Lee et al.; "A Propionate-Inducible Expression System for Enteric Bacteria"; Applied and Environmental Microbiology; bearing a date of Nov. 2005; pp. 6856-6862; vol. 71, No. 11; American Society for Microbiology.
Lee et al.; "A Type I-Secreted, Sulfated Peptide Triggers XA21-Mediated Innate Immunity"; Science; bearing a date of Nov. 6, 2009; pp. 850-853.

Lee et al.; "Preparation of hydroxyapatite spheres with an internal cavity as a scaffold for hard tissue regeneration"; J Mater Sci: Mater Med; bearing a date of 2008; pp. 3029-3034; vol. 19; Springer Science+Business Media, LLC.
Lee et al.; "Hypoxia-inducible gene expression system using the erythropoietin enhancer and 3'-untranslated region for the VEGF gene therapy"; Abstract; 3 pgs.; Journal of Controlled Release; bearing a date of Sep. 28, 2006; pp. 113-119; vol. 115, No. 1.
León Y León, Carlos A.; "New Perspectives in Mercury Porosimetry"; Advances in Colloid and Interface Science; bearing a date of 1998; pp. 341-372; vol. 76-77; Elsevier Science B.V.
Li et al.; "Engineered Recombinant Peanut Protein and Heat-Killed Listeria monocytogenes Coadministration Protects Against Peanut-Induced Anaphylaxis in a Murine Model"; The Journal of Immunology; bearing a date of 2003; pp. 3289-3295; vol. 170; The American Association of Immunologies, Inc.
Lin et al.; "Hydrogels in controlled release formulations: Network design and mathematical modeling"; Advanced Drug Delivery Reviews; bearing a date of 2006; pp. 1379-1408; vol. 58; Elsevier B.V.
Lin et al.; "Functional Bone Engineering Using ex Vivo Gene Therapy and Topology-Optimized, Biodegradable Polymer Composite Scaffolds"; Tissue Engineering; bearing a date of 2005; pp. 1589-1598; vol. 11, No. 9/10; Mary Ann Liebert, Inc.
Linhart et al.; "Biologically and Chemically Optimized Composites of Carbonated Apatite and Polyglycolide as Bone Substitition Materials"; Journal of Biomedical Materials Research; bearing a date of Feb. 2001; pp. 162-171; vol. 54, No. 2; John Wiley & Sons, Inc.; located at: http://www3.interscience.wiley.com/cgi-bin/abstract/75501642/ABSTRACT?CRETRY=1&SRETRY=0.
Liu et al.; "Biomedical nanoparticle carriers with combined thermal and magnetic responses"; Nano Today; bearing a date of 2009; pp. 52-65; vol. 4; Elsevier Ltd.
Liu et al.; "Less harmful acidic degradation of poly(lactic-co-glycolic acid) bone tissue engineering scaffolds through titania nanoparticle addition"; International Journal of Nanomedicine; bearing a date of 2006; pp. 541-545; vol. 1, No. 4; Dove Medical Press Limited.
Lopez et al.; "Prospects in Diatom Research"; Current Opinion in Biotechnology; bearing a date of 2005; pp. 180-186; vol. 16; Elsevier Ltd.; located at: www.sciencedirect.com.
Losic et al.; "Research Article: Pore Architecture of Diatom Frustules: Potential Nanostructured Membranes for Molecular and Particle Separations"; Journal of Nanoscience and Nanotechnology; bearing a date of Apr. 2006; pp. 982-989; vol. 6, No. 4; American Scientific Publishers.
Luke et al.; "Rationale and plans for developing a non-replicating, metabolically active, radiation-attenuated *Plasmodium falciparum* sporozoite vaccine"; The Journal of Experimental Biology; bearing a date of 2003; pp. 3803-3808; vol. 206; The Company of Biologists Ltd.
Lutz et al.; "Biomimetic Silica Formation: Analysis of the Phosphate-Induced Self-Assembly of Polyamines"; Physical Chemistry Chemical Physics; bearing a date of Jul. 2005; pp. 2812-2815; vol. 7, No. 14; The Owner Societies 2005; located at www.rsc.org/pccp.
Maassen et al.; "Instruments for oral disease-intervention strategies: recombinant *Lactobacillus casei* expressing tetanus toxin fragment C for vaccination or myelin proteins for oral tolerance induction in multiple sclerosis"; Vaccine; bearing a date of Apr. 23, 1999; pp. 2117-2128; vol. 17, No. 17; Abstract, 1 pg.
Madsen et al.; "Two acid-inducible promoters from *Lactococcus lactis* require the *cis*-acting ACiD-box and the transcription regulator RcfB"; Molecular Biology; bearing a date of May 2005; pp. 735-746; vol. 56, No. 3; Abstract, 1 pg.; Blackwell Publishing.
Magnani et al.; "Erythrocyte-mediated delivery of drugs, peptides and modified oligonucleotides"; Gene Therapy; bearing a date of 2002; pp. 749-751; vol. 9; Nature Publishing Group.
Maillard et al.; "Structural diversity in twin-arginine signal peptide-binding proteins"; PNAS; bearing a date of Oct. 2, 2007; pp. 15641-15646; vol. 104, No. 40; The National Academy of Sciences of the USA.

(56) References Cited

OTHER PUBLICATIONS

Maki et al.; "Treatment of Diabetes by Xenogeneic Islets Without Immunosuppression: Use of a Vascularized Bioartificial Pancreas"; Diabetes; bearing a date of Mar. 1996; pp. 342-347; vol. 45.

Mallonee et al.; "Cloning and Sequencing of a Bile Acid-Inducible Operon from *Eubacterium* sp. Strain VPI 12708"; Journal of Bacteriology; bearing a date of Dec. 1990; pp. 7011-7019; vol. 172, No. 12; American Society for Microbiology.

Marx, Christopher J.; "Getting in Touch with Your Friends"; Science; bearing a date of May 29, 2009; pp. 1150-1151; vol. 324, No. 5931; Abstract, 1 pg.

Marx, Jean; "Piecing Together Human Aging: Coming to Grips With Bone Loss"; Science; bearing a date of Sep. 3, 2004; pp. 1420-1422; vol. 305; AAAS; located at: www.sciencemag.org.

Matter et al.; "Functional analysis of tight junctions"; Methods; bearing a date of 2003; pp. 228-234; vol. 30; Elsevier Science; located at: www.elsevier.com/locate/ymeth and at: www.sciencedirect.com.

McElhaney, Ronald N.; "Membrane Lipid, Not Polarized Water, is Responsible for the Semipermeable Properties of Living Cells"; Biophysical Journal; bearing a date of 1975; pp. 777-784; vol. 15.

McGraw-Hill Encyclopedia of Science and Technology; Definition of "Bone"; bearing a date of Aug. 6, 2007; 4 pages; taken from Answers.com; http://www.answers.com/topic/bone.

Meyer et al.; "Biological and biophysical principles in extracorporal bone tissue engineering Part III"; International Journal of Oral & Maxillofacial Surgery; bearing a date of 2004; pp. 635-641; vol. 33; Elsevier Ltd.

Meyer et al.; "Biological and biophysical principles in extracorporal bone tissue engineering—Part 1"; International Journal of Oral & Maxillofacial Surgery; bearing a date of 2004; pp. 325-332; vol. 33; Elsevier Ltd.

Michejda, Maria; "Which Stem Cells Should be Used for Transplantation?"; Fetal Diagnosis and Therapy; bearing a date of 2004; pp. 2-8; vol. 19; S. Karger Medical and Scientific; located at: www.karger.com/fdt.

Ming et al.; "Azide-alkyne 'click' reaction performed on oligonucleotides with the universal nucleoside 7-octadiynyl-7-deaza-2'-deoxyinosine"; Nucleic Acids Symposium; bearing a date of Sep. 2008; pp. 471-472; Series No. 52; Oxford University Press.

Minn et al.; "Drug Metabolizing Enzymes in the Brain and Cerebral Microvessels"; Brain Research Reviews; bearing a date of 1991; pp. 65-82; vol. 16; Elsevier Science Publishers B. V.

Mironov et al.; "Cardiovascular Tissue Engineering I. Perfusion Bioreactors: A Review"; Journal of Long-Term Effects of Medical Implants; bearing a date of 2006;.pp. 111-130; vol. 16, No. 2; Begell House, Inc.; located at: http://begellhouse.com.

Misch et al.; "Mechanical Properties of Trabecular Bone in the Human Mandible: Implications for Dental Implant Treatment Planning and Surgical Placement"; J. Oral Maxillofac Surg; bearing a date of 1999; pp. 700-708; vol. 57.

Mishra et al.; "Folate Conjugated Doxorubicin-Loaded Membrane Vesicles for Improved Cancer Therapy"; Drug Delivery; bearing a date of 2003; pp. 277-282; vol. 10; Taylor & Francis Inc.

Mohan et al.; "Bone Growth Factors"; Clinical Orthopaedics and Related Research; bearing a date of Feb. 1991; pp. 30-48; vol. 263.

Montsant et al.; "Comparative Genomics of the Pennate Diatom *Phaeodactylum tricornutum*"; Plant Physiology; bearing a date of Feb. 2005; pp. 500-513; vol. 137; American Society of Plant Biologists; located at: www.plantphysiol.org.

Montsant et al.; "Review: Diatomics: Toward Diatom Functional Genomics"; Journal of Nanoscience and Nanotechnology; bearing a date of 2005; pp. 5-14; vol. 5, No. 1; American Scientific Publishers.

Monzavi-Karbassi et al.; "Peptide mimotopes as surrogate antigens of carbohydrates in vaccine discovery"; Trends in Biotechnology; bearing a date of May 2002; pp. 207-214; vol. 20, No. 5; Elsevier Science Ltd.

Moon et al.; "Biologic Modification of Ligamentum Flavum Cells by Marker Gene Transfer and Recombinant Human Bone Morphogenetic Protein-2"; SPINE; bearing a date of 2004; pp. 960-965; vol. 29, No. 9; Lippincott Williams & Wilkins, Inc.

Morin et al.; "Preferential Binding Sites for Interferon Regulatory Factors 3 and 7 Involved in Interferon-A Gene Transcription"; J. Mol. Biol.; bearing a date of 2002; pp. 1009-1022; vol. 316; Elsevier Science Ltd.

Müller et al., "Microbial Degradation of Halogenated Hydrocarbons: A Biological Solution to Pollution Problems?"; Angewandt Chemie Int Ed English; bearing a date of 1986; pp. 779-789; vol. 25, No. 9; Abstract, 1 pg.; Wiley-VCH Verlag GmbH, Weinheim.

Müller et al.; "Review article—Solid lipid nanoparticles (SLN) for controlled drug delivery —a review of the state of the art"; European Journal of Pharmaceutics and Biopharmaceutics; bearing a date of 2000; pp. 161-177; vol. 50; Elsevier Science B.V.

Mundy, Gregory R.; "Cytokines and Growth Factors in the Regulation of Bone Remodeling"; Journal of Bone and Mineral Research; bearing a date of 1993; pp. S505-S510; vol. 8, Supplement 2; Mary Ann Liebert, Inc.

Muraglia et al.; "Clonal mesenchymal progenitors from human bone marrow differentiate in vitro according to a hierarchical model"; Journal of Cell Science; bearing a date of 2000; pp. 1161-1166; vol. 113; The Company of Biologists Limited.

Murphy et al.; "Live-attenuated virus vaccines for respiratory syncytial and parainfluenza viruses: applications for reverse genetics"; The Journal of Clinical Investigation; bearing a date of Jul. 2002; pp. 21-27; vol. 110, No. 1.

Murphy et al.; "Principles Underlying the Development and Use of Live Attenuated Cold-Adapted Influenza A and B Virus Vaccines"; Viral Immunology; bearing a date of 2002; pp. 295-323; vol. 15, No. 2.

Myers et al.; "MtrB Is Required for Proper Incorporation of the Cytochromes OmcA and OmcB into the Outer Membrane of *Shewanella putrefaciens* MR-1"; Applied and Environmental Microbiology; bearing a date of Nov. 2002; pp. 5585-5594; vol. 68, No. 11; American Society for Microbiology.

Myles et al.; "An assessment of the portability of ancestry informative markers between human populations"; BMC Medical Genomics; bearing a date of 2009; pp. 1-10, vol. 2, No. 45; BioMed Central Ltd.

Nagy et al.; "Human Cerebral Microvessel Endothelial Cell Culture as a Model System to Study the Blood-Brain Interface in Ischemic/Hypoxic Conditions"; Cellular and Molecular Neurobiology; bearing a date of Feb. 2005; pp. 201-210; vol. 25, No. 1; Springer Science + Business Media, Inc.

Nakamura et al.; "Dendritic Cells Genetically Engineered to Simultaneously Express Endogenous Tumor Antigen and Granulocyte Macrophage Colony-stimulating Factor Elicit Potent Therapeutic Antitumor Immunity"; Clinical Cancer Research; bearing a date of Aug. 2002; pp. 2742-2749; vol. 8.

National Center Biotechnology Information (NCBI) Single Nucleotide Polymorphisms, on the worldwide web at www.ncbi.nlm.nih.gov/projects/SNP/; 2 pgs.; printed on May 21, 2010.

Neumann et al.; "Generation of influenza A viruses entirely from cloned cDNAs"; Proc. Natl. Acad. Sci. USA; bearing a date of Aug. 1999; pp. 9345-9350; vol. 96; PNAS.

Nierodzik et al.; "Thrombin Stimulates Tumor-Platelet Adhesion In Vitro and Metastasis In Vivo"; J. Clin. Invest.; bearing a date of Jan. 1991; pp. 229-236; vol. 87; The American Society for Clinical Investigation, Inc.

Nishioka et al.; "Enhancement of drug delivery to bone: Characterization of human tissue-nonspecific alkaline phosphatase tagged with an acidic oligopeptide"; Mol Genet Metab.; bearing a date of Jul. 2006; pp. 1-25; vol. 88, No. 3; National Institutes of Health.

Novellino et al.; "A listing of human tumor antigens recognized by T cells: Mar. 2004 update"; Abstract plus excerpt (total of 14 pages); Cancer Immunol Immunother.; bearing a date of Mar. 2005; pp. 187-207; vol. 54, No. 3.

Nusrat et al.; "Tight Junctions are Membrane Microdomains"; Journal of Cell Science; bearing a date of 2000; pp. 1771-1781; vol. 113; The Company of Biologists Limited.

O'Brien et al.; "Formulation of Poly(DL-Lactide-Co-Glycolide) Microspheres and Their Ingestion by Bovine Leukocytes"; Journal of Dairy Science; bearing a date of 1996; pp. 1954-1959; vol. 79.

(56) References Cited

OTHER PUBLICATIONS

O'Donoghue et al.; "Fetal stem cells"; Best Practice & Research Clinical Obstetrics and Gynaecology; bearing a date of 2004; pp. 853-875; vol. 18, No. 6; Elsevier Ltd; located at: http://www.sciencedirect.com.

O'Hara et al.; "The gut flora as a forgotten organ"; EMBO reports; bearing a date of 2006; pp. 688-693; vol. 7, No. 7; European Molecular Biology Organization.

O'Shea et al.; "BBA Report: Prolonged Survival of Transplanted Islets of Langerhans Encapsulated in a Biocompatible Membrane"; Biochimica et Biophysica Acta; bearing a date of 1984; pp. 133-136; vol. 804; Elsevier Science Publishers B.V.

Ogura et al.; "Differentiation of the human mesenchymal stem cells derived from bone marrow and enhancement of cell attachment by fibronectin"; Journal of Oral Science; bearing a date of 2004; pp. 207-213; vol. 46, No. 4.

Ohgawara, Hisako; "Strategies for immunoisolation in islet transplantation: challenges for the twenty-first century"; J Hepatobiliary Pancreat Surg; bearing a date of 2000; pp. 374-379; vol. 7; Springer-Verlag.

Okada et al.; "Inhibition of Biofilm Formation using Newly Developed Coating Materials with Self-Cleaning Properties"; Dental Materials Journal; bearing a date of 2008; pp. 565-572; vol. 27, No. 4.

Oldendorf et al.; "The Large Apparent Work Capability of the Blood-Brain Barrier: A Study of the Mitochondrial Content of Capillary Endothelial Cells in Brain and Other Tissues of the Rat"; Annals of Neurology; bearing a date of May 1977; pp. 409-417; vol. 1, No. 5.

Oldendorf et al.; "Greater Number of Capillary Endothelial Cell Mitochondria in Brain Than in Muscle (38889)"; Proceedings of the Society for Experimental Biology and Medicine; bearing a date of 1975; pp. 736-738; vol. 149; Society for Experimental Biology and Medicine.

Orive et al.; "Cell encapsulation: Promise and progress"; Nature Medicine; bearing a date of Jan. 2003; pp. 104-107; vol. 9, No. 1; Nature Publishing Company.

Orson et al.; "Substance Abuse Vaccines"; Ann N.Y. Acad. Sci.; bearing a date of 2008; pp. 257-269; vol. 1141; New York Academy of Sciences.

Pappas, Janice L.; "Research Article: Geometry and Topology of Diatom Shape and Surface Morphogenesis for Use in Applications of Nanotechnology"; Journal of Nanoscience and Nanotechnology; bearing a date of 2005; pp. 120-130; vol. 5, No. 1; American Scientific Publishers.

Parrish-Novak et al.; "Interleukin-21 and the IL-21 receptor: novel effectors of NK and T cell responses"; Journal of Leukocyte Biology; bearing a date of Nov. 2002; pp. 856-863; vol. 72.

PCT International Search Report; International App. No. PCT/US 08/01436; pp. 1-2; Apr. 22, 2009.

Peeters et al.; "Resistance of planktonic and biofilm-grown *Burkholderia cepacia* complex isolates to the transition metal gallium"; Journal of Antimicrobial.Chemotherapy; bearing a date of 2008; pp. 1062-1065; vol. 61; Oxford University Press.

Peppas et al.; "Polymers and Gels as Molecular Recognition Agents"; Pharmaceutical Research; bearing a date of May 2002; pp. 578-587; vol. 19, No. 5; Plenum Publishing Corporation.

Perizzolo et al.; "Interaction between topography and coating in the formation of bone nodules in culture for hydroxyapatite- and titanium-coated micromachined surfaces"; J Biomed Mater Res; bearing a date of 2001; pp. 494-503; vol. 56; John Wiley & Sons, Inc.

Pinkel et al.; "Array comparative genomic hybridization and its applications in cancer"; Nature Genetics Supplement; bearing a date of Jun. 2005; pp. S11-S17; vol. 37; Nature Publishing Group.

Pittenger et al.; "Reports: Multilineage Potential of Adult Human Mesenchymal Stem Cells"; Science; bearing a date of Apr. 2, 1999; pp. 143-147; vol. 284; located at: www.sciencemag.org.

Pondaven et al.; "Original Paper: Grazing-Induced Changes in Cell Wall Silicification in a Marine Diatom"; Protist; bearing dates of Nov. 7, 2006 and 2007; pp. 21-28; vol. 158, No. 1; Elsevier GmbH; located at: www.sciencedirect.com.

"Portion"; Definition from Merriam-Webster Online Dictionary; bearing a date of 2009; located at http://www.merriam-webster.com/dictionary/portion.

Poulsen et al.; "Molecular Genetic Manipulation of the Diatom *Thalassiosira pseudonana* (Bacillariophyceae)"; Journal of Phycology; bearing a date of Oct .2006; pp. 1059-1065; vol. 42, No. 5; Phycological Society of America; located at www.ingentaconnect.com.

Poulsen et al.; "A New Molecular Tool for Transgenic Diatoms Control of mRNA and Protein Biosynthesis by an Inducible Promoter-Terminator Cassette"; FEBS Journal (Federation of European Biochemical Societies); bearing a date of Jul. 2005; pp. 3413-3423; vol. 272, No. 13; FEBS; located at: http://www.blackwell-synergy.com/doi/abs/10.1111/j.1742-4658.2005.04760.x.

Prieto et al.; "The Report and Recommendations of ECVAM Workshop 49: Blood-Brain Barrier In Vitro Models and Their Application in Toxicology"; Alternatives to Laboratory Animals; bearing a date of 2004; pp. 37-50; vol. 32, No. 1; ECVAM, Institute for Health & Consumer Protection, European Commission Joint Research Centre.

Pronk, Jack T.; "Auxotrophic Yeast Strains in Fundamental and Applied Research"; Applied and Environmental Microbiology; bearing a date of May 2002; pp. 2095-2100; vol. 68, No. 5; American Society for Microbiology.

Pulanić et al.; "The Past Decade: Fibrinogen"; Coll. Antropol.; bearing a date of 2005; pp. 341-349; vol. 29, No. 1.

Pulendran et al.; "Translating Innate Immunity into Immunological Memory: Implications for Vaccine Development"; Cell; bearing a date of Feb. 24, 2006; pp. 849-863; vol. 124; Elsevier Inc.

Ramos et al.; "The behavior of bacteria designed for biodegradation."; Biotechnology; bearing a date of Dec. 1994; pp. 1349-1356; vol. 12, No. 13; Abstract; 1 pg.

Rao et al.; "Toward a live microbial microbicide for HIV: Commensal bacteria secreting an HIV fusion inhibitor peptide"; PNAS; bearing a date of Aug. 23, 2005; pp. 11993-11998; vol. 102, No. 34.

Rao et al.; "Medical Sciences: Choroid plexus epithelial expression of MDR1 P glycoprotein and blood-cerebrospinal-fluid drug-permeability barrier"; Proc. Natl. Acad. Sci. USA; bearing a date of Mar. 1999; pp. 3900-3905; vol. 96.

Read et al.; "Local endostatin treatment of gliomas administered by microencapsulated producer cells"; Nature Biotechnology; bearing a date of Jan. 2001; pp. 29-34; vol. 19; Nature Publishing Group.

Remington: The Science and Practice of Pharmacy; $20^{th}$ Edition; Cover page (3 pgs.); printed on May 19, 2010; Lippincott Williams & Wilkins, Baltimore, Maryland.

Rensberger et al.; "Letters to nature: Fine structure of bone in dinosaurs, birds and mammals"; Nature; bearing a date of Aug. 10, 2000; pp. 619-622; vol. 406; Macmillan Magazines Ltd.; located at: www.nature.com.

Reszka et al.; "Mechanism of Action of Bisphosphonates"; Current Osteoporosis Reports; bearing a date of 2003; pp. 45-52; vol. 1; Current Science Inc.

Reynolds et al.; "Vaccine-induced CD8+ T-cell Responses to MAGE-3 Correlate with Clinical Outcome in Patients with Melanoma"; Clinical Cancer Research; bearing a date of Feb. 2003; pp. 657-662; vol. 9.

Richter et al.; "Determination of the minimal acid-inducible promoter region of the *lipF* gene from *Mycobacterium tuberculosis*"; Gene; bearing a date of 2006; Abstract; 2 pgs.; Elsevier B.V.

Robbins et al.; "A Mutated β-Catenin Gene Encodes a Melanoma-specific Antigen Recognized by Tumor Infiltrating Lymphocytes"; J. Exp. Med; bearing a date of Mar. 1996; pp. 1185-1192; vol. 183.

Roger et al.; "Critical role for Ets, AP-1 and GATA-like transcription factors in regulating mouse Toll-like receptor 4 (Tlr4) gene expression"; Biochem. J.; bearing a date of 2005; pp. 355-365; vol. 387; Biochemical Society.

Roodman, G. David; "Role of Cytokines in the Regulation of Bone Resorption"; Calcified Tissue International; bearing a date of 1993; pp. S94-S98; vol. 53 (Suppl. I); Springer-Verlag New York Inc.

Rorrer et al.; "Biosynthesis of Silicon-Germanium Oxide Nanocomposites by the Marine Diatom Nitzschia Frustulum"; Journal of Nanoscience and Nanotechnology; bearing a date of 2005; pp. 41-49; vol. 5, No. 1; American Scientific Publishers.

(56) References Cited

OTHER PUBLICATIONS

Rossi et al.; "Review: Erythrocyte-based drug delivery"; Expert Opinion on Drug Delivery; bearing a date of 2005; pp. 311-322; vol. 2, No. 2; Ashley Publications; located at: www.ashely-pub.com.

Roy et al.; "Virus-like particles as a vaccine delivery system"; Human Vaccines; bearing a date of Jan./Feb. 2008; pp. 5-8; vol. 4, No. 1; Landes Bioscience.

Rumpler et al.; "The effect of geometry on three-dimensional tissue growth"; J. R. Soc. Interface; bearing a date of 2008; pp. 1173-1180; vol. 5; The Royal Society.

Runte et al.; "Optical Data Acquisition for Computer-Assisted Design of Facial Prostheses"; The International Journal of Prosthodontics; bearing a date of Mar./Apr. 2002; pp. 129-132; vol. 15, No. 2.

Ryu et al.; "Bacterial volatiles promote growth in Arabidopsis"; PNAS; bearing a date of Apr. 15, 2003; pp. 4927-4932; vol. 100, No. 8.

Salazar-Onfray et al.; "Synthetic Peptides Derived from the Melanocyte-stimulating Hormone Receptor MC1R Can Stimulate HLA-A2-restricted Cytotoxic T Lymphocytes That Recognize Naturally Processed Peptides on Human Melanoma Cells"; Cancer Research; bearing a date of Oct. 1, 1997; pp. 4348-4355; vol. 57.

Sambrook et al.; "Molecular Cloning: A Laboratory Manual"; $3^{rd}$ ed.; bearing a date of Dec. 5, 2000; 4 pgs.; Cold Spring Harbor Laboratory Press, N.Y.

Sangha et al.; "L-BLP25: A Peptide Vaccine Strategy in Non-Small Cell Lung Cancer"; Clin Cancer Res; bearing a date of Aug. 1, 2007; pp. 4652s-4654s; vol. 13; 15 Suppl.

Sargent et al.; "Studies on Foliar Penetration; VI. Factors Controlling The Penetration of 4-Amino-3,5,6-Tri-Chloropicolinic Acid (Picloram) into the Leaves of *Phaseolus vulgaris*"; Journal of Experimental Botany; bearing a date of 1970; pp. 219-227; vol. 21, No. 1; Abstract, 2 pgs.; Oxford University Press.

Scaglione et al.; "Engineering of Osteoinductive Grafts by Isolation and Expansion of Ovine Bone Marrow Stromal Cells Directly on 3D Cermaic Scaffolds"; Biotechnology and Bioengineering; bearing a date of Jan. 5, 2005; pp. 181-187; vol. 93, No. 1; Wiley Periodicals, Inc.

Scala et al.; "Genome Analysis: Genome Properties of the Diatom Phaeodactylum Tricornutum"; Plant Physiology; bearing a date of Jul. 2002; pp. 993-1002; vol. 129; American Society of Plant Biologists; located at: www.plantphysiol.org.

Schantz et al.; "Osteogenic differentiation of mesenchymal progenitor cells in computer designed fibrin-polymer-ceramic scaffolds manufactured by fused deposition modeling"; Journal of Materials Science: Materials in Medicine; bearing a date of 2005; pp. 807-819; vol. 16; Springer Science + Business Media, Inc.

Schett et al.; "Review: Mechanisms of Disease: the link between RANKL and arthritic bone disease"; Nature Clinical Practice: Rheumatology; bearing a date of Nov. 2005; pp. 47-54; vol. 1, No. 1; Nature Publishing Group; located at: www.nature.com/clinicalpractice/rheum.

Schneeberger et al.; "Substructure of Intercellular Junctions in Freeze-Fractured Alveolar-Capillary Membranes of Mouse Lung" Circulation Research; bearing a date of May 1976; pp. 404-411; vol. 38, No. 5; American Heart Association; located at: http://circres.ahajournals.org.

Schweitzer et al.; Gender-Specific Reproductive Tissue in Ratites and *Tyrannosaurus rex*; Science; bearing a date of Jun. 3, 2005; pp. 1456-1460; vol. 308; located at: www.sciencemag.org.

Schweitzer et al.; "Soft-Tissue Vessels and Cellular Preservation in *Tyrannosaurus rex*"; Science; bearing a date of Mar. 25, 2005; pp. 1952-1955; vol. 307; located at: www.sciencemag.org.

Shibata et al.; "Development of a hypoxia-responsive vector for tumor-specific gene therapy"; Gene Therapy; bearing a date of 2007; pp. 493-498; vol. 7; Macmillan Publishers Ltd.

Shim et al.; "Rhizosphere Competitiveness of Trichloroethylene-Degrading, Poplar-Colonizing Recombinant Bacteria"; Applied and Environmental Microbiology; bearing a date of Nov. 2000; pp. 4673-4678; vol. 66, No. 11; American Society for Microbiology.

Shively et al.; "CEA-Related Antigens: Molecular Biology and Clinical Significance"; CRC Critical Reviews in Onocology/Hematology; pp. 355-399; vol. 2, Issue 4; printed on May 18, 2010.

Shou et al.; "Synthetic cooperation in engineered yeast populations"; PNAS; bearing a date of Feb. 6, 2007; pp. 1877-1882; vol. 104, No. 6; The National Academy of Sciences of the USA.

Skarpos et al.; "Synthesis of functionalized bisphosphonates via click chemistry"; Org. Biomol. Chem.; bearing a date of 2007; pp. 2361-2367; vol. 5; The Royal Society of Chemistry.

Slingluff, JR. et al.; "Phase I Trial of a Melanoma Vaccine with $gp100_{280-288}$ Peptide and Tetanus Helper Peptide in Adjuvant: Immunologic and Clinical Outcomes"; Clinical Cancer Research; bearing a date of Oct. 2001; pp. 3012-3024; vol. 7.

Smith et al.; "Cerebrovascular Permeability Coefficients to Sodium, Potassium, and Chloride"; J. Neurochem., bearing a date of 1986; pp. 1732-1742; vol. 46, No. 6; International Society for Neurochemistry.

Smith et al.; "Functional expression of plant acetolactate synthase genes in *Escherichia coli*"; Genetics; bearing a date of Jun. 1989; pp. 4179-4183; vol. 86; PNAS USA.

Sokolov et al.; "Swimming bacteria power microscope gears"; PNAS; Abstract, 1 pg.; bearing a date of Jan. 19, 2010.

Spector, Myron; "Bone Repair and Regeneration: Anorganic Bovine Bone and Ceramic Analogs of Bone Mineral as Implants to Facilitate Bone Regeneration"; Clinics in Plastic Surgery—An International Quarterly; bearing a date of Jul. 1944; pp. 437-444; vol. 21, No. 3; W.B. Saunders Company.

Steidler et al.; "Biological containment of genetically modified *Lactococcus lactis* for intestinal delivery of human interleukin 10"; Nature Biotechnology; bearing a date of Jul. 2003; pp. 785-789; vol. 21, No. 7; Nature Publishing Group.

Steidler et al.; "Mucosal Delivery of Murine Interleukin-2 (IL-2) and IL-6 by Recombinant Strains of *Lactococcus lactis* Coexpressing Antigen and Cytokine"; Infection and Immunity; bearing a date of Jul. 1998; pp. 3183-3189; vol. 66, No. 7; American Society for Microbiology.

Sterrenburg et al.; "Research Article: Valve Morphogenesis in the Diatom Genus Pleurosigma W. Smith (Bacillariophyceae): Nature's Alternative Sandwich"; Journal of Nanoscience and Nanotechnology; bearing a date of 2005; pp. 140-145; vol. 5, No. 1; American Scientific Publishers.

Stevens et al.; "Materials and Biology—Review: Exploring and Engineering the Cell Surface Interface"; Science; bearing a date of Nov. 18, 2005; pp. 1135-1138; vol. 310; located at www.sciencemag.org.

Steward, Michael W.; "The Development of a Mimotope-based Synthetic Peptide Vaccine Against Respiratory Syncytial Virus"; Abstract; 2 pgs.; Biologicals; bearing a date of Sep. 2001; pp. 215-219; vol. 29, Issues 3-4.

Stritzker et al.; "Tumor-specific colonization, tissue distribution, and gene induction by probiotic *Escherichia coli* Nissle 1917 in live mice"; International Journal of Medical Microbiology; bearing a date of 2007; pp. 151-162; vol. 297; Elsevier GmbH.

Sumper et al.; "Biomineralization in Diatoms: Characterization of Novel Polyamines Associated with Silica"; FEBS Letters (Federation of European Biochemical Societies); bearing a date of Jul. 4, 2005; pp. 3765-3769; vol. 579, No. 17; Federation of European Biochemical Societies; Elsevier B.V.; located at www.sciencedirect.com.

Sumper et al.; "Silica Pattern Formation in Diatoms: Species-Specific Polyamine Biosynthesis"; Chembiochem: A European Journal of Chemical Biology; bearing a date of Sep. 2006; pp. 1419-1427; vol. 7, No. 9; Wiley-VCH Verlag GmbH & Co. KGaA, Wienheim; located at: http://www3.interscience.wiley.com/cgi-bin/abstract/112747021/ABSTRACT?CRETRY=1&SRETRY=0.

Sun et al.; "Normalization of Diabetes in Spontaneously Diabetic Cynomologus Monkeys by Xenografts of Microencapsulated Porcine Islets without Immunosuppression"; J. Clin. Invest.; bearing a date of Sep. 1996; pp. 1417-1422; vol. 98, No. 6; The American Society for Clinical Investigation, Inc.

Suyama et al.; "Phylogenetic Affiliation of Soil Bacteria That Degrade Aliphatic Polyesters Available Commercially as Biodegrad-

(56) References Cited

OTHER PUBLICATIONS able Plastics"; Applied and Environmental Microbiology; bearing a date of Dec. 1998; pp. 5008-5011; vol. 64, No. 12; American Society for Microbiology.
Swindell et al.; "Genetic Manipulation of the Pathway for Diacetyl Metabolism in *Lactococcus lactis*"; Applied and Environmental Microbiology; bearing a date of Jul. 1996; pp. 2641-2643; vol. 62, No. 7; American Society for Microbiology.
Syed-Picard et al.; "Three-Dimensional Engineered Bone from Bone Marrow Stromal Cells and Their Autogenous Extracellular Matrix"; Tissue Engineering: Part A; bearing a date of 2009; pp. 187-195; vol. 15, No. 1.
Syvänen, Ann-Christine; "Toward genome-wide SNP genotyping"; Nature Genetics Supplement; bearing a date of Jun. 2005; pp. S5-S10; vol. 37; Nature Publishing Group.
Taghavi et al.; "Genome Survey and Characterization of Endophytic Bacteria Exhibiting a Beneficial Effect on Growth and Development of Poplar Trees"; Applied and Environmental Microbiology; bearing a date of Feb. 2009; pp. 748-757; vol. 75, No. 3; American Society for Microbiology.
Tamura et al.; "Interaction of Recombinant Norwalk Virus Particles with the 105-Kilodalton Cellular Binding Protein, a Candidate Receptor Molecule for Virus Attachment"; Journal of Virology; bearing a date of Dec. 2000; pp. 11589-11597; vol. 74, No. 24; American Society for Microbiology.
Tawata et al.; "Screening for Genetic Mutations. A Review"; Combinatorial Chemistry & High Throughput Screening; bearing a date of 2000; pp. 1-9; vol. 3; Bentham Science Publishers B.V.
Taylor et al.; "Transcription from a heat-inducible promoter causes heat shock regulation of the sigma subunit of *E. coli* RNA polymerase"; Cell; bearing a date of Sep. 1984; pp. 371-381; vol. 38, No. 2; Abstract; 1 pg.
Teixeira et al.; "Laser surface treatment of hydroxyapatite for enhanced tissue integration: surface characterization and osteoblastic interaction studies"; Journal of Biomedical Materials Research Part A; bearing a date of 2007; pp. 920-929; Wiley Periodicals, Inc.
Terasaki et al.; "Conditionally Immortalized Cell Lines as a New In Vitro Model for the Study of Barrier Functions"; Biological & Pharmaceutical Bulletin; bearing a date of Feb. 2001; pp. 111-118; vol. 24, No. 2; Pharmaceutical Society of Japan.
Thamatrakoln et al.; "Research Article: Approaches for Functional Characterization of Diatom Silicic Acid Transporters"; Journal of Nanoscience and Nanotechnology; bearing a date of 2005; pp. 158-166; vol. 5, No. 1; American Scientific Publishers.
The International Hapmap Consortium; "A second generation human haplotype map of over 3.1 million SNPs"; Nature; bearing a date of Oct. 18, 2007; pp. 851-861; vol. 449; Nature Publishing Group.
Treys et al.; "Tumor-Specific Gene Delivery Using Genetically Engineered Bacteria"; Current Gene Therapy; bearing a date of Jun. 2003; pp. 207-221; vol. 3, No. 3; Abstract, 2 pgs.; www.ingentaconnect.com.
Thompson et al.; "The low-toxicity versions of LPS, MPL® adjuvant and RC529, are efficient adjuvants for CD4+ T cells"; Journal of Leukocytee Biology; bearing a date of Dec. 2005; pp. 1273-1280; vol. 78; Society for Leukocyte Biology.
Thomson et al.; "Fabrication of biodegradable polymer scaffolds to engineer trabecular bone"; Abstract, 1 page; J Biomater Sci Polym Ed.; bearing a date of 1995; pp. 23-38; vol. 7, No. 1.
Thorwarth et al.; "Bioactivation of an anorganic bone matrix by P-15 peptide for the promotion of early bone formation"; Biomaterials; bearing a date of 2005; pp. 5648-5657; vol. 26; Elsevier Ltd.; located at: www.elsevier.com/locate/biomaterials and at: www.sciencedirect.com.
Tiffany, Mary Ann; "Research Article: Diatom Auxospore Scales and Early Stages in Diatom Frustule Morphogenesis: Their Potential for Use in Nanotechnology"; Journal of Nanoscience and Nanotechnology; bearing a date of 2005; pp. 131-139; vol. 5, No. 1; American Scientific Publishers.
Tomai et al.; "Resiquimod and other immune response modifiers as vaccine adjuvants"; Expert Rev. Vaccines; bearing a date of 2007; pp. 835-847; vol. 6, No. 5; Future Drugs Ltd.
Tomas et al.; "Identifying Marine Phytoplankton"; bearing a date of Jul. 1997; Abstract and Table of Contents (2 pages total); 1$^{st}$ Edition; Elsevier Science.
Touloukian et al.; "Mining the Melanosome for Tumor Vaccine Targets: P.polypeptide Is a Novel Tumor-associated Antigen"; Cancer Res.; bearing a date of Nov. 15, 2001; pp. 8100-8104; vol. 61, No. 22.
Toussaint et al.; "A Mathematical Framework for the Selection of an Optimal Set of Peptides for Epitope-Based Vaccines"; PL$_o$S Computational Biology; bearing a date of Dec. 2008; pp. 1-10; vol. 4, Issue 12.
Tse et al.; "Suppression of Allogenic T-Cell Proliferation by Human Marrow Stromal Cells: Implications in Transplantation"; Transplantation; bearing a date of Feb. 15, 2003; pp. 389-397; vol. 75; Lippincott Williams & Wilkins, Inc.
Tsukita et al.; "Occludin and Claudins in Tight-Junction Strands: Leading or Supporting Players?"; Trends in Cell Biology; bearing a date of Jul. 1999; pp. 268-273; vol. 9, No. 7; Elsevier Science.
Turner et al.; "Review Article: Biomechanics of Bone: Determinants of Skeletal Fragility and Bone Quality"; Osteoporos International; bearing a date of 2002; pp. 97-104; vol. 13; International Osteoporosis Foundation and National Osteoporosis Foundation.
Vacanti et al.; "The Efficacy of Periosteal Cells Compared to Chondrocytes in the Tissue Engineered Repair of Bone Defects"; Tissue Engineering; bearing a date of 1995; pp. 301-308; vol. 1, No. 3; Mary Ann Liebert, Inc.
Valentini et al.; Maxillary Sinus Grafting with Anorganic Bovine Bone: A Clinical Report of Long-term Results; The International Journal of Oral & Maxillofacial Implants; bearing a date of 2003; pp. 556-560; vol. 18, No. 4; Quintessence Publishing Co., Inc.
Van Dongen et al.; "Single-Step Azide Introduction in Proteins via an Aqueous Diazo Transfer"; Bioconjugate Chem.; bearing a date of 2009; pp. 20-23; vol. 20; American Chemical Society.
Van Slooten et al.; "Liposomes as cytokine-supplement in tumor cell-based vaccines"; International Journal of Pharmaceuticals; bearing a date of 1999; pp. 33-36; vol. 183; Elsevier Science B.V.
Van Slooten et al.; "Liposomes Containing Interferon-Gamma as Adjuvant in Tumor Cell Vaccines"; Pharmaceutical Research; bearing a date of 2000; pp. 42-48; vol. 17, No. 1; Plenum Publishing Corporation.
Velayudhan et al.; "Extrusion of hydroxyapatite to clinically significant shapes"; Material Letters; bearing d date of Nov. 2000; pp. 142-146; vol. 46; Elsevier Science B.V.
Vrieling et al.; "Controlled Silica Synthesis Inspired by Diatom Silicon Biomineralization"; Journal of Nanoscience and Nanotechnology; bearing a date of 2005; pp. 68-78; vol. 5, No. 1; American Scientific Publishers.
Wadolkowski et al.; "Colonization of the Streptomycin-Treated Mouse Large Intestine by a Human Fecal *Escherichia coli* Strain: Role of Growth in Mucus"; Infection and Immunity; bearing a date of May 1988; pp. 1030-1035; vol. 56, No. 5; American Society for Microbiology.
Wang et al.; "Characterization of two temperature-inducible promoters newly isolated from B. subtillis"; Biochemical and biophysical research communications; bearing a date of 2007; pp. 1148-1153; vol. 358, No. 4; Abstract; 1 pg.
Wang et al.; "Cloning and expression of a lignin peroxidase gene from *Streptomyces viridosporus* in *Streptomyces lividans*"; Journal of Biotechnology; bearing a date of 1990; pp. 131-144; vol. 13; Elsevier Science Publishers B.V.
Wang et al.; "Identification of TRP-2 as a Human Tumor Antigen Recognized by Cytotoxic T Lymphocytes"; The Journal of Experimental Medicine; bearing a date of Dec. 1996; pp. 2207-2216; vol. 184.
Warfield et al.; "Ebola virus-like particles protect from lethal Ebola virus infection"; PNAS; bearing a date of Dec. 23, 2003; pp. 15889-15894; vol. 100, No. 26; The National Academy of Sciences of the USA.
Warfield et al.; "Ebola Virus Inactivation with Preservation of Antigenic and Structural Integrity by a Photoinducible Alkylating

(56) References Cited

OTHER PUBLICATIONS

Agent"; The Journal of Infectious Diseases; bearing a date of 2007; pp. S276-S283; vol. 196, Suppl 2; Infectious Diseases Society of America.
Warren et al.; "Discussion: Tissue-Engineered Bone Using Mesenchymal Stem Cells and a Biodegradable Scaffold"; The Journal of Craniofacial Surgery; bearing a date of Mar. 2002; pp. 240-243; vol. 13, No. 2; Mutaz Habal, MD.
Weber et al.; "A biotin-triggered genetic switch in mammalian cells and mice"; Metabolic Engineering; bearing a date of 2009; pp. 117-124; vol. 11; Elsevier Inc.
Wee et al.; "Research Article: Engineering and Medical Applications of Diatoms";.Journal of Nanoscience and Nanotechnology; bearing a date of 2005; pp. 88-91; vol. 5, No. 1; American Scientific Publishers.
Widdick et al.; "The twin-arginine translocation pathway is a major route of protein export in *Streptomyces coelicolor*"; PNAS; bearing a date of Nov. 21, 2006; pp. 17927-17932; vol. 103, No. 47.
Widmer et al.; "Chapter II.5 Fundamentals and Methods of Tissue Engineering: Fabrication of Biodegradable Polymer Scaffolds for Tissue Engineering"; Frontiers in Tissue Engineering; bearing a date of 1998; pp. 107-120; Elsevier Science Ltd.
Wiedmann-Al-Ahmad et al.; "Search for ideal biomaterials to cultivate human osteoblast-like cells for reconstructive surgery"; Journal of Materials Science: Materials in Medicine; bearing a date of 2005; pp. 57-66; vol. 16; Springer Science + Business Media, Inc.
Wiesmann et al.; "Biological and biophysical principles in extracorporal bone tissue engineering—Part II"; International Journal of Oral & Maxillofacial Surgery; bearing a date of 2004; pp. 523-530; vol. 33; Elsevier Ltd.; located at: http://www.sciencedirect.com.
Wilcock et al.; "Anti-Aβ immunotherapy in Alzheimer's disease; relevance of transgenic mouse studies to clinical trials"; J Alzheimer's Dis.; bearing a date of Dec. 2008; pp. 555-569; vol. 15, No. 4.
Williams et al.; "Look who's talking: communication and quorum sensing in the bacterial world"; Phil. Trans. R. Soc. B; bearing a date of 2007; pp. 1119-1134; vol. 362; The Royal Society.
Wilson et al.; "Species-specific detection of hydrocarbon-utilizing bacteria"; Journal of Microbiological Methods; bearing a date of Dec. 1999; pp. 59-78; vol. 39, No. 1; Abstract, 2 pgs.; Elsevier Science B.V.
Win et al.; "Higher-Order Cellular Information Processing with Synthetic RNA Devices"; Science; bearing a date of Oct. 17, 2008; pp. 456-460; vol. 322, No. 5900; Abstract, 1 pg.
Xin et al.; "Intracerebral xenotransplantation of semipermeable membrane-encapsulated pancreatic islets"; World J Gastrointestinal; bearing a date of 2005; pp. 5714-5717; vol. 11, No. 36; Elsevier Inc.
Xu et al.; "Fast-setting calcium phosphate scaffolds with tailored macropore formation rates for bone regeneration"; J Biomed Mater Res; bearing a date of 2004; pp. 725-734; vol. 68A; Wiley Periodicals, Inc.
Yang et al.; "Engineering Target-Responsive Hydrogels Based on Aptamer—Target Interactions"; J. Am. Chem. Soc.; bearing a date of 2008; pp. 6320-6321; vol. 130; American Chemical Society.
Ye et al.; "Molecularly imprinted polymers as antibody and receptor mimics for assays, sensors and drug discovery"; Anal Bioanal Chem; bearing a date of 2004; pp. 1887-1897; vol. 378; Springer-Verlag.
Yoshikawa et al.; "Bone tissue engineering with porous hydroxyapatite ceramics"; J Artif Organs; bearing a date of 2005; pp. 131-136; vol. 8; The Japanese Society for Artificial Organs.
Zaborina et al.; "Dynorphin Activates Quorum Sensing Quinolone Signaling in *Pseudomonas aeruginosa*"; PLoS Pathogens; bearing a date of Mar. 2007; pp. 0001-0015; vol. 3, No. 3.
Zaslavskaia et al.; "Reports: Trophic Conversion of an Obligate Photoautotrophic Organism Through Metabolic Engineering"; Science; bearing a date of Jun. 15, 2001; pp. 2073-2075 plus cover page (total of 4 pages); vol. 292, No. 5524; located at: www.sciencemag.org.
Zavazava, Nicholas; "Review: Cell- & Tissue-based Therapy: Embryonic stem cells and potency to induce transplantation tolerance"; Expert Opin. Biol. Ther.; bearing a date of 2003; pp. 5-13; vol. 3, No. 1; Ashley Publications; located at: www.ashley-pub.com.
Zeigler et al.; "Microscopic platelet size and morphology in various hematologic disorders"; Blood; bearing a date of 1978; pp. 479-486; vol. 51; The American Society of Hematology.
Zhang et al.; "Human gut microbiota in obesity and after gastric bypass"; PNAS; Feb. 17, bearing a date of 2009; pp. 2365-2370; vol. 106, No. 7; The National Academy of Sciences of the USA.
Zhang et al.; "The histidine utilization (hut) genes of *Pseudomonas fluorescens* SBW25 are active on plant surfaces, but are not required for competitive colonization of sugar beet seedlings"; Microbiology; bearing a date of 2006; pp. 1867-1875; vol. 152; SGM.
Zheng et al.; "Primary Culture of Choroidal Epithelial Cells: Characterization of an in vitro Model of Blood-CSF Barrier"; In Vitro Cell. Dev. Biol.—Animal; bearing a date of Jan. 1998; pp. 40-45; vol. 34; Society for In Vitro Biology.
www.nottinham.ac.uk/quorum/AHIS.htm; Structures of AHLs; 2 pgs.; last accessed on Nov. 10, 2009.
www.nottingham.ac.uk/quorum/table.htm; Table of organisms; 3 pgs.; last accessed on Nov. 10, 2009.
Fulton, George P.; "Diatomaceous earth filtration for safe drinking water"; ASCE Publications; bearing a date of 2000; pp. 1-3.
Reinholt, Finn P. et al.; "Osteopontin—a possible anchor of osteoclasts to bone"; Proc. Natl. Acad. Sci. USA; bearing a date of Jun. 1990; pp. 4473-4475; vol. 87.
Definition from Biology Online; "Cell Membrane"; Biology Online Dictionary; total of 1 page; located at: www.biology-online.org/dictionary/Cell_membrane.
Excerpt from Encyclopedia Britannica; "Compact Bone"; Encyclopedia Britannica Online; printed on Feb. 10, 2011; total of 1 page; located at: http://www.britannica.com/EBchecked/topic/129490/compact-bone.
Ogden, John A.; "Skeletal Injury in the Child"; bearing a date of 2000; total of 2 pages; 3rd Edition; Springer-Verlag New York, Inc.
Toto et al.; "Fate of Subcutaneous Anorganic Bone Implants"; Journal of Dental Research; bearing a date of Nov.-Dec. 1961; pp. 1127-1135; vol. 40, No. 6; Sage Publications.
Komlev et al.; "Porous hydroxyapatite ceramics of bi-modal pore size distribution"; Journal of Materials Science: Materials in Medicine; 2002; pp. 295-299; vol. 13; Kluwer Academic Publishers.
Lu et al.; "Controllable porosity hydroxyapatite ceramics as spine cage: fabrication and properties evaluation"; Journal of Materials Science: Materials in Medicine; 2003; pp. 1039-1046; vol. 14; Kluwer Academic Publishers.
Millipore.com; "Pore Density"; 1 page; screen shot taken on Sep. 7, 2011 from http://www.millipore.com/membrane/fix4/filter_characterization_hm&tab1=1&tab2=2#tab2=2:tab1=1.
Anderson et al.; "KIESELGUHRS Suitability as Carriers in Catalysts"; Industrial and Engineering Chemistry; bearing a date of Dec. 1947; pp. 1618-1628; vol. 39, No. 12; U.S. Bureau of Mines.
Shin, Jennifer; "Intro to Diatoms: General Information"; Monterey Bay Aquarium Research Institute; bearing a date of 1999; pp. 1-2; MBARI; located at: www.mbari.org/staff/conn/botany/diatoms/jennifer/introa.htm.
Narváez-Vásquez et al.; "Systemins and AtPeps: Defense-Related Peptide signals"; Induced Plant Resistance to Herbivory: Chapter 15; bearing a date of 2008; pp. 313-328; Springer Science+Business Media B. V.
Nichol et al.; "Effectiveness of Live, Attenuated Intranasal Influenza Virus Vaccine in Healthy, Working Adults"; JAMA; Jul. 14, 1999; pp. 137-144; vol. 281, No. 2; American Medical Association.
Qiu et al.; "Environment-sensitive hydrogels for drug delivery"; Advanced Drug Delivery Reviews; bearing a date of Aug. 14, 2001; pp. 321-339; vol. 53; Elsevier Science B. V.
Syto et al.; "Structural and Biological Stability of the Human Interleukin 10 Homodimer"; Biochemistry; bearing dates of Jun. 30, 1998 and Sep. 23, 1998; pp. 16943-16951; vol. 37; American Chemical Society.
The American Heritage® Dictionary of the English Language; "auxotrophic"; located at: http://www.credoreference.com/entry/hmdictenglang/auxotrophic ; Sep. 2, 2012; bearing a date of 2007; © 2007, 2000 Houghton Mifflin Company.

(56) References Cited

OTHER PUBLICATIONS

The Columbia Encyclopedia; "Soil"; located at: http://www.credoreference.com/topic/soil; Aug. 24, 2012; 3 pages; Columbia University Press 2008.

The Columbia Encyclopedia; "Virus"; located at: http://www.credoreference.com/entry/columency/virus ; Sep. 2, 2012; bearing a date of 2008; 1 page.

Balda et al; "Tight junctions"; Journal of Cell Science; bearing a date of 1998; pp. 541-547; vol. 111; The Company of Biologists Limited; Great Britain.

Buchert et al.; "Method to Examine Tight Junction Physiology in Cancer Stem Cells: TEER, Paracellular Permeability, and Dilution Potential Measurements"; Stem Cell Rev and Rep; bearing a date of Dec. 3, 2011; pp. 1030-1034; vol. 8; Springer Science+Business Media, LLC.

Pinto De Silva et al.; "On Tight-Junction Structure"; Cell; bearing a date of Mar. 1982; pp. 441-450; vol. 28; MIT.

Tsukita et al.; "Multifunctional Strands in Tight Junctions"; Nature Reviews | Molecular Cell Biology; bearing a date of Apr. 2001; pp. 285-293; vol. 2; Macmillan Magazines Ltd.

Djeha et al.; "Combined Adenovirus-Mediated Nitroreductase Gene Delivery and CB1954 Treatment: A Well-Tolerated Therapy for Established Solid Tumors"; Molecular Therapy; bearing a date of Feb. 2001, accepted in revised form Dec. 21, 2000; pp. 233-240; vol. 3, No. 2; The American Society of Gene Therapy.

Chou et al.; "Characterization of a pH-Inducible Promoter System for High-Level Expression of Recombinant Proteins in *Escherichia coli*"; Biotechnology and Bioengineering; Jul. 20, 1995; pp. 186-192; vol. 47, No. 2; John Wiley & Sons, Inc.

\* cited by examiner

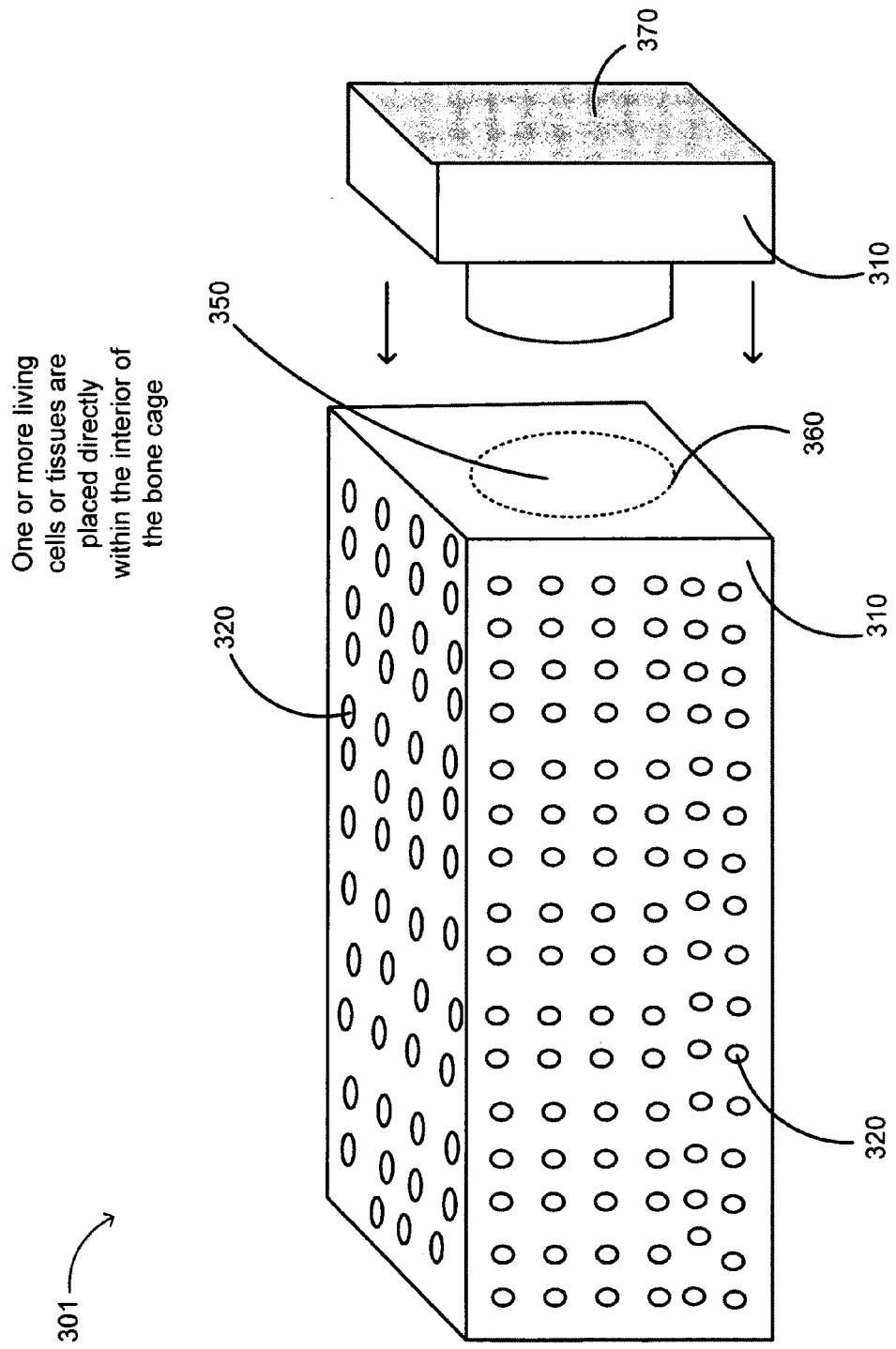

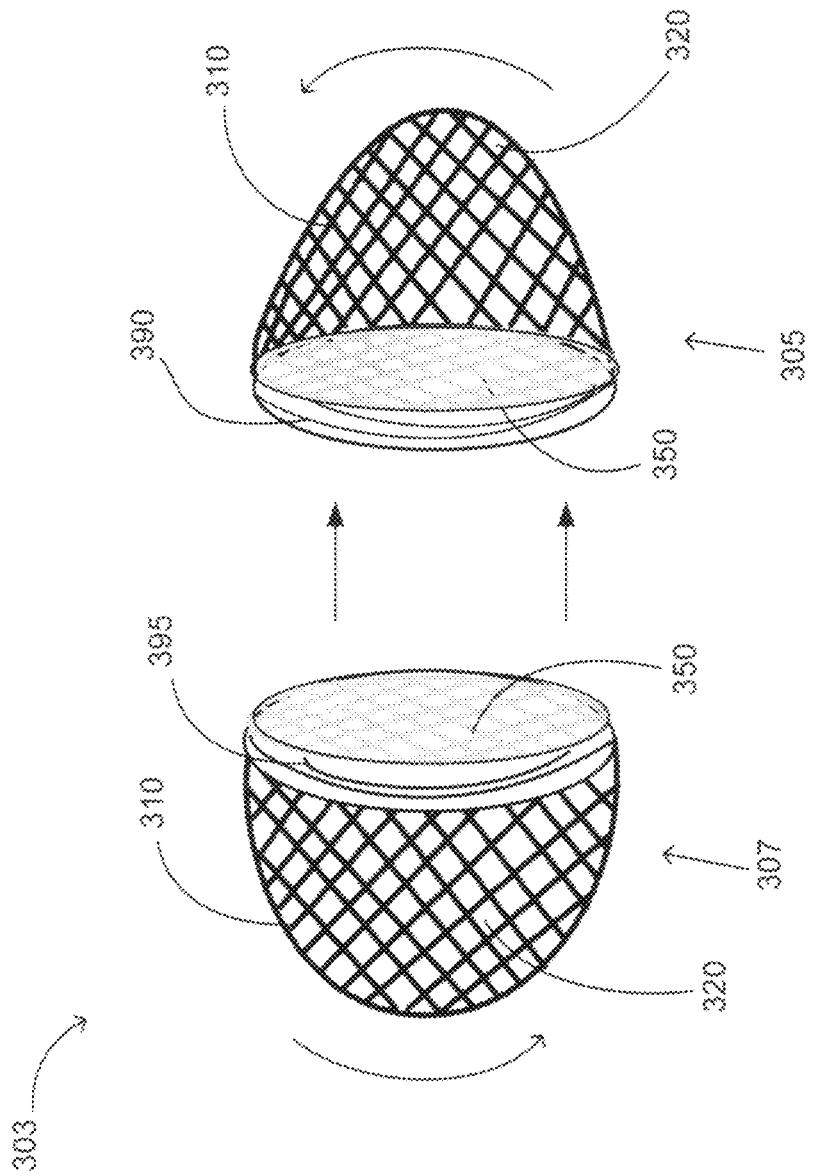

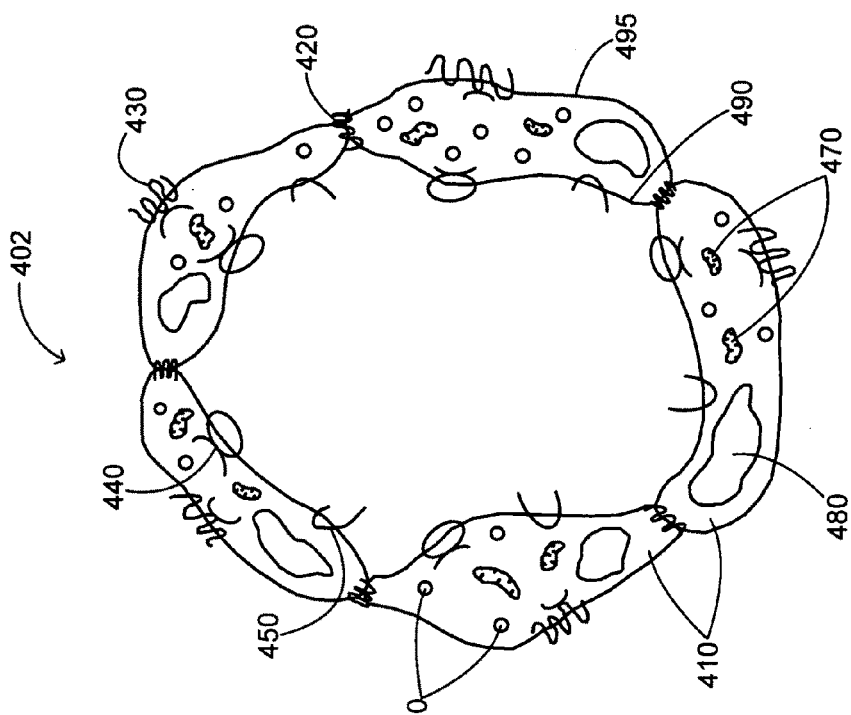
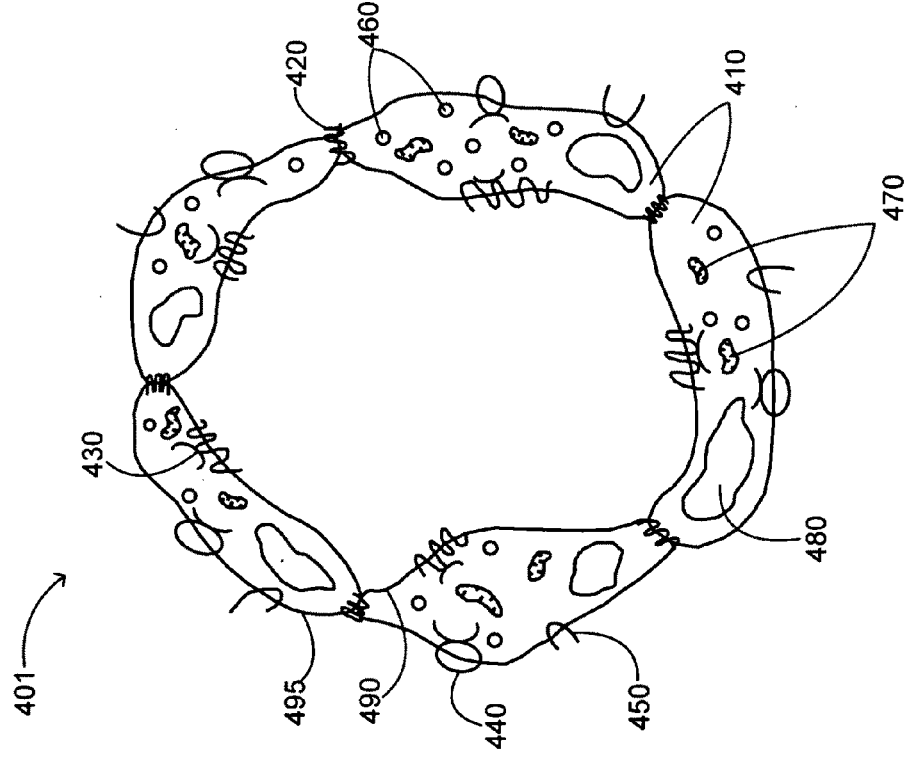
FIGURE 4

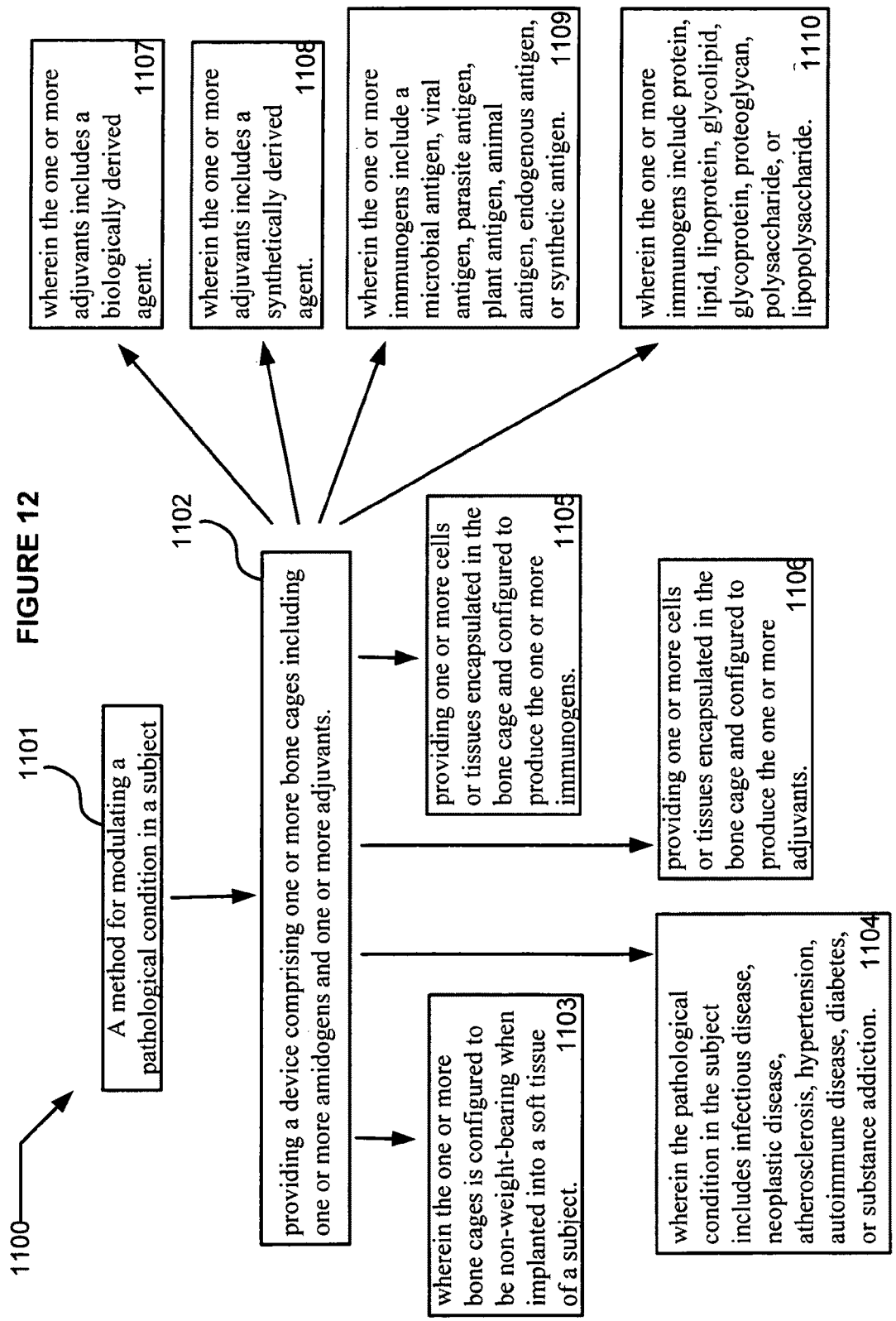

FIGURE 13

1300 A system, comprising:

1310 at least one computing device; at least one treatment device including at least one semi-permeable barrier substantially enclosing at least one auxotrophic microorganism, the at least one auxotrophic microorganism including at least one nucleic acid construct encoding at least one therapeutic agent, the barrier defining an interior region and exterior region; wherein the device includes at least one metabolite required by the at least one auxotrophic microorganism; the treatment device further comprising at least one pump for dispensing at least one therapeutic agent, the pump including electronic circuitry configured to send or receive signals from the computing device; and one or more instructions on a recordable medium that when executed on the computing device cause the computing device to regulate dispensing of the at least one therapeutic agent from the at least one treatment device 1320 wherein the at least one computing device includes one or more of a desktop computer, phone, personal digital assistant, remote controller, workstation computer, or computing system 1330 wherein the at least one computing system includes one or more of a cluster of processors, a networked computer, a tablet personal computer, a laptop computer, a mobile device, a mobile telephone, or a personal digital assistant computer 1340 further comprising one or more instructions on a recordable medium that when executed on the at least one computing device cause the at least one computing device to generate at least one output to a user readable display

FIGURE 14

1400 wherein the at least one output includes at least one graphical illustration of the at least one auxotrophic microorganism, at least one component thereof, or at least one product thereof; at least one property of the treatment device; or at least one property of dispensing the at least one therapeutic agent from the treatment device 1410 wherein the at least one output includes at least one protocol for administering the at least one treatment device to at least one biological tissue 1420 wherein the user includes at least one entity 1430 wherein the entity includes at least one person, or computer 1440 wherein the user readable display includes a human readable display 1450 wherein the user readable display includes one or more active displays 1460 wherein the user readable display includes one or more passive displays 1470 wherein the user readable display includes one or more of a numeric format, graphical format, or audio format 1480 further comprising one or more instructions on a recordable medium that when executed on the computing device cause the computing device to evaluate the at least one biological tissue for one or more indicators prior to, during, or subsequent to administering the at least one treatment device to the at least one biological tissue

FIGURE 15

1500 wherein to evaluate at least one biological tissue for one or more indicators includes to evaluate at least one of an assay, image, or gross assessment of the at least one biological tissue prior to, during, or subsequent to administering the at least one treatment device to the at least one biological tissue 1510 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 1520 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation 1530 further comprising one or more instructions on a recordable medium that when executed on the computing device cause the computing device to alter at least one microorganism isolated from at least one biological tissue

FIGURE 16

1600 further comprising one or more instructions on a recordable medium that when executed on the computing device cause the computing device to amplify the at least one microorganism isolated from the at least one biological tissue 1610 further comprising one or more instructions on a recordable medium that when executed on the computing device cause the computing device to reinstate the at least one microorganism to the biological tissue from which it was isolated subsequent to alteration 1620 further comprising one or more instructions on a recordable medium that when executed on the computing device cause the computing device to predetermine at least one microorganism strain or type for altering in order to produce at least one therapeutic agent based on at least one feature of at least one biological tissue 1630 wherein the at least one feature of the at least one biological tissue includes at least one property of one or more microorganism populations associated with the at least one biological tissue 1640 further comprising one or more instructions for delivering at least one agent sufficient to induce death in the at least one auxotrophic microorganism 1650 wherein the one or more instructions for delivering at least one agent sufficient to induce death in the at least one auxotrophic microorganism includes one or more instructions for delivering the at least one agent at least one of locally or systemically

FIGURE 17

1700 further comprising a cryptographic logic component 1710 wherein the cryptographic logic component is configured to implement at least one cryptographic process or cryptographic logic 1720 wherein the cryptographic logic component is configured to implement one or more processes associated with at least one of a cryptographic protocol, decryption protocol, or encryption protocol 1730 wherein the cryptographic logic component is configured to implement one or more processes associated with at least one of a regulatory compliance protocol, regulatory protocol, or authentication protocol 1740 wherein the cryptographic logic component is configured to implement one or more processes associated with at least one of an authorization protocol, activation protocol, or treatment regimen protocol 1750 wherein the cryptographic logic component includes one or more of a crypto-algorithm, signal-bearing media, crypto controller, or cryptographic module

FIGURE 18

1800 wherein the cryptographic logic component is configured to generate information associated with at least one of an authentication protocol, authorization protocol, anti-microbial agent reservoir delivery protocol, activation protocol, encryption protocol, decryption protocol authorization instruction, prescription dosing instruction, or prescribed regimen instruction 1810 wherein the cryptographic logic component is configured to generate information associated with at least one of an activation code, error code, command code, or authorization code 1820 wherein the cryptographic logic component is configured to generate information associated with at least one of a cryptographic protocol, decryption protocol, encryption protocol, regulatory compliance protocol, or regulatory use protocol

FIGURE 19

1900 A system, comprising:

1910 at least one computing device;

one or more instructions on a recordable medium that when executed on the at least one computing device cause the at least one computing device to receive a first input associated with a first possible dataset, the first possible dataset including data representative of at least one parameter for making or administering at least one treatment device to at least one biological tissue, wherein the at least one treatment device includes at least one semi-permeable barrier structured to substantially enclose at least one auxotrophic microorganism;

wherein the at least one auxotrophic microorganism includes at least one nucleic acid construct encoding at least one therapeutic agent; and one or more instructions on a recordable medium that when executed on the at least one computing device cause the computing device to generate an output to a user readable display 1915 further comprising one or more instructions on a recordable medium that when executed on the at least one computing device cause the at least one computing device to compare a value associated with the first possible dataset with a second dataset including values of at least one predictive parameter 1920 wherein the first input includes one or more values derived from at least one property of the at least one treatment device

FIGURE 20

| |
|---|
| 2000 wherein the first input includes at least one parameter for generating the at least one auxotrophic microorganism |

| |
|---|
| 2010 wherein the first input includes at least one parameter for making the at least one treatment device |

| |
|---|
| 2020 wherein the at least one parameter for making the at least one treatment device includes one or more of constitution of the at least one treatment device, configuration of the at least one treatment device, formulation of the at least one therapeutic agent, type of auxotrophic microorganism, strain of auxotrophic microorganism, configuration of the at least one inducible genetic element of the auxotrophic microorganism, or alteration of the at least one auxotrophic microorganism |

| |
|---|
| 2030 wherein the second input includes one or more values related to the at least one parameter for administering at least one treatment device to the at least one biological tissue |

| |
|---|
| 2040 wherein the at least one parameter for administering the at least one treatment device includes one or more of: biological tissue type; biological tissue function; biological tissue size; biological tissue constitution; biological tissue architecture; biological tissue durability; biological tissue temperature; temperature of administration conditions; depth of administration of the at least one treatment device; biological tissue source; one or more temporal coordinates; one or more spatial coordinates; angle of administration of the at least one treatment device; force of administration of the at least one treatment device; velocity of administration of the at least one treatment device; quantity of treatment devices administered; rate of administration of more than one treatment device; method of administration of the at least one treatment device; timing of administration of the at least one treatment device; rate of production of the at least one therapeutic agent of the at least one treatment device, or rate of dispensing of the at least one therapeutic agent from the at least one treatment device |

FIGURE 21

2100 further comprising one or more instructions on a recordable medium that when executed on the at least one computing device cause the at least one computing device to determine a graphical illustration of the second possible dataset 2120 further comprising one or more instructions on a recordable medium that when executed on the at least one computing device cause the at least one computing device to determine from the comparison at least one parameter for making or administering the at least one treatment device 2130 further comprising one or more instructions on a recordable medium that when executed on the at least one computing device cause the at least one computing device to access the first possible dataset in response to the first input 2140 further comprising one or more instructions on a recordable medium that when executed on the at least one computing device cause the at least one computing device to generate the first possible dataset in response to the first input 2150 further comprising one or more instructions on a recordable medium that when executed on the at least one computing device cause the at least one computing device to determine a graphical illustration of the first possible dataset 2160 wherein the at least one computing device includes one or more of a desktop computer, workstation computer, phone, personal digital assistant, remote controller, or computing system 2170 wherein the at least one computing system includes one or more of a cluster of processors, a networked computer, a tablet personal computer, a laptop computer, a mobile device, a mobile telephone, or a personal digital assistant computer

FIGURE 22

2200 wherein the output includes at least one graphical description of the at least one treatment device, at least one component thereof, or at least one cell or substance associated with at least one biological tissue 2210 wherein the user includes at least one entity 2220 wherein the entity includes at least one person, or computer 2230 wherein the user readable display includes a human readable display 2240 wherein the user readable display includes one or more active displays 2250 wherein the user readable display includes one or more passive displays 2260 wherein the user readable display includes one or more of a numeric format, graphical format, or audio format 2270 further comprising one or more instructions for receiving a third input associated with at least one feature of at least one subject 2280 wherein the at least one feature of the at least one subject includes one or more of a physiological condition; genotype; phenotype; genetic profile; proteomic profile; lipidomic profile; glycomic profile; system biology profile; circulatory condition; respiratory condition; lymph condition; anatomic, genetic or proteomic characteristic; response to previous treatment; weight; height; medical diagnosis; familial background; results of one or more medical tests; ethnic background; body mass index; age; presence or absence of at least one disease or condition; species; ethnicity; race; allergies; gender; presence or absence of at least one biological, chemical, or therapeutic agent in the subject; pregnancy status; lactation status; medical history; or blood condition

FIGURE 23

2300 wherein the user readable display includes one or more of a display of one or more differences in the comparison of at least one value related to the first input and at least one value related to at least one property of the at least one treatment device 2310 wherein the user readable display includes one or more of a display of one or more differences in the comparison of at least one value related to the second input and at least one value related to at least one parameter for administration of the at least one treatment device to the at least one biological tissue 2320 further comprising means for transmitting one or more signals that include information related to the processing of the first input and the second input 2330 wherein the means for transmitting one or more signals includes means for transmitting one or more signals associated with selection of at least one parameter for making the at least one treatment device 2340 wherein the means for transmitting one or more signals includes means for transmitting one or more signals associated with selection of at least one parameter for administering the at least one treatment device to the at least one biological tissue 2350 wherein the means for transmitting one or more signals includes means for transmitting one or more signals associated with comparing the information related to the processing of the first input and the second input 2360 further comprising means for generating the at least one auxotrophic microorganism 2370 further comprising means for administering the at least one treatment device to at least one biological tissue

FIGURE 24

| |
|---|
| 2400 further comprising means for evaluating the at least one biological tissue for one or more indicators prior to, during, or subsequent to administering the at least one treatment device to at least one biological tissue |

| |
|---|
| 2410 wherein the one or more indicators include at least one of an assay, image, or gross assessment of the at least one biological tissue prior to, during, or subsequent to at least one administration of the at least one treatment device |

| |
|---|
| 2420 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay |

| |
|---|
| 2430 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation |

| |
|---|
| 2440 further comprising one or more instructions on a recordable medium that when executed on the computing device cause the computing device to evaluate the at least one biological tissue for one or more indicators relating to one or more of: administering the at least one device, at least one component thereof, or at least one product thereof, cell or tissue formation; cell or tissue growth; cell or tissue apoptosis; cell or tissue necrosis; cell division; cellular cytoskeletal rearrangement; cell or tissue secretion; cell or tissue differentiation; status of the at least one auxotrophic microorganism of the at least one treatment device; status of the at least one treatment device; or status of the at least one therapeutic agent |

FIGURE 25

| 2500 further comprising means for transmitting one or more signals that include information relating to the accepting a first input or a second input and information related to the evaluating the at least one biological tissue |

| 2510 wherein the means for transmitting one or more signals includes means for transmitting one or more signals associated with selection of at least one parameter for making the at least one treatment device |

| 2520 wherein the means for transmitting one or more signals includes means for transmitting one or more signals associated with selection of at least one parameter for administering the at least one treatment device |

| 2530 further comprising means for obtaining genetic sequence information from at least one microorganism isolated from at least one biological tissue |

| 2540 further comprising means for altering the at least one microorganism isolated from the at least one biological tissue |

| 2550 further comprising means for amplifying the at least one microorganism isolated from the at least one biological tissue |

| 2560 further comprising means for reinstating the at least one microorganism isolated from the at least one biological tissue subsequent to alteration |

| 2570 further comprising means for predetermining at least one microorganism strain or type for altering to produce at least one therapeutic agent based on at least one feature of at least one biological tissue |

| 2580 wherein the at least one feature of the at least one biological tissue includes at least one property of one or more microorganism populations associated with the at least one biological tissue |

FIGURE 26

2600 A computer-implemented method, comprising:

2610 executing one or more instructions located on a recordable medium for regulating dispensing of at least one treatment device including at least one semi-permeable barrier substantially enclosing at least one auxotrophic microorganism, the at least one auxotrophic microorganism including at least one nucleic acid construct encoding at least one therapeutic agent, the barrier defining an interior region and exterior region; wherein the device includes at least one metabolite required by the at least one auxotrophic microorganism 2620 further comprising generating at least one output to a user readable display 2630 wherein the generating the at least one output includes generating at least one graphical illustration of one or more of the at least one auxotrophic microorganism, at least one component thereof, or at least one product thereof; at least one property of the at least one treatment device; or at least one property of dispensing the at least one treatment device 2640 wherein the generating the at least one output includes generating at least one protocol for generating the at least one auxotrophic microorganism 2650 wherein the at least one output includes at least one protocol for administering the at least one treatment device to at least one biological tissue 2660 wherein the user includes at least one entity 2670 wherein the entity includes at least one person, or computer 2680 wherein the user readable display includes a human readable display

FIGURE 27

| |
|---|
| 2700 wherein the user readable display includes one or more active display |
| 2710 wherein the user readable display includes one or more passive displays |
| 2720 wherein the user readable display includes one or more of a numeric format, graphical format, or audio format |
| 2730 further comprising executing one or more instructions for evaluating at least one biological tissue for one or more indicators prior to, during, or subsequent to administering the at least one treatment device to the at least one biological tissue |
| 2740 wherein the evaluating at least one biological tissue for one or more indicators includes evaluating at least one of an assay, image, or gross assessment of the at least one biological tissue prior to, during, or subsequent to administering the at least one treatment device to the at least one biological tissue |
| 2750 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay |
| 2760 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or *in silico* generation |

FIGURE 28

2800 further comprising executing one or more instructions for evaluating the at least one biological tissue for one or more indicators relating to one or more of: administering the at least one treatment device, at least one component thereof, or at least one product thereof; cell or tissue formation; cell or tissue growth; cell or tissue apoptosis; cell or tissue necrosis; cell division; cellular cytoskeletal rearrangement; cell or tissue secretion; cell or tissue differentiation; status of the at least one auxotrophic microorganism of the at least one treatment device; status of the at least one treatment device; or status of the at least one therapeutic agent 2810 further comprising executing one or more instructions for obtaining genetic sequence information from at least one microorganism isolated from at least one biological tissue 2820 further comprising executing one or more instructions for altering the at least one microorganism isolated from the at least one biological tissue 2830 further comprising executing one or more instructions for amplifying the at least one microorganism isolated from the at least one biological tissue 2840 further comprising executing instructions for replacing the at least one microorganism isolated from the at least one biological tissue subsequent to alteration 2850 further comprising executing one or more instructions for predetermining at least one microorganism strain or type for altering to produce at least one therapeutic agent based on at least one feature of at least one biological tissue 2860 wherein the at least one feature of the at least one biological tissue includes at least one property of one or more microorganism populations associated with the at least one biological tissue

FIGURE 29

2900 A computer program product, comprising:

2910 a recordable medium bearing one or more instructions for regulating dispensing of at least one treatment device including an semi-permeable barrier structured to substantially enclose at least one auxotrophic microorganism, and wherein the at least one auxotrophic microorganism includes at least one nucleic acid construct encoding at least one therapeutic agent 2920 wherein the recordable medium includes a computer-readable medium 2930 wherein the recordable medium includes a communications medium 2940 further comprising one or more instructions for evaluating the at least one biological tissue for one or more indicators prior to, during, or subsequent to administering the at least one treatment device 2950 further comprising one or more instructions for evaluating the at least one biological tissue for one or more indicators relating to one or more of: administering the at least one treatment device, at least one component thereof, or at least one product thereof; cell or tissue formation; cell or tissue growth; cell or tissue apoptosis; cell or tissue necrosis; cell division; cellular cytoskeletal rearrangement; cell or tissue secretion; cell or tissue differentiation; status of the at least one auxotrophic microorganism of the at least one treatment device; status of the at least one treatment device; or status of the at least one therapeutic agent 2960 wherein the first input includes at least one parameter for generating the at least one auxotrophic microorganism 2970 wherein the second input includes at least one parameter for administering the at least one treatment device to at least one biological tissue

FIGURE 30

3000 wherein the output includes at least one protocol for generating the at least one auxotrophic microorganism 3010 wherein the output includes at least one protocol for administering the at least one treatment device to the at least one biological tissue 3020 wherein the at least one output includes at least one graphical illustration of one or more of the at least one auxotrophic microorganism, at least one component thereof, or at least one product thereof; at least one property of the at least one treatment device; or at least one property of dispensing the at least one treatment device 3030 wherein the user includes at least one entity 3040 wherein the entity includes at least one person, or computer 3050 wherein the user readable display includes a human readable display 3060 wherein the user readable display includes one or more active displays 3070 wherein the user readable display includes one or more passive displays 3080 wherein the user readable display includes one or more of a numeric format, graphical format, or audio format 3090 further comprising one or more instructions for obtaining genetic sequence information from at least one microorganism isolated from the at least one biological tissue

FIGURE 31

3100 further comprising one or more instructions for altering the at least one microorganism isolated from the at least one biological tissue 3110 further comprising one or more instructions for amplifying the at least one microorganism isolated from the at least one biological tissue 3120 further comprising one or more instructions for reinstating the at least one microorganism isolated from the at least one biological tissue subsequent to modification 3130 further comprising one or more instructions for predetermine at least one microorganism type for altering to produce at least one therapeutic agent based on at least one feature of the at least one biological tissue 3140 wherein the at least one feature of the at least one biological tissue includes at least one property of one or more microorganism populations associated with the at least one biological tissue

DEVICE INCLUDING ALTERED MICROORGANISMS, AND METHODS AND SYSTEMS OF USE

RELATED APPLICATIONS

For purposes of the USPTO extra-statutory requirements, the present application constitutes a continuation-in-part of U.S. patent application Ser. No. 12/802,149, entitled DEVICE INCLUDING ALTERED MICROORGANISMS, AND METHODS AND SYSTEMS OF USE, naming Dario G. Amodei, Mahalaxmi Gita Bangera, Xiaoyan Robert Bao, Anna Bershteyn, Brett Bethke, Philip A. Eckhoff, Kevin Michael Esvelt, Kyle Gustafson, Edward K. Y. Jung, William Michael Kaminsky, Jordin T. Kare, Lily Yvonne Kim, Eric C. Leuthardt, Erez Lieberman, Ankur Moitra, Christopher Somogyi, Clarence T. Tegreene, Lowell L. Wood, Jr. and Jeremiah James Zartman as inventors, filed 28 May 2010 now U.S. Pat. No. 8,682,619, or is an application of which a currently co-pending application is entitled to the benefit of the filing date.

For purposes of the USPTO extra-statutory requirements, the present application constitutes a continuation-in-part of U.S. patent application Ser. No. 12/806,637, entitled DEVICE INCLUDING ALTERED MICROORGANISMS, AND METHODS AND SYSTEMS OF USE, naming Dario G. Amodei, Mahalaxmi Gita Bangera, Xiaoyan Robert Bao, Anna Bershteyn, Brett Bethke, Philip A. Eckhoff, Kevin Michael Esvelt, Kyle Gustafson, Edward K. Y. Jung, William Michael Kaminsky, Jordin T. Kare, Lily Yvonne Kim, Eric C. Leuthardt, Erez Lieberman, Ankur Moitra, Christopher Somogyi, Clarence T. Tegreene, Lowell L. Wood, Jr. and Jeremiah James Zartman as inventors, filed 28 May 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,604, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr. and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,605, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr. and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,606, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr. and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,607, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr. and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,608, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr. and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/657,609, entitled COMPOSITIONS AND METHODS FOR THERAPEUTIC DELIVERY WITH MICROORGANISMS, naming Roderick A. Hyde, Edward K. Y. Jung, Royce A. Levien, Robert W. Lord, Mark A. Malamud, John D. Rinaldo, Jr. and Lowell L. Wood, Jr. as inventors, filed 22 Jan. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/462,114 now U.S. Pat. No. 8,551,750, entitled DEVICE INCLUDING BONE CAGE AND METHOD FOR TREATMENT OF DISEASE IN A SUBJECT, naming Ed Harlow, Edward K. Y. Jung, Robert Langer, Eric C. Leuthardt, Elizabeth A. Sweeney and Lowell L. Wood, Jr. as inventors, filed 28 Jul. 2009, or is an application of which a currently co-pending application is entitled to the benefit of the filing date.

For purposes of the USPTO extra-statutory requirements, the present application constitutes a continuation-in-part of U.S. patent application Ser. No. 11/975,605 now U.S. Pat. No. 8,114,647, entitled BLOOD BRAIN BARRIER DEVICE, naming Ed Harlow, Roderick A. Hyde, Edward K. Y. Jung, Robert Langer, Eric C. Leuthardt, and Lowell L. Wood, Jr. as inventors, filed 18 Oct. 2007, or is an application of which a currently co-pending application is entitled to the benefit of the filing date.

For purposes of the USPTO extra-statutory requirements, the present application constitutes a continuation-in-part of U.S. patent application Ser. No. 11/974,750 now U.S. Pat. No. 8,304,220, entitled BONE SEMI-PERMEABLE DEVICE, naming Ed Harlow, Edward K. Y. Jung, Robert Langer, Eric C. Leuthardt, and Lowell L. Wood, Jr. as inventors, filed 15 Oct. 2007, or is an application of which a currently co-pending application is entitled to the benefit of the filing date.

For purposes of the USPTO extra-statutory requirements, the present application constitutes a continuation-in-part of U.S. patent application Ser. No. 11/974,852 now U.S. Pat. No. 8,367,384, entitled BONE SEMI-PERMEABLE DEVICE, naming Ed Harlow, Edward K. Y. Jung, Robert Langer, Eric C. Leuthardt, and Lowell L. Wood, Jr. as inventors, filed 15 Oct. 2007, or is an application of which a currently co-pending application is entitled to the benefit of the filing date.

For purposes of the USPTO extra-statutory requirements, the present application constitutes a continuation-in-part of U.S. patent application Ser. No. 11/974,798, entitled BONE SEMI-PERMEABLE DEVICE, naming Ed Harlow, Edward K. Y. Jung, Robert Langer, Eric C. Leuthardt, and Lowell L. Wood, Jr. as inventors, filed 15 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/906,664, entitled BONE CELL DELIVERY DEVICE, naming Ed Harlow, Edward K. Y. Jung, Robert Langer, Eric C. Leuthardt, and Lowell L. Wood, Jr. as inventors, filed 2 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/906,581, entitled BONE CELL DELIVERY DEVICE, naming Ed Harlow, Edward K. Y. Jung, Robert Langer, Eric C. Leuthardt, and Lowell L. Wood, Jr. as inventors, filed 2 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/906,580, entitled BONE CELL DELIVERY DEVICE, naming Ed Harlow, Edward K. Y. Jung, Robert Langer, Eric C. Leuthardt, and Lowell L. Wood, Jr. as inventors, filed 2 Oct. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/900,870, entitled BONE DELIVERY DEVICE, naming Ed Harlow, Edward K. Y. Jung, Robert Langer, Eric C. Leuthardt, and Lowell L. Wood, Jr. as inventors, filed 12 Sep. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/900,776, entitled BONE DELIVERY DEVICE, naming Ed Harlow, Edward K. Y. Jung, Robert Langer, Eric C. Leuthardt, and Lowell L. Wood, Jr. as inventors, filed 12 Sep. 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/900,773 now U.S. Pat. No. 8,252,570, entitled BONE DELIVERY DEVICE, naming Ed Harlow, Edward K. Y. Jung, Robert Langer, Eric C. Leuthardt, and Lowell L. Wood, Jr. as inventors, filed 12 Sep. 2007, or is an application of which a currently co-pending application is entitled to the benefit of the filing date.

For purposes of the USPTO extra-statutory requirements, the present application constitutes a continuation-in-part of U.S. patent application Ser. No. 11/701,163, entitled DIATOM DEVICE, naming Edward K. Y. Jung, Robert Langer, and Eric C. Leuthardt as inventors, filed 31 Jan. 2007 now U.S. Pat. No. 8,354,258, or is an application of which a currently co-pending application is entitled to the benefit of the filing date.

For purposes of the USPTO extra-statutory requirements, the present application constitutes a continuation-in-part of U.S. patent application Ser. No. 11/452,019, entitled BLOOD BRAIN BARRIER DEVICE, naming Ed Harlow, Roderick A. Hyde, Edward K. Y. Jung, Robert Langer, Eric C. Leuthardt, and Lowell L. Wood, Jr. as inventors, filed 12 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/451,994, entitled CHOROID PLEXUS DEVICE, naming Ed Harlow, Roderick A. Hyde, Edward K. Y. Jung, Robert Langer, Eric C. Leuthardt, and Lowell L. Wood, Jr. as inventors, filed 12 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/451,986 now U.S. Pat. No. 8,053,220, entitled CHOROID PLEXUS DEVICE, naming Ed Harlow, Roderick A. Hyde, Edward K. Y. Jung, Robert Langer, Eric C. Leuthardt, and Lowell L. Wood, Jr. as inventors, filed 12 Jun. 2006, or is an application of which a currently co-pending application is entitled to the benefit of the filing date.

For purposes of the USPTO extra-statutory requirements, the present application constitutes a continuation-in-part of U.S. patent application Ser. No. 11/389,268, entitled BLOOD BRAIN BARRIER DEVICE, naming Ed Harlow, Roderick A. Hyde, Edward K. Y. Jung, Robert Langer, Eric C. Leuthardt, and Lowell L. Wood, Jr. as inventors, filed 24 Mar. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/304,499, entitled BONE SEMI-PERMEABLE DEVICE, naming Ed Harlow, Edward K. Y. Jung, Robert Langer, Eric C. Leuthardt, and Lowell L. Wood, Jr. as inventors, filed 14 Dec. 2005 now U.S. Pat. No. 8,278,094, or is an application of which a currently co-pending application is entitled to the benefit of the filing date.

For purposes of the USPTO extra-statutory requirements, the present application constitutes a continuation-in-part of U.S. patent application Ser. No. 11/304,492, entitled BONE CELL DELIVERY DEVICE, naming Ed Harlow, Edward K. Y. Jung, Robert Langer, Eric C. Leuthardt, and Lowell L. Wood, Jr. as inventors, filed 14 Dec. 2005 now U.S. Pat. No. 7,855,062, or is an application of which a currently co-pending application is entitled to the benefit of the filing date.

For purposes of the USPTO extra-statutory requirements, the present application constitutes a continuation-in-part of U.S. patent application Ser. No. 11/304,486, entitled BONE DELIVERY DEVICE, naming Ed Harlow, Roderick A. Hyde, Edward K. Y. Jung, Robert Langer, Eric C. Leuthardt, and Lowell L. Wood, Jr. as inventors, filed 14 Dec. 2005 now U.S. Pat. No. 8,198,080, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

SUMMARY

The present disclosure relates to various devices, systems, methods (including computer-implemented methods), and computer program products relating to administering altered microorganisms to a biological tissue.

In an embodiment, a device, comprises at least one semi-permeable barrier substantially enclosing at least one auxotrophic microorganism, the at least one auxotrophic microorganism including at least one nucleic acid construct encoding at least one therapeutic agent, the barrier defining an interior region and exterior region; and wherein the device includes at least one metabolite required by the at least one auxotrophic microorganism.

In an embodiment, an implantable device, comprises an semi-permeable barrier substantially enclosing at least one auxotrophic microorganism, the barrier defining an interior region and exterior region of the device; the interior region including at least one reservoir configured for containing the at least one auxotrophic microorganism, wherein the at least one auxotrophic microorganism includes at least one nucleic acid construct encoding at least one therapeutic agent; at least one port configured to allow transport of the at least one therapeutic agent to the exterior region of the device; and at least one osmotic pump configured to facilitate transport of the at least one therapeutic agent through the at least one port.

In an embodiment, a method of treating a disease or condition in a subject, comprises administering at least one implantable device including an semi-permeable barrier structured to substantially enclose at least one auxotrophic microorganism, the structure defining an interior region and an exterior region of the device; wherein the at least one auxotrophic microorganism includes at least one nucleic acid construct encoding at least one therapeutic agent; and wherein the at least one implantable device dispenses to the subject an effective amount of the at least one therapeutic agent.

In an embodiment, a composition, comprises at least one auxotrophic microorganism including at least one pH inducible promoter operably coupled to at least one heterologous genetic element encoding at least one therapeutic agent for at least one biological tissue, and including at least one genetic element inducible to initiate death of the at least one auxotrophic microorganism; and wherein the at least one composition includes at least one metabolite required by the at least one auxotrophic microorganism.

In an embodiment, a system comprises at least one computing device; at least one treatment device including at least one semi-permeable barrier substantially enclosing at least one auxotrophic microorganism, the at least one auxotrophic microorganism including at least one nucleic acid construct encoding at least one therapeutic agent, the barrier defining an interior region and exterior region; wherein the device includes at least one metabolite required by the at least one auxotrophic microorganism; the treatment device further comprising at least one pump for dispensing at least one therapeutic agent, the pump including electronic circuitry configured to send or receive signals from the computing device; and one or more instructions on a recordable medium that when executed on the computing device cause the computing device to regulate dispensing of the at least one therapeutic agent from the at least one treatment device.

In an embodiment, a system comprises at least one computing device; one or more instructions on a recordable medium that when executed on the at least one computing device cause the at least one computing device to receive a first input associated with a first possible dataset, the first possible dataset including data representative of at least one parameter for making or administering at least one treatment device to at least one biological tissue, wherein the at least one treatment device includes at least one semi-permeable barrier structured to substantially enclose at least one auxotrophic microorganism; wherein the at least one auxotrophic microorganism includes at least one nucleic acid construct encoding at least one therapeutic agent; and one or more instructions on a recordable medium that when executed on the at least one computing device cause the computing device to generate an output to a user readable display.

In an embodiment, a computer-implemented method comprises executing one or more instructions located on a recordable medium for regulating dispensing of at least one treatment device including at least one semi-permeable barrier substantially enclosing at least one auxotrophic microorganism, the at least one auxotrophic microorganism including at least one nucleic acid construct encoding at least one therapeutic agent, the barrier defining an interior region and exterior region; wherein the device includes at least one metabolite required by the at least one auxotrophic microorganism.

In an embodiment, a computer program product, comprises a recordable medium bearing one or more instructions for regulating dispensing of at least one treatment device including an semi-permeable barrier structured to substantially enclose at least one auxotrophic microorganism, and wherein the at least one auxotrophic microorganism includes at least one nucleic acid construct encoding at least one therapeutic agent.

BRIEF DESCRIPTION OF THE FIGURES

FIGS. 3A, 3B, and 3C depict a diagrammatic view of an aspect of an embodiment of a device with closable openings.

FIGS. 4A and 4B depict a diagrammatic view of an aspect of an embodiment of a device. FIG. 4A shows a cross-sectional view with the endothelial cell ablumenal surface oriented toward the exterior of the device. FIG. 4B shows a cross-sectional view with the endothelial cell ablumenal surface oriented toward the internal cavity.

FIG. 5A shows a cross-sectional view with the epithelial cell apical surface oriented toward the exterior of the device. FIG. 5B shows a cross-sectional view with the epithelial cell apical surface oriented toward the internal cavity.

FIG. 6A shows frustules and girdle bands of a centric diatom, *Biddulphia reticulata* (size bar=10 μm). FIG. 6B shows frustules, raphes, and girdle bands of two *Diploneis* sp. pennate diatoms (size bar=10 μm). FIG. 6C shows frustules of a centric diatom, *Eupodiscus radiatus* (size bar=20 μm). FIG. 6D shows frustules and girdle bands of a centric diatom, *Melosira varians* (size bar=10 μm). (PLoS Biol. (2004) 2(10):e306: 1512-1515).

FIG. 7A shows *Cymatoseira belgica*. FIG. 7B shows *Aulacoseira italica* (left) and *Aulacoseira valida* (right).

FIG. 10C is a cross-sectional view of FIG. 10A.

FIG. 12 depicts a partial view of a method relating to various aspects of embodiments disclosed herein.

FIG. 13 depicts a partial view of a system relating to various aspects of the embodiments disclosed herein.

FIG. 14 depicts a partial view of FIG. 13.

FIG. 15 depicts a partial view of FIG. 13.

FIG. 16 depicts a partial view of FIG. 13.

FIG. 17 depicts a partial view of FIG. 13.

FIG. 18 depicts a partial view of FIG. 13.

FIG. 19 depicts a partial view of a system relating to various aspects of the embodiments disclosed herein.

FIG. 20 depicts a partial view of FIG. 19.

FIG. 21 depicts a partial view of FIG. 19.

FIG. 22 depicts a partial view of FIG. 19.

FIG. 23 depicts a partial view of FIG. 19.

FIG. 24 depicts a partial view of FIG. 19.

FIG. 25 depicts a partial view of FIG. 19.

FIG. 26 depicts a partial view of a computer-implemented method relating to various aspects of the embodiments disclosed herein.

FIG. 27 depicts a partial view of FIG. 26.

FIG. 28 depicts a partial view of FIG. 26.

FIG. 29 depicts a computer program product relating to various aspects of the embodiments disclosed herein.

FIG. 30 depicts a partial view of FIG. 29.

FIG. 31 depicts a partial view of FIG. 29.

DETAILED DESCRIPTION

Figure 1A:
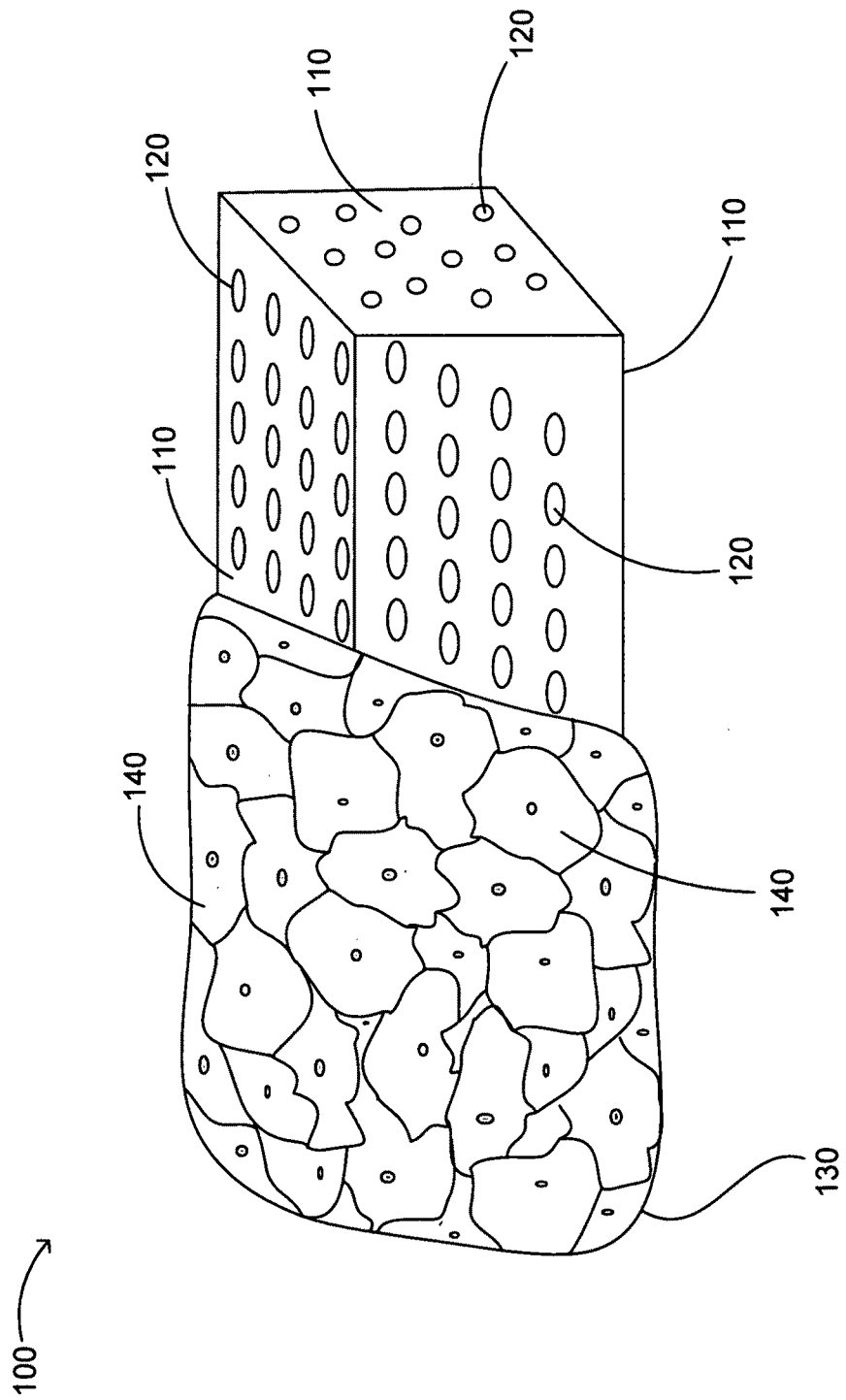
FIGS. 1A and 1B depict a diagrammatic view of an aspect of an embodiment of a device that substantially encloses at least one altered microorganism.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

Devices, methods, and systems are disclosed herein that relate to delivering at least one therapeutic agent to a biological tissue or organ. In an embodiment, the biological tissue or organ is part of a subject, as described herein.

Devices, methods, and systems are disclosed herein for stimulating an immune response in a subject. Devices, methods, and systems for preventing or treating an infectious disease or a pathological condition in the subject are disclosed. The pathological condition includes, but is not limited to, infectious disease, neoplastic disease, atherosclerosis, hypertension, autoimmune disease, diabetes, or substance addiction.

In an embodiment, the device includes a semi-permeable barrier substantially enclosing at least one altered microorganism, the semi-permeable barrier defining an interior region and an exterior region of the barrier. In an embodiment, the at least one altered microorganism includes at least one auxotrophic microorganism. In an embodiment, the device includes at least one metabolite (e.g., an essential nutrient) required by the at least one altered microorganism. In an embodiment, the device includes at least one semi-permeable barrier substantially enclosing at least one auxotrophic microorganism, the at least one auxotrophic microorganism including at least one nucleic acid construct encoding at least one therapeutic agent, the barrier defining an interior region and exterior region; and wherein the device includes at least one metabolite required by the at least one auxotrophic microorganism.

In an embodiment, the semi-permeable barrier provides selectivity for egress from the interior region to the exterior region of the barrier. In an embodiment, the semi-permeable barrier provides selectivity for ingress from the exterior region to the interior region of the barrier. In an embodiment, the device includes one or more bone barriers, diatom barriers, polymer or copolymer barriers, protein barriers, element barriers, vitamin barriers, mineral barriers, chloroplast barriers, or carbohydrate barriers. In an embodiment, the bone barrier includes a bone cage. In an embodiment, the diatom barrier includes a diatom cage. In an embodiment, the polymer or copolymer barrier includes a polymer or copolymer cage.

In an embodiment, the device is useful in a method for vaccinating a subject. In an embodiment, the device is useful in a method for treating any disease or condition where an increase in the immune response in the subject is desired. The device is useful in a method for treating an infectious disease or neoplastic disease in the subject. In an aspect, stem cells or tissues or other cell or tissue types can be configured to restructure the one or more semi-permeable barriers.

The device including one or more semi-permeable barriers is configured for implantation in a soft tissue of the subject. In an embodiment, the device is configured for injection into the soft tissue of a subject using a syringe. In an embodiment, the device is configured to be at least one of biocompatible or biodegradable. In an embodiment, the device including one or more semi-permeable barriers can remain in the soft tissue over an extended period of time to deliver at least one therapeutic agent to the subject to treat a pathological condition. The device including one or more cages can deliver a dosage of the immunogen and the adjuvant over a long term. Following injection into a soft tissue of the subject, the device including one or more bone cages can deliver a temporal series of vaccinations or booster vaccinations as may be required for a specific vaccination schedule. The device can be configured to provide one or more chambers and/or multiple pore sizes for controlled release of the one or more immunogens and one or more adjuvants.

In an embodiment, the device including one or more semi-permeable barriers refers to a rigid, semi-rigid, or otherwise structurally supportive structure with one or more external walls, and at least one internal cavity. In an embodiment, the device including one or more semi-permeable barriers refers to a pliable structure. In an embodiment, the device includes at least one of a rigid, semi-rigid, or pliable structure. In an embodiment, the semi-permeable barrier includes at least one interior region and at least one exterior region.

In an embodiment, one or more semi-permeable barriers can be structurally supportive to include, or contain biologically active molecules, e.g., one or more immunogens and one or more adjuvants, or one or more cells or tissues configured to produce at least one therapeutic agent, such as one or more immunogens and/or one or more adjuvants. In an embodiment, the device including one or more cages can be configured to deliver the at least one therapeutic agent, such as one or more immunogens and the one or more adjuvants to the soft tissue of a subject and to raise an immune response to the immunogen providing a method for treating a pathological condition in the subject. In an embodiment, the device including one or more cages can be configured to be non-weight-bearing to the skeletal structure when implanted into a soft tissue of a subject. In an embodiment, the device including one or more cages is not configured to provide intrinsic support to the bone or skeletal structure of the subject.

In an embodiment, one or more immunogens and one or more adjuvants, optionally in combination with a semi-permeable membrane and/or one or more cells or tissues, can be placed within the internal cavity of the semi-permeable barrier. In an embodiment, one or more immunogens and the one or more adjuvants in combination with the one or more cells or tissues may not include bone tissue. In an aspect, the cells or tissue may include stem cells or progenitor cells, e.g., mesodermal cells, osteoblasts or osteoclasts, configured to synthesize or degrade bone tissue. In an aspect, the one or more cells or tissues are modified to produce one or more immunogens and/or one or more adjuvants. The external wall of the device can be any shape, including, but not limited to, spherical, oval, rectangular, square, trapezoidal or modified versions of these shapes. The internal cavity, or interior of the device, can also be any shape, including, but not limited to, spherical, oval, rectangular, square, trapezoidal or modified versions of these shapes. Moreover, the internal cavity of the device can be configured to include or define one or more portions that are in fluid communication or are isolated portions from each other. The device including one or more semi-permeable barriers can be configured to release the at least one therapeutic agent (e.g., one or more immunogens and the one or more adjuvants) in a timed release manner over an extended time frame according to desired or recommended dosage and timing of a vaccination schedule.

In an embodiment, the release of the at least one therapeutic agent from the semi-permeable barrier can be temporally controlled. Temporal release can be controlled by the properties of the semi-permeable barrier, e.g., compartments, wall thickness, or pores in the cage, the formulation of the at least one therapeutic agent, or a combination thereof. Temporally controlled release of the at least one therapeutic agent from the device is useful for vaccines or other therapeutic agents requiring multiple doses (e.g., primary immunization and secondary immunization to establish memory cells responsive to the pathogenic organism or pathogenic condition). For example, vaccines recommended for multiple doses can include providing one dosage of the device including the one or more bone cages to the subject maintaining the temporally controlled release of the one or more immunogen and the one or more adjuvant for up to 24 months.

The release of the at least one therapeutic agent from the device can be controlled, for example, by a trigger, a pump, a biomolecule, a specific analyte, a pathogen or tumor cell, pulse of radiation, or an externally-administered compound. The trigger can stimulate immediate release of the at least one therapeutic agent from the device. Alternatively, the trigger can stimulate the synthesis of the at least one therapeutic agent by cells incorporated in the device. The trigger can be a biomolecule. Examples of trigger biomolecules include, but are not limited to, pathogen associated biomolecules (e.g., toxins, polysaccharides, double stranded RNA, CpG polynucleotides), tumor associated biomolecules (e.g., tumor antigens, tumor markers), other disease associated biomolecules (e.g., (β-amyloid), allergens (e.g., food allergen), or other biomolecules (e.g., drugs of abuse). Alternatively, the trigger can be a physiological change induced by the pathogen, tumor, disease, or allergic response. Examples of a physiological change include, but are not limited to, changes in pH, temperature, osmolarity, hypoxia, and ion concentrations. Examples of a physiological change further include, but are not limited to, increases in concentrations of endogenous compounds in the subject such as radical oxygen species, cytokines, nitric oxide, anti-microbial peptides, or pro-inflammatory molecules.

The device can be implantable indicating it is able to be placed within a subject. The device including one or more semi-permeable barriers can be implanted by methods including, but not limited to, surgery, injection, suppository, and inhalation. The device including one or more semi-permeable barriers can be placed, for example, subcutaneously, intramuscularly, intraperitoneally, intravenously, intravitreally, intra-arterially, intraarteriolarly, in capillary beds, subdermally, intradermally, orally, rectally, or nasally. The device including one or more semi-permeable barriers can be implanted during a surgical procedure, or can be injected using, for example, a hollow bore needle, such as those used for biopsies. Alternatively, injection can be by a gun, such as those used for anesthetic darts. The device including one or more semi-permeable barriers can be implanted in any location in a subject appropriate for the desired treatment, such locations are well-known to health care workers including, but not limited to, physicians and nurses, as well as veterinary, animal husbandry, fish, game, zoo, bird, reptile, and exotic animal officials.

The device including one or more semi-permeable barriers can be implanted in well-vascularized soft tissue, including, but not limited to, liver, kidney, muscle, lung, cardiac and/or brain tissue. In an aspect, the device including one or more semi-permeable barriers is implanted in less well-vascularized tissue including, but not limited to, joints, cartilage, and fat. The device including one or more semi-permeable barriers can be implanted behind the blood brain barrier. The device including a semi-permeable barrier can be implanted in the bladder, uterus, or vagina.

Biocompatible refers to a material the body generally accepts without a significant immune response/rejection or excessive fibrosis. In an aspect, some immune response and/or fibrosis is desired. In an aspect, vascularization is desired. In an aspect, vascularization is not desired.

The device including one or more semi-permeable barriers can be implanted in a subject including mammal, reptile, bird, amphibian, or fish. In an aspect, the subject includes domesticated, wild, research, zoo, sports, pet, primate, marine, and farm animals. The animal can be a mammal. The mammal can be a primate. In a further aspect, the primate can be a human. Animals include, but are not limited to, human, bovine, porcine, swine, ovine, murine, canine, avian, feline, equine, or rodent. Domesticated and/or farm animals include, but are not limited to, chickens, horses, cattle, pigs, sheep, donkeys, mules, rabbits, goats, ducks, geese, chickens, and turkeys. Wild animals can include, but are not limited to, non-human primates, bear, deer, elk, raccoons, squirrels, wolves, coyotes, opossums, foxes, skunks, and cougars. Research animals include, but are not limited to, rats, mice, hamsters, guinea pigs, rabbits, pigs, dogs, cats, and non-human primates. Pets include, but are not limited to, dogs, cats, gerbils, hamsters, guinea pigs and rabbits. Reptiles include, but are not limited to, snakes, lizards, alligators, crocodiles, iguanas, and turtles. Avian animals include, but are not limited to, chickens, ducks, geese, owls, sea gulls, eagles, hawks, and falcons. Fish include, but are not limited to, farm-raised, wild, pelagic, coastal, sport, commercial, fresh water, salt water, and tropical. Marine animals include, but are not limited to, whales, sharks, seals, sea lions, walruses, penguins, dolphins, and fish.

As discussed herein, in an embodiment the semi-permeable barrier includes at least one external wall. In an embodiment, the external wall of the one or more semi-permeable barriers can be any dimension, preferably an integer µM from about 1 µm to about 1,000 µM including approximately, but not limited to, 2 µm, 3 µm, 4 µm, 5 µm, 8 µm, 12 µm, 15 µm, 20 µm, 25 µm, 50 µm, 100 µm, 200 µm, 300 µm, 500 µm, 600 µm, 800 µm and 1,000 µm. In an aspect, the external wall can be approximately 1 µm to 1,000 µm, 2 µm to 500 µm, 3 µm to 250 µm, 4 µm to 100 µm, 5 µm to 50 µm, 5 µm to 10 µm, 2 µm to 20 µm, 1 µm to 50 µm, 5 µm to 25 µm, or 2 µm to 8 µm in width. In an aspect, the width is not uniform throughout the structure.

In an embodiment, the semi-permeable barrier includes an internal cavity. In an embodiment, the diameter of the internal cavity of the one or more semi-permeable barriers can be any integer µm from approximately 1 to approximately 1,000 including, but not limited to approximately, 2 µm, 3 µm, 4 µm, 5 µm, 8 µm, 10 µm, 12 µm, 15 µm, 20 µm, 25 µm, 50 µm, 100 µm, 200 µm, 300 µm, 500 µm, 600 µm, 800 µm or 1,000 µm. In an aspect, the diameter of the internal cavity can be approximately 1 µm to 1,000 µm, 2 µm to 800 µm, 5 µm to 750 µm, 10 µm to 500 µm, 20 µm to 250 µm, 10 µm to 100 µm, 5 µm to 50 µm, 1 µm to 10 µm, 2 µm to 20 µm, 1 µm to 50 µm, 50 µm to 500 µm, or 250 µm to 1,000 µm in width. In an aspect, the diameter of the internal cavity can be approximately up to 1 mm to 1 cm in width, including, but not limited to, up to 1 mm, up to 10 mm, up to 100 mm, or up to 1 cm or more in width. In an aspect, the internal diameter is not uniform throughout the structure. For example, the internal diameter can be up to 1 mm in one dimension and up to 3 cm in a second dimension.

The volume of the internal cavity can be any integer cubic µm from about 1 µm$^3$ to about $10^{12}$ µm$^3$ including, but not limited to, 1 cubic µm, 8 cubic µm, 27 cubic µm, 64 cubic µm, 125 cubic µm, 512 cubic µm, 1000 cubic µm, 1700 cubic µm, 3400 cubic µm, 8000 cubic µm, $1.5 \times 10^4$ cubic µm, $1.25 \times 10^5$ cubic µm, $10^6$ cubic µm, $8 \times 10^6$ cubic µm, $3 \times 10^7$ cubic µm, $10^8$ cubic µm, $2 \times 10^8$ cubic µm, $5 \times 10^8$ cubic µm, $10^9$ cubic µm, $10^{10}$ cubic µm $10^{11}$ cubic µm, and $10^{12}$ cubic µm. In an aspect, the volume of the internal cavity can be approximately up to 100 cubic µm, up to 1000 cubic µm, up to $10^4$ cubic µm, $10^5$ cubic µm, up to $10^6$ cubic µm, up to $10^7$ cubic µm, up to $10^8$ cubic µm, up to $10^9$ cubic µm, up to $10^{10}$ cubic µm, up to $10^{11}$ cubic µm, or up to $10^{12}$ cubic µm.

The liquid volume capacity of the internal cavity can be any integer microliter (µL) from about 10 µL to about 1000 µl, including approximately, but not limited to, $10^{-9}$ µL, $10^{-4}$ µL, $10^{-7}$ µL, $10^{-6}$ µL, $10^{-5}$ µL, $10^{-4}$ µL, $10^{-3}$ µL, 0.01 µL, 0.1 µL, 1 µL, 10 µL, 100 µL and 1000 µL. In an aspect, the liquid volume capacity can be approximately up to $10^{-8}$ µL, up to $10^{-7}$ µL, up to $10^{-6}$ µL, up to $10^{-5}$ µL, up to $10^{-4}$ µL, up to $10^{-3}$ µL, up to 0.01 µL, up to 0.1 µL, up to 1 µL, up to 10 µL, up to 100 µL or up to 1000 µL.

The internal cavity of the semi-permeable barrier can hold one or more cells. In an aspect, the cell can be the immunogen, e.g., a live, attenuated or inactivated pathogen or tumor cell. In an aspect, the cell can be engineered to generate one or more immunogen and/or one or more adjuvant. Examples of cell types that can be included in the cavity of the semi-permeable barrier include, but are not limited to, a virus, a bacterium, a fungus, a parasite, or a mammalian cell. The type of cell depends upon the nature of the vaccine and the immunogen. In an aspect, the type of cell and the number of cells held in the cavity may be dependent upon the size of the cells relative to the size of the cavity. Viruses can range in diameter from about 20 nm to about 400 nm. The human immunodeficiency virus (HIV) is approximately 90 to 160 nm in diameter. Bacteria can range in size from about 0.1 µm to about 600 µm over a single dimension. *Escherichia coli* represent a *bacillus* of about average size measuring 1 to 1.5 µm in width and 2 to 6 µm in length. In an aspect, the cell can be a fungus that is a genetically engineered yeast strain. *Saccharomyces cerevisiae*, a common yeast strain, ranges in diameter from 3 to 6 µm. In an aspect, the cell can be a blood borne parasite, e.g., *Plasmodium*. In another example, blood borne parasites range in size from about 1 to 30 µm by about 1 to 5 µm depending upon the type of parasite and the stage of development. *Plasmodium* sporozoites are about 1 µm in width and about 5 µm in length. Mammalian cells can range in diameter from about 3 µm to about 100 µm. For example, circulating human tumor cells of epithelial origin are about 15 to 20 µm in diameter. Chinese hamster ovary (CHO) cells, a cell type commonly used for genetic engineering, are about 14.5 µm in diameter. The volume of an average human cell ranges from about 500 to about 4000 cubic µm. As an example, a spherical mammalian cell with a diameter of 10 µm has a calculated volume of approximately 523 cubic µm while a spherical bacterium with a diameter of 1 µm has a calculated volume of approximately 0.523 µm, suggesting that 1000 bacteria may be loaded into a space that accommodates one mammalian cell.

Additionally, implantable devices are disclosed herein that include a semi-permeable barrier substantially enclosing at least one altered microorganism, the barrier defining an interior region and an exterior region, as described herein. In an embodiment, the at least one altered microorganism includes at least one nucleic acid construct encoding at least one therapeutic agent. In an embodiment, the altered microorganism includes an auxotrophic microorganism. In an embodiment, the device includes at least one metabolite (e.g., an essential nutrient) required by the at least one altered microorganism (e.g., auxotrophic microorganism).

As described herein, in an embodiment, the semi-permeable barrier includes one or more of a bone barrier, diatom barrier, polymer or co-polymer barrier, protein barrier, element barrier, vitamin barrier, mineral barrier, chloroplast barrier, or carbohydrate barrier. In an embodiment, the semi-permeable barrier includes one or more of collagen, elastin, albumin, gelatin, extracellular matrix, acrylate, methacrylate, fibrinogen, thrombin, fibrin, cellulose, poly(hydroxyalkanoate), poly (ε-caprolactone), polysaccharide, polythioester, starch, amylase, polylactone, polyphosphazene, polycyanaoacrylate, poly(lactic acid), poly(glycolic acid), polycaprolactone, plasticized cellulose materials, polyvinyl chloride, polyvinylidene fluoride, polyurethane isocyanate, polyalginate, polysulfone, polystyrene, polyvinyl alcohol, polyacrylonitrile, polymethylene oxide, polyethylene oxide, polytetrafluoroethylene, polymethyl methacrylate, polyamide, polyether-polyamino copolymer, thermoplastic copolymer, polyanhydride, polydioxanone, polyorthoester, poly(propylene fumarate), polyesteramide, polyamido amine, polythioester, nylon, polyacrylamide, acrylamide, nylon, urethane, polytetrafluoroethylene, polyurethane, dimethylsiloxane/methylvinylsiloxane copolymer, acetate, polyester, dextran, calcium, silicon, phosphorous, iron, magnesium, manganese, sodium, potassium, chromium, titanium, nickel, zinc, copper, cobalt, tungsten, silver, gold, platinum, enzyme, acid, amino acid, peptide, polypeptide, protein, oligonucleotide, nucleic acid, ribonucleic acid, oligosaccharide, monosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, cell ligand, cell receptor, or chlorophyll.

In an embodiment, the semi-permeable barrier includes a diatom barrier. In an embodiment, the diatom barrier includes a diatom cage. Diatom cages may include various parts or whole diatom skeletons from which organic matter has been removed. Diatoms exhibit a multitude of shapes and patterns in their siliceous valve structure (J. Nanosci. and Nanotech. (2005) 5:108-119). Shape and form are inherited in diatoms as a result of auxospore formation and vegetative reproduction. Diatom shapes include, but are not limited to cylindrical, ellipsoid, cubic and needle-shaped, and include features such as, but not limited to, radial, concentric, and/or traversal ribs, honeycomb structures, Warren trusses, radial and/or concentric undulations, hollow spines, and/or bulging, dome-shaped protuberances as shown for example in *Fragilariopsis, Thalassiosira, Asteromphalus, Coscinodiscus, Arachnoidiscusm, Asteromphalus, Navicula, Chaetoceros, Chorethron,* and/or *Odontella* as well as most other diatoms.

Diatom frustules include pores, optionally surrounded by silica structures, presumably to allow efficient nutrient uptake (J. Nanosci. and Nanotech. (2005) 5:108-119; J. Nanosci. and Nanotech. (2006) 8: 982-989). Illustrative pore sizes include 0.8 μm areolae, and cribra of 160 nm and 35 nm in *Coscinodiscus wailesii*.

Diatom spines can be siliceous or made of chitan (J. Nanosci. and Nanotech. (2005) 5:108-119). The siliceous spines can be extensive, and highly structured, including, for example, barbs and lattice work.

The geometry of the diatom siliceous structures is determined by specialized organelles, the silica deposition vesicles (J. Nanosci. and Nanotech. (2005) 5:108-119). An organic matrix of proteins/peptides and polysaccharides cause polycondensation of the silica, and remain an integral part of the 3-dimensional structure of the material formed.

Methods for removing some, most or all organic material from a diatom skeleton are known in the art and include, but are not limited to, treatment with a variety of oxidizing agents, such as $KMnO_4$ and HCl or sulfuric and nitric acid, as well as acid treatment to according to the method of von Storsch as described in Hasle and Syvertsen (Marine Diatoms (1997) Ed. Tomas. Academic Press. San Diego, Calif., Chapter 2; J. Nanosci. and Nanotech. (2005) 5:131-139; J. Nanosci. and Nanotech. (2005) 5:108-119; J. Nanosci. and Nanotech. (2006) 6:982-989).

In an embodiment, the diatom skeleton includes one or more of three porous layers, such as but not limited to, the cribellum, the cribrum, and a foramen layer. The pore sizes of the layers differ among diatoms, as does the order of the layers. In illustrative embodiments, in *Coscinodiscus* sp. the cribellum is the outer porous layer, followed by a second porous layer the cribrum, which is connected to a third layer, a porous silica plate containing the foramen holes. The pores of the cribellum (approx. 45 nm) are smaller than the pores of the cribrum (approx. 192 nm), which are smaller than the foramen holes (approx. 1150 nm). In illustrative embodiments, in *Thalassiosira eccentrica*, the foramen pores (approx. 770 nm) are part of the external layer, while the internal layer includes pores of approx. 43 nm, similar to the cribellum layer, above (Methods for identifying the layers, and retaining one or more of the layers are known in the art (J. Nanosci. and Nanotech. (2006) 6:982-989).

In an embodiment, diatom cages include a rigid, semi-rigid, or other structural support with at least one external wall, and at least one internal cavity including at least part of one or more of a diatom cell wall, valve, or frustule. In an embodiment, the internal cavity includes at least one of a semi-permeable membrane, one or more living cells or tissues, or one or more biologically active molecules.

In an embodiment, a method for making a diatom cage includes, for example, micromanipulation or nanomanipulation (e.g., micromachining or nanomachining). In an embodiment, surface organic materials are removed from the frustules of diatoms, and the paired frustules make up the diatom cage. The paired frustules may be sealed using one or more standard methods, including but not limited to, at least one of sealants such as glue, bands, wraps or attachments such as screws, nails, hook and eye or any other closure methods (optionally removable) used by a medical professional such as sutures.

In an embodiment, the diatom cage has a shape selected from the group consisting of cylindrical, ellipsoid, cubic, and needle-shaped. The diatom skeleton, or cage may optionally include features such as, but not limited to, radial, concentric, or transversal ribs, honeycomb structures, Warren trusses, radial or concentric undulations, hollow spines, or bulging, dome shaped protuberances.

In an embodiment, the size of the diatom skeleton, or cage is at least approximately 0.5 μm, at least approximately 1 μm, least approximately 2 μm, at least approximately 3 μm, at least approximately 4 μm, at least approximately 5 μm, at least approximately 6 μm, at least approximately 7 μm, at least approximately 8 μm, at least approximately 9 μm, at least approximately 10 μm, at least approximately 11 μm, at least approximately 12 μm, at least approximately 15 μm, at least approximately 18 μm, at least approximately 20 μm, at least approximately 25 μm, at least approximately 30 μm, at least approximately 35 μm, at least approximately at least approximately 40 μm, at least approximately 50 μm, at least approximately 60 μm, at least approximately 75 μm, at least approximately 90 μm, at least approximately 100 μm, at least approximately 125 μm, at least approximately 150 μm, at least approximately 175 μm, at least approximately 200 μm, at least approximately 250 μm, at least approximately 300 μm, at least approximately 350 μm, at least approximately 400 μm, at least approximately 500 μm, at least approximately 600 μm, at least approximately 750 μm, at least approximately 1000 μm, at least approximately 1250 μm, at least approximately 1500 μm, at least approximately 1750 μm, at least approximately 2000 μm, at least approximately 2500 μm, at least approximately 3000 μm, at least approximately 3500 μm, at least approximately 4000 μm, at least approximately 4500 μm, or at least approximately 5000 μm.

In an embodiment, the diatom cage is at least partially isolated from a naturally-occurring diatom, cultured diatom, or modified diatom (a physical, genetic, or chemical modification, for example). In an embodiment, the diatom includes at least one of centric or pinnate. In an embodiment, the diatom includes at least one of eucentric, eccentric, araphid, eunotioid, monoraphid, naviculoid, cymbelloid, epithemoid, nitzschioid, or surirelloid. In an embodiment, the diatom includes at least one of *Fragilariopsis, Thalassiosira, Asteromphalus, Coscinodiscus, Arachnoidiscusm, Asteromphalus, Navicula, Chaetoceros, Chorethron*, or *Odontella*.

Methods for obtaining diatoms from nature are known in the art. For example, diatoms can be obtained from a wide variety of habitats including, but not limited to, bodies of water including salt water (e.g. oceans) and fresh water (e.g. ponds), as well as soil (Appl. Microbiol. Biotechnol. (2003) 60:612-623). Centric diatoms are essentially planktonic algae, and are found in all open water masses. Pennate diatoms are frequently, but not exclusively, benthic, and are found growing on sediments or attached to rocks or microalgae in their benthic form. Some species are also found in soil. Diatoms are abundant in the beginning of spring and autumn when nutrients are not limiting, and light intensity and daylength are optimal for diatom photosynthesis.

Methods for culturing diatoms are known in the art, and include, for example, laboratory scale and commercial scale cultivation using small-scale, closely controlled photobioreactors, and large-scale, open air systems, (Appl. Microbiol. Biotechnol. (2003) 60:612-623; Appl. Microbiol. Biotechnol. (2003) 60:624-632). Diatoms cultured in small-scale, closely controlled bioreactors include, but are not limited to, *Phaeodactylum tricornutum, Skeletonema costatum, Chaetoceros* spp., *Nitzchia laevis, Cyclotella cryptica*, or *Haslea ostrearia*. Diatoms cultured in large-scale, open air systems include, but are not limited to, *Skeletonema, Thalassiosira, Phaeodactylum, Chaetoceros, Cylindrotheca, Bellerochea, Actinocyclus, Nitzschia*, or *Cyclotella*. Although most microalgae are obligate photoautotrophs and their growth is dependent on the generation of photosynthetically derived energy, genetically engineered diatoms may be grown in fermenters.

In some embodiments, the diatom skeleton or cage is designed or treated to, at least partially or completely, prevent or reduce restructuring. In some embodiments, the diatom skeleton, structure or cage is designed or treated to be at least partially, or completely, restructured. Diatom restructuring includes, but is not limited to, influx and growth of the subject's cells (including, but not limited to, bone cells) in or on the diatom skeleton, structure or cage. Mechanisms of restructuring, treatments to modify restructuring, genes governing restructuring and methods for detecting and measuring changes in bone are known in the art and described herein.

In illustrative embodiments, compounds to mediate deposition and/or resorption of cells (e.g. bone) can be administered locally by being applied to, or made part of, the diatom skeleton, structure, and/or cage either globally, or in localized areas, depending on, for example, whether complete or partial restructuring is desired. In illustrative embodiments, compounds can be administered by incorporation in the diatom skeleton, structure and/or cage as one of the one or more biologically active molecules and/or part of the living cells and/or tissues, as discussed herein.

In an embodiment, the pore sizes of a diatom cage range from about 1 nm, about 5 nm, about 10 nm, about 25 nm, about 30 nm, about 50 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, about 210 nm, about 220 nm, about 230 nm, about 240 nm, about 250 nm, about 260 nm, about 270 nm, about 280 nm, about 290 nm, about 300 nm, about 320 nm, about 340 nm, about 360 nm, about 380 nm, about 400 nm, about 420 nm, about 440 nm, about 460 nm, about 480 nm, about 500 nm, about 520 nm, about 540 nm, about 560 nm, about 580 nm, about 600 nm, about 700 nm, about 800 nm, about 900 nm, about 1000 nm, about 1500 nm, about 2000 nm, or any value less than or therebetween.

In an embodiment, the diatom cage porosity is approximately 1%, approximately 3%, approximately 5%, approximately 10%, approximately 15%, approximately 20%, approximately 30%, approximately 40%, approximately 50%, approximately 60%, approximately 70%, approximately 80%, approximately 90%, or any value greater than or therebetween.

In an embodiment, the diatom cage is at least partially non-immunogenic. In general, diatoms are chemically inert and bio-compatible (PLoS Biol. (2004) 2(10):e306: 1512-1515). Methods of modifying the immunogenicity of the diatom cage are known in the art, and include but are not limited to, modifications relating to the immunogenicity of associated tissue (such as, for example, the semi-permeable component, bone tissue, other tissue, or cells), biological materials (such as, immune modulatory compounds known in the art and discussed herein), or genetic modifications.

In an embodiment, the diatom is modified (e.g., physically, chemically, or genetically modified). Biotechnological methods of genetic and non-genetic modification and manipulation of nucleic acids and proteins are known in the art (Sambrook and Russell. (2001) *Molecular Cloning: A Laboratory Manual* 3rd edition. Cold Spring Harbor Laboratory Press; Sambrook, Fritsch, Maniatis. *Molecular Cloning: A Laboratory Manual* $3^{rd}$ edition. includes a spiral bound, 3 volume set, associated with a web site as an on-line laboratory manual (on the world wide web at MolecularCloning.com).

Methods for genetic engineering are known in the art for a variety of diatom species, including but not limited to, *P. tricornutum, Cyclotella cryptica, Cylindrotheca fusiformis, Navicula saprophila*, and *Thalassiosira weissflogii* (J. Phycol. (1995) 31:1004-1012; Mol. Gen. Genetics (1996) 252: 572-579; Appl. Biochem. Biotechnol. (1996) 57/58:223-231; J. Phycol. (1999) 35:113-120; Mar. Biotech. (1999) 1:239-251; Science (2001) 292:2073-2075; Appl. Microbiol. Biotechnol. (2003) 60:612-623; J. Nanosci. and Nanotech. (2005) 5:5-14; FEBS J. (2005) 272:3413-3423; J. Physiol. (2006) 42:1059-1065). Recombinant methods include, but are not limited to, mutagenesis and transformation techniques, including transient and stable transfection. Stable transfection has been achieved in both inducible and constitutive manners. Co-transformation is effective in allowing introduction of a non-selective gene as well as a selection marker gene of which a variety are available for use in diatoms. Transfection methods include, for example, microparticle bombardment.

In an embodiment, cell wall and membrane proteins were targeted and covalently modified by heterologous expression in *Cylindrotheca fusiformis* (J. Phycol. (1999) 35:113-120). In an embodiment, *P. tricornatum* was transformed with a gene encoding a glucose transporter (glut 1 from human erythrocytes or hup 1 from the microalga *Chlorella kessleri*) that allowed growth on exogenous glucose in the absence of light (Science (2001) 292:2073-2075), and *C. cryptica* was genetically engineered for further biodiesel production (Appl. Biochem. Biotechnol. (1996) 57/58:223-231). In an embodiment, diatom multipartite plastid targeting signals were characterized in vivo (J. Cell Sci. (2002) 115:4061-4069; Plant J. (2005) 41:175-183).

The complete genome sequence is known for at least one diatom species, *Thalassiosira pseudonana*, and is in progress for at least one other diatom species, *Phaeodactylum tricornutum* (Science (2004) 306:79-86; Plant Physiol. (2005) 137:

500-513; J. Nanosci. and Nanotech. (2005) 5:5-14). In addition, EST databases of nonredundant cDNAs have been created and at least partially analyzed for at least *P. tricornatum* and *Thalassiossira pseudonana* (Plant Physiol. (2002) 129:993-1002; J. Nanosci. and Nanotech. (2005) 5:5-14).

In an embodiment, the diatom is genetically engineered to alter at least one of growth under fermentation conditions, glucose uptake, or expression of a glucose transporter. Although most microalgae are obligate photoautotrophs and their growth is dependent on the generation of photosynthetically derived energy, diatoms may be genetically engineered (or undergo mutagenesis) to allow growth under conditions suitable for fermentation cultivation. In an example, *Phaeodactylum tricornutum* was genetically engineered to express a glucose transporter through gene transfer of glut 1 or hup 1 and was cultured with the addition of exogenous glucose in the absence of light in a microbial fermenter (Science (2001) 292:2073-2075).

In an embodiment, the diatom frustules, silica nanostructure, cell wall, or membrane is modified through genetic or non-genetic engineering. In an embodiment, the diatom silica nanostructure is modified through genetic or non-genetic engineering. In an embodiment, the diatom is genetically engineered to express one or more modified cell wall proteins, membrane proteins, or transporters. In an embodiment, the diatom is genetically engineered to express one or more modified silaffins, silaffin-related genes, polyamines, polyamine-related genes, or silicic acid transporters. A variety of diatom cell wall and membrane proteins as well as their encoding nucleic acid sequences are known in the art, including but not limited to, polyamines, silaffins, and silicic acid transporters (ChemBioChem (2006) 7:1419-1427; Mol. & Cell. Proteomics (2006) 5:182-193; FEBS Lett. (2005) 579: 3765-3769; J. Nanosci. and Nanotech. (2005) 5:146-157; J. Nanosci. and Nanotech. (2005) 5:158-166). In an embodiment, cell wall and membrane proteins were targeted and covalently modified by heterologous expression in *Cylindrotheca fusiformis* (J. Phycol. (1999) 35:113-120).

In an embodiment, a method for non-genetic modification of diatoms includes cell wall modifications, are known in the art (Protist (2006) 158:21-28; J. Nanosci. and Nanotech. (2005) 5:92-95; J. Nanosci. and Nanotech. (2005) 5:68-78; J. Nanosci. and Nanotech. (2005) 5:41-49). In an embodiment, cell wall silification can be modified by changes in the growth environment, including, but not limited to, pH, nutrient levels, light levels, temperature, and grazing. In an embodiment, cell wall silification can be modified by zeolitisation. In an embodiment, cell wall silification can be modified by culture conditions including metals other than silica, including but not limited to, germanium.

In an embodiment, the device may be implanted by standard methods known in the art including, but not limited to, surgery, injection, suppository, and inhalation. The device may be placed, for example, subcutaneously, intra-muscularly, intra-peritoneally, intra-venously, intra-arteriolar, in capillary beds, subdermally, intradermally, orally, rectally, nasally, into the cerebrospinal fluid space, intracranially, intraperitoneal, transurethral, or transvaginal. The device may be implanted during a surgical procedure, or may be injected using, for example, a hollow bore needle, such as those used for biopsies. Alternatively, injection may be by a gun, such as those used for anesthetic darts. The device can be implanted in any location in a subject appropriate for the desired treatment, such locations are well-known to health care workers including, but not limited to, physicians and nurses, as well as veterinary, animal husbandry, fish, game, zoo, bird, reptile, and exotic animal officials.

In an embodiment, the device includes at least one of an infusion pump, osmotic delivery system, peristaltic pump, or simple diffusion delivery system for administering the at least one therapeutic agent. In an embodiment, at least two therapeutic agents are administered by way of the device. In an embodiment, the device includes separate chambers configured to hold multiple different microorganisms, such that each chamber includes a different agent, or a different altered microorganism. See, for example, U.S. Pat. App. Pub. No. 20090202608, which is incorporated herein by reference.

In an embodiment, the device includes one or more gears. For example, published reports indicate that a solution of *Bacillus subtilis* are capable of rotating gears that are approximately 380 microns in size. See, for example, Sokolov, et al., ABSTRACT, PNAS, vol. 106, no. 51, online at 0913015107 (2009), which is incorporated herein by reference. As described in the publication, the bacteria suspended in a solution can turn microgears by manipulation of oxygen in the solution. Also as reported, since the bacteria utilized were aerobic, decreasing the level of oxygen resulted in a decrease in movement of the gears, while increasing the oxygen level resulted in increasing movement of the gears. In an embodiment, at least one gear, such as described herein, is utilized to operate a pump, such as a peristaltic pump, for dispensing the at least one therapeutic agent.

Altered Microorganisms

The compositions, methods, devices, and systems described herein relate to at least one altered microorganism (e.g., an auxotrophic microorganism) that is configured to deliver at least one agent (e.g., a therapeutic agent) to at least one substrate (e.g., biological tissue). In an embodiment, the at least one agent is produced by at least one nucleic acid construct included in the at least one altered microorganism. In an embodiment, the device provides at least one metabolite required by the at least one altered microorganism. In an embodiment, the at least one altered microorganism includes at least one inducible genetic element configured to initiate death of the altered microorganism.

In an embodiment, an altered microorganism includes a microorganism that has been chemically, physically, or genetically modified from a naturally occurring microorganism, or a microorganism that has been artificially synthesized. In an embodiment, the altered microorganism includes an auxotrophic microorganism. For example, in an embodiment, an auxotrophic microorganism includes at least one modification that renders it dependent on at least one metabolite or other essential nutrient, that the microorganism is unable to manufacture for itself, and instead must be provided to the microorganism (e.g., by the device). Examples of particular metabolites are described herein, and include but are not limited to, energy sources or other metabolic pathway requirements.

In an embodiment, the growth of the altered microorganism can be directed. In one example, by allowing selective growth of the microorganism, or selective agent production (e.g., lactic acid suppressor gene), the microorganism can be directed or controlled. In another example, the altered microorganism includes a recombinant microorganism with a mutation that renders the microorganism dependent on an external factor for survival (e.g., thymidylate synthase gene). In another example, the altered microorganism contains an essential gene and a control sequence that regulates expression such that an essential gene is expressed in a permissive environment and not expressed in a nonpermissive environment. In another example, the altered microorganism contains a lethal gene and a control sequence that regulates expression such that the lethal gene is expressed in a nonpermissive environment, and not expressed when in a permissive environment. See, for example, U.S. Patent Application Publication No. 20080253990, and U.S. Patent Application Publication No. 20080254014, each of which is incorporated herein by reference.

In an embodiment, the at least one altered microorganism includes at least one of a prokaryote or a eukaryote. In an embodiment, the at least one altered microorganism includes at least one of bacteria, protozoa, rotifers, algae, or fungi. In an embodiment, the at least one altered microorganism includes at least one of a non-pathogenic strain, transgenic microorganism, magnetotactic microorganism, anaerobic or aerobic microorganism, food grade strain, obligate microorganism, attenuated microorganism strain, facultative anaerobe, non-invasive strain, probiotic, colonizing microorganism, element-modifying microorganism, or photosynthetic microorganism. In an embodiment, the at least one element-modifying microorganism includes at least one of a nitrogen-fixing microorganism, nitrifying microorganism, denitrifying microorganism, hydrocarbon-utilizing microorganism, dechlorinating microorganism, or a sulfate-reducing microorganism.

In an embodiment, the at least one altered microorganism includes at least one of *Bifidobacterium, Lactococcus, Lactobacillus, Salmonella, Clostridium, Escherichia, Listeria, Streptococcus, Staphlococcus, Bacillus, Marinobacter, Micrococcus, Dietzia, Oceanobacillus, Citriococcus, Georgenia, Microbacterium, Stappia, Isoptericola, Cellulomonas, Rhizobia, Frankia, Klebsiella, Nocardioform Actinomycetes, Cytophagacia, Corynebacterium, Vibrionacia, Cyanobacteria, Pseudomonas, Rhastonia, Sphaerotilus, Shewanella, Wolbachia,* or *Azotobacter, Azospirillum*. In an embodiment, the at least one altered microorganism includes at least one of *Saccharomyces, Candida, Brettanomyces, Zygosaccharomyces, Yarrowia, Schizosaccharomyces, Torulaspora, Neotyphodium,* or *Cryptococcus*.

Some non-limiting examples of microorganisms that can be modified according to various embodiments described herein include: *Lactococcus garvieae, Lactococcus lactis, Lactococcus lactis* subsp. *cremoris, Lactococcus lactis* subsp. *hordniae, Lactococcus lactis, Lactococcus lactis* subsp. *Lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius* subsp. *araffinosus, Lactobacillus aviarius* subsp. *aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus collinoides, Lactobacillus confusus, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus divergens, Lactobacillus farciminis, Lactobacillus fermentum, Lactobacillus fornicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefuranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rimae, Lactobacillus rogosae, Lactobacillus ruminis, Lactobacillus sakei, Lactobacillus sakei* subsp. *carnosus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis* subsp. *mali, Lactobacillus yamanashiensis* subsp. *Yamanashiensis, Lactobacillus zeae, Clostridium novyi, Clostridium sordellii, Bifidobacterium longum, Escherichia coli, Salmonella typhimurium, Salmonella paratyphi, Salmonella pneumoniae, Salmonella enterica, Streptococcus pneumoniae, Streptococcus pyogenes, Streptococcus* group B, *Streptococcus mutans, Streptococcus sobrinus, Streptococcus equi, Staphylococcus* ssp., *Erysipelothrix rhusiopathiae, Bacillus anthracis, Listeria monocytogenes, Mycobacterium leprae, Mycobacterium tuberculosis, Clostridium tetani, Clostridium botulinum, Clostridium difficile, Clostridium perfringens, Corynebacterium diphtheriae, Mycoplasma* ssp., *Rhodococcus, Nocardia, Gordona, Jensenia, Shewanella, Shewandella oneidensis, Dehalococcoides, Burkholderia zenovorans, Comamonas, Cupriavidus, Sphingomonas, Acidovorax, Desulfovibrio, Anabaena cylindrica, Plectonema, Nostoc commune, Rhodobacter sphaeroides, Rhodopseudomonas palustris,* or *Rhodobacter capsulatus, Escherichia coli* Nissle 1917, *Salmonella typhimurium* 14028, *Salmonella typhimurium* SL1344, *Salmonella typhi, Salmonella abortus-ovi, Salmonella abortus-equi, Salmonella Dublin, Salmonella gallinarum, Salmonella pullorum, Shigella fexneri, Shigella sonnei, Haemophilus influenzae, Bordetella pertussis, Nisseria meningitides, Nisseria gonorrohia, Pasteuralla multocida, Yersinia pestis, Escherichia coli* 4608-58, *Salmonella flexneri* 2a SC602, *Escherichia coli* CFT073, *Escherichia coli* Top10, *Escherichia coli* MC1000, *Escherichia coli* NF1815, *Escherichia coli* NF1830, *Escherichia coli* HB101, *Escherichia coli* BD3364, *Escherichia coli* BD3364, *Escherichia coli* HfrC, *Escherichia coli* BD3342, *Escherichia coli* BD3346, *Escherichia coli* XAC, *Escherichia coli* BD71, *Escherichia coli* BD76, *Escherichia coli* 517.1, *Lactococcus lactis* MG1363, *Lactococcus lactis*-Thy12, *Clostridium novyi*-NT, *Lactobacillus plantarum* NC1 MB8826, *Lactobacillus plantarum* NCIMB8826Int1, *Lactobacillus fermentum* KLD, *Lactobacillus plantarum* MD007, *Lactobacillus plantarum* MD007Int6, *Lactococcus lactis* NZ3900, MC-1 magnetotactic bacteria, *Lactococcus lactis* PH3960, *Streptococcus gor-*

*donii, Lactobacillus zeae, Streptococcus mutans, Bacteroides ovatus, Bacteroides fragilis, Prevotella, Saccharomyces boulardii, Firmicutes, Gammaproteobacteria, Prevotellaceae, Archaea, Listeria innocua, Staphylococcus xylosus, Staphylococcus carnosus, Listeria monocytogenes, Klebsiella pneumoniae, Azotobacter vinlandii, Anabaena cylindrica, Plectonema, Nostoc commune, Rhodobacter sphaeroides, Rhodopseudomonas palustris, Rhodobacter capsulatus, Clavibacter, Alcaligenes, Sphingobacterium, Phyllobacterium, Aeromonas, Stenotrophomonas, Acidovorax, Comamonas, Desulfovibrio, Stentrophomonas, Serratia, Pseudomonas aeruginosa, Stentrophomonas maltophilia, Serratia marsescens, Variovorax, Chryseobacterium, Comamonas, Acidovorax, Stenotrophomonas, Sphingobacterium, Xanthomonas, Frateuria, Zoogloea, Alcaligenes, Flavobacterium, Derxia, Lampropedia, Brucella, Xanthobacter, Thermus, Thermomicrobium, Halomonas, Alteromonas, Serpens, Janthinobacterium, Bordetella, Paracoccus, Beijerinckia, Francisella, Eubacteria, Actinomycetes, Nocardia, Rhodococcus, Gordona, Nocardioides, Saccharopolyspora, Micropolyspora, Promicromonospora, Intrasporangium, Pseudonocardia, Oerskovia, Stomatococcus, Planococcus, Aerococcus, Peptococcus, Peptostreptococcus, Coprococcus, Gemella, Pediococcus, Leuconostoc, Ruminococcus, Sarcina, Aeromonas, Photobacterium, Vibrio, Plesiomonas, Zymomonas, Chromobacterium, Cardiobacterium, Calymmatobacterium, Streptobacillus, Eikenella, Gardnerella, Phyllobacterium, Rhizobium, Bradyrhizobium, Agrobacterium, Cytophaga, Flexibacter, Saprospira, Flexithrix, Herpetosiphon, Capnocytophaga, Sporocytophaga, Aureobacterium, Agromyces, Arachnia, Rothia, Acetobacterium, Actinomyces, Arthrobactera, Arcanobacterium, Lachnospira, Propionibacterium, Eubacterium, Butyrivibria, Brevibacterium, Bifidobacterium, Microbacterium, Caseobacter,* or *Thermoanaerobacter, Enterobacter* sp. 638, or *Burkholderia cepacia* BU72, or other strain.

In an embodiment, the at least one altered microorganism includes MC-1 magnetotactic bacteria. For example, magnetotactic bacteria have flagella that provide for mobilization, and can be combined with nanoparticles of magnetite or magnetosome chains embedded in the bacteria for directing the microbes. See, for example, Felfoul, et al., IEEE Xplore Abstract, issue 22-26, pp. 1463-1466 (2007), which is incorporated herein by reference.

In an embodiment, the altered microorganism includes at least one microorganism with the designation of "generally regarded as safe" (GRAS) status in the food industry.

Many microorganism strains are registered with the American Type Culture Collection (ATCC, Rockville, Md., USA), and can be adapted for use with various embodiments described herein.

In an embodiment, any microorganism for which at least a portion of the genome has been sequenced is utilized. For example, by sequencing the genome of a particular microorganism, regulatory elements and sites for chromosomal insertion can be identified. Furthermore, bioinformatics and promoter-trapping strategies can assist in locating endogenous promoters to further regulate production of the at least one therapeutic agent.

In an embodiment, at least one altered microorganism includes a microorganism that is isolated from at least one biological tissue, environmental medium, subject, or other substrate. The microorganism is modified, and placed into at least one biological tissue, subject, or other substrate (which may be the same or different substrate as the source of the microorganism).

In an embodiment, the altered microorganism includes at least one microorganism strain that naturally resides in the gut of a subject, or has been modified to survive and/or proliferate in the gut of a subject. In an embodiment, the semi-permeable barrier is implanted into the gut of a subject for delivery of at least one therapeutic agent produced by the microorganism.

In an embodiment, the microorganism or the device includes at least one inducible genetic element configured to initiate death in the at least one microorganism. For example, in an embodiment, the microorganism includes inducible suicide genetic elements that are configured to initiate or induce death in the microorganism upon encountering at least one inducer that regulates the genetic elements. In an embodiment, the genetic elements that regulate the induction of death of the microorganism are incorporated as part of the microorganism's own chromosomal or genetic constitution. In an embodiment, the genetic elements that regulate the induction of death of the microorganism are included as part of a vector (e.g., plasmid, cosmid, etc.). See, for example, U.S. Patent Application No. 20050276788, which is incorporated herein by reference.

In an embodiment, the device itself is configured to induce apoptosis or necrosis in the at least one altered microorganism. For example, in an embodiment, the device (e.g., semi-permeable barrier) is configured to include or release at least one molecule that induces apoptosis or necrosis in the at least one altered microorganism.

In an embodiment, a conditional lethal system for eukaryotic cells (e.g., fungal cells such as yeast, or other eukaryotic cells) is utilized by providing intracellular production of the *Serratia marcescens* nuclease in the cell, which destroys the genetic material in the cell. See, for example, Balan and Schenberg, Yeast, vol. 22, pp. 203-212 (2005), which is incorporated herein by reference. As reported, under normal conditions, the nuclease, encoded by the nucA gene, is secreted into the extracellular medium. Cloning it without the signal sequence, however, results in killing the yeast cell upon glucose depletion from the medium. Id. The conditional lethal system also disfavors horizontal gene transfer from recombinant yeast cells to other microorganisms found in the environment. Id.

In an embodiment, a lac-hok cassette is utilized for inducing death, wherein the hok gene from plasmid R1 belongs to a family of genes encoding small polypeptides (about 50 amino acids) which, when overexpressed, collapse the membrane potential and lead to cell death. See, for example, Contreras, et al., App. Env. Microbiol. vol. 57, no. 5, pp. 1504-1508 (1991), which is incorporated herein by reference. In an embodiment, a gef system, a chromosomally encoded *E. coli* gene highly homologous to hok, is utilized for inducing death in the altered microorganism. For example, the altered microorganism survives only in the presence of effectors of the meta-cleavage pathway encoded by the TOL plasmid of *P. putida*. Id. For example, in an embodiment, microorganisms configured to degrade substituted benzoates utilize a Lad protein (Lac repressor) expressed from a Pm::lacI fusion represses transcription from a Ptac::gef cassette in the presence of XylS effectors (coding for the regulator necessary to activate transcription from Pm, in the presence of an effector such as 3-methylbenzoate, in this example), whereas in the absence of XylS effectors, expression of the gef gene is no longer repressed, leading to cell killing. Id. Substitution of XylS for another protein expands the range of response. Id. Thus, in an embodiment, a similar construct is developed for regulation of production of a particular therapeutic agent in an altered microorganism, as described herein.

In an embodiment, the at least one altered microorganism includes at least one inducible genetic element configured to initiate death of the at least one microorganism. In an embodiment, the inducible genetic element includes at least one secretory signal sequence. Various mechanisms can be employed to initiate death of the microorganism. For example, the inducible genetic element can be configured to initiate programmed cell death, to initiate autophagocytosis of the at least one microorganism, to lyse the at least one microorganism, or by other means.

In an embodiment, the at least one inducible genetic element configured to initiate death of the at least one altered microorganism includes at least one of programmed cell death 1 gene (PDCD1), programmed cell death 2 gene (PDCD2), programmed cell death 3 gene (PDCD3), programmed cell death 4 gene (PDCD4), programmed cell death 5 gene (PDCD5), programmed cell death 6 gene (PDCD6), programmed cell death 7 gene (PDCD7), programmed cell death 8 gene (PDCD8), programmed cell death 9 gene (PDCD9), programmed cell death 10 gene (PDCD10), programmed cell death 11 gene (PDCD11), programmed cell death 12 gene (PDCD12), caspase gene, rel gene, hok gene, sok gene, diaminopimelate gene, nuclease gene, methylase gene, DNA ligase gene, DNA gyrase gene, toxin-antitoxin module, relF gene, triclosan, lysine, or lysine-holin. In an embodiment, the toxin-antitoxin module includes at least one of masEF, chpBIK, relBE, yefM-yoeB, dinJ-yaf1, barnase-barstar, or ecnA-ecnB. In an embodiment, the at least one inducible genetic element configured to lyse the at least one auxotrophic microorganism includes at least one of a nuclease gene, or lysis gene E.

In an embodiment, the at least one inducible genetic element configured to initiate death of the altered microorganism includes at least one of extracellular death factor, mazF, or mazEF. For example, toxin-antitoxin modules are generally gene pairs specifying for a toxin and its antitoxin, and are found on the chromosomes of many bacteria. For example, in E. coli, mazF encodes a stable toxin (MazF), and mazE encodes a labile antitoxin (mazE) which prevents the lethal effect of MazF. See, for example, J. Bacteriol., vol. 186, no. 24, pp. 8295-8300, (2004), which is incorporated herein by reference. As published, the quorum sensing peptide, Extracellular Death Factor, is a signal molecule required for mazEF-mediated cell death. Id. In an embodiment, a microbial biofilm is desired, and the device includes means for measuring biofilm formation. In an embodiment, a microbial biofilm is not desired, and the device includes means for inhibiting biofilm formation (e.g., $Ga(NO_3)_3$; coating materials such as fluoroalkylated acrylic acid oligomer). See, e.g., Peeters, et al., J. Antimicrob. Chemo. Vol. 61, pp. 1062-1065 (2008); and Okada et al, Dental Mat. J. vol. 27, no. 4, pp. 565-572 (2008), each of which is incorporated herein by reference.

Figure 8:
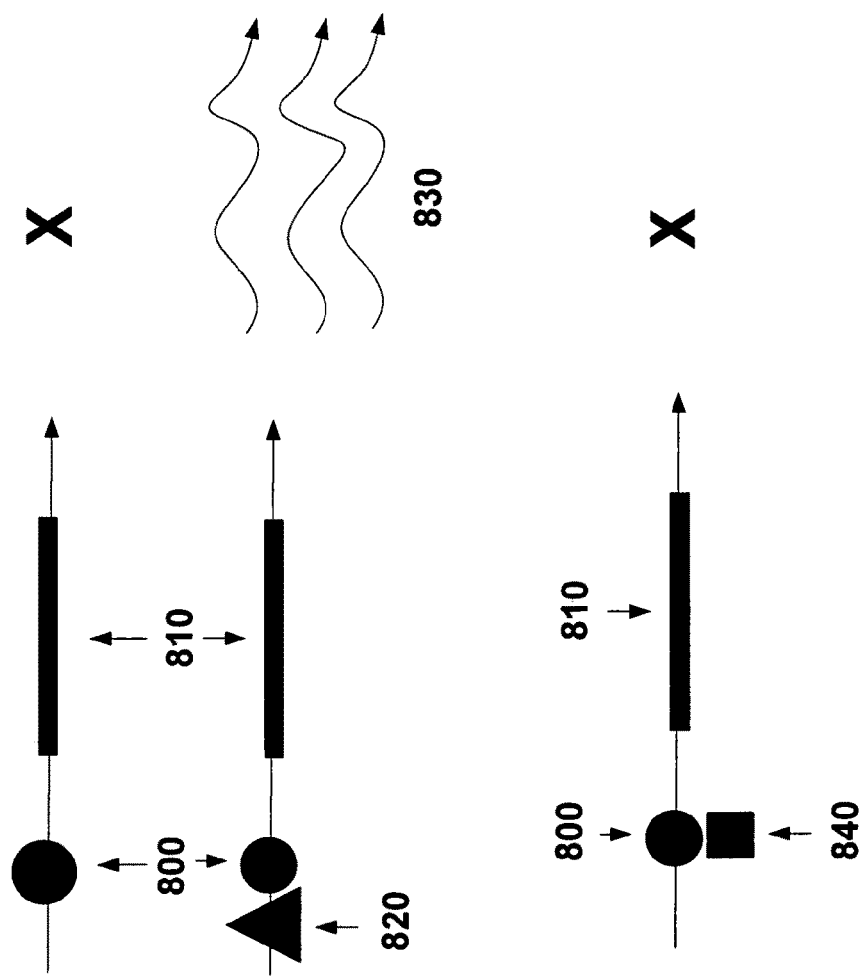
FIG. 8 depicts a partial view of particular genetic elements utilized in various embodiments disclosed herein.

As illustrated in FIG. 8, an example of an inducible genetic element, including an inducible promoter 800 capable of regulating expression of at least one gene 810. In the absence of an inducer 820, the gene 810 is not transcribed (as indicated by the "X"). However, in the presence of the inducer 820, the promoter 800 directs transcription of the gene 810, resulting in production of at least one transcript 830. Likewise, in the presence of a repressor 840, the promoter 800 does not support gene transcription of the gene 810 (as indicated by the "X").

As described herein, in an embodiment the at least one composition includes at least one essential nutrient, such as a metabolite, that is required by the at least one altered microorganism. In an embodiment, the altered microorganism has a strict requirement for at least one metabolite that is not present or is present at low concentrations in the external environment (e.g., auxotrophic). For example, the at least one essential nutrient includes, but is not limited to, at least one of an organic or inorganic small molecule, nucleic acid, amino acid, peptide, polypeptide, protein, glycopeptide, glycoprotein, glycolipid, lipopolysaccharide, peptidoglycan, proteoglycan, lipid, fatty acid, metalloprotein, metal, liposome, carbohydrate, or radiation. In an embodiment, the at least one essential nutrient includes at least one of arabinose, lactose, maltose, sucrose, glucose, xylose, galactose, rhamnose, fructose, melibiose, starch, inunlin, lipopolysaccharide, arsenic, cadmium, hydrocarbon, chromium, ultra-violet radiation, infrared radiation, electromagnetic radiation, visible radiation, antibiotic, oxygen, carbon dioxide, nitrogen, xylan, or nisin. Other non-limiting examples of essential nutrients include at least one of L-arabinose, allolactose, D-glucose, D-xylose, D-galactose, ampicillin, tetracycline, penicillin, pristinamycin, retinoic acid, or interferon. In an embodiment, the at least one essential nutrient includes the at least one therapeutic agent. In certain instances, the at least one essential nutrient is also supplied or produced by the at least one biological tissue.

In an embodiment, the at least one nucleic acid construct includes at least one regulatory sequence. In an embodiment, the at least one regulatory sequence includes at least one of a promoter, enhancer, or repressor. In an embodiment, the at least one regulatory element is regulated by at least one inducer. In an embodiment, the at least one inducer includes at least one quorum-sensing molecule. Particular non-limiting examples of quorum-sensing molecules are described herein.

In an embodiment, the at least one essential nutrient is configured to be supplied or provided by at least one other modified biological cell located in the device. The modified biological cell can include, for example, at least one of bacteria, protozoa, rotifers, algae, or fungi. In an embodiment, the modified biological cell includes at least one prokaryote cell or eukaryote cell. In an embodiment, the modified biological cell includes at least one altered microorganism. In an embodiment, the modified biological cell includes at least one blood cell, muscle cell, nerve cell, fibroblast, adipose cell, stem cell, pluripotent cell, epithelial cell, secretory cell, skin cell, neoplastic cell, or other biological tissue or organ cell. In an embodiment, the modified biological cell includes at least one autologous cell or modified autologous cell. In an embodiment, the modified biological cell is at least part of at least one cell mass. In an embodiment, the at least one cell mass includes at least one tumor, scar, pore, pit, eschar, granuloma, keloid, artheromatous plaque, abscess, pustule, scaling (e.g., psoriasis or eczema), infected tissue, hair follicle, necrotic tissue, stratum corneum, wrinkle, wound, tumor, skin structure, nevus, cyst, lesion, callus, neoplastic tissue, gangrenous tissue, or cellular deposit.

In an embodiment, the modified biological cell is modified for at least one of a commensal or cooperative relationship with the at least one altered microorganism. In an embodiment, the modified biological cell is modified for obligatory cooperation with the at least one altered microorganism.

Developing a modified biological cell that is modified to be in a cooperative relationship can be conducted using routine laboratory procedures. For example, populations of Saccharomyces cerevisiae have been modified to create obligatory cooperation by mutating each strain in such a manner as to render each strain nutritionally deficient without the other. See, for example, Shou, et al. PNAS, vol. 104, no. 6, pp. 1877-1882 (2007), which is incorporated herein by reference.

For example, a first *S. cerevisiae* strain was modified in order to require adenine to grow and overproduce lysine, while a second *S. cerevisiae* strain was modified to require lysine to grow and overproduce adenine. Id. These modified, nonmating yeast strains compose a synthetic obligatory cooperative system, termed COSMO (cooperation that is synthetic and mutually obligatory) by providing an essential metabolite to the other strain. Id. As published, persistent cooperation could be established with the modified yeast strains, and was mathematically and experimentally shown to be viable over a wide range of initial conditions, with oscillating population ratio settling to a value predicted by nutrient supply and consumption. Id. In another example, as described herein, quorum-sensing molecules are utilized for regulating production of the at least one therapeutic agent.

Furthermore, even in the absence of explicitly engineered mechanisms to stabilize cooperation, the system can consistently develop increased ability to survive reductions in population density. Id. For example, members of a microorganism consortium can exert both positive and negative control over one another's activities by exchanging metabolic intermediates that either assist or compromise the growth of their neighbors. In one example, engineered acyl-HSL communication has been used in biological "circuits" that coordinate population-wide behaviors ranging from population density dependent fluorescence, cell suicide, and invasion of cancer cells, to pattern formation. Id. In one example, upon induction of the biological circuit that encodes the communication and the programmed cellular response, one population (predator) dies out win the absence of the other (prey). Communication between the two populations directs the prey to rescue the predator, but once the predator recovers to a sufficiently high density, it begins to kill the prey. Id.

In an embodiment, a cooperative relationship includes, but is not limited to biofilm formation, colonization, virulence, proliferation, communication, and other activities. See, for example, Brenner, et al., Trends Biotech. vol. 26, no. 9, pp. 483-489 (2008), which is incorporated herein by reference. For example, the at least one altered microorganism can participate in at least one microbial consensus consortium for cross-talk and cell-cell signaling. See, for example, Brenner, et al., PNAS, vol. 104, no. 44, pp. 17300-17304 (2007), which is incorporated herein by reference.

Published studies describe that synthetic ecosystems of at least one microbial population can communicate bi-directionally through quorum sensing and regulate gene expression and survival of other population members, by way of engineered gene circuits. See, for example, Balagadde, et al., Mol. Sys. Biol. vol. 4, no. 187, pp. 1-8 (2008), which is incorporated herein by reference. As discussed herein, in an embodiment, the predator cells kill the prey by inducing expression of a killer protein in the prey, while the prey rescue the predators by eliciting expression of an antidote protein in the predator. Thus, extinction, coexistence and oscillatory dynamics of the predator and prey populations are possible depending on the operating conditions, which can be determined mathematically. Id. In an embodiment, the predator includes the at least one modified biological cell, and the prey includes the at least one altered microorganism. In an embodiment, the predator includes the at least one altered microorganism, and the prey includes the at least one modified biological cell.

In an embodiment, the at least one altered microorganism is in a syntrophic relationship with at least one other altered microorganism. See, for example, Marx, Science vol. 324, pp. 1150-1151 (2009), which is incorporated herein by reference. For example, one altered microorganism may convert the primary resource to an intermediate that can be used by another altered microorganism. In an embodiment, one altered microorganism provides motility for another altered microorganism, which may in turn provide a nutrient source. Id.

In an embodiment, the altered microorganism includes at least one nucleic acid construct, including a nucleic acid construct that includes at least one artificial operon. In an embodiment, the at least one artificial operon encodes at least one polycistronic mRNA transcript.

In an embodiment, the altered microorganism includes at least one nucleic acid construct encoding at least one therapeutic agent. In an embodiment, the nucleic acid construct includes at least one inducible promoter or enhancer. In an embodiment, the at least one nucleic acid construct includes at least one promoter, enhancer, or repressor that is regulated by at least one inducer. In an embodiment, the at least one inducer includes at least one quorum-sensing molecule.

Microorganisms produce, release, exchange, and detect quorum-sensing molecules in response to population density, and respond to alteration in gene expression. See, for example, Bassler and Losick, Cell, vol. 125, pp. 237-246 (2006), which is incorporated herein by reference. In an embodiment, quorum-sensing molecules regulate at least one of competence, bioluminescence, virulence factor secretion, biofilm formation, sporulation, morphological differentiation, secondary metabolite production, cell-to-cell signaling, or protein production. Id.

In an embodiment, the quorum-sensing signal is produced in response to an environmental signal or growth event. In an embodiment, the quorum-sensing signal is secreted and recognized by other microorganisms. In an embodiment, the quorum-sensing signal accumulates to a threshold concentration before it stimulates a response. In an embodiment, the response includes a concerted response. In an embodiment, the response includes a cellular response that is in addition to or instead of metabolic or detoxification processes. See, for example, Diggle, et al., Curr. Biol., vol. 117, no. 21, pp. R907-R910 (2007), which is incorporated herein by reference.

In an embodiment, the at least one quorum-sensing molecule includes thiolactone. In an embodiment, the at least one quorum-sensing molecule includes homoserine lactone. In an embodiment, the at least one quorum-sensing molecule includes at least one of N-acylhomoserine lactone, or γ-butyrolactone. In an embodiment, the at least one quorum-sensing molecule includes at least one of 3-oxo-acylhomoserine lactone, N-(3-oxoacyl)homoserine lactone, 3-hydroxy-acylhomoserine lactone, N-3-hydroxyacyl) homoserine lactone, 2-isocapryloyl-3-hydroxy-methyl-γ-butyrolactone, furanosyl borate ester, *Pseudomonas* quinolone signal, 2-heptyl-3-hydroxy-4(1H)-quinolone, paraoxonase, methyl dodecenoic acid, hydroxyl-palmitic acid methyl ester, N-(3-oxohexanoyl)homoserine lactone (3-oxo-C6-HSL), N-(3-oxododecanoyl)-L-homoserine lactone, nisin, dihydroxyacetone phosphate, glyceraldehydes 3-phosphate, or 2-alkyl-4-quinolone.

The following non-limiting examples indicate particular structures of homoserine lactone (HSL) compounds utilized by various microorganisms as quorum-sensing molecules. See, for example, the worldwide web at nottingham.ac.uk/quorum/AHLs.htm, the content of which is incorporated herein by reference.

Additional examples of chemical structures of particular quorum-sensing molecules are provided below.

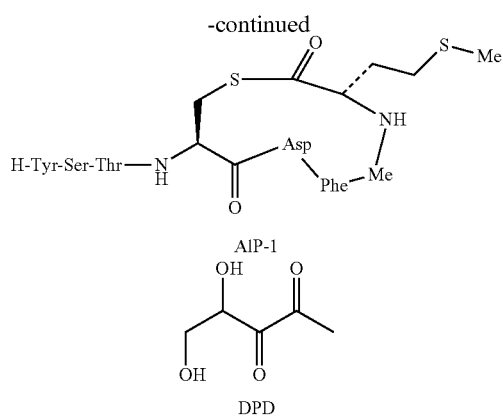

AIP-1

DPD

A-Factor is 2-isocapryloyl-3-hydroxy-methyl-γ-butyrolactone, PQS is *Pseudomonas* quinolone signal (2-heptyl-3-hydroxy-4-(1H)-quinolone), DSF is "diffusible factor" (methyl dodecenoic acid), AIP-1 is "autoinducing peptide 1" (thiolactone peptide), DPD is 4,5-dihydroxy-2,3-pentanedione, HHQ is 4-hydroxy-2-heptylquinoline, and PAME is hydroxyl-palmitic acid methyl ester. See, for example, the worldwide web at gcat.davidson.edu, the content of which is incorporated herein by reference.

Table 1 below is a non-limiting list of examples of specific acylhomoserine lactone (AHL) compounds utilized by particular bacteria.

TABLE 1

| Bacterium | LuxR/I homologues with links to Swissprot | GenBank Accsession Number | Major AHL | Phenotype | Reference |
|---|---|---|---|---|---|
| *Aeromonas hydrophila* | AhyR, AhyI | X89469 | C4-HSL | Extracellular protease, biofilm formation | Swift et al 1997, 1999b, c, Lynch et al 1999 |
| *Aeromonas salmonicida* | AsaR, AsaI | U65741 | C4-HSL | Extracellular protease | Swift et al 1997 |
| *Agrobacterium tumefaciens* | TraR, TraI | L17024, L22207 | 3-oxo-C8-HSL | Conjugation | Fuqua et al 1994, Piper et al 1999, |
| *Burkholderia cepacia* | CepR, CepI | AF330018, AF330012 | C8-HSL | Protease, siderophore | Lewenza et al 1999 |
| *Chromobacterium violaceum* | CviR, CviI | no link available | C6-HSL | Antibiotics, violacein, exoenzymes, cyanide | McClean et al 1997, Chernin et al 1998 |
| *Enterobacter agglomerans* | EagR, EagI | X74300 | 3-oxo-C6-HSL | Unknown | Swift et al 1993 |
| *Erwinia carotovora* Subsp *carotovora* | CarR, ExpR ExpI (CarI) | X74299, X80475, X72891 | 3-oxo-C6-HSL | Carbapenem antibiotic, exoenzymes | Bainton et al 1992, Swift et al 1993, Pirhonen et al 1993 |
| *Erwinia chrysanthemi* | ExpR, ExpI (EchR, EchI) | X96440 | 3-oxo-C6-HSL | Pectinases | Nasser et al 1998 |
| *Escherichia coli* | SdiA | AE005414 | Unknown | Cell division | Sitnikov et al 1996 |
| *Nitrosomas europaea* | Unknown | — | 3-oxo-C6-HSL | Emergence from lag phase | Batchelor et al 1997 |
| *Obesumbacterium proteus* | OprR, OprI | no link available | 3-oxo-C6-HSL | Unknown | Swift et al 1999 |
| *Pantoea stewartii* | EsaR, EsaI | L32183, L32184 | 3-oxo-C6-HSL | Exopolysaccharide | Beck von Bodman & Farrand 1995 |
| *Pseudomonas aeruginosa* | LasR, LasI | M59425 | 3-oxo-C12-HSL | Exoenzymes, Xcp, biofilm formation, RhlR, cell-cell spacing. | Chapon-Hervé et al 1997, Gambello & Iglewski 1991, Passador et al 1993, Glessner et al 1999 |
| | RhlR, RhlI (VsmR, VsmI) | L08962, U11811, U15644 | C4-HSL | Exoenzymes, cyanide, RpoS, lectins, pyocyanin, rhamnolipid, type 4 pili. | Latifi et al 1995, 1996, Winson et al 1995, Pearson et al 1997, Glessner et al 1999. |
| *Pseudomonas aureofaciens* | PhzR, PhzI | L32729, L33724 | C6-HSL | Phenazine antibiotic | Pierson et al 1994, Wood et al 1997 |
| *Pseudomonas fluorescens* | PhzR, PhzI | L48616 | Unknown | Phenazine antibiotic | Shaw et al 1997 |
| *Pseudomonas syringae pv. tabaci* | PsyR, PsyI | U39802 | Unknown | Unknown | Swift et al 1999 |
| *Ralstonia solanacearum* | SolR, SolI | AF021840 | C8-HSL | Unknown | Flavier et al 1997 |
| *Rhizobium etli* | RaiR, RaiI | U92713 | Unknown | Restriction of nodule number | Gray et al 1996, Rosemeyer et al 1998 |
| *Rhizobium leguminosarum* | RhiR | M98835 | 3-hydroxy-7-cis-C14-HSL | Nodulation, bacteriocin, stationary phase survival | Gray 1997, Rodelas et al 1999, Thorne and Williams 1999 |
| *Rhodobacter sphaeroides* | CerR, CerI | AF016298 | 7-cis-C14-HSL | Community escape | Puskas et al 1997 |
| *Serratia liquefaciens* | SwrR, SwrI | U22823 | C4-HSL | Swarming, protease | Eberl et al 1996, Givskov et al 1997 Lindum et al 1998 |

TABLE 1-continued

| Bacterium | LuxR/I homologues with links to Swissprot | GenBank Accsession Number | Major AHL | Phenotype | Reference |
|---|---|---|---|---|---|
| Vibrio anguillarum | VanR, VanI | U69677 | 3-oxo-C10-HSL | Unknown | Milton et al 1997 |
| Vibrio fischeri | LuxR, LuxI | M19039, M96844, M25752 | 3-oxo-C6-HSL | Bioluminescence | |
| Xenorhabdus nematophilus | Unknown | — | 3-hydroxy-C4-HSL or an agonist | Virulence, bacterial lipase | Dunphy et al 1997 |
| Yersinia enterocolitica | YenR, YenI | X76082 | C6-HSL | Unknown | Throup et al 1995 |
| Yersinia pestis | YpeR, YpeI | AF071401 | Unknown | Unknown | Swift et al 1999a, b |
| Yersinia pseudotuberculosis | YpsR, YpsI | AF079973 | 3-oxo-C6-HSL | Motility, clumping | Atkinson et al 1999 |
| | YtbR, YtbI | AF079136 | C8-HSL | Unknown | Atkinson et al 1999 |
| Yersinia ruckeri | YukR, YukI | AF079135 | Unknown | Unknown | Atkinson et al 1999 |

See, for example, the worldwide web at nottingham.ac.uk/quorum/table.htm, the subject matter of which is incorporated herein by reference. In an embodiment, the at least one nucleic acid construct includes at least one neutral, base or acid inducible promoter. Examples of acid inducible promoters include, but are not limited to HVA1 promoter (plant cells), P170, P1, or P3 (*Lactococcus*), baiA1, baiA3 (*Eubacteria*), lipF promoter (*Mycobacteria*), $F_1F_0$-ATPase promoter (*Lactobacillus, Streptococcus*, or *Enterococcus*), gadC, gad D (*Lactococcus, Shignella*), glutamate decarboxylase promoter (*Mycobacteria, Clostridium, Listeria, Lactobacillus*), or similar operons. See, for example, Cotter and Hill, Microbiol. and Mol. Biol. Rev. vol. 67, no. 3, pp. 429-453 (2003); Hagenbeek, et al., Plant Phys., vol. 123, pp. 1553-1560 (2000); Madsen, et al., Abstract, Mol. Microbiol. vol. 56, no. 3, pp. 735-746 (2005); U.S. Pat. No. 6,242,194; Richter, et al., Abstract, Gene, vol. 395, no. 1-2, pp. 22-28 (2007), Mallonee, et al., J. Bacteriol., vol. 172, no. 12, pp. 7011-7019 (1990); each of which is incorporated herein by reference. Examples of base inducible promoters include, but are not limited to, alkaline phosphatase promoters.

In an embodiment, the acid inducible genetic element is inducible at a pH of approximately 0.0, approximately 0.5, approximately 1.0, approximately 1.5, approximately 2.0, approximately 2.5, approximately 3.0, approximately 3.5, approximately 4.0, approximately 4.5, approximately 5.0, approximately 5.5, approximately 6.0, approximately 6.5, approximately 6.6, approximately 6.7, approximately 6.8, approximately 6.9, or any value therebetween or less.

In an embodiment, the base inducible genetic element is inducible at a pH of approximately 7.1, approximately 7.5, approximately 8.0, approximately 8.5, approximately 9.0, approximately 9.5, approximately 10.0, approximately 10.5, approximately 11.0, approximately 11.5, approximately 12.0, approximately 12.5, approximately 13.0, approximately 13.5, approximately 14.0, or any value therebetween or greater. In an embodiment, the neutral inducible genetic element is inducible at a pH of approximately 7.0.

The pH level of a particular biological tissue can affect the inducibility of the pH inducible promoter. For example, the gastric pH of humans is between 1.5 (fasting state), and 3.0-5.0 (following feeding). Id. Likewise, human urine has a pH of approximately 6.0, human skin has a pH of approximately 5.5, human ear canal has a pH of approximately 4.5, while blood and cerebrospinal fluid tend to have a pH of approximately 7.3-7.4. See, for example, Boron, et al., Medical Physiology: A Cellular and Molecular Approach. Elsevier/Saunders. (2004), ISBN 1-4160-2328-3, which is incorporated herein by reference. Furthermore, dental caries and tooth demineralization is initiated at a pH of approximately 5.2. Cotter and Hill, Ibid. Thus, a composition that is activated at various pH levels is useful for particular embodiments. In an embodiment, the pH inducible promoter is induced at a particular pH (e.g., chewing gum containing the composition described herein which is inducible at low pH in the mouth). The pH level of plant leaves is approximately 4.2. See, for example, Sargent and Blackman, Abstract, J. Exp. Botany, vol. 21, no. 1, pp. 219-227 (2005), which is incorporated herein by reference.

As described herein for various inducible genetic elements, the inducible genetic elements can include at least one inducible promoter, enhancer, or repressor. As previously described, in an embodiment, the inducible genetic element is regulated by an inducer, such as a quorum-sensing molecule. Other examples of the at least one inducer include, but are not limited to, at least one of radiation, temperature change, alcohol, antibiotic, steroid, metal, salicylic acid, ethylene, benzothiadiazole, or other compound. In an embodiment, the at least one inducer includes at least one of arabinose, lactose, maltose, sucrose, glucose, xylose, galactose, rhamnose, fructose, melibiose, starch, inulin, lipopolysaccharide, arsenic, cadmium, chromium, temperature, light, antibiotic, oxygen level, xylan, nisin, L-arabinose, allolactose, D-glucose, D-xylose, D-galactose, ampicillin, tetracycline, penicillin, pristinamycin, retinoic acid, or interferon. Other examples of inducers include, but are not limited to, at least a portion of one of an organic or inorganic small molecule, clathrate or caged compound, protocell, coacervate, microsphere, Janus particle, proteinoid, laminate, helical rod, liposome, macroscopic tube, niosome, sphingosome, toroid, vesicular tube, vesicle, small unilamellar vesicle, large unilamellar vesicle, large multilamellar vesicle, multivesicular vesicle, lipid layer, lipid bilayer, micelle, organelle, nucleic acid, peptide, polypeptide, protein, glycopeptide, glycolipid, lipoprotein, lipopolysaccharide, sphingolipid, glycosphingolipid, glycoprotein, peptidoglycan, lipid, carbohydrate, metalloprotein, proteoglycan, chromosome, nucleus, acid, buffer, protic solvent, aprotic solvent, nitric oxide, vitamin, mineral, nitrous oxide, nitric oxide synthase, amino acid, micelle, polymer, copolymer, monomer, prepolymer, cell receptor, adhesion molecule, cytokine, chemokine, immunoglobulin, antibody, antigen, extracellular matrix, cell ligand, zwitterionic material, cationic material, oligonucleotide, nanotube, piloxymer, transfersome, gas, element, contaminant, radioactive particle, radiation, hormone, virus, quantum dot, temperature change, thermal energy, or contrast agent. See, for example, Theys, et al., Abstract, Curr. Gene Ther. vol. 3, no. 3 pp. 207-221 (2003), which is incorporated herein by reference. In an embodiment, the at least one inducer is produced by at least one microorganism.

In an embodiment, the at least one inducible genetic element is temperature-inducible. For example, various heat shock protein promoters have been isolated from microorganisms, animal and plant cells (including maize and soybeans), and other temperature-inducible promoters have been isolated from various organisms and microorganisms. Some non-limiting examples of promoters induced by a change in temperature include hsp70 (e.g., animal cells, maize), Gmhsp17.5-E (e.g., soybeans), Gmhsp17.6-L, HS6871 (e.g., soybeans), HSP18.2 (Arabidopsis), HSP18.1 (Arabidopsis), Hsp70B, P2 (Bacillus), P7 (Bacillus), PhS (*E. coli*), *Tetrahymena therophila* promoter (protozoan), *Hansenula polymorpha* promoter (yeast), *Schizosaccharomyces pombe* promoters (yeast), or $P_L$(lambda phage). See, for example, Taylor, et al, Cell, Abstract, vol. 38, no. 2, pp. 371-381 (1984); U.S. Pat. No. 4,352,581; U.S. Pat. No. 6,852,511, Wang, et al., Biochem. and Biophys. Res. Commun. Abstract, vol. 358, no. 4, pp. 1148-1153 (2007), U.S. Pat. No. 7,462,708, each of which is incorporated herein by reference.

In an embodiment, the implantable device is configured to be implanted into at least one biological tissue or organ. In an embodiment, the at least one biological tissue or organ is located in at least one of in vitro, in vivo, in situ, in utero, ex vivo, in planta, or in silico. In an embodiment, the at least one biological tissue includes at least one of one mucosal surface. In an embodiment, the at least one biological tissue includes at least one of cartilage, skin, scalp, hair, nail, nail bed, teeth, eye, ear, ovary, oviduct, tongue, tonsil, adenoid, liver, bone, pancreas, stomach, duct, valve, smooth muscle, appendix, blood vessel, bone marrow, heart, lung, brain, breast, kidney, bladder, urethra, ureter, gall bladder, uterus, prostate, testes, vas deferens, fallopian tubes, large intestine, small intestine, esophagus, oral cavity, nasal cavity, otic cavity, connective tissue, muscle tissue, adipose tissue, or mucosa-associated lymphoid tissue (MALT). In an embodiment, the device is configured to be implanted in at least one body cavity of a subject. For example, in an embodiment, the at least one body cavity includes at least one of an otic cavity, oral cavity, vaginal cavity, anal cavity, nasal cavity, esophagus, or eyelid. In an embodiment, the at least one body cavity includes the gastrointestinal tract of a subject. In an embodiment, the gastrointestinal tract includes at least one of a stomach, large intestine, small intestine, appendix, or any part thereof.

In at least one embodiment, the at least one biological tissue is at least partially located in a subject. In an embodiment, as discussed herein, a subject includes, but is not limited to, a vertebrate or invertebrate, including a fish, reptile, mammal, amphibian, or bird. In at least one embodiment, the subject includes at least one human. In an embodiment, the at least one subject includes at least one of livestock, pet, zoo animal, undomesticated herd animal, wild animal, aquatic plant or animal, or product animal.

In an embodiment, the at least one subject includes at least one of a sheep, goat, frog, dog, cat, rat, mouse, vermin, monkey, horse, cow, pig, chicken, shellfish, fish, turkey, llama, alpaca, bison, buffalo, ape, primate, ferret, wolf, fox, coyote, deer, rabbit, guinea pig, yak, chinchilla, mink, reindeer, elk, camel, fox, elk, deer, raccoon, donkey, or mule. In an embodiment, the at least one subject includes at least one anthozoan species. In an embodiment, the at least one subject includes at least one of a sea anemone, coral, mollusk, fish, whale, dolphin, porpoise, seal, otter, beaver, seabird, gull, pelican, albatross, duck, swan, or goose. In an embodiment, the at least one subject includes at least one insect (e.g., fly, mosquito, beetle, moth, butterfly, etc.). In an embodiment, the at least one subject includes at least one arachnid. In an embodiment, the at least one subject includes at least one crustacean.

In an embodiment, the subject includes a plant. In an embodiment, the at least one biological tissue includes one or more of a stalk, stem, leaf, root, plant, or tendril. In an embodiment, the at least one biological tissue includes at least one food product. In an embodiment, the at least one food product includes one or more animal, plant, fungal or other biological food product. In an embodiment, the food product includes meat. In an embodiment, the at least one biological tissue includes at least one cell mass or wound.

In an embodiment, the at least one composition is self-administered by the at least one subject. In an embodiment, the at least one composition is ingested by the at least one subject. In an embodiment, the at least one biological tissue includes at least one implantable or transplantable biological tissue. In an embodiment, the at least one biological tissue is transplanted or implanted into at least one subject. In an embodiment, the at least one biological tissue is from at least one donor or recipient. In an embodiment, the at least one biological tissue includes at least one bodily orifice of a subject.

Selection of the particular microorganism can be based on calculations of sub-populations in a population, a particular subject, a particular state of health of the subject, a particular organ, a particular biological tissue, or a particular biological cell type. For example, the intestinal microflora can contribute to pathogenesis in susceptible subjects, or it can contribute to the metabolism and overall health of the subject. See, for example, O'Hara and Shanahan, EMBO reports, vol. 7, no. 7, pp. 688-693 (2006), which is incorporated herein by reference. Microorganism populations vary according to age, disease state or health state, and diet. Id. For example, *Lactobacilli* are dominant among microflora associated with the urogenital tract of healthy women but are almost completely absent in patients who develop most forms of urinary tract infections. See, for example, Hanniffy, et al., Adv. Applied Microbiol., vol. 56, pp. 1-64 (2004), which is incorporated herein by reference.

Published reports indicate that the human gut microbiota affects nutrition, development, metabolism, pathogen resistance, and regulation of immune responses; and the microbiota community changes with antibiotic use. See, Dethlefsen, et al., PLOS Biol., vol. 6, no. 11, pp. 2383-2400 (2008), which is incorporated herein by reference. For example, approximately 3300-5700 bacterial taxa were identified as accounting for over 99% of the variable region sequence tags obtained. Id. Antibiotic use of ciprofloxacin influenced the abundance of about one third of the bacterial taxa in the gut. Id.

Further published reports indicate high diversity of microorganisms located in the human mouth, with a small majority in common amongst any particular geographical region group. See, for example, Myles, et al., Abstract, BMC Med. Gen. vol. 2, no. 45 (2009), which is incorporated herein by reference. For example, the populations of individual groups of bacteria located in the saliva of one person tested were not largely common with other people located in a similar geographical region. Id.

In an embodiment, at least one microorganism (or a population thereof) is obtained from at least one subject, modified, and returned to the at least one subject, and possibly others (e.g., members of a household). In an embodiment, the at least one altered microorganism (or a population thereof) is returned to approximately the same location of the subject from which it was extracted. In an embodiment, the at least one altered microorganism (or a population thereof) is returned to a different location of the subject source. For example, at least one microorganism can be extracted from the intestine of a subject, modified, and returned to the oral cavity, otic cavity, stomach, or intestine of that same subject. In an embodiment, at least one microorganism is extracted, modified, and returned to the subject at approximately the same location from where it was extracted, and the altered microorganism is able to translocate to another location within the subject or to another subject (e.g., maternal transfer). In an embodiment, at least some genetic sequence information from the microorganism is obtained prior to or subsequent to modifying it. In an embodiment, the at least one altered microorganism is amplified prior to reinstating it in the at least one biological tissue, or subject.

Published studies indicate that the human gut contains distinct differences in the microflora of obese subjects, normal weight subjects, and subjects who have undergone gastric bypass surgery. See, for example, Zhang, et al., PNAS, pp. 2365-2370; available online at 10.10973/pnas.0812600106 (printed 2009, available 2008), which is incorporated herein by reference. Further, these studies indicate a shift in microbiota populations following gastric bypass surgery. Id.

In an embodiment, a microorganism is selected from at least one subject based on a desired state of health, modified, and placed in the same or different subject. Selection of a particular microorganism can be conducted utilizing conventional techniques, including but not limited to barcoded 16S pyrosequencing. See, for example, Andersson, et al., PLOS One vol. 3, no. 7, pp. 1-8 (2008), which is incorporated herein by reference. The relatively small genome size of microorganisms, and the availability of high-throughput sequencing facilities has allowed the sequencing of more than 90 bacterial genomes for the public domain. Id.

In an embodiment, the at least one altered microorganism includes at least one vector including at least one genetic element for producing an agent, or initiating death in the microorganism. Various vectors can be utilized, as described herein, including at least one of a plasmid, bacteriophage, cosmid, artificial chromosome, or other vector. In an embodiment, the altered microorganism includes multiple vectors, some of which can be the same or different from the other vectors. In an embodiment, the altered microorganism includes at least one vector that is able to regulate initiation of death of the at least one altered microorganism, and also generate the at least one therapeutic agent.

Vectors suitable for microbiological applications are well known in the art, and are routinely designed and developed for particular purposes. Some non-limiting published examples of vectors that have been used to transform bacterial strains include the following plasmids: pMW211, pBAD-DEST49, pDONRP4-P1R, pENTR-$P_{BAD}$, pENTR-DUAL, pENTR-term, pBR322, pDESTR4-R3, pBGS18-N9uc8, pBS24Ub, pUbNuc, pIXY154, pBR322DEST, pBR322DEST-$P_{BAD}$-DUAL-term, pJIM2093, pTG2247, pMEC10, pMEC46, pMEC127, pTX, pSK360, pACYC184, pBO E93, pBR327, pDW205, pKCL11, pKK2247, pMR60, pOU82, pR2172, pSK330, pSK342, pSK355, pUHE21-2, pEHLYA2-SD. See, for example, Stritzker, et al. Intl. J. Med. Microbiol. Vol. 297, pp. 151-162 (2007); Grangette et al., Infect. Immun. vol. 72, pp. 2731-2737 (2004), Knudsen and Karlstrom, App. and Env. Microbiol. pp. 85-92, vol. 57, no. 1 (1991), Rao et al., PNAS pp. 11993-11998, vol. 102, no. 34 (2005), each of which is incorporated herein by reference.

Therapeutic Agents

In an embodiment, the at least one altered microorganism produces at least one therapeutic agent. In an embodiment, the at least one therapeutic agent includes at least a portion of one of an organic or inorganic small molecule, proteinoid, nucleic acid, peptide, polypeptide, protein, glycopeptide, glycolipid, lipoprotein, lipopolysaccharide, sphingolipid, glycosphingolipid, fatty acid, glycoprotein, peptidoglycan, lipid, carbohydrate, metalloprotein, proteoglycan, vitamin, mineral, amino acid, polymer, copolymer, monomer, prepolymer, cell receptor, adhesion molecule, cytokine, chemokine, immunoglobulin, antibody, antigen, extracellular matrix component, cell ligand, oligonucleotide, element, chromosome, nucleus, acid, base, buffer, protic solvent, aprotic solvent, hormone, metabolite, or contrast agent.

In an embodiment, the fatty acid includes at least one of a short chain fatty acid, long chain fatty acid, unsaturated fat, or saturated fat. In an embodiment, the at least one lipid includes at least one of a monounsaturated fat, polyunsaturated fat, trans fat, cis fat, omega fatty acid. In an embodiment, the at least one fatty acid includes at least one of an arachidic fatty acid, stearic fatty acid, palmitic fatty acid, erucic fatty acid, linoleic fatty acid oleic fatty acid, or linolenic fatty acid. In an embodiment, the fatty acid includes at least one of myristoleic acid, palmitoleic acid, sapienic acid, oleic acid, linoleic acid, alpha-linolenic acid, arachidonic acid, eicosapentaenoic acid, erucic acid, or docosahexaenoic acid. For example, it has been published that oleic acid protects against the development of ulcerative colitis. See, for example, Punyanganie, et al., no. 100 AGA Abstracts, S-18 (2010).

In an embodiment, the polymer or co-polymer includes at least one of polyester, polylactic acid, polyglycolic acid, cellulose, nitrocellulose, urea, urethane, or other polymer. For example, in an embodiment, at least one microorganism that is capable of synthesizing at least one thermoplastic polymer (e.g., polyester) is utilized. See, for example, U.S. Pat. No. 5,663,063, which is incorporated herein by reference. For example, as described in U.S. Pat. No. 5,663,063, *E. coli* strains can be modified to produce polyhyroxybutyrate and polyhydroxyalkanoate polyesters. Id.

In an embodiment, at least one microorganism that is capable of degrading at least one polymer (e.g., aliphatic polyester) is utilized. See, for example, Suyama, et al., App. Env. Microbiol. vol. 64, no. 12, pp. 5008-5011 (1998), which is incorporated herein by reference. For example, in an embodiment, the at least one microorganism is capable of degrading at least one of poly (beta-hydroxyalkanoate), poly (epsilon-caprolactone), or poly (hexamethylene carbonate). Id.

In an embodiment, the polymer or co-polymer includes at least one of polyester, polylactic acid, polyglycolic acid, cellulose, nitrocellulose, urea, urethane, or other polymer, as described herein. In an embodiment, the at least one therapeutic agent includes one or more of anti-tumor agent, antimicrobial agent, anti-coagulant, anti-viral agent, analgesic, antiseptic, anesthetic, diagnostic agent, anti-inflammatory agent, vaccine, cell growth inhibitor, cell growth promoter, chemical debridement agent, immunogen, antigen, radioactive agent, apoptosis promoting factor, angiogenic factor, anti-angiogenic factor, hormone, enzymatic factor, enzyme, papain, collagenase, protease, peptidase, elastase, urea, vitamin, mineral, nitrite, nitrate, nutraceutical, histatin, honey, alcium alginate, angiogenic factor, hormone, vitamin, mineral, nutraceutical, cytokine, chemokine, probiotic, sterol, contraceptive, coagulant, anti-coagulant, phage, prodrug, prebiotic, blood sugar stabilizer, smooth muscle cell activator, epinephrine, adrenaline, neurotoxin, neuro-muscular toxin, Botulinum toxin type A, microbial cell or component thereof, or virus or component thereof. In an embodiment, the nutraceutical includes one or more of a flavonoid, antioxidant, beta-carotene, anthocyanin, alpha-linolenic acid, omega-3 fatty acids, plant products, or animal products.

In an embodiment, the analgesic or anesthetic includes one or more of any aminoamid or aminoester local anesthetic, ibuprofen, morphine, codeine, aspirin, acetaminophen, lidocaine/lignocaine, ropivacaine, mepivacaine, benzocaine, chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, piperocaine, prilocalne, trimecaine, saxitoxin, or tetrodotoxin. In an embodiment, the nutraceutical includes one or more of a flavonoid, antioxidant, beta-carotene, anthocyanin, alpha-linolenic acid, omega-3 fatty acids, plant products, or animal products.

In an embodiment, the at least one therapeutic agent includes one or more of an antimicrobial agent, and includes at least one of an anti-fungal agent, antibiotic agent, anti-bacterial, anti-parasitic agent, or anti-worm agent. In an embodiment, the at least one therapeutic agent includes one or more of penicillin, cephalosporin, polymixin, sulfonamide, beta-lactam antibiotic, beta-lactamase inhibitor, enediynes, lincosamide antibiotic, nitroimidazole antibiotic, pleuromutilin antibiotic, polyketide antibiotic, polymyxin antibiotic, polypeptide antibiotic, antimicrobial peptides, quinolone antibiotic, rifamycin antibiotic, sulfonamide antibiotic, tetracycline antibiotic, aminoglycoside antibiotic, macrolide, tetracycline, cyclic lipopeptide, glycylcycline, oxazolidinone, amoxicillin, tobramycin, levofloxacin, gatifloxacin, moxifloxacin, streptomycin, oxytetracycline, chloramphenicol, or ampicillin.

In an embodiment, the therapeutic agent includes at least one of calcium, carbon, nitrogen, sulfur, nitrate, nitrite, copper, magnesium, selenium, boron, sodium, aluminum, phosphorus, potassium, titanium, chromium, manganese, iron, nickel, zinc, silver, barium, lead, vanadium, tin, strontium, or molybdenum.

In an embodiment, the at least one therapeutic agent includes at least one enzyme able to convert at least one prodrug or precursor compound into an active state. In an embodiment, the at least one enzyme includes at least one of beta glucuronidase, cytosine deaminase, or nitroreductase.

In an embodiment, the at least one therapeutic agent is pH dependent. Thus, in certain embodiments, the agent can be administered to one particular location and remain inactive until conditions change that result in alteration of the pH of the location (or the altered microorganism travels to another location with a different pH), and the agent becomes active. The activity of the agent can be gradual (along a gradation), or sudden.

In an embodiment, the at least one therapeutic agent is capable of modulating at least one immune response. In an embodiment, wherein the at least one immune response includes at least one allergic or autoimmune response. In an embodiment, the at least one therapeutic agent is capable of inducing apoptosis in one or more cells of the at least one biological tissue. In an embodiment, the at least one administered therapeutic agent modulates the viability, proliferation, or metastasis of at least one tumor cell in the at least one biological tissue.

In an embodiment, the at least one therapeutic agent includes at least one of insulin, clacitonin, lutenizing hormone, parathyroid hormone, somatostatin, thyroid stimulating hormone, vasoactive intestinal polypeptide, tumor necrosis metabolite, endostatin, angiostatin, anti-angiogenic antithrombin II, fibronectin, prolactin, thrombospondin I, laminin, procollagen, collagen, integrin, steroid, corticosteroid, virus antigen, microorganism antigen, trefoil protein, or lipase.

The trefoil peptide can include, but not be limited to, TFF1 (also known as pS2, or breast cancer estrogen inducible gene), TFF2 (also known as SP, or spasmolytic peptide), or TFF3 (also known as ITF, or intestinal trefoil factor). See, for example, U.S. Patent Application Publication Nos. 20070110723, and 20070122427; each of which is incorporated herein by reference. See also, U.S. Pat. No. 7,220,418, which is incorporated herein by reference. The vaccine can include but not be limited to antigenic peptides, proteins, or carbohydrates. For example, the vaccine can include but not be limited to envelope proteins, capsid proteins, surface proteins, toxins, polysaccharides, oligosaccharides, or enzymes needed to make at least one thereof.

In an embodiment, the virus antigen includes at least one antigen from one or more of a double-stranded DNA virus, single-stranded DNA virus, double-stranded RNA virus, (+) single-strand RNA virus, (−) single-strand RNA virus, single-strand RNA-Reverse Transcriptase virus, or double-stranded DNA-Reverse Transcriptase virus. In an embodiment, the virus antigen includes at least one antigen of a virus from one or more of the family of Adenoviridae, Arenaviridae, Bunyaviridae, Calciviridae, Circoviridae, Coronaviridae, Filoviridae, Flaviviridae, Hepadnaviridae, Herpesviridae, Orthomyxoviridae, Papovaviridae, Papillomaviridae, Polyomaviridae, Paramyxoviridae, Parvoviridae, Picornaviridae, Poxyiridae, Reoviridae, Retroviridae, Rhabdoviridae, Pseudoviridae, or Togaviridae. In an embodiment, the virus antigen includes at least one antigen from one or more of human immunodeficiency virus (HIV) type I, HIV-type 2, simian immunodeficiency virus (SIV), or feline leukemia virus. In an embodiment, the virus antigen includes at least one antigen from one or more of respiratory syncytial virus (RSV), influenza (flu), adenovirus, rhinovirus, enterovirus, poliovirus, rubella virus, paramyxovirus, herpes simplex virus type I (HSV-1), Herpes simplex virus 2 (HSV-2), rotavirus, neurotropic virus, coxsackie virus, hepatitis virus type A, hepatitis virus type B, hepatitis virus type C, or oncovirus. In an embodiment, the at least one antigen includes at least one antigen from one or more of *Brucella, Chlamydia, Citrobacter, Coxiella brunetii, Escherichia coli, Francisella tularensis, Haemophilus, Legionella,* mycobacterium, *Neisseria, Pseudomonas, Rickettsia, Salmonella, Shigella, Staphylococcus, Streptococcus, Candida, Cryptococcus, Aspergillus, Blastomyces, Histoplasma, Paracoccidioides, Nosema, Encephalitozoon, Torulopsis, Pneumocystis, Trypanosoma, Leishmania, Theileria, Plasmodium, Cryptosporidium,* or *Toxoplasma.*

In an embodiment, the at least one therapeutic agent includes at least one vaccine. In an embodiment, the at least one vaccine includes at least one of an antigenic peptide, antigenic protein, or antigenic carbohydrate. In an embodiment, the at least one vaccine includes at least one of an envelope protein, capsid protein, surface protein, toxin, polysaccharide, oligosaccharide, or enzyme needed to make at least one thereof. In an embodiment, the vaccine composition further comprises at least one adjuvant. In an embodiment, the at least one therapeutic agent includes at least one anti-inflammatory cytokine.

In an embodiment, at least one therapeutic agent includes at one of Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, Interleukin-13, Interleukin-14, Interleukin-15, Interleukin-16, Interleukin-17, Interleukin-18, Interleukin-19, Interleukin-20, Interleukin-21, Interleukin-22, Interleukin-23, Interleukin-24, Interleukin-25, Interleukin-26, Interleukin-27, Interleukin-28, Interleukin-29, Interleukin-30, Interleukin-31, Interleukin-32, Interleukin-33, Interleukin-34, Interleukin-35, Interleukin-36, Interleukin-37, Interleukin-38, Interleukin-39, Interleukin-40, Interleukin-41, Interleukin-42, Interferon-γ, Interferon-α, Interferon-β, Transforming Growth factor, Granulocyte Macrophage-Colony Stimulating Metabolite, Macrophage-Colony Stimulating Metabolite, Scarecrow, Erythropoietin, Granulocyte-Colony Stimulating Metabolite, Leukemia Inhibitory Metabolite, Oncostatin M, Ciliary Neurotrophic Metabolite, Growth Hormone, Prolactin, Fibroblast Growth factor, Nerve Growth factor, Platelet Derived Growth factor, Epidermal Growth factor, Fas, Fas ligand, CD40, CD27, CD4, CD8, CD2, CD3, Tumor Necrosis Metabolite-α, or Tumor Necrosis Metabolite-β.

Chemokines are biochemical signaling molecules that act to attract other particular molecules, including but not limited to cells, to a specific site. In at least one embodiment, the therapeutic agent includes one or more chemokines. In at least one embodiment, the one or more chemokines include at least one of a CC chemokine, CXC chemokine, C chemokine, or CX3C chemokine. In an embodiment, the at least one therapeutic agent includes at least one of CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CCL29, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CXCL18, CXCL19, CXCL20, CXCL21, CXCL22, XCL1, XCL2, XCL3, XCL4, XCL5, CX3CL1, CX3CL2, or CX3CL3.

In an embodiment, administration of the at least one therapeutic agent results in at least one of nucleic acid transcription, protein translation, cell division, apoptosis, necrosis, cytoskeletal rearrangement, or secretion in the at least one biological tissue.

In an embodiment, the at least one therapeutic agent includes at least one prodrug or precursor compound. For example, the at least one prodrug or precursor compound includes at least one glucuronide prodrug, such as at least one glucuronide of epirubicin, 5-fluorouracil, 4-hydroxycyclophosphamide, or 5-fluorocytosine. In another example, the at least one prodrug or precursor compound includes 5-(aziridin-1-yl)-2,4-dinitrobenzamide. In an embodiment, the at least one therapeutic agent includes at least one prodrug. In an embodiment, at least one altered microorganism delivers at least one prodrug, while at least one other altered microorganism delivers at least one enzyme capable of converting the at least one prodrug into active form. For example, published studies demonstrating strains of recombinant *Saccharomyces cerevisiae* expressing plant P450 73A1 show that the enzyme is active and able to convert trans-cinnamic acid into p-coumaric acid in vivo. See, for example, Garrait, et al., Applied Env. Microbiol. vol. 73, no. 11, pp. 3566-3574 (2007), and Blanquet, et al., Applied Env. Microbiol. vol. 69, no. 5, pp. 2884-2892 (2003), each of which is incorporated herein by reference.

In an embodiment, the at least one therapeutic agent includes at least one factor related to digestion of food, for example insulin resistance, blood glucose regulation, caloric use or caloric intake of a subject. For example, in an embodiment the therapeutic agent includes at least one of fasting-induced adipocyte factor (FIAF or ANGPTL4), peroxisome proliferator-activated receptor-γ (PPARγ), or similar agents. See, for example, Jia, et al., Nature Rev., vol. 7, pp. 123-129 (2008), which is incorporated herein by reference.

In an embodiment, the at least one altered microorganism delivers at least two different therapeutic agents. In certain cases, the at least two different therapeutic agents are regulated by at least one different promoter. In an embodiment, at least one therapeutic agent includes at least one antigen, and at least one cytokine. In an embodiment, the at least one antigen includes tetanus toxin fragment. In an embodiment, the at least one cytokine includes at least one of IL-2 or IL-6. In an embodiment, the antigen is contained within the at least one altered microorganism, while the cytokine is secreted. See, for example, Steidler, et al. Infect. Immun. pp. 3183-3189, vol. 66, no. 7 (1998), and U.S. Pat. No. 6,605,286; each of which is incorporated herein by reference. In another example, published studies show secretion of human myelin basic protein (hMBP) or hMBP as a fusion protein with beta-glucuronidase from *E. coli*. The heterologous products are produced by *L. casei*. See, for example, Maassen, et al., Vaccine, Abstract, vol. 17, no. 17, pp. 2117-2128 (1999), which is incorporated herein by reference.

The at least one altered microorganism includes at least one nucleic acid construct encoding at least one therapeutic agent by at least one of mode, including but not limited to synthesizing the at least one agent, expressing the at least one agent on its surface, or extracellular secretion of the at least one therapeutic or agent.

In an embodiment, the at least one altered microorganism includes at least one nucleic acid construct encoding at least one therapeutic agent and expresses at least a portion of the agent (e.g. antibody) on its surface. In an embodiment, the at least one altered microorganism expresses at least a portion of a carbohydrate-binding motif on its surface. In one example, the at least one altered microorganism expresses at least one of a heparin or mannose binding motif its surface.

Figure 9:
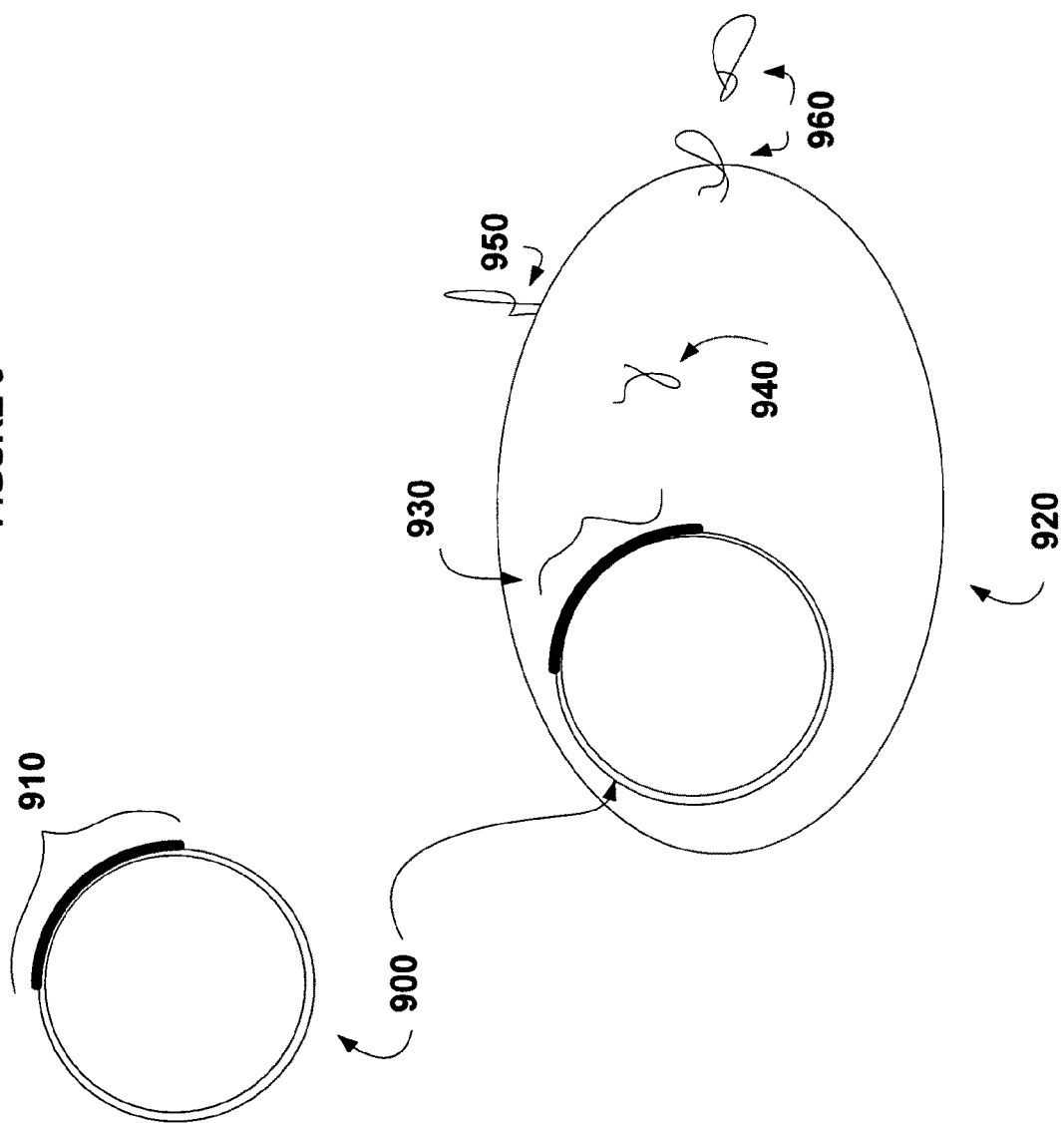
FIG. 9 depicts a partial view of particular genetic elements utilized in various embodiments disclosed herein.

For example, as illustrated in FIG. 9, in an embodiment, a vector 900 including at least one nucleic acid construct 910 is placed into at least one microorganism 920 by methods known in the art (e.g., electroporation, transformation, etc.). Once incorporated into the microorganism 920, the nucleic acid construct 910 is transcribed, resulting in production of at least one transcript 930, which is converted intracellularly into at least one protein 940. In an embodiment, the protein can remain intracellularly 940 or be secreted into a periplasmic space (not shown). Thus, the protein is obtained through lysis of the microorganism 920. In an embodiment, the protein is expressed on the surface 950 of the microorganism 920. In an embodiment, the protein is secreted extracellularly 960.

In an embodiment, the at least one altered microorganism includes at least one synthetic protein scaffold positioned to modulate the stoichiometry of the synthesis of the at least one therapeutic agent. For example, in an embodiment, the at least one synthetic protein scaffold is positioned to spatially or temporally recruit at least one protein or fragment thereof. For example, synthetic protein scaffolds that spatially recruit metabolic enzymes can be designed and modulate the stochiometry of a biosynthetic pathway. See, for example, Dueber et al., Nat. Biotech. vol. 27, no. 8, pp. 753-759 (2009), which is incorporated herein by reference. In one example, at least one flux of an enzymatic reaction of a particular biosynthetic pathway can be balanced to, for example, limit the accumulation of intermediates, optimize production levels, prevent loss of intermediates, protect unstable intermediates from degradation, circumvent unfavorable equilibria and kinetics imposed by bulk-phase metabolite concentration, etc. Id. In an embodiment, scaffolds provide a means for controlling design by physically separating catalytic activities from binding element, which allows modification (i.e., single interaction to each enzyme) to the enzyme needed for attaining modular control over complex formation. Id. Designing such scaffolds can be performed by tethering a short peptide ligand to the enzyme, for example an SH2 domain, SH3 domain, GTPase binding domain, etc. In one particular embodiment, a synthetic complex is designed by attaching a varying number of SH3 interaction ligands to the C terminus of one enzyme (e.g., synthase), and attaching an SH3 domain to the N terminus of another enzyme (e.g., reductase). Id.

In an embodiment, the at least one altered microorganism includes at least one riboregulated transcriptional cascade counter. See, for example, Friedland, et al., Science, vol. 324, pp. 1199-1202, (2009), which is incorporated herein by reference. In an embodiment, the at least one riboregulated transcriptional cascade counter is positioned to produce at least one product upon exposure to at least one inducer.

Various inducers are described herein. Several non-limiting examples include physical or chemical inducers, such as radiation, temperature, carbohydrate, peptide, protein, alcohol, antibiotic, steroid, metal, salicylic acid, ethylene, benzothiadiazole, or other compound. In an embodiment, the at least one antibiotic includes at least one of ampicillin, tetracycline, penicillin, pristinamycin, or other antibiotic.

In an embodiment, the at least one riboregulated transcriptional cascade counter is positioned to produce at least one sequence of products upon exposure to at least one sequence of inducers. In an embodiment, the at least one riboregulated transcriptional cascade counter is positioned to produce at least one product that is different than at least one other consecutive product. In an embodiment, the at least one riboregulated transcriptional cascade counter is positioned to produce at least one first product upon exposure to at least one first inducer. In an embodiment, the at least one riboregulated transcriptional cascade is inducible to produce at least one second product upon exposure to at least one second inducer. In an embodiment, the at least one riboregulated transcriptional cascade is inducible to produce at least one third product upon exposure to at least one third inducer, etc.

In an embodiment, the at least one altered microorganism is inducible to produce the at least one agent by at least one twin-arginine translocation system. See, for example, Widdick, et al., PNAS, vol. 103, no. 47, pp. 17927-17932 (2006), which is incorporated herein by reference. For example, in most bacteria, the general secretory pathway (Sec) is the predominant route for protein export. Id. Proteins exported via Sec are translocated across the membrane in an unfolded state through a membrane-embedded translocon, to which they are targeted by cleavable N-terminal signal peptides. Id. A second export pathway designated Tat (for twin-arginine translocation), transports prefolded protein substrates. Id. Proteins are targeted to the Tat pathway by tripartitie N-terminal signal peptides, which contain a conserved twin-arginine motif in the N region of Tat signal peptides. Id. The motif is described as R—R-x-Φ-Φ, where Φ represents a hydrophobic amino acid. The consecutive arginine residues are almost invariant and believed to be important for transport by this pathway. Id. The Tat system is capable of producing large proteins, and proteins with lipid anchors, which are sometimes difficult to produce by way of the Sec system. Id. According to published studies, the twin arginine translocation system has been demonstrated to be usable in various microorganisms. See, for example, Maillard, et al., PNAS, vol. 104, no. 40, pp. 15641-15646; U.S. Pat. No. 7,447,595; each of which is incorporated herein by reference.

In an embodiment, the at least one altered microorganism is inducible to produce the at least one agent by at least one prepro signal sequence. See, for example, Eiden-Plach, et al., App. and Env. Microbiol., vol. 70, no. 2, pp. 961-966, which is incorporated herein by reference. In an embodiment, the at least one altered microorganism is inducible to produce the at least one agent by at least one Aga2p display. See, for example, U.S. Pat. No. 6,696,251, which is incorporated herein by reference. In an embodiment, the displayed agent is cleaved from the yeast by at least one protease.

In an embodiment, the at least one altered microorganism includes a microorganism having one or more non-reverting mutations. For example, a non-reverting mutation can involve a polynucleotide of greater than about 1 nucleotide, about 2 nucleotides, about 3 nucleotides, about 4 nucleotides, about 5 nucleotides, about 10 nucleotides, about 15 nucleotides, about 20 nucleotides, or any value therebetween or greater. In an embodiment, the non-reverting mutation blocks at least one biosynthetic pathway of the microorganism. For example, the non-reverting mutation can include a deletion, insertion, inversion, or any combination of these. Developing altered microorganisms containing non-reverting mutations is a routine practice, and is based on several non-limiting factors, including the ability to mutate a particular gene without destroying the viability of the microorganism, the nature of the at least one therapeutic agent that is to be delivered by the altered microorganism, the nature of the microorganism, and in some cases, the nature of the subject that will host the altered microorganism. For example, in an embodiment the mutated gene prevents production of at least one enzyme that is required for a biosynthetic pathway of a metabolite needed for replication or protein synthesis, without sacrificing viability of the microorganism (e.g., aro genes, pab genes, pur genes, etc.). See, for example, U.S. Pat. No. 4,837,151, which is incorporated herein by reference. Standard methods for making non-reverting mutants include, but are not limited to, introducing transposable elements, site directed mutagenesis, congugational crossing, or other form of mutagenesis. The altered microorganism is produced by transduction, transformation, or other means.

In an embodiment, the at least one therapeutic agent is able to translocate to at least one other location in the biological tissue or subject. For example, in an embodiment, the at least one altered microorganism delivers at least one therapeutic agent to the gastro-intestinal region of a subject, where it is absorbed and utilized at a distant location in the same subject (e.g., lungs, heart, etc.). In an embodiment, the at least one therapeutic agent translocates systemically. In an embodiment, the at least one therapeutic agent translocates selectively to a location (e.g., by utilizing particular cell ligand-receptor interactions, oxygen or other gas levels, magnetic particles tagged to the microorganism, or other mechanism for directing the microorganism, etc.).

In an embodiment, the altered microorganism produces at least one treatment or therapeutic agent catalyzes the conversion of a prodrug to its active state. For instance, in an embodiment, the at least one anaerobic microorganism is administered to a tumor that has a largely anaerobic environment. The anaerobic microorganism is allowed to proliferate and produce an enzyme or other factor. Prior to, during, or after administration of the at least one anaerobic microorganism, at least one prodrug is administered to the tumor (e.g., by way of a microorganism or other delivery method). The enzyme or other factor secreted by the at least one anaerobic microorganism is convert the at least one prodrug to an active state (e.g., to a cytotoxic agent). For example, the at least one enzyme includes at least one of beta glucuronidase or cytosine deaminase. In an embodiment, the at least one prodrug includes at least one glucuronide prodrug. In an embodiment, the at least one glucuronide prodrug includes at least one glucuronide of epirubicin, 5-fluorouracil, 4-hydroxycyclophosphamide, or 5-fluorocytosine. See, for example, U.S. Pat. No. 6,652,849, which is incorporated herein by reference.

In another example, the enzyme includes nitroreductase, and the prodrug includes 5-(aziridin-1-yl)-2,4-dinitrobenzamide (CB1954). See, for example, U.S. Pat. No. 6,416,754, which is incorporated herein by reference.

Figure 10:
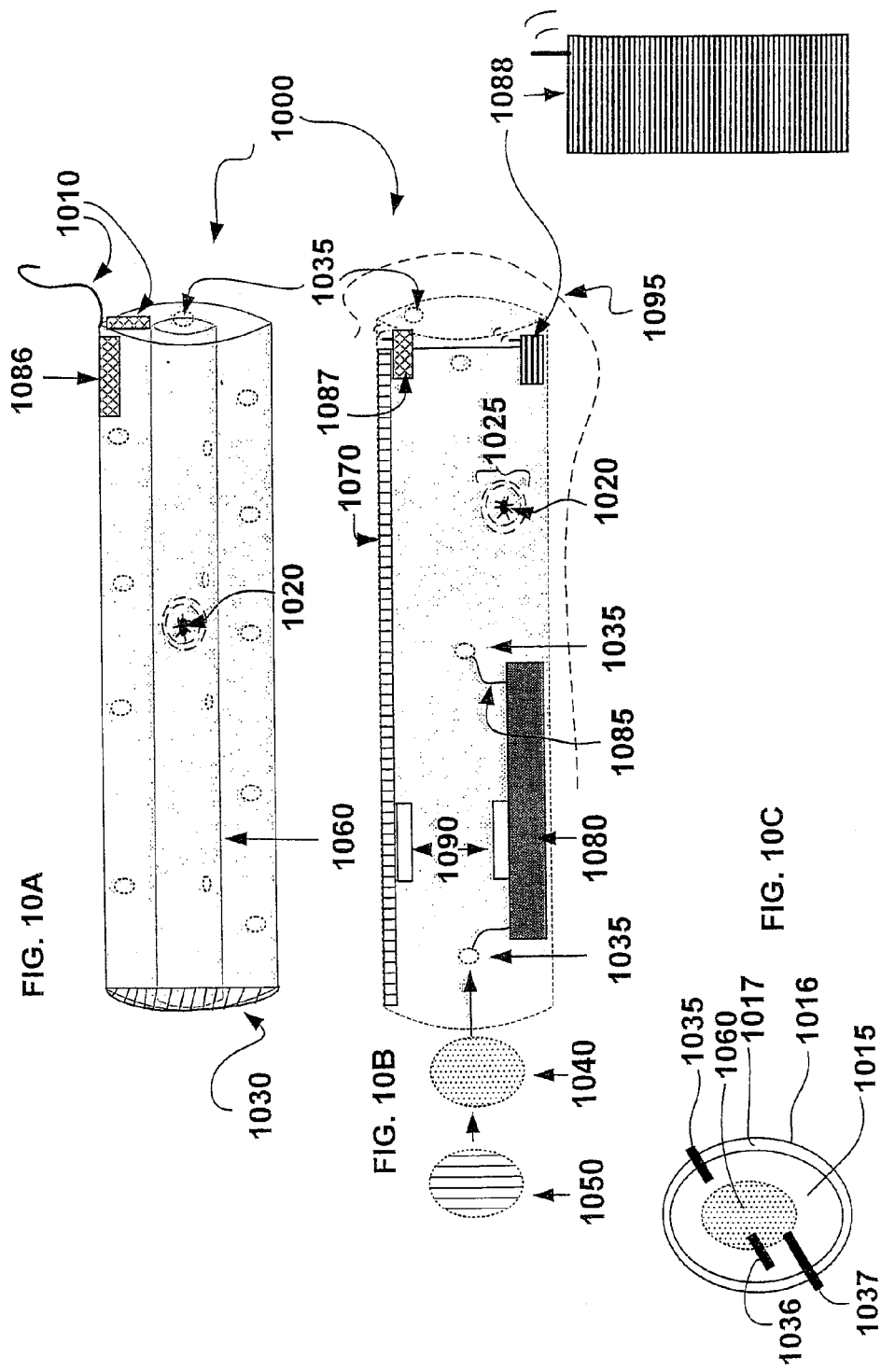
FIGS. 10A, 10B, and 10C depict diagrammatic views of various aspects of a device.

As illustrated in FIG. 10, an implantable device 1000 comprises an semi-permeable barrier 1017 structured to substantially enclose at least one altered microorganism 1020, the semi-permeable barrier 1017 defining an interior region 1015 and an exterior region or external wall 1016 of the device 1000. In an embodiment, the at least one altered microorganism 1020 includes at least one nucleic acid construct encoding at least one therapeutic agent. In an embodiment, production of the at least one therapeutic agent 1025 (indicated as concentric circles emanating from the at least one altered microorganism 1020), results in release of the therapeutic agent to the interior 1015 of the semi-permeable barrier 1017. In an embodiment, the at least one therapeutic agent 1025 is transported to the exterior of the semi-permeable barrier 1017. In an embodiment, the device 1000 further comprises at least one anchoring component 1010 from which to secure the device to at least one biological tissue or organ 1095. In an embodiment, the anchoring component 1010 includes at least one latch, hook or tether. In an embodiment, the anchoring component 1010 includes at least one adhesive or Velcro attachment.

As described herein, in an embodiment, the implantable device 1000 is biocompatible. In an embodiment, the implantable device 1000 is biodegradable. In an embodiment, the semi-permeable barrier includes at least one of a bone cage, diatom cage, polymer or co-polymer cage, protein cage, element cage, vitamin cage, mineral cage, chloroplast cage, or carbohydrate cage, as described herein. In an embodiment, the semi-permeable barrier includes one or more collagen, elastin, albumin, gelatin, extracellular matrix, acrylate, methacrylate, fibrinogen, thrombin, fibrin, cellulose, poly(hydroxyalkanoate), poly (ε-caprolactone), polysaccharide, polythioester, starch, amylase, polylactone, polyphosphazene, polycyanaoacrylate, poly(lactic acid), poly(glycolic acid), polycaprolactone, polyanhydride, polydioxanone, polyorthoester, poly(propylene fumarate), plasticized cellulose materials, polyvinyl chloride, polyvinylidene fluoride, polyurethane isocyanate, polyalginate, polysulfone, polystyrene, polyvinyl alcohol, polyacrylonitrile, polymethylene oxide, polytetrafluoroethylene, polymethyl methacrylate, polyamide, polyether-polyamino copolymer, thermoplastic copolymer, polyesteramide, polyamido amine, polythioester, nylon, polyacrylamide, acrylamide, nylon, urethane, polytetrafluoroethylene, polyurethane, dimethylsiloxane/methylvinylsiloxane copolymer, acetate, polyester, dextran, calcium, silicon, phosphorous, iron, magnesium, manganese, sodium, potassium, chromium, titanium, nickel, zinc, copper, cobalt, tungsten, silver, gold, platinum, enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, cell ligand, cell receptor, or chlorophyll.

In an embodiment, the semi-permeable barrier includes at least one pore or port component 1035 configured to selectively limit access between the interior and the exterior of the semi-permeable barrier 1017. In an embodiment, the semi-permeable barrier includes a homogenous surface or construction material. In an embodiment, the semi-permeable barrier includes a heterogenous surface or construction material. As described herein, bone cages, diatom cages, and other semi-permeable barriers discussed herein may be naturally porous. In an embodiment including a semi-permeable barrier, pores or ports are utilized to restrict access to the interior or internal cavity of the device. In an embodiment, the pores or ports can be naturally occurring, manufactured in the device, or both. In an embodiment, the device includes multiple ports 1035 at various locations. In an embodiment, the semi-permeable barrier 1017 includes at least one size exclusion component 1050 (larger view of optional component of the port 1035). In an embodiment, the at least one size exclusion component 1050 includes at least one size exclusion membrane, screen, or filter.

In an embodiment, the semi-permeable barrier 1017 includes at least one charge exclusion component 1040 (larger view of optional component of the port 1035). In an embodiment, the at least one charge exclusion component 1040 includes at least one charge exclusion membrane. In an embodiment, the semi-permeable barrier includes at least one semi-permeable component (indicated by dotted lines). In an embodiment, the device 1000 includes at least one internal port component 1036 configured to selectively limit access between layers or internal modules located in the interior of the device 1000. In an embodiment, the at least one internal port component 1037 traverses one or more semi-permeable barriers and actively or passively transports the therapeutic agent 1025 from an internal compartment 1060 containing the at least one altered microorganism 1020, to the exterior of the device 1016. In an embodiment, the device 1000 includes at least one end cap 1030. In an embodiment, the at least one semi-permeable component includes at least one semi-permeable membrane. In an embodiment, the at least one semi-permeable component includes at least one microporous or nanoporous material. In an embodiment, the semi-permeable barrier 1017 includes means to deter or restrict ingress (e.g., a semi-permeable membrane, nanopore membrane, etc.) of at least one of an immune cell or immune-system related material from the subject.

In an embodiment, the at least one altered microorganism is located in a compartment that is at least partially separated from another compartment of the device (e.g., the compartments can be linearly arranged, concentrically arranged, or any other arrangement). The compartments can be separated, for example, by a semi-permeable component, where it is desired to allow movement of the contents of one compartment to another. In an embodiment, the at least one therapeutic agent is allowed to pass through to another compartment or to the exterior of the device, while the at least one altered microorganism producing the at least one therapeutic agent is prohibited from leaving its compartment. Regulatory control of the therapeutic agent or altered microorganism can be implemented, for example, by a semi-permeable component, size exclusion component, or other means.

In an embodiment, the flow rate of fluid through the device can be regulated. For example, in an embodiment the flow rate can be altered depending on at least one of the materials utilized for the device, use of a pump, or varying the number of pores or ports in the device. In an embodiment, the flow rate of fluid through the device can be adjusted to alter the delivery of the at least one therapeutic agent.

In an embodiment, the device 1000 further comprises at least one sensor 1070. In an embodiment, the at least one sensor 1070 includes an optical density sensor. Optical density sensors are well known in the art, and include, for example, TruCell™ or TruCell2™, that are molded optical sensors for measuring cell counts in cell cultures or other media. In an embodiment, the device 1000 further includes at least one pump 1080. In an embodiment, the at least one pump 1080 includes at least one osmotic or peristaltic pump. In an embodiment, the osmotic pump includes a semi-permeable membrane incorporated into a portion of the wall of the device (or wall of the compartment, if utilized to move therapeutic agent from an inner compartment to an outer compartment of the device). In an embodiment, an osmotically active agent is mixed with the therapeutic agent. In an embodiment, the pump 1080 is connected to at least one component (e.g., a port 1035), by a channel 1085, for example. In an embodiment, no connection 1085 is required between the pump 1080 and the at least one component.

In an embodiment, the semi-permeable barrier is configured to actively or passively transport at least a portion of the at least one therapeutic agent 1025 to the exterior of the semi-permeable barrier 1017 (e.g., via a port 1035). In an embodiment, the semi-permeable barrier is configured to actively or passively transfer at least a portion of the at least one therapeutic agent 1025 based on at least one chemical gradient. In an embodiment, the semi-permeable barrier 1017 is configured to actively or passively transfer at least a portion of the at least one therapeutic agent 1025 based on one or more of pH differential, salt concentration gradient, electrical charge gradient, therapeutic agent concentration gradient, endocytosis, exocytosis, diffusion, altered microorganism concentration gradient, or condensation. For example, in an embodiment, the semi-permeable barrier allows certain molecules or ions to pass through it depending on at least one of the pressure, concentration, or temperature of the molecules or solutes on either side, as well as the permeability of the barrier to each solute. In an embodiment, the semi-permeable barrier includes at least one lipid bilayer, thin film composite membrane, cellulose ester membrane, charge mosaic membrane, bipolar membrane, anion exchange membrane, alkali anion exchange membrane, or proton exchange membrane.

In an embodiment, the semi-permeable barrier 1017 is configured to alter the at least one therapeutic agent 1025 prior to, during, or after transfer to the exterior of the semi-permeable barrier 1017. In an embodiment, the semi-permeable barrier 1017 is configured to alter the at least one therapeutic agent 1025 by at least one of altering at least one physical or chemical property of the at least one therapeutic agent 1025. In an embodiment, the at least one semi-permeable barrier 1017 includes at least one of an emulsion, lipid, dispersion, or micelle. In an embodiment, the at least one semi-permeable barrier 1017 includes one or more cells. In an embodiment, the at least one semi-permeable barrier 1017 includes one or more cell junctions. In an embodiment, the one or more cell junctions include at least one of a tight junction, zonula adherens, macula adherens, or gap junction. In an embodiment, the semi-permeable barrier 1017 is at least one of expandable, compressible, rigid, or pliable.

In an embodiment, the device 1000 further comprises at least one detection material 1086. In an embodiment, the at least one detection material 1086 includes at least one of a contrast agent, or electronic identification device. In an embodiment, the at least one electronic identification device includes at least one radio frequency identification device. In an embodiment, the at least one detection material 1086 includes at least one of a radioactive, luminescent, colorimetric or odorous substance. In an embodiment, the at least one detection material 1086 includes at least one of a diamagnetic particle, ferromagnetic particle, paramagnetic particle, super paramagnetic particle, particle with altered isotope, or other magnetic particle. In an embodiment, the device 1000 further comprises at least one transmitter 1087 that can send signals to a receiver 1088 (that can be located in the interior or exterior of the device 1000). In an embodiment, the device 1000 further comprises at least one circuit 1090 operably coupled to one or more of the components of the device.

As described elsewhere herein, the semi-permeable bather structured with an angle of enclosure of approximately 10 degrees, approximately 20 degrees, approximately 30 degrees, approximately 40 degrees, approximately 50 degrees, approximately 60 degrees, approximately 70 degrees, approximately 80 degrees, approximately 90 degrees, approximately 100 degrees, approximately 110 degrees, approximately 120 degrees, approximately 130 degrees, approximately 140 degrees, approximately 150 degrees, approximately 160 degrees, approximately 170 degrees, approximately 180 degrees, approximately 190 degrees, approximately 200 degrees, approximately 210 degrees, approximately 220 degrees, approximately 230 degrees, approximately 240 degrees, approximately 250 degrees, approximately 260 degrees, approximately 270 degrees, approximately 280 degrees, approximately 290 degrees, approximately 300 degrees, approximately 310 degrees, approximately 320 degrees, approximately 330 degrees, approximately 340 degrees, approximately 350 degrees, approximately 360 degrees, or any value less than or therebetween.

In an embodiment, the semi-permeable barrier is structured to be permeable to material less than or approximately equal to 50 nm, less than or approximately equal to 40 nm, less than or approximately equal to 30 nm, less than or approximately equal to 20 nm, less than or approximately equal to 10 nm, less than or approximately equal to 5 nm, less than or approximately equal to 1 nm, less than or approximately equal to 100 µm, less than or approximately equal to 50 µm, less than or approximately equal to 25 µm, less than or approximately equal to 10 µm, less than or approximately equal to 5 µm, less than or approximately equal to 1 µm, or any value therebetween.

In an embodiment, the at least one altered microorganism 1020 includes at least one auxotrophic microorganism. In an embodiment, the device 1000 includes at least one essential nutrient required by the at least one auxotrophic microorganism. In an embodiment, the at least one essential nutrient is in limited supply. In an embodiment, the at least one altered microorganism 1020 is responsive tout least one of pH, light, or heat.

In an embodiment, the device is configured to induce apoptosis in the at least one altered microorganism. In an embodiment, the device is configured to induce apoptosis in the at least one altered microorganism 1020 by at least one of altering pH of the interior of the semi-permeable barrier, or altering the temperature of the interior of the semi-permeable barrier. Thus, in an embodiment, the device is configured to increase or decrease the pH of the interior by release of an acidic or basic substance, respectively. For example, in an embodiment, the semi-permeable barrier includes poly(lactic-co-glycolic) acid (PLGA). Published reports indicate that the degradation of PLGA results in a reduction in the local pH when implanted into a biological tissue. See, for example, Liu, et al. Int'l J. Nanomed. vol. 1(4), pp. 541-545 (2006), which is incorporated herein by reference. Furthermore, the rate of degradation (and thus, the pH) can be regulated by adding titanium nanoparticles to the barrier. Id. For example, the addition of titanium nanoparticles slows the rate of degradation of the PLGA device, and thus, does not drop the localized pH as rapidly. Id.

In an embodiment, the device includes heating capacity (e.g., battery powered electrical heat) that can be remotely controlled. In an embodiment, the device includes power generated from the biological tissue or subject for which it serves. For example, in an embodiment the device is configured to increase the local temperature near the device at least about one degree Celsius, at least about two degrees Celsius, at least about three degrees Celsius, at least about four degrees Celsius, at least about five degrees Celsius, at least about six degrees Celsius, at least about seven degrees Celsius, at least about eight degrees Celsius, at least about nine degrees Celsius, at least about ten degrees Celsius, or any value therebetween or greater. In an embodiment, this increase temperature is held for a matter of about a few seconds, about a few minutes, about a few hours, or about a few days.

In an embodiment, the at least one altered microorganism 1020 includes at least one inducible genetic element configured to initiate death of the at least one altered microorganism 1020.

In an embodiment, the device is configured for administration to at least one biological tissue by at least one route including peroral, topical, transdermal, epidermal, intravenous, intraocular, tracheal, transmucosal, intracavity, subcutaneous, intramuscular, inhalation, fetal, intrauterine, intragastric, placental, intranasal, interdermal, intradermal, enteral, parenteral, surgical, or injection. In an embodiment, the intracavity route includes at least one of oral, vaginal, uterine, rectal, nasal, peritoneal, ventricular, or intestinal. The delivery may include inhalation, depot injections, implants, or other mode of delivery by way of an apparatus.

In an embodiment, a device includes a time-release formulation. In at least one embodiment, a device includes at least one of an suspension, mixture, solution, sol, clathrate, colloid, emulsion, microemulsion, aerosol, ointment, capsule, micro-encapsule, powder, tablet, suppository, cream, device, paste, resin, liniment, lotion, ampule, elixir, spray, syrup, foam, pessary, tincture, detection material, polymer, biopolymer, buffer, adjuvant, diluent, lubricant, disintegration agent, suspending agent, solvent, light-emitting agent, colorimetric agent, glidant, anti-adherent, anti-static agent, surfactant, plasticizer, emulsifying agent, flavor, gum, sweetener, coating, binder, filler, compression aid, encapsulation aid, preservative, granulation agent, spheronization agent, stabilizer, adhesive, pigment, sorbent, nanoparticle, microparticle, or gel.

In an embodiment, the device is configured to be included with at least part of one or more of dentures or other oral implants, contact lens or other ocular implants, orifice insert, orifice spray or inhaler, prosthetics, sutures, surgical staples, dental floss, stents, shunts, bandages, absorbable mesh, or oral implant.

Figure 11:
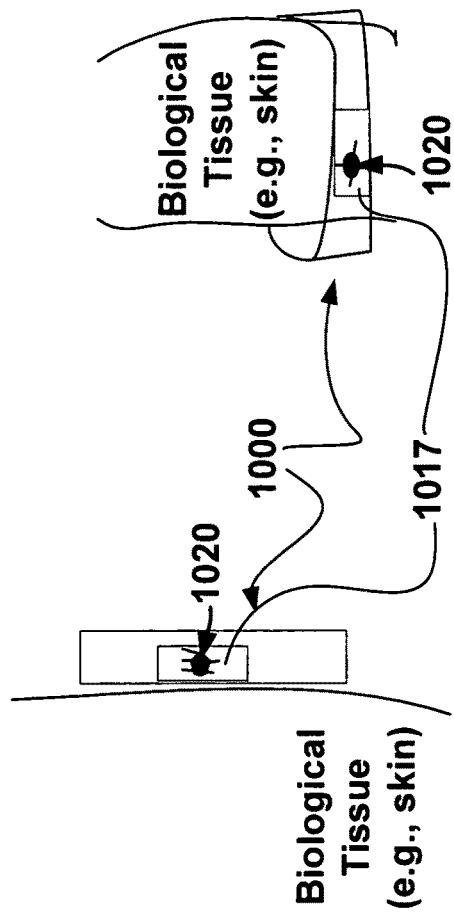
FIG. 11 depicts diagrammatic views of various aspects of a device.

As depicted in FIG. 11, other embodiments of the device 1000 disclosed herein include devices that are external to a biological tissue, or reside on the surface of the subject (e.g., bandages, etc.). As depicted in FIG. 11, the semi-permeable membrane 1017 at least partially encloses at least one altered microorganism 1020 that has been modified to deliver at least one agent (e.g., therapeutic agent).

The therapeutic agent described herein may be formulated neat or may be combined in the device with one or more acceptable carriers, diluents, excipients, and/or vehicles such as, for example, buffers, surfactants, preservatives, solubilizing agents, isotonicity agents, and stabilizing agents as appropriate. A pharmaceutically acceptable carrier, for example, may be approved by a regulatory agency of the state and/or Federal government such as, for example, the United States Food and Drug Administration (US FDA) or listed in the U.S. Pharmacopeia or other generally recognized pharmacopeia for use in animals, and more particularly in humans. Conventional formulation techniques generally known to practitioners are described in Remington: The Science and Practice of Pharmacy; $20^{th}$ Edition; Cover page (3 pgs.); printed on May 19, 2010; Lippincott Williams & Wilkins, Baltimore, Md. which is incorporated herein by reference.

Acceptable pharmaceutical carriers can be present in the same compartment as the at least one altered microorganism, or in a different compartment (e.g., the at least one altered microorganism can be located in an inner compartment and the at least one carrier can be located in an outer compartment). Examples of pharmaceutical carriers include, but are not limited to, the following: sugars, such as lactose, glucose and sucrose; starches, such as corn starch and potato starch; cellulose, and its derivatives, such as sodium carboxymethyl cellulose, ethyl cellulose, bovine serum albumin, keyhole limpet hemocyanin, tetanus toxoid, cellulose acetate, and hydroxymethylcellulose; polyvinylpyrrolidone; cyclodextrin and amylose; powdered tragacanth; malt; gelatin, agar and pectin; talc; oils, such as mineral oil, polyhydroxyethoxylated castor oil, peanut oil, cottonseed oil, safflower oil, sesame oil, olive oil, corn oil and soybean oil; polysaccharides, such as alginic acid and acacia; fatty acids and fatty acid derivatives, such as stearic acid, magnesium and sodium stearate, fatty acid amines, pentaerythritol fatty acid esters; and fatty acid monoglycerides and diglycerides; glycols, such as propylene glycol; polyols, such as glycerin, sorbitol, mannitol and polyethylene glycol; esters, such as ethyl oleate and ethyl laurate; buffering agents, such as magnesium hydroxide, aluminum hydroxide and sodium benzoate/benzoic acid; water; isotonic saline; Ringer's solution; ethyl alcohol; phosphate buffer solutions; other non-toxic compatible substances employed in pharmaceutical compositions. The pharmaceutical compositions are generally formulated as sterile, substantially isotonic and in full compliance with all Good Manufacturing Practice (GMP) regulations of the U.S. Food and Drug Administration.

In an embodiment, the at least one sensor includes at least one biosensor. In an embodiment, the at least one biosensor includes at least one altered microorganism. In an embodiment, the at least one altered microorganism detects the at least one agent. For example, in an embodiment, a biosensor microorganism is express green fluorescent protein (or another measurable material) upon exposure to the at least one agent. See, for example, Hansen et al., App. Env. Microbiol. vol. 67, no. 1, pp. 239-244 (2001), which is incorporated herein by reference. In an embodiment, the biosensor microorganism is expresses a measurable material upon exposure to at least one byproduct of the altered microorganism. For example, as set forth in Hansen, et al., an altered microorganism expresses green fluorescent protein in the presence of tetracycline, which is produced by a naturally occurring bacterial strain. Id. As indicated, testing was conducted by inoculating soil with the biosensor microorganisms, and detecting the biosensor microorganisms by flow cytometry. Id. For example, induced biosensor bacteria were isolated using fluorescence-activated cell sorting (FACS) and examined by epifluorescence microscopy. Id.

In an embodiment, a method of treating a disease or condition in a subject comprises administering at least one implantable device including an semi-permeable barrier structured to substantially enclose at least one altered microorganism, the structure defining an interior region and an exterior region of the device; wherein the at least one altered microorganism includes at least one nucleic acid construct encoding at least one therapeutic agent; and wherein the at least one implantable device dispenses to the subject an effective amount of the at least one therapeutic agent.

In an embodiment, the subject is afflicted with or suspected of being afflicted with at least one disease or condition. As described herein, the at least one disease or condition may include one or more of a pathogenic infection, parasitic infection, autoimmune disease, sepsis, systemic inflammatory response syndrome, septic shock, multiple organ dysfunction syndrome, allergic reaction, or cancer. In at least one embodiment, the at least one inflammatory disease or condition includes one or more of anaphylaxis, viral infection, bacterial infection, *plasmodium* infection, protozoan infection, nematode infection, or other worm infection. In at least one embodiment, the at least one inflammatory disease or condition includes malaria. In at least one embodiment, the parasitic infection includes at least one infection or infestation of one or more of a phytoparasite, zooparasite, ectoparasite, endoparasite, or one or more of parasitic cysts, larvae, or eggs.

Particular non-limiting examples of diseases or conditions are listed in Table 2 below.

TABLE 2

| Disease or Condition | Therapeutic Agent |
|---|---|
| Obesity/Diabetes | Ghrelin antagonists, PYY, Leptin, Obestatin, GLP-1, Exendin, Amylin, G protein coupled receptor GRP 119 agonists, selective Melanin Concentrating Hormone (MCH) receptor blockers, Cannabinoid-1 agonists, Lipase inhibitors, Neuropeptide Y (NPY) blocker, Oxymodulin, Silent Mating Type Information Regulation 2 homolog-1 (SIRT-1/sirtuin) activators, Oxyntomodulin, Cholecystokinin (CCK) agonists, Gastric Inhibitory Polypeptide (GIP) agonists |
| Hepatitis | interferons; protease inhibitors, e.g., Telaprevir (VX-950; Vertex Pharmaceuticals, Inc.); antibodies (e.g., monoclonal, humanized, polyclonal, single-chain) |
| Alzheimer's disease | secretase inhibitor, gamma secretase inhibitor, gamma secretase modulators, alpha secretase stimulators, serotonin inhibitors Alzheimer's disease Metal protein attenuation compounds, Ion channel blockers, Oligomeric amyloid beta formation inhibitors Alzheimer's disease RAGE inhibitors (Receptor for Advance Glycation endproducts), Antibodies targeting amyloid beta Alzheimer's disease GSK-3B Kinase inhibitors, Cdk5/p25 Kinase inhibitors, Extracellular signal-regulated kinase 2 (ERK2) inhibitors, C-abl Kinase inhibitors, MARK Kinase inhibitors, Protein phosphate promoters (PP-2A) Alzheimer's disease Modulators of Amyloid beta production (e.g., secretase inhibitor, gamma secretase inhibitor, gamma secretase modulators, or alpha secretase stimulators), Inhibitors of inhibit amyloid beta aggregation (e.g., Metal protein attenuation compounds, Ion channel blockers, or Oligomeric amyloid beta |

TABLE 2-continued

| Disease or Condition | Therapeutic Agent |
|---|---|
| | formation inhibitors), Amyloid beta load reducer (e.g., RAGE inhibitors (Receptor for Advance Glycation endproducts), or Antibodies targeting amyloid beta), Tau-related microtubule destabilization inhibitors (GSK-3B Kinase inhibitors, Cdk5/p25 Kinase inhibitors, ERK2 Kinase inhibitors, C-abl Kinase inhibitors, MARK Kinase inhibitors, Protein phosphate promoters (PP-2A)) |
| Bone Fractures Receptor | activator of NF-.kappa.B ligand (RANKL) activators, Bone Morphogenetic Protein-7 (BMP-7) Bone loss during cancer (RANKL, activator and Bisphosphonates) and (Aromatase treatment inhibitors for breast cancer OR Anti-androgens for prostate cancer OR luteinizing hormone-releasing hormone (LHRH) agonists for prostate cancer) |
| Rheumatoid Arthritis | an anti-CD 20 agent, a JAK3 (janus kinase 3) inhibitor, a CCR1 (chemokine [c-c motif] receptor 1) antagonist, a Syk (spleen tyrosine kinase) inhibitor, a P38 MAP kinase inhibitor, CTLA-4 (cytotoxic T-lymphocyte antigen 4), a Tumor necrosis factor (TNF)-alpha antagonist, a TNF-alpha ligand, a steroid, an inhibitor of the IL-12 Superfamily of cytokines (IL-1, 6, 12, 15, 17, 18, 32) |
| Cancer | (Vascular endothelial growth factor (VEGF) blocker or VEGF receptor ligand), (Platelet-derived growth factor (PDGF) blocker or PDGF receptor ligand), a receptor tyrosine kinase inhibiting (rtki) compound Cancer (a RAS kinase inhibitor or a RAF kinase inhibitor or a MEK kinase inhibitor or an ERK kinase inhibitor) and (an AKT kinase inhibitor or an inhibitor of the mammalian target of rapamycin (mTOR) kinase or S6k1 or 4E-BP1), angiogenesis inhibitor (e.g., VEGF blocker, VEGF receptor ligand, PDGF blocker, PDGF receptor ligand, EGF blocker, a receptor tyrosine kinase inhibiting (rtki) compound), a tumor cell pathway inhibitor (e.g., a RAS kinase inhibitor or a RAF kinase inhibitor or a MEK kinase inhibitor, an ERK kinase inhibitor, a RAS kinase inhibitor or a RAF kinase inhibitor or a MEK kinase inhibitor, an ERK kinase inhibitor), inhibitors of chromatin modification (e.g., an inhibitor of Histone Deacetylase (HDAC), an inhibitor of histone acetyltransferase (HAT)), TNF-alpha antagonist, a TNF-related apoptosis inducing ligand (TRAIL) antibody, Wnt inhibitor, a Hh (hedgehog) inhibitor, PI-3 Kinase inhibitor, a MEK kinase inhibitor, PI-3 Kinase inhibitor, an mTOR kinase inhibitor, epidermal growth factor receptor tyrosine kinase inhibitor (EGFr-TKI), a B-cell leukemia/lymphoma 2 (BCL-2) blocker, TRAIL receptor antibody, a traditional cytotoxic compound, P38 MAP kinase inhibitor and (a Raf kinase inhibitor, a MEK kinase inhibitor, or an ERK kinase inhibitors), EGFr TKI, an ERB2 inhibitor |

See, for example, U.S. Patent App. Pub. No. 20090202608, which is incorporated herein by reference.

In an aspect, the immunogen and/or adjuvant can be produced by cells, e.g., COS cells, incorporated into the internal cavity of the semi-permeable barrier. The number of cells producing the immunogen and/or adjuvant can be approximately up to $10^3$ cells, up to $10^4$ cells, up to $10^5$ cells, up to $10^6$ cells, up to $10^7$ cells, up to $10^8$ cells, or up to $10^9$ cells. In an aspect, the number of cells incorporated into the semi-permeable barrier can be dependent upon the amount of immunogen and adjuvant needed for immunization, the efficiency of the incorporated cells, and the size of the semi-permeable barrier cavity. For example, studies describe synthesis and secretion of recombinant tick-borne encephalitis virus protein E in COS cells in yields ranging from 1 to 5 μg per $10^6$ COS cells. Allison, et al., *J. Virol.* 69: 5816-5820, 1995, which is incorporated herein by reference. As such, up to $5 \times 10^6$ cells would be needed to generate 25 μg of protein E for immunization. In the case of a COS cell with an estimated cellular volume of 500 cubic μm, the $5 \times 10^6$ cells could be accommodated in a semi-permeable barrier with an internal cavity measuring at least $2.5 \times 10^9$ cubic μm in volume with approximate dimensions of at least 1350 μm×1350 μm×1350 μm. The total number of cells producing the immunogen and/or adjuvant can be incorporated into one semi-permeable barrier for implantation or distributed in a number of semi-permeable barriers for implantation.

The internal cavity of the semi-permeable barrier can hold non-cellular particles of varying size. In an aspect, the particles are the immunogen, for example, virus-like particles. In an aspect, the particles can incorporate and/or encapsulate an immunogen that is a biomolecule or a live, attenuated or inactivated pathogen or tumor cell. In an aspect, the particles can encapsulate one or more cells that have been genetically engineered to express an immunogen and/or antigen. The size of the particles depends upon the composition of the particles and the intended contents thereof as well as the size of the semi-permeable barrier cavity.

The diameter of the particles can be any integer nm from approximately 1 nm to $10^7$ nm including approximately, but not limited to, 1 nm; 5 nm, 10 nm, 25 nm, 50 nm, 100 nm, 250 nm, 500 nm, 1000 nm, $10^4$ nm, $10^5$ nm, $10^6$ nm, and $10^7$ nm. In an aspect, the diameter of the particles can be approximately up to 10 nm, up to 50 nm, up to 100 nm, up to 500 nm, up to 1000 nm, up to $10^4$ nm, up to $10^5$ nm, up to $10^6$ nm, or up to $10^7$ nm. Virus-like particles derived from self-aggregation of genetically engineered viral proteins are in the sub-micromolar size range. For example, Tamura, et al., describe the preparation of viral particles derived from recombinant expression of the Norwalk virus capsid protein that are 38 nm in size. Tamura, et al., *J. Virol.* 74:11589-11597, 2000, which is incorporated herein by reference. Kallinteri & Carnett describe a number of polymeric nanoparticles used for drug delivery including vaccine delivery ranging in average size from 100 nm to over 600 nm Kallinteri & Garnett. Polymeric "Nanoparticle for Drug Delivery". *Nanomaterials for Medical Diagnosis and Therapy*. Ed. by Challa Kumar. Wiley-VCH, Weinheim, 409-470, 2007, which is incorporated herein by reference. Particles encapsulating cells can be greater than 1 mm and as small as a single cell. For example, Breguet et al., describe the encapsulation of Chinese hamster ovary (CHO) cells into alginate/poly-L-lysine particles of 500 μm and 800 μm with as many as 17,000 cells per particle. Breguet, et al., *Cytotechnology* 53:81-93, 2007, which is incorporated herein by reference.

The amount of immunogen used for immunization can be an integer microgram (μg) from approximately 0.1 μg to 1,000 μg including approximately, but not limited to approximately, 0.1 μg, 0.5 μg, 1 μg, 5 μg, 10 μg, 25 μg, 30 μg, 35 μg, 40 μg, 45 μg, 50 μg, 100 μg, 250 μg, 500 μg, and 1000 μg. In an aspect, the amount of immunogen can be approximately up to 0.1 μg, up to 0.5 μg, up to 1 μg, up to 5 μg, up to 10 μg, up to 25 μg, up to 50 μg, up to 100 μg, up to 250 μg, up to 500 μg, or up to 1000 μg. As an example, GARDASIL® for immunization against the human papillomavirus includes 20 μg of recombinant HPV 6 L1 protein, 40 μg of recombinant HPV 11 μl protein, 40 μg of recombinant HPV 16 μl protein, and 20 μg of recombinant HPV 18 L1 proteins. See, e.g., GARDASIL® HPV vaccine Prescribing Information, U.S. Food & Drug Administration. In an aspect, the total amount of immunogen needed for immunization can be incorporated into one semi-permeable barrier and implanted into a subject. In an aspect, the total amount of immunogen needed for immunization can be distributed in a number of semi-permeable barriers, all or part of which are implanted into a subject.

In an aspect, the immunogen can be a live, attenuated or dead pathogen or tumor cell. In an aspect, the amount of immunogen can be expressed as the number of cells used for immunization. The number of cells can be approximately up to $10^3$, up to $10^4$, up to $10^5$, up to $10^6$, up to $10^7$, up to $10^8$, or up to $10^9$. For example, Berger, et al., describe using $7 \times 10^7$ autologous prostate tumor cells for immunization against locally advanced or metastatic prostrate cancer. Berger, et al., *J. Pharm. Pharmaceut. Sci.* 10:144-152, 2007, which is incorporated herein by reference. In an aspect, the amount of immunogen can be expressed as the number of infectious units, a measure of the concentration of live, attenuated pathogen in a given amount of fluid. The number of infectious units can be approximately up to $10^3$ IU, up to $10^4$, up to $10^5$, up to $10^6$, up to $10^7$, up to $10^8$, or up to $10^9$. For example, the FluMist® influenza live virus vaccine contains $10^{6.5-7.5}$ infectious units of each of three influenza strains for the 2008-2009 season. See, e.g., FluMist®, Prescribing Information, U.S. Food & Drug Administration. The total number of cells and/or infectious units needed for immunization can be incorporated into a single semi-permeable barrier for implantation or distributed in a number of semi-permeable barriers for implantation.

The external wall of the one or more semi-permeable barriers can be porous. Porosity refers to the percentage of void space in a solid. *Adv. Colloid Interface Sci.* 76-77:341-372, 1998, which is incorporated herein by reference. Porosity is a morphological property independent of the material. Porosity can be created by, for example, salt leaching, gas foaming, phase separation, freeze-drying, and sintering, depending on the material used to fabricate the access-limiting scaffold.

The porosity can be any integer percentage from approximately 1% to approximately 99% including, but not limited to, approximately 2%, 3%, 4%, 7%, 10%, 12%, 15%, 20%, 35%, 50%, 60%, 75%, and/or 90%. In an aspect, the porosity can be approximately 1% to 99%, 1% to 15%, 3% to 12%, 5% to 10%, 40% to 95%, 50% to 90%, 60% to 75%, 3% to 90%, 10% to 75%, 15% to 90%, and 25% to 90%. The porosity may not be uniform throughout the barrier. The porosity of trabecular barrier can be approximately 50% to 90%, while that of cortical access-limiting can be approximately 3% to 12%. *Biomaterials* 26: 5474-5491, 2005, which is incorporated herein by reference.

The pore size of the one or more semi-permeable barriers can be any integer nm from approximately 1 nm to approximately 10,000 nm including, but not limited to, approximately 2 nm, 3 nm, 4 nm, 5 nm, 8 nm, 10 nm, 12 nm, 15 nm; 20 nm, 25 nm, 50 nm, 100 nm, 200 nm, 300 nm, 500 nm, 600 nm, 800 nm, 1,000 nm, 2,000 nm, 5,000 nm, or 10,000 nm. In an aspect, the pore size can be approximately 1 nm to 10,000 nm, 10 nm to 5,000 nm, 25 nm to 1,000 nm, 50 nm to 750 nm, 100 nm to 500 nm, 10 nm to 100 nm, 5 nm to 50 nm, 1 nm to 10 nm, 2 nm to 20 nm, 500 nm to 5,000 nm, 1,000 nm to 10,000 nm, or 250 nm to 1,000 nm in width. In an aspect, the pore size can be approximately 10 μm up to approximately 100 μm in width. In an aspect, the pore size may not be uniform throughout the structure.

In an embodiment, the semi-permeable barrier is structured to be permeable to biological or chemical material greater than or approximately equal to 50 Daltons, greater than or approximately equal to 100 Daltons, greater than or approximately equal to 101 Daltons, greater than or approximately equal to 102 Daltons, greater than or approximately equal to 103 Daltons, greater than or approximately equal to 104 Daltons, greater than or approximately equal to 105 Daltons, greater than or approximately equal to 106 Daltons, greater than or approximately equal to 107 Daltons, greater than or approximately equal to 108 Daltons, greater than or approximately equal to 109 Daltons, greater than or approximately equal to 110 Daltons, or any value greater than or therebetween.

Device Including One or More Bone Cages Derived from Natural or Synthetic Materials Natural Source of Bone Materials.

Organic bone can encompass multiple kinds of bone obtained from donors including cortical, trabecular and cancellous. The bone can be autologous, allogeneic, or xenogeneic, with respect to a subject within whom the bone is implanted. Autologous tissue can be excised from one part of an individual and implanted into another part of the same individual. Allogeneic tissue can be harvested from one individual donor and implanted into a genetically different recipient individual within one species. A xenogeneic tissue would be harvested from an individual in one species and implanted in an individual recipient from a different species.

In an aspect, the bone cage can be comprised of autologous bone excised from, e.g., the iliac crest, skull, or fibula. Autologous tissues do not typically elicit immune rejection. In an aspect, the bone cage can be comprised of allogeneic bone harvested from a cadaver from any location in the body and optionally frozen prior to re-implantation to decrease immunogenicity. Examples of uses for allogeneic bone include, but are not limited to, Allogro® demineralized bone matrix, AlloSource, Centennial Colo.; Orthoblast®, demineralized bone matrix and cancellous bone in reverse phase medium, Isotis Orthobiologics, Irvine Calif.; Opteform® demineralized bone matrix based allograft, Exactech, Inc., Gainesville Fla.; and Grafton® demineralized bone matrix, Osteotech, Inc., Eatontown N.J. Allograft bone substitutes can include allograft bone of a variety of material sources, both natural and synthetic, or a composite.

Xenogeneic bone tissue can be obtained from animals and can be used for implantation in humans. For example, Surgibone®, sterile, extracellular composite of hydroxyapatite and collagen of bovine bone (Unilab, Inc., Mississauga, ON, Canada) for surgical implantation in humans is prepared from bovine bone and has been used to augment autografts for hip revision surgery. *Acta Orthop.* 76:544-549, 2005, which is incorporated herein by reference. Studies of the immunological mechanisms underlying the rejection of pig organs implanted into primates has resulted in the development of novel lines of genetically engineered pigs that are more immunologically compatible with man. *J. Nephrol.* 16 (suppl 7):S16-21, 2003, which is incorporated herein by reference.

The bone cage can be comprised of anorganic bone. Anorganic bone or anorganic bone matrix has been used for bone repair. *Clin. Plast. Surg.* 21:437-444, 1994; J. Long Term Eff. Med. Implants 8:69-78, 1998, which are incorporated herein by reference. Anorganic bone or anorganic bone matrix includes autologous, allogeneic, or xenogeneic bone (with respect to a subject within whom the bone is implanted) that has been deorganified. Examples of the use of such tissues include, but are not limited to, Bio-Oss® natural bone substitute (Geistlich Pharma Ag, Wolhusen, Switzerland), that is composed of anorganic bovine bone, or an anorganic bone matrix. *Arch Oral. Biol.* (2005) Jul. 29 Epub ahead of print); *Biomaterials* 26: 5648-5657, 2005, which are incorporated herein by reference.

The bone cage can be comprised of demineralized bone. Demineralized bone has been used as allografts for bone repair. *Cell Tissue Bank* 6:3-12, (2005) which is incorporated herein by reference. Demineralized bone can include autologous, allogeneic, or xenogeneic bone (with respect to a subject within whom the bone is implanted) that has been demineralized. An example of the use of demineralized, freeze-dried bone together with anorganic bovine bone for maxillary sinus grafting is presented in *Int. J. Oral Maxillofac. Implants* 18:556-60, 2003, which is incorporated herein by reference.

Once the organic, anorganic, freeze-dried and/or demineralized bone is obtained, the cage can be created by a variety of techniques. The bone can be machined using, for example, microtomes such as the Leica SP 2600 (or 1600) Saw Microtome (Leica Microsystems Nussloch GmbH, Postfach 1120, Heidelberger Strasse 17-19, D-69226 Nussloch, Germany) that can slice bone to a finished thickness of approximately 20-30 µm. Lasers, such as the YAG laser rod, can be used to cut bone with a minimum width of approximately 10 µm for deeper beam penetrations and less than 1 µm for thin coatings (Laserod, Inc., Gardena, Calif. 90247-5252). Micro tweezers, such as those from MEMS Precision Instruments, can be used to assemble the pieces as necessary. Methods for preparing 2-50 µm thick sections of undecalcified hard tissues, for example those found in e.g., *Histochem Cell. Biol.* 113:331-339, 2000 can be used.

An example of a method to make bone cages of FIG. 1 and/or FIG. 3A is described below. The bone cage can be constructed by excising a portion of cortical bone approximately 3 mm by 1 mm from the iliac crest of a subject using a microsaw. This portion of bone is then micromachined to a desired size, for example about 30 µm by 90 µm, using a microsaw. The shape is rectangular, or smoothed to an oblong, although other shapes may be implemented. The interior cavity of the bone cage is hollowed using a micromachining laser, leaving an approximately 5 µm thick bone wall. The bone wall can be perforated with approximately 1 to 2 µm holes using a micromachining laser. A second piece of bone can be micromachined and shaped to form a bone cap or plug.

Figure 2A:
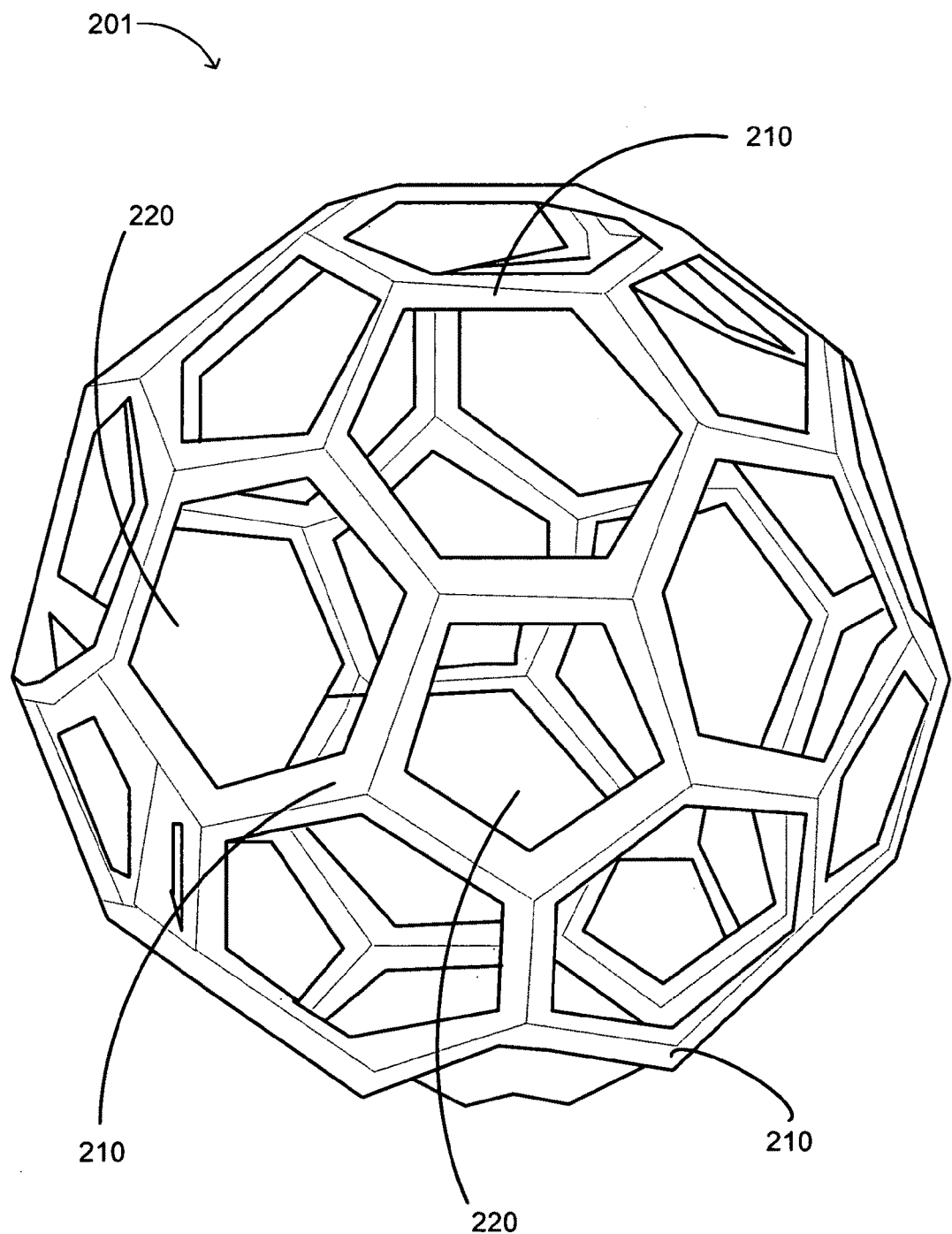
FIGS. 2A, 2B, and 2C depict a diagrammatic view of an aspect of an embodiment of a device that substantially encloses at least one altered microorganism.
Figure 2B:
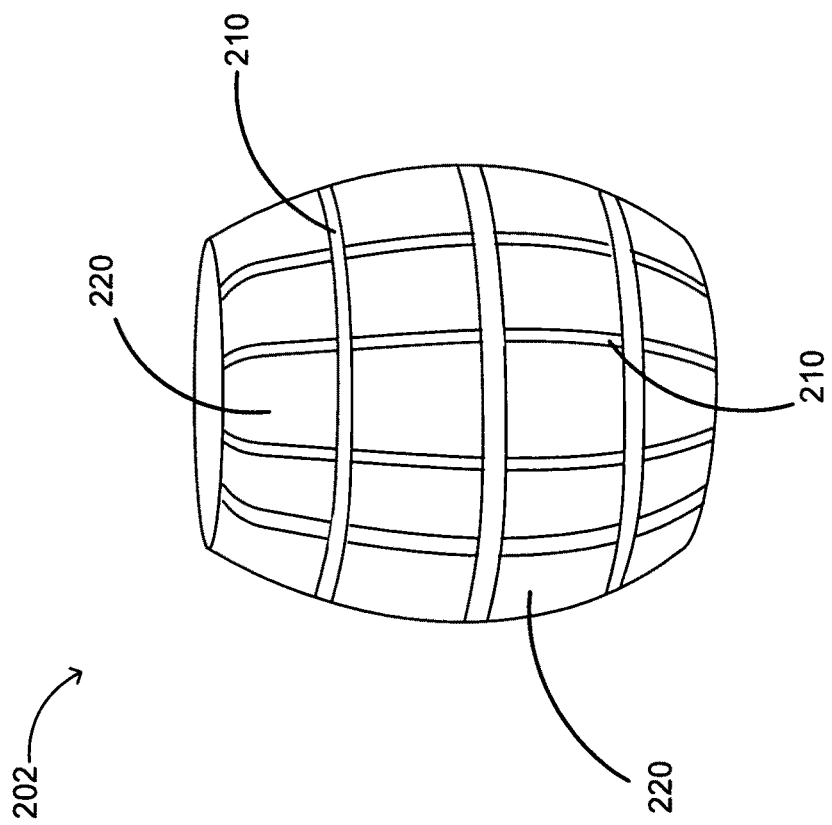
Figure 2C:
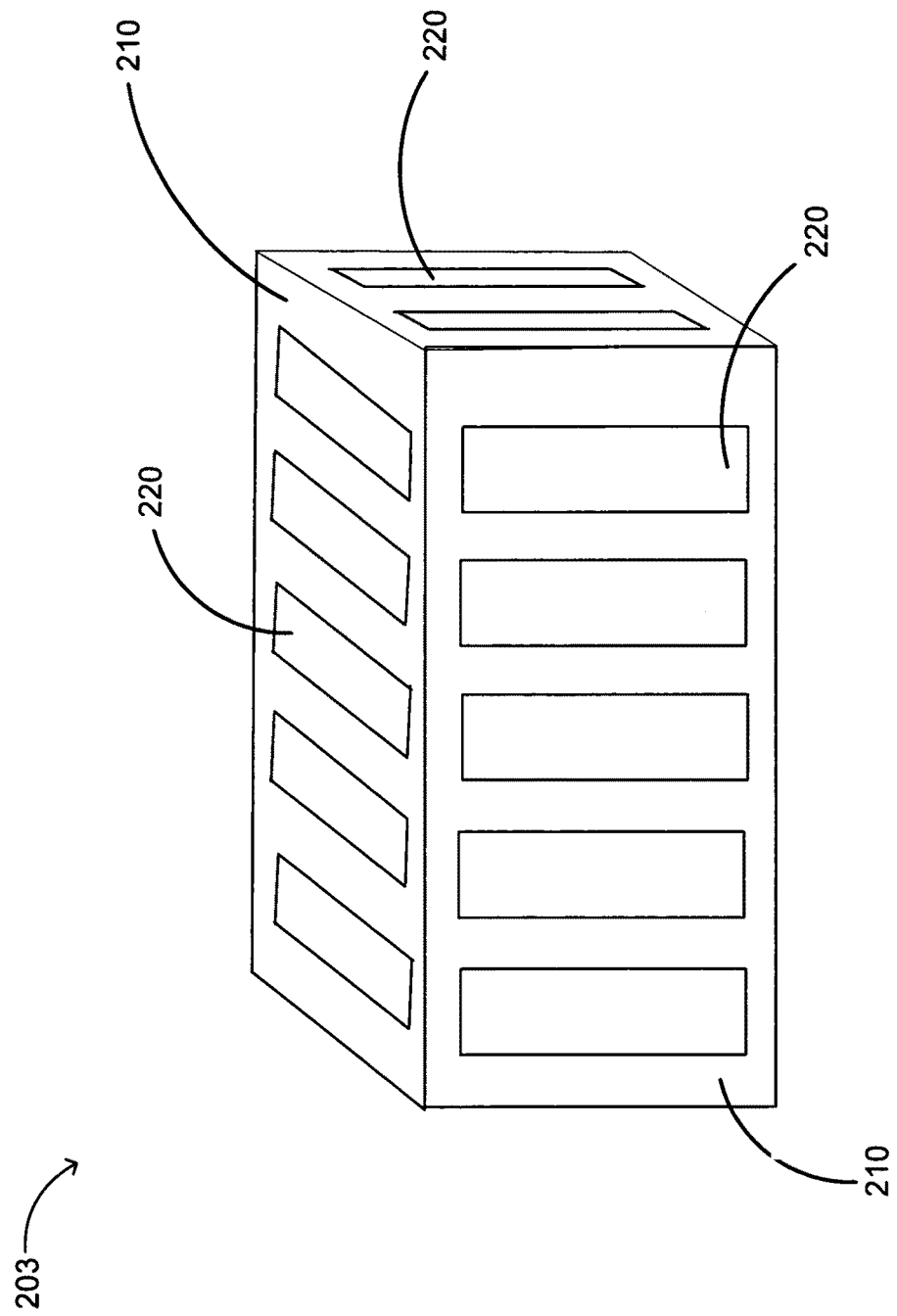

An example of a bone cage that can be constructed using these techniques is shown in FIG. 2C. Bone formed in a tubular structure can be sliced into sections, for example perpendicular to the tubular Haversian systems that make up cortically dense bone, to produce very thin bone rings. These rings can then be further sectioned into barrel staves to form a barrel-shaped construct, laid side by side to form a tube-shaped construct, or overlapped to make smaller portal structures. Further holes and smaller cutting can create joints to allow the various components to fit together and be assembled using micro tweezers.

In an alternative aspect, bone cages can be constructed by excising a portion of bone, followed by micromachining to the desired size and/or shape. The orientation of the construct can be selected to align the natural pores of the bone to form a natural internal cavity for the bone cage. The interior cavity of the bone cage can be further refined using focused beam machining to enlarge or re-shape the interior cavity of the bone cage. Additional pores can be added as described herein, if the natural porosity of the bone is not sufficient to allow the desired amount and/or type of nutrients and/or other materials to reach and/or elute from the internal cavity.

The methods for making a bone cage described herein are illustrative and are not intended to be limiting. In addition, these and other methods can be used in combination as well as separately.

The bone cage can be comprised of biocompatible and/or implantable artificial bone substitutes containing metals, ceramics and/or polymers. Artificial bone scaffolding can be used in bone repair. *Int. J. Oral Maxillofac. Surg.* 33:325-332; 2004; *Int. J. Oral Maxillofac. Surg.* 33:523-530, 2004, which are incorporated herein by reference. Artificial bone includes any bone substitute composites or scaffolds with a structural rigidity substantially equal to or greater than that of cartilage, and with pores that allow at least fluid passage. The pores can allow passage of macromolecules, but not cells. The cells may produce and secrete one or more immunogens and/or one or more adjuvants. In an aspect, the pores can allow passage of cells as well as macromolecules. Passage refers to processing including, but not limited to, diffusion, release, extrusion, and/or migration.

The mechanical properties of naturally occurring bone, including stiffness and tensile strength, can be provided by the bone tissue "scaffold" that contains significant amounts of non-living material, such as organic minerals, as well various proteins of the extracellular matrix.

Synthetic Source of Bone Materials.

A variety of bone substitutes can be used in tissue engineering to create scaffolds. Synthetic Biodegradable Polymer Scaffolds (1997) Boston, Mass.: Birkhauser; *J. Biomed. Mater. Res.* 54:162-171, 2001; *Int. J. Oral Maxillofac. Surg.* 33:523-530, 2004, which are incorporated herein by reference. These include, but are not limited to, synthetic organic materials such as clinically used nondegradable and biodegradable and bioresorbable polymers including polyglycolide, optically active and racemic polylactides, polydioxanone, and polycaprolactone, polymers under clinical investigation including polyorthoester, polyanhydrides, and polyhydroxyalkanoate, early stage polymeric biomaterials including ploy(lactic acid-co-lysine), as well as biodegradable polymer ceramic scaffolds. *J. Mater. Sci. Mater. Med.* 16:807-819; 2005; *Biomaterials* 19:1405-1412, 1998, which are incorporated herein by reference. Examples include, but are not limited to, Cortoss® self-setting synthetic ceramic composite, Orthovita, Malvern, Pa.; 3D open cell polylactic acid (OPLA); and Immix® amorphous D, L-Polylactide-co-glycolide synthetic bone graft scaffold, Osteobiologics Inc, San Antonio, Tex.

Synthetic inorganic molecules can also be used in scaffolding, including hydroxyapatite, calcium/phosphate composites, calcium sulfate, and glass ceramics. *Biotechnol. Bioeng.* (2005); *J. Artif. Organs* 8:131-136, 2005; *J. Biomed. Mater Res. A.* 68:725-734, 2005; *J. Long Term Eff. Med. Implants* 8:69-78, 1998, which are incorporated herein by reference. Examples include, but are not limited to, Norian® SRS® fast set putty, Norian Corp., Cupertino Calif.; ProOsteon® hydroxyapatite bone substitute, Biomet, Inc. Warsaw, Ind.; Osteograf® hydroxyapatite bone material, and Osteoset® calcium sulfate bone substitute, Dentsply, UK; Wright Medical Technology, Inc., Arlington, Tenn.

Organic materials of natural origin including collagen, fibrin, and hyaluronic acid can be used, as can inorganic material of natural origin including, for example, coralline hydroxyapatite. A variety of metals can be used in artificial scaffolds for bone, including silicon, titanium and aluminum. *J. Biomed. Mater. Res. A.* 70: 206-218, 2004; *J. Biomed. Mater. Res.* 56: 494-503, 2001; *J. Biomed. Mater. Res. A.* 72: 288-295, 2005, which are incorporated herein by reference.

In addition to the methods for making bone cages discussed above, design and prototyping of scaffolds can be performed digitally, and the material can be processed as sponge-like sheets, gels, or highly complex structures with intricate pores and channels. *Int. J. Prothodont.* 15: 129-132, 2002; Ann. NY Acad. Sci. 961: 83-95, 2002, which is incorporated herein by reference. A biocompatible three-dimensional internal architectural structure with a desired material surface topography, pore size, channel direction and trabecular orientation can be fabricated. *Biomaterials* 23: 4437-4447, 2002, which is incorporated herein by reference. Fabrication of scaffolding can be accomplished using conventional manual-based fabrication techniques or computer-based solid free form fabrication technologies. *Frontiers in Tissue Engineering*, New York, Elsevier Science 107-120, 1998; *J. Biomed. Mater. Res.* 51: 376-382, 2000; *J. Biomater. Sci. Polymer. E.*, Vol. 7, No. 1, pp. 23-38, 1995, *Br. J. Plast. Surg.* 53: 200-204, 2000, which are incorporated herein by reference. See, e.g., U.S. Application Numbers 2007/0184088; 2007/0134346; 2007/0134345; 2007/0134225; 2007/0134224; 2007/0134223; 2007/0134222; and 2007/0134216, which are incorporated herein by reference.

Device Including One or More Bone Cages Generated Using Hydroxyapatite

The device including one or more bone cages can be generated using hydroxyapatite either alone or in combination with other agents. Hydroxyapatite is synthesized by precipitation after the mixing of a calcium-containing solution and a phosphate-containing solution (see, e.g., U.S. Pat. No. 5,858,318; U.S. Pat. No. 6,592,989, which are incorporated herein by reference). For example, hydroxyapatite can be formed by combining solutions of calcium nitrate and ammonium phosphate with a calcium to phosphate ratio of about 10:6. The pH of the solution is adjusted to a pH of about 2.0 with dilute acid or to about 10.0 with dilute base. The resulting precipitate is collected by centrifugation at about 9,000 to 10,000 rpm, washed several times with distilled water, filtered and dried. In some instances, the slurry of hydroxyapatite granules in water can be extruded through a spray nozzle under pressure and in the presence heat to form smaller and more uniform granules (see, e.g., U.S. Pat. No. 5,858,318, which is incorporated herein by reference). The characteristics of the resulting hydroxyapatite powder are assessed using X-ray diffraction, Fourier transform infrared spectroscopy (FTIR), scanning electron microscopy (SEM), and/or transmission electron microscopy (TEM). Alternatively, granular hydroxyapatite is purchased from a commercial source (from, e.g., Clarkson Chromatography Products, Inc., South Williamsport, Pa.). Hydroxyapatite granules of uniform size can also be generated using any of a number of commercially available milling and/or grinding systems (from, e.g., Hosokawa Micron, Summit, N.J.) followed by sizing through a series of sub-millimeter mesh sieves. Particle size is assessed using laser light scattering instrumentation (e.g., Mastersizer 2000, Malvern Instruments, Inc., Malvern, Worcestershire, UK).

The powdered hydroxyapatite can be shaped into appropriate structures using slurry cast molding. See, e.g., Rumpler, et al. *J. R. Soc. Interface* 5:1173-1180, 2008, which is incorporated herein by reference. Casting molds can be designed using computer-aided design (CAD) software and produced using a three-dimensional wax printer (e.g., Model Maker II 3D modeling system, Solidscape, Merrimack, N.H.). The molds are filled with a slurry of hydroxyapatite particles, heated to 600° C. to remove the wax mold, and sintered at 1300° C. for 1 hour.

Alternatively, hydroxyapatite spheres with an internal cavity are generated using methods described by Lee, et al., *J. Mater. Sci. Mater. Med.* 19:3029-3034, 2008, which is incorporated herein by reference. Hydroxyapatite powder (20% by weight) is vigorously mixed in dichloromethane containing polyvinyl butyral (5% by weight) and then dropped into a water bath containing 2% polyvinyl alcohol. The slurry is stirred while the solvent is evaporated. The resulting microspheres (0.1 to 1 millimeter in diameter) are collected by filtration, dried overnight and then heat treated from several hours at a temperature ranging from about 600° C. to about 1200° C.

In some instances, the powdered hydroxyapatite is compressed into blocks, discs or other structures that are further machined to form the bone cage. For example, hydroxyapatite powder can be dry blended with ethylene vinyl acetate (EVA) powder and low density polyethylene and pressed into ceramic blocks by hot pressing at 150° C. for 5 minutes at a pressure varying from 30-70 MPa. See, e.g., Velayudhan, et al., *Materials Letters* 46:142-146, 2000, which is incorporated herein by reference. Alternatively, preformed blocks, discs, or other structures of hydroxyapatite can be purchased from a commercial source (from, e.g., Clarkson Chomatography Products, Inc., South Williamsport, Pa.; Berkeley Advanced Biomaterials, Inc., Berkeley, Calif.).

One or more cavities are formed in the block of hydroxyapatite using a drill with a micro drill bit (e.g., drill bits ranging in size from 50-250 micrometers from Union Tools, Co., Buena Park, Calif.). Micro-holes in the wall of the block of hydroxyapatite can be generated using a focused laser. A laser can be used to cut and shape hydroxyapatite. See, e.g., Teixeira, et al., *J. Biomed. Mater. Res. A*, 81:920-929, 2007, which is incorporated herein by reference. The block of hydroxyapatite is further machined to create micro-holes as small as 1 micrometer in the wall of the block using a laser micromachining system with a pulsed diode pumped solid state laser (from, e.g., Oxford Lasers, Oxon, UK).

Cross-Linking an Immunogen and an Adjuvant to Bone Cage Device

A device including one or more bone cages can include the one or more immunogens and/or one or more adjuvants attached to a surface of the one or more bone cages. The one or more immunogens and/or one or more adjuvants can be non-covalently attached to the bone cage by simple adsorption. For example, hydroxyapatite, a bone replacement material with a crystal structure similar to the inorganic matrix of bone, can be used as an adsorption matrix. Studies describe the adsorption and release of a recombinant human protein to a hydroxyapaptite-based implant for use in delivering a therapy to a bone graft. Boix, et al., *J. Inorg. Biochem.* 99:1043-1050, 2005, which is incorporated herein by reference. The binding to hydroxyapatite can be enhanced by incorporating an acidic oligopeptide (e.g., six to eight residues of L-aspartic acid) into the binding biomolecule. See, e.g., Nishioka, et al., *Mol. Genet. Metab.* 88:244-55, 2006, which is incorporated herein by reference.

The one or more immunogens and/or one or more adjuvants can be linked to the bone cage through a chemical linkage between one or more components of the immunogen and/or adjuvant and one or more components of the bone cage. Chemical linkers may be used to link together proteins, carbohydrates, oligonucleotides, small biomolecules, or combinations thereof. In an aspect, the chemical linker can bind directly to the mineral component of the bone.

Chemical linkers such as homobifunctional, heterofunctional, and/or photoreactive cross-linking agents can be used to link the immunogen and/or the adjuvant to biomolecules associated with a surface of the bone cage. The immunogen and/or the adjuvant can be linked to biomolecules associated with a surface of the bone cage through amine groups, sulfhydryl groups, carbohydrate groups, or a combination thereof. Examples of homobifunctional cross linkers include, but are not limited to, primary amine/primary amine linkers such as BSOCES ((bis(2-[succinimidooxy-carbonyloxy] ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2' pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-γ-maleimidobutyryl-oxysuccinimide ester), Sulfo GMBS (N-γ-maleimidobutyryloxysulfosuccinimide ester), EMCS (N-(ε-maleimidocaproyloxy) succinimide ester), Sulfo EMCS(N-(ε-maleimidocaproyloxy) sulfo succinimide), SIAB (N-succinimidyl(4-iodoacetyl)aminobenzoate), SMCC (succinimidyl 4-(N-maleimidomethyl)cyclohexane-1-carboxylate), SMPB (succinimidyl 4-(rho-maleimidophenyl) butyrate), Sulfo SLAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH(N-(s-maleimidocaproic acid) hydrazide); and amine/carboxyl linkers such as EDC (1-ethyl-3-(3-dimethylaminopropyl) carbodiimide hydrochloride).

In an aspect, the one or more immunogens and/or the one or more adjuvants can be linked directly to the bone cage through a bisphosphonate linkage. Bisphosphonates bind to the mineral phase of bone and have been used in the treatment of osteoporosis for antiresorptive therapy. An amino group can be added to bisphosphonate by chemical synthesis and used to functionalize the bisphosphonate with a heterologous cross-linking agent such as those described herein. The heterologous cross-linking agent can be used to link the amino-bisphosphonate to a biomolecule. The biomolecule-modified aminobisphosphonate can bind to the surface of bone as well as to the surface of bone substitutes, e.g., hydroxyapatite. See, e.g., Ehrick et al, *Bioconjugate Chem.* 19:315-321, 2008, which is incorporated herein by reference.

In an aspect, the immunogen and/or the adjuvant can be linked to the bone cage through an azide-alkyne mediated linkage. The copper-catalyzed azide-alkyne cycloaddition is a 1,3-dipolar cycloaddition between an azide and a terminal alkyne to form a triazole. A copper-free cycloaddition reaction has also been described for use in living cells. See, e.g., Baskin et al., *Proc. Natl. Acad. Sci., USA.* 104:16793-16797, 2007, which is incorporated herein by reference. To link one or more components, one component is derivatized with azide while the other component is derivatized with alkyne. The components can be readily snapped together using "click chemistry." Viral particles, oligonucleotides, carbohydrates, lipids, proteins, and peptides can be functionalized with azide and/or alkyne for use in "click chemistry" reactions in which building block components are readily "snapped" together. See, e.g., Hein et al., *Pharm. Res.* 25:2216-2230, 2008; Ming, et al., *Nucleic Acids Symp. Ser. (Oxf).* 52:471-472, 2008; Van Dongen et al., *Bioconjugate Chem.* 20:20-23, 2009; Godeau, et al, *J. Med. Chem.* 51:4374-4376, 2008, which are incorporated herein by reference.

Cellular Restructuring a Device Including One or More Bone Cages

The device including one or more bone cages can be constructed utilizing cells cultured in vitro including, but not limited to, stem cells, fibroblasts, endothelial cells, osteoblasts and/or osteoclasts. The in vitro cultured cells can be configured to form the bone cage structure or configured to restructure the bone cage wall or inner compartment. Restructuring the device including one or more bone cages is useful to design compartments that can provide temporal release or triggered release of the one or more immunogens and one or more adjuvants from the bone cage. Restructuring or restructured, as it relates to the bone cage, refers to a change in the physical structure of the bone cage, including, but not limited to, bone size, shape, architecture and quality. Bone restructuring includes, but is not limited to, bone resorption, osteoconduction, or bone deposition. Timed release can depend upon the size of the bone cage compartment and the thickness of the bone cage wall. The bone cage wall can be slowly degraded to release one or more of the one or more immunogens and the one or more adjuvants. In an aspect, the non-stem cells can be isolated from a subject. Bone cell populations can be derived from all bone surfaces by a variety of techniques, including, but not limited to, mechanical disruption, explantation, and enzyme digestion. *Tissue Eng.* 1:301-308, 1995, which is incorporated herein by reference. Methods can be used to culture and/or propagate osteoprogenitor cells and/or osteoblast-like cells in vitro. *Int. J. Oral Maxillofac. Surg.* 33:325-332, 2004, which is incorporated herein by reference. Culture conditions can be used for manufacturing bone tissue including, but not limited to, temperature, culture medium, biochemical and mechanical stimuli, fluid flow and perfusion. *Int. J. Oral Maxillofac. Surg.* 33:523-530, 2004, which is incorporated herein by reference.

The non-stem cells can be differentiated from stem cells, including, but not limited to, fetal, embryonic, cord blood, mesenchymal and/or hematopoeitic stem cells. In an aspect, the numbers of stem cells can be increased in culture in vitro prior to differentiation. Methods can be used for isolation, culturing and transplantation of stem cells. *Fetal Diagn. Ther.* 19:2-8, 2004; *Best Pract. Res. Clin. Obstet. Gynaecol.* 18:853-875, 2004, which are incorporated herein by reference.

In an aspect, the stem cells can be mesenchymal stem cells. Mesenchymal stem cells are multipotent cells found in several, perhaps most, adult tissues. *Blood* 105:1815-1822, 2005, which is incorporated herein by reference. Mesenchymal stem cells can be reliably isolated and cultured in therapeutic quantities. *Bone* 13:81-88, 1992, which is incorporated herein by reference. Several methods can be used to isolate mesenchymal stem cells from, for example, bone marrow, adipose tissue, and muscle, based on the physical and immunological characteristics. *Basic & Clinical Pharmacology & Toxicology* 95:209, 2004; *Ann. Biomed. Eng.* 32:136-147, 2004, which are incorporated herein by reference. Mesenchymal stem cells can differentiate into various lineages including osteoblasts in vitro. *Science* 284:143-147, 1999; *J. Cell Sci.* 113:1161-1166, 2000; *Int. J. Oral Maxillofac. Surg.* 33:325-332, 2004, which are incorporated herein by reference.

The bone cage can be comprised of cells cultured in vitro on bone scaffolding. In an aspect, the bone scaffolding can be degradable in vitro and/or in vivo. Porosity and pore size of the scaffold can play a role in bone formation, osteogenesis and osteoconduction in vitro and in vivo. Methods of measuring and controlling porosity and pore size in artificial scaffolds can be used. *Biomaterials* 26:5474-5491, 2005, which is incorporated herein by reference.

Stem cells and/or osteoblast progenitor cells can be propagated on scaffolds of a variety of shapes including, those shown in FIG. 2. The cells are grown until fusion, or partially grown to result in a lattice shape. The bone cells cultured in vitro include autologous, allogeneic, or xenogeneic cells, with respect to a subject within whom the bone cage is implanted. A method of making a bone cage using mesenchymal stem cells is described herein and, for example, FIG. 3B. An artificial scaffold, for example, of degradable polymer, can be laid down in the desired open lattice-work shape of the two halves of the bone structure. Expanded mesenchymal stem cells (autologous, allogeneic, or xenogeneic) are cultured in the latticework shapes, in vitro, and encouraged to differentiate into osteoblasts. Once the cells have populated the lattice structure, other optional components of the device including the one or more bone cages is added, and the device is implanted.

The bone cage can comprise living tissue. Living tissue refers to the presence of living bone cells such as, but not limited to, osteoblasts, or osteoclasts within the bone scaffold. Living tissue includes living bone cells in artificial bone scaffolding. The living tissue can be autologous, allogeneic, or xenogeneic, with respect to a subject within whom the bone cage is implanted. The bone cage can comprise dead tissue. "Dead tissue" refers to the absence of living bone cells, such as, but not limited to, osteoblasts, or osteoclasts within the bone scaffold. The dead tissue can be autologous, allogeneic, or xenogeneic, with respect to a subject within whom the bone cage is implanted.

The bone cage can be designed and/or treated, at least partially or completely, to prevent restructuring. In the case of a bone cage with artificial scaffolding, autologous, or non-autologous bone, bone restructuring can include, but is not limited to, the influx and growth of the subject's bone cells in the artificial, autologous, or non-autologous bone scaffold. Mechanisms of restructuring, treatments to modify restructuring, and genes governing restructuring can be used. *Nature* 1:47-54, 2005, which is incorporated herein by reference.

Methods for detecting and measuring changes in the device including one or more bone cages is described. The change can result, for example, from global or discrete increases or decreases in bone mass. Alternatively, the change can result, for example, from global or discrete increases or decreases in the relative ratios of cells, including, but not limited to, the number of osteoblasts as compared with the number of osteoclasts. The change can also result, for example, from global or discrete increases or decreases in bone pore size and/or porosity. Increase and/or decrease in bone mass, relative ratio of cells, or pore size and/or porosity, for example, can be measured as any integer percent change from 1% to 99%, for example, 10%, 25%, 50%, 75%, and 95%, as compared with the original bone mass, relative ratio of cells, or pore size and/or porosity, respectively, either globally or in a discrete location.

Bone restructuring, a combination of bone resorption by osteoclasts and bone deposition by osteoblasts, can be modified. Resorption as it relates to the bone cage refers to a decrease in bone mass from either global or discrete reductions in, for example, the extracellular matrix and/or cells. Bone resorption can be mediated by osteoclasts, so treatments that inhibit the activity of osteoclasts decrease bone resorption. Methods for detecting and measuring these changes are described. *Biomaterials* 26:5474-5491, 2005, which is incorporated herein by reference.

In an aspect, restructuring of the bone cage can be partially or completely reduced or prevented. In an aspect, the bone can be designed and/or treated to be at least partially, or completely, restructured. Modifications of bone restructuring can result, for example, from administration of compounds that influence bone resorption and/or deposition, by the selection of the pore size and/or porosity of the bone, by the selection of the type of bone, by the selection of the location of implantation, as a result of inherent, induced, or genetically modified immunogenicity, and as a result of other genetic modification. In an aspect, the bone is partially or completely resorbable.

Compounds that influence bone restructuring through modifications in bone resorption and/or deposition can be applied before, during, or after implantation of the bone cage. Compounds can be administered at the discretion of the health professional and depend on the desired timing and the extent of the modification of a subject's bone restructuring. Administration of the compounds can be systemic or localized. Systemic and local administration includes any method used in the art for pharmaceutical administration.

The device including one or more bone cages including one or more immunogens and one or more adjuvants can be administered locally by being applied in the subject in the vicinity of the bone either globally, or in localized areas, depending on whether complete or partial restructuring is desired. An example is the incorporation of the cell binding peptide P-15 on anorganic bovine bone matrix. *Biomaterials* 25:4831-4836, 2004; *J. Biomed. Mater. Res. A.* 74:712-721, 2005; *Biomaterials* 26:5648-5657, 2005, which are incorporated herein by reference. Other examples include, but are not limited to, addition of TGF-β, platelet-derived growth factor, fibroblast growth factor, and bone morphogenic proteins.

In an aspect, compounds can be administered by incorporation in the bone cage including one or more immunogens and one or more adjuvants optionally in combination with living cells and/or tissues, as discussed herein.

Bis-phosphonates, used systemically to prevent bone resorption can be applied before, during, or after implantation of the bone cage to partially or completely modify bone restructuring. Osteoporos Int 13: 97-104, 2002; *Curr. Osteoporos. Rep.* 1: 45-52, 2003, which are incorporated herein by reference. Such therapies can also be administered locally by treating the bone cage, or by placing them inside the cage in combination with one of the one or more immunogens and one or more adjuvants, or optionally one or more cells or tissues that produce the one or more immunogen and/or the one or more adjuvant, to elute over time. Alternatively, discrete portions of the bone cage can be coated to selectively prevent restructuring as discussed herein.

One or more hormones and/or related compounds, including, but not limited to, estrogen, growth hormone, calcitonin, vitamin D, and/or calcium, that encourage bone growth, can be administered before, during, or after implantation of the bone cage to partially or completely modify bone restructuring. In an aspect, the bone cage can be treated globally or discretely with a thin layer of one or more of these hormones to encourage bone growth throughout or in discrete locations.

Anabolic therapies including, but not limited to, hormones such as parathyroidhormone (PTH-(1-84)), teriparatide (PTH-(1-34)), and/or excess glucocorticoid, that can increase bone turnover and porosity can be administered systemically to partially or completely modify restructuring. *Osteoporosis Int.* 13:97-104, 2002. In an aspect, these hormones can be administered locally by treating the entire bone cage, or discrete portions of the bone cage, to allow selective restructuring. These hormones can be administered by placing them inside the cage as one of the one of the one or more immunogens and one or more adjuvants and/or one or more cells or tissues.

Bone resorption can be influenced by the administration of cytokines that increase osteoclast activity including, but not limited to, interleukin-1, M-CSF, tumor nevrosis factor, and/ or interleukin-6. Bone resorption can be influenced by the administration of cytokines that decrease osteoclast activity including, but not limited to, interleukin-4, interferon-γ, and/ or transforming growth factor-β. In an aspect, bone resorption can be influenced by other humoral factors including, but not limited to, leukotrienes, arachidonic metabolites, and/or prostaglandins and their inhibitors and including β-lipoxygenase enzyme inhibitors.

Bone formation can be influenced by the administration of factors that promote osteoblast activity and proliferation including, but not limited to, insulin-like growth factors I and II, transforming growth factor-β, acidic and basic fibroblast growth factor, platelet-derived growth factor, and/or bone morphogenic proteins.

Bone formation can be influenced by the administration of factors that promote osteoblast activity and proliferation including, but not limited to, growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GM-CSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin or vascular endothelial cell growth factor (VEGF).

Bone pore size and porosity influence bone restructuring through modifications in bone resorption and/or deposition. Since the size of the pores in the bone impacts new bone growth, decreasing the pore size and/or the percent of porosity of the bone in the cage reduces or prevents restructuring. In contrast, increasing the pore size and/or the percent porosity of the bone in the cage enhances restructuring. The bone cage can be constructed such that the pore size and porosity is approximately uniform through out the cage, or that the pore size and porosity varies depending on the location. Varying the pore size and/or porosity in discrete locations leads to partial restructuring (either partial enhancement or partial prevention).

In an aspect, the pore size of the one or more bone cages can be approximately 1 nm to 10 nm, approximately 1 nm to 20 nm, approximately 1 nm to 25 nm, approximately 1 nm to 50 nm, approximately 1 nm to 100 nm, approximately 1 nm to 150 nm, approximately 15 nm to 50 nm, approximately 50 nm to 100 nm, approximately 25 nm to 100 nm, approximately 50 nm to 150 nm, or approximately 25 nm to 150 nm. In an aspect, the pore size can be larger, for example, approximately 150 nm to 500 nm, approximately 250 nm to 750 nm, or approximately 500 nm to 1,500 nm, in one or more locations. This can allow partial restructuring in these one or more locations.

In a further aspect, the pore size of the one or more bone cages can be approximately 150 nm to 500 nm, approximately 250 nm to 750 nm, or approximately 500 nm to 1,500 nm. In an aspect, the pore size can be smaller, for example, approximately 1 nm to 20 nm, approximately 1 nm to 25 nm, approximately 1 nm to 50 nm, approximately 1 nm to 100 nm, approximately 1 nm to 150 nm, approximately 15 nm to 50 nm, approximately 50 nm to 100 nm, approximately 25 nm to 100 nm, approximately 50 nm to 150 nm, or approximately 25 nm to 150 nm. This can prevent or reduce restructuring in these one or more locations.

The porosity can be approximately 1% to 15%, approximately 3% to 12%, approximately 5% to 10%, approximately 1% to 3%, approximately 1% to 5%, or approximately 1% to 10% in one or more locations. In an aspect, the porosity can be a greater percentage in one or more locations, for example approximately 40% to 95%, approximately 50% to 90%, approximately 60% to 75%, approximately 15% to 90%, and approximately 25% to 90%. This can allow partial restructuring in these one or more locations.

The type of bone used in the fabrication of the one or more bone cages influences bone restructuring through modifications in bone resorption and/or deposition. Measurements of the influence on bone restructuring of each type of bone can be performed in vitro, as well as in pre-clinical and clinical studies. Different bone types and/or sources have a differential ability to support restructuring. As a result, bone restructuring can be partially or completely reduced, or alternatively, partially or completely enhanced depending on the bone chosen. In addition, different bone types/sources can be used in discrete locations in the bone cage to enhance or prevent/decrease bone restructuring.

Studies assessing the ability of new bone or bone cells to restructure a variety of artificial and/or anorganic bone in bone transplant patients or in vitro culture have shown, for example, that implantation of Bio-Oss® anorganic bovine bone (Geistlich, Wolhusen, Switzerland) leads to limited, reduced or absent restructuring compared with other artificial or natural organic bone options such as Algipore® porous fluorohydroxyapatitic biomaterial. *Clin. Oral Implants Res.* 15:96-100, 2004; *J. Mater. Sci. Mater. Med.* 16:57-66, 2005, which are incorporated herein by reference. Since these studies have also identified artificial bone that encourages restructuring, as does natural bone, the bone cage can be designed with portions that are resistant to restructuring as well as portions that encourage restructuring as desired.

Bone restructuring can be modified by making the bone cage from cortical bone, or trabecular or cancellous bone. The choice of bone will impact the extent of restructuring since cortical bone is generally less porous than trabecular or cancellous bone. In addition, discrete parts of the bone cage can be formed from one type of bone or another to influence the restructuring of discrete locations.

Bone restructuring can be modified by the location of implantation. Bone restructuring can be greater when the bone is implanted in bone rather than other locations. The type of bone the bone cage is implanted in will also influence the extent of restructuring. The bone cage can be implanted in non-bone soft tissues including, but not limited to, liver, muscle, lung, or fat.

Immunogenicity of the bone cage influences bone restructuring through modifications in bone resorption and/or deposition by osteoblasts and osteoclasts, as well as through immune mechanisms. Methods of influencing the immunogenicity of cells can be used. Examples include, but are not limited to, the immuno-compatibility of donor and recipient, the inherent immunogenicity of the bone material or cells, the presence of immune modulatory compounds, and genetic modifications.

The device including one or more bone cages can be partially or completely non-immunogenic with respect to a subject within whom the device is implanted, or alternatively, can be partially or completely recognized as self. In an aspect, the one or more bone cages can be partially or completely immunogenic with respect to a subject within whom the device is implanted, or alternatively, can be partially or completely recognized as non-self. Non-immunogenic means that the immune response, if any, is not such that immune suppressive drugs would be required following implantation of the bone cage.

Bone cage restructuring and immunogenicity can be modified by the immuno-compatibility of donor and recipient. In a further aspect, bone cages completely or partially made from bone derived from a donor autologous to the recipient of the bone cage, are non-immunogenic and recognized as self. Previously frozen allogeneic bone, as well as xenogeneic or allogeneic anorganic bone, is considered non-immunogenic.

The device including one or more bone cages can be completely or partially made from bone derived from a donor allogeneic to the recipient of the bone cage. In an aspect, in which the bone is from cadavers, and frozen, de-mineralized, and/or deorganified, immuno-suppressive therapy is not generally required although some recipients may develop anti-HLA antibodies (The Merck Manual of Diagnosis and Therapy. Sec. 12, Ch. 149). In an aspect, in which the allogeneic bone is not frozen, deorganified or demineralized, for example, an immune response may result unless modified by other means, such as immuno-suppressive therapy.

The device including one or more bone cages can be completely or partially made from bone derived from a donor xenogeneic to the recipient of the bone cage. In an aspect, in which the bone is anorganic bovine bone, for example, immuno-suppressive therapy is not required, although some recipients may experience a transient macrophage infiltrate, but no systemic or local immune response. *J. Periodontol.* 65:1008-15, 1994, which is incorporated herein by reference. In an aspect, in which the bone cage is made from xenogeneic bone that is not anorganic or pre-frozen, the bone cage can be immunogenic and not recognized as self.

The device including one or more bone cages can be partially made from non-immunogenic bone including, but not limited to, autologous bone and/or pre-frozen, de-organified, and/or demineralized allogeneic bone, and/or anorganic xenogeneic bone, and partially made from immunogeneic bone including, not limited to, allogeneic bone that is not pre-frozen, de-organified, and/or de-mineralized and/or xenogeneic bone that is not anorganic. The immunogenic bone can be placed in discrete locations to encourage restructuring. In an aspect, the non-immunogenic bone can be placed in discrete locations to prevent or reduce restructuring.

Bone cage restructuring and immunogenicity can be modified by the inherent immunogenicity of the bone material or cells. In an aspect, the one or more bone cages can be completely or partially made from stem cells including, but not limited to, mesenchymal, fetal, cord blood, and/or hematopoietic stem cells. Bone cages can be completely or partially made from differentiated stem cells such as bone cells, including, but not limited to, osteoblasts and/or osteoclasts, fibroblasts, or endothelial cells. The cells can be autologous, allogeneic, or xenogeneic as relates to a subject in whom they are implanted.

The one or more bone cages can be composed of autologous, allogeneic, xenogeneic and/or artificial bone in which autologous, allogeneic, and/or xenogeneic stem cells have been cultured. The stem cells can be induced to differentiate into, for example, bone cells including, but not limited to, osteoblasts and/or osteoclasts. Stem cells can be cultured in discrete areas of the bone cage. The autologous, allogeneic and/or xenogeneic mesenchymal stem cells can partially or completely decrease the immunogenicity of part, or all, of the bone cage.

Stem cells generally have decreased immunogenicity and can induce transplant tolerance. For example, hematopoietic stem cells can induce tolerance as can embryonic stem cells. *Expert Opin. Biol. Ther.* 3:5-13, 2003, which is incorporated herein by reference. In addition, transplanted allogeneic mesenchymal stem cells demonstrate a lack of immune recognition and clearance. *Blood* 105:1815-1822, 2005; *Bone Marrow Transplant* (22) 30:215-222; *Proc. Natl. Acad. Sci. USA*

99:8932-8937, 2002 as well as being useful in graft-versus-host disease (*Lancet* 363:1439-1441, 2004), which are incorporated herein by reference. Mesenchymal stem cells do not activate alloreactive T cells even when differentiated into various mesenchymal lineages (*Exp. Hematol.* 28:875-884, 2000; *Exp. Hematol.* 31:890-896, 2003, and suppress proliferation of allogeneic T cells in an MHC-independent manner. *Transplantation* 75:389-397, 2003; *Blood* 105:1815-1822, 2005, which are incorporated herein by reference.

The one or more bone cages can be composed of autologous, allogeneic, xenogeneic and/or artificial bone in which autologous, allogeneic, and/or xenogeneic bone cells have been cultured. The bone cells can include, but are not limited to osteoblasts and osteoclasts. In an aspect, the bone cells can be cultured in discrete areas of the bone cage. Bone cages created from autologous, allogeneic, xenogeneic and/or artificial bone, in which allogeneic or xenogeneic (to a subject in which it is to be implanted) bone cells can be propagated, increases the immunogenicity of the bone cage when implanted in the subject.

Bone cage restructuring and/or immunogenicity can be modified by the presence of immuno-modulatory compounds. These include immuno-suppressive as well as immuno-stimulatory compounds. Immuno-suppressive compounds decrease immunogenicity and hence decrease restructuring, while immuno-stimulatory compounds increase immunogenicity and hence increase restructuring. The immuno-modulatory compounds can be administered systemically to a subject before, during and/or after implantation of the bone cage using methods known in the art. The compounds can be adsorbed onto the surface of the bone cage, placed inside it as the one or more immunogens and one or more adjuvants, or secreted from the one or more cells or tissues. In an aspect in which the one or more immunomodulatory compounds can be adsorbed onto the bone cage, they can be adsorbed to one or more discrete locations on the bone cage, The immunosuppressive compounds include, but are not limited to, corticosteroids, such as prednisolone or methylprednisolone. In an aspect, the immune stimulatory and/or inflammatory molecules include, but not limited to, tumor necrosis factor α, interferon γ, interleukin 2 (IL-2), IL-12, IL-21, and/or one or more selectins. Other appropriate compounds can be used by health professionals and can be found, for example, in the Physician's Desk Reference.

Immunostimulatory and/or inflammatory molecules can be applied to discrete locations on the bone cage. This can result in partial or complete restructuring of the discrete area. Immunosuppressive compounds can be applied to discrete locations on the bone cage. This can prevent or reduce restructuring of the bone cage in at least those locations.

The bone cage can comprise cells that have been genetically modified. In an aspect, the genetically modified cells include, but are not limited to, stem cells, bone cells, cells comprising the semi-permeable component, and/or one or more cells or tissues.

Genetic modification of cells can influence bone restructuring and/or immunogenicity. Genetic modification of cells influences bone resorption and/or deposition. In an aspect, genetic modification of cells stimulates or inhibits immune reactions. Genetic modification of cells influences the permeability and/or the immuno-isolatory aspects of the semi-permeable component. Genetic modification of cells results in the release, secretion, diffusion and/or deposition of one or more immunogens and one or more adjuvants. Genetic modification of cells influences the binding of one or more immunogens and one or more adjuvants to the bone cage including, but not limited to, the bone wall and/or the semi-permeable component.

The bone cage comprises genetically modified stem cells including, but not limited to, embryonic, fetal, mesenchymal, and/or hematopoietic stem cells. The stem cells can be non-differentiated. The stem cells can be stimulated to differentiate. The stem cells can be non-differentiated mesenchymal stem cells. The mesenchymal stem cells can be differentiated into cells including, but not limited to, osteoblast, osteoclast or endothelial cells.

Cells can be genetically modified to increase or decrease bone restructuring. Stem cells, such as mesenchymal stem cells, can be genetically modified to be more or less osteoconductive when differentiated into osteoblasts or other components of bone. Methods for genetic modification of mesenchymal stem can be used. *Ann. Biomed. Eng.* 32:136-47, 2004; *Cloning Stem Cells* &:154-166, 2005, which are incorporated herein by reference.

Methods for modifying the osteoconduction of cells are described. For example, bone morphogenetic protein-2 (BMP-2) an osteoinductive agent, up-regulates the expression of osteogenic phenotypes, and induces bone nodule formation in a dose-dependent manner. *Spine* 29:960-5, 2004, which is incorporated herein by reference. Ciz, an inhibitor of osteoblast differentiation, interferes with bone morphogenic protein signaling, that leads to increased bone mass. In a further aspect, a BMP and/or Ciz gene can be transduced into cells and/or its expression up-regulated. Alternatively, a BMP and/or Ciz gene can be deleted from the cells by genetic knock out, RNAi, or antisense nucleic acid, and/or its expression down-regulated by genetic inactivation methods.

Cells can be genetically modified to increase or decrease immunogenicity and/or an immune response. In an aspect, the cells including, but not limited to, stem cells, bone cells, cells of the semi-permeable component, and/or the one or more cells or tissues, can be genetically modified to express immune recognition markers of the host, to secrete and/or express anti-inflammatory molecules, and/or to express or secrete immune-stimulatory molecules.

Device Including One or More Bone Cages Including a Semipermeable Component

The bone cage partially or completely surrounds and/or is surrounded by a semi-permeable component. The bone cage partially or completely encloses and/or is enclosed by a semi-permeable component. The semi-permeable component can be partially or completely comprised of the bone wall of the bone cage. The semi-permeable component can be partially or completely external to the bone wall of the bone cage. The semi-permeable component can be partially or completely internal to the bone wall or the bone cage. The semi-permeable component partially or completely encloses one or more immunogens and one or more adjuvants, optionally in combination with one or more cells or tissues that produce the one or more immunogen and/or the one or more adjuvant. The semi-permeable component can include, but is not limited to, artificial membrane, cells with tight junctions, plasma membrane, micelles, liposomes, virosomes, intracellular membranes, red blood cells, red blood cell ghosts, or aggregated platelets. In an aspect, the device including one or more bone cages can include red blood cells loaded with one or more immunogens and/or one or more adjuvants. Red blood cells loaded with one or more immunogens and/or one or more adjuvants can be useful in treatment of HIV infection by targeting immunogen and adjuvant to viral reservoirs carrying replication-competent HIV, including monocytes/macrophages. Cervasi et al., *J. Virol.* 80: 10335-10345, 2006; M.

Magnani, *Erythrocyte Engineering for Drug Delivery and Targeting*, Landes Bioscience, Austin Tex., 2002; "Erythrocyte-based drug delivery", *Expert Opinion on Drug Delivery*, 2: 311-322, 2005, which are incorporated herein by reference.

Semi-permeable component refers to a selective impediment to the passage of fluids and/or substances in the fluids. In an aspect, the semi-permeable component can prevent the passage of macromolecules and cells, but allows the passage of oxygen and/or nutrients. The passage of one or more immunogens and one or more adjuvants from the cage and/or products can be released by the one or more cells or tissues in the cage can be allowed. In an aspect, the passage of macromolecules, or macromolecules and cells can be allowed.

The semi-permeable component can include, but is not limited to, the bone wall, one or more semi-permeable membranes, cells with tight junctions, one or more plasma membranes, one or more intracellular membranes, one or more red blood cell ghosts, and one or more aggregated platelets or other cells. The semi-permeable component can be comprised of cells that are autologous, allogeneic, or xenogeneic with respect to a subject within whom the semi-permeable component may be implanted.

In an aspect, part or all of the semi-permeable component can be partially or completely non-immunogenic and/or can be recognized as self by a subject within whom it is implanted. In an aspect, part or all of the semi-permeable component can be partially or completely immunogenic and/or can be recognized as non-self by a subject within whom it is implanted.

The semi-permeable component can be comprised of cells that are cultured in vitro. The semi-permeable component can be comprised of cells that are genetically engineered. In an aspect, some or all of the cells can be genetically engineered to release, secrete, deliver, diffuse, and/or provide one or more immunogens and one or more adjuvants. In an aspect, some or all of the cells can be genetically engineered to be less immunogenic or to be more immunogenic. In yet other aspects, some or all of the cells can be genetically engineered to increase or decrease bone restructuring including, but not limited to, bone deposition and bone resorption. The semi-permeable component can be designed to at least partially or completely enhance restructuring.

The semi-permeable component can be a semi-permeable membrane. The semi-permeable membrane can include, but is not limited to, artificial membranes, biological membranes, and/or a combination of artificial and biologically-derived components. The manufacture and use of artificial semi-permeable membranes can be used. *Cell Transplant* 10:3-24, 2001, which is incorporated herein by reference. Artificial semi-permeable membranes include, but are not limited to, hydrogel membranes. *Biochim. Biophys. Acta* 804:133-136, 1984; *Journal of Biomedical Materials Research* 26:967-977, 1992; *J. Biomed. Mater. Res.* 26:967-977, 1992 and ultrafiltration membranes *Diabetes* 45:342-347, 1996; *J. Clin. Invest.* 98:1417-1422, 1996; *Transplantation* 59:1485-1487, 1995; *J. Biomech. Eng.* 113:152-170, 1991, both of which can be employed in the immuno-isolation of xenografts, for example *Ann. NY Acad. Sci.* 875:7-23, 1999. The membranes can be made, for example, from polymer films and thermoplastic hollow fibers. In addition, biological semi-permeable membranes can be used to encapsulate islet cells followed by implantation. *World J. Gastroenterol.* 11:5714-5717, 2005, which is incorporated herein by reference.

The semi-permeable component can be partially or completely composed of cells with tight junctions. Tight junction or zonula occludens refers to the intercellular junction that regulates diffusion between cells and allows the formation of barriers that can separate compartments of different composition. The intercellular gate formed by tight junctions is size and ion selective, among other things.

The cells with tight junctions can include, but are not limited to, epithelial and/or endothelial cells, or a combination. Both epithelial cells and endothelial cells can form tight junctions between cells. *Methods* 30:228-234, 2003, which is incorporated herein by reference.

The semi-permeable component can be comprised of cells with tight junctions where the cells are stem cells, or are differentiated from stem cells. Stem cells can be cultured in vitro to confluency on the interior and/or exterior of a bone scaffold of the desired shape and composition. The stem cells can include, but are not limited to, one or more of mesenchymal, embryonic, fetal, or hematopoietic stem cells. The stem cells can be stimulated to differentiate. The stem cells can differentiate into one or more of endothelial cells and epithelial cells. The stem cells can differentiate into bone cells, including, but not limited to, osteoblasts or osteoclasts. The stem cells do not differentiate into bone cells.

Methods for differentiating mesenchymal stem cells into endothelial cells *Basic & Clin. Pharmacol. & Toxicol.* 95:209-214, 2004 and hematopoietic stem cells into epithelial stem cells can be used. Stem cells can be relatively non-immunostimulatory, and to retain this characteristic following differentiation.

The semi-permeable component can be a plasma membrane. The plasma membrane can be made from red cell ghosts. Red cell ghosts can be created by removal of the erythrocyte cytoplasm by lysis followed by size-exclusion chromatography. In an aspect, one or more red cell ghosts encapsulate the one or more immunogens and one or more adjuvants optionally in combination with the one or more living cells and/or tissues. Methods of using red cell ghosts for drug delivery have been described. *Expert Opinion on Drug Delivery* 2:311-322, 2005; *Drug Delivery*, 2003 Taylor & Francis eds. 10(4):277-282; *BioDrugs* 18:189-198, 2004, which are incorporated herein by reference.

The one or more red cells ghosts can be fused to form an internal or external continuous or semi-continuous membrane. The fused red blood cell ghosts encapsulate the one or more immunogens and one or more adjuvants optionally in combination with the one or more living cells and/or tissues.

The semi-permeable component can include an aggregate of platelets. The bone cage is coated internally and/or externally with a platelet aggregating compound on which platelets aggregate in vitro and/or in vivo. The platelet aggregating compound includes, but is not limited to, fibrin, fibrinogen and/or thrombin. For example, fibrinogen is known to play a role in platelet aggregation. *Coll. Anthropol.* 29:341-9, 2005, which is incorporated herein by reference.

The device including one or more bone cages can comprise one or more immunogens and one or more adjuvants. The one or more immunogens and one or more adjuvants can be surrounded by the semi-permeable component. In an aspect, the one or more immunogens and one or more adjuvants can be adsorbed to the bone cage. The bone cage binds one or more immunogens and one or more adjuvants. The bone cage can bind covalently or ionically to one or more immunogens and one or more adjuvants. The bone cage can bind these molecules following their release from the bone cage and/or living cells and/or tissues. The one or more immunogens and one or more adjuvants comprise part of the bone wall. The one or more immunogens and one or more adjuvants can be bound to the semi-permeable component and/or one or more cells or tissues. The one or more immunogens and one or more adjuvants can be released from, provided by, secreted from, and/or diffuse from cells of the bone wall, the semi-permeable component, and/or one or more cells or tissues.

Biologically active molecules, e.g., one or more immunogens and one or more adjuvants, include any molecule that has a measurable biological action in a subject. For example, biologically active molecules would include, but not be limited to, any molecules described in this disclosure including, but not limited to, molecules that enhance or reduce bone restructuring including bone resorption and deposition, and/ or that enhance or reduce an immune response. These biologically active molecules would include, but not be limited to, pharmaceutically acceptable compounds including parenteral drugs, nutrients, and vitamins including, but not limited to, those described in this disclosure for the treatment of particular diseases or disorders.

The device including one or more bone cages includes one or more immunogens and one or more adjuvants optionally wherein one or more cells or tissues produce the one or more immunogens and/or the one or more adjuvants. A semi-permeable component can surround the one or more immunogens and one or more adjuvants optionally in combination with one or more cells or tissues. The cells can be autologous, allogeneic, or xenogeneic with respect to a subject within whom they may be implanted. The cells can be cultured in vitro. In an aspect, the cells can be non-immunogenic and/or are configured to be recognized as self by a subject within whom they is implanted. In an aspect, the one or more cells or tissues can be genetically engineered. The one or more cells or tissues can be genetically engineered to release, provide, diffuse and/or extrude the one or more immunogens and/or one or more adjuvants.

The one or more living cells and/or tissues can include, but are not limited to, cells and/or tissues that produce, express and/or secrete immune/inflammation-related, biochemical function-related, metabolism-related, and/or hormone-related biologically active molecules. The one or more living cells and/or tissues can include, but are not limited to, bacteria, yeast, islet cells, liver cells, thyroid cells, bone cells, and/or neural cells.

Other aspects include methods for delivering one or more immunogens and one or more adjuvants to a subject. The one or more immunogens and one or more adjuvants to be delivered to the subject are identified and/or selected, for example by health care workers including, but not limited to, physicians responsible for the health of the subject. One or more of the bone cages described above can be selected for delivery of the one or more immunogens and one or more adjuvants. The one or more immunogens and one or more adjuvants can be provided with or added to the bone cages, and/or released from one or more cells or tissues provided with or added to the bone cages, and/or released from the cells comprising the semi-permeable component provided with or added to the bone cages. The device including one or more bone cages including the one or more immunogens and one or more adjuvants optionally in combination with cells or tissues and/ or semi-permeable component can be implanted in the subject to allow delivery of the one or more immunogens and one or more adjuvants.

Bone Cage Device Including Immunogen and Adjuvant as a Vaccine

The device including one or more bone cages includes one or more immunogens provided in combination with one or more adjuvants, for active immunization of a subject against a pathological condition, e.g., infectious disease or neoplastic disease. An immunogen is a substance that, as a result of coming in contact with appropriate tissues of an animal body, can induce an immune response, for example formation of antibodies and/or cell-mediated immunity. Information and examples of immune responses can be found in Delves et al, *Roitt's Essential Immunology*, 11th edition, Wiley-Blackwell, 2006, which is incorporated herein by reference. An immunogen includes any type of biological or synthetic compound including, but not limited to, a compound from a pathogenic organism, a substance endogenous to the subject causing a pathological condition in the subject, or a synthetic substance.

Immunogens from Pathogens.

The device including one or more bone cages can be used to administer one or more immunogens and one or more adjuvants that constitute a vaccine against a pathogen, e.g., viruses, bacteria, fungi, and parasites. Examples of pathogens include, but are not limited to, viruses, e.g., herpes simplex virus (HSV), hepatitis A virus, hepatitis B virus (HBV), hepatitis C virus (HCV), cytomegalovirus (CMV), dengue virus, flavivirus, Epstein-Barr virus (EBV), influenza virus, measles virus, human immunodeficiency virus (HIV), human papilloma virus (HPV), Japanese encephalitis virus, norovirus, polio virus, rotavirus, respiratory syncytial virus (RSV), ebola virus, rabies virus, Sendai virus, severe acute respiratory syndrome (SARS) coronavirus, smallpox virus, West Nile virus, yellow fever virus; bacteria, e.g., *Mycobacterium tuberculosis* (tuberculosis), *Chlamydia trachomatis* (trachoma), *Haemophilus influenzae* (otitis media), *Neisseria meningitidis* (meningitis), *Streptococcus pneumoniae* (pneumonia), *Escherichia coli* (intestimal disorders) *Staphylococcus aureus, Bacillus anthracic* (anthrax), *Borrelia burgdorferi* (Lyme's disease); and parasites, e.g., *Plasmodium* (malaria), *Leishmania, Trypanosoma cruzi, Trypanosoma brucei, Ascaris lumbricoides* (ascariasis), hookworm, *Onchocerca volvulus* (river blindness), *Schistosoma* (schistosomasis), *Trichuris trichiura* (trichurasis).

Immunogens used with the device including one or more bone cages as a vaccine against a pathogen can be derived from any of a number of sources including, but not limited to, living microorganisms that are naturally avirulent or that have been modified to attenuate their virulence while retaining adequate immunogenic properties; heat and/or chemically inactivated/killed virulent microorganisms; immunogens extracted from or secreted by an infectious agent; immunogens produced by recombinant DNA technology; a live, recombinant vector producing immunogens in vivo in the vaccinated host; plasmid DNA; immunogens produced by chemical synthesis in vitro. Examples of commonly administered vaccines containing live, attenuated microorganisms include those for yellow fever, measles, oral polio, varicella, rubella, mumps, and rotavirus. Examples of commonly administered vaccines containing inactivated/killed microorganisms include those for influenza, cholera, bubonic plague, polio, rabies and hepatitis A. Examples of commonly administered vaccines derived from toxins include those for tetanus and diphtheria. Examples of vaccines using one or more isolated immunogens from a microorganism include the hepatitis B vaccine that is composed of only the surface proteins of the virus and the virus-like particle (VLP) vaccine against human papillomavirus (HPV).

The immunogen can be a live, attenuated pathogen, e.g., a live, attenuated virus, bacteria, or parasite. In some instances, the live attenuated pathogen can be naturally-occurring. In an aspect, the live attenuated pathogen is generated by environmental and/or genetic manipulation. Examples of environmental manipulation include, but are not limited to, chemical or radiation induced attenuation of the virulent strain or extensive passage of the virulent strain at suboptimal temperatures. For example, cold adapted strains of influenza A and influenza B have been developed by multiple passages at progressively lower temperatures in primary chicken kidney cells, resulting in attenuated influenza strains that only replicate at 25° C. or well below normal mammalian body temperature. Murphy & Coelingh, *Viral Immunol.* 15:295-323, 2002, which is incorporated herein by reference. As another example, non-replicating, but metabolically active *Plasmodium falciparum* sporozoites for malaria vaccination have been generated by irradiation. Luke & Hoffman, *J. Exp. Biol.* 206:3803-3808, 2003, which is incorporated herein by reference. Alternatively, live, attenuated pathogen can be generated by reverse genetics, whereby the infectious pathogen is produced entirely from recombinant cDNA and predetermined changes in the nucleotide sequence are introduced by site-directed mutagenesis to generate a new, attenuated vaccine strain. See, e.g., Murphy & Collins, *J. Clin. Invest.* 110: 21-27, 2002; Neumann, et al., *Proc. Natl. Acad. Sci. USA.* 96:9345-9350, 1999, which are incorporated herein by reference.

The immunogen can be an inactivated pathogen, e.g., an inactivated virus, bacteria, or parasite, in which the ability of the pathogen to replicate has been eliminated, but the ability to mount an immune response remains intact. An inactivated virus, bacteria or parasite can be generated using heat, UV irradiation, formalin or other chemicals such as β-propiolactone or a photoinducible agent. For example, the Ebola virus can be inactivated with the photoinducible alkylating agent 1,5-iodonaphthylazide without compromising immunogenicity and structural integrity. See, e.g., Warfield, et al., *J. Infect. Dis.* 196 Suppl 2:S276-S283, 2007, which is incorporated herein by reference.

In an aspect, the immunogen can be all or part of a cell lysate generated, for example, from a microbial antigen, viral antigen, parasite antigen, fungal antigen, plant antigen, animal antigen, endogenous antigen, or synthetic antigen. A cell lysate can be generated by mechanical methods, non-mechanical methods, or a combination thereof. Examples of mechanical methods for generating a cell lysate include, but are not limited to, sonication, homogenization by dounce or glass beads, and osmotic lysis. Examples of non-mechanical methods include, but are not limited to, detergents, alkali, and enzymatic degradation (e.g., lysozyme, lysostaphin, zymolyase, lyticase). The immunogen can be a whole cell lysate. Alternatively, the immunogen can be a subfraction of the whole cell lysate, e.g., the cell wall subfraction. A whole cell lysate can be subfractionated by differential centrifugation to generate a cell wall/membrane fraction. Alternatively, a whole cell lysate can be subfractionated using beads or other particles that include one or more antibody directed to a biomolecule associated with one or more cell subfraction. Immunogens can include all or parts of viruses, bacteria, parasites, and other microorganisms, e.g., coats, capsules, cells walls, flagella, fimbrae, and toxins.

The immunogen can be one or more specific biomolecules associated with the pathogen, particularly biomolecules expressed on the surface of the pathogen. Pathogen associated biomolecules can be purified from a natural source. Alternatively, pathogen associated biomolecules, for example, proteins, can be generated by recombinant DNA technology using standard methodologies. Recombinant DNA technology can also be used to produce enzymes required for modification to endogenous proteins, lipids, polysaccharides or lipopolysaccharides. For example, cDNA encoding all or part of an immunogen or one or more enzyme required for modification or production thereof, can be isolated using polymerase chain reaction (PCR) amplification in combination with primers based on DNA sequence available in the Genbank Database. Benson, et al., *Nucleic Acids Res.* 36:D25-30, 2008, which is incorporated herein by reference. Production or modification of an immunogen can include, e.g., cDNA encoding glycosylation enzymes for glycosylation of a protein, glycoprotein, or lipopolysaccharide. cDNA encoding glycosylation enzymes can be configured to correct abberant glycosylation in protein, glycoprotein, or lipopolysaccharide associated with tumor cells. The modification may only be needed for surface expression or may be part of the immunogen itself. In some instances, the recombinant expression of one or more pathogen protein can result in formation of viral-like particles in which expressed capsid proteins, for example, spontaneously assemble into particles that are structurally similar to authentic virus. *Roy & Noad Human Vaccines* 4:5-8, 2008, which is incorporated herein by reference.

The immunogen can be produced by cells encapsulated in the bone cage. The cells encapsulated in the bone cage may naturally express the immunogen, or the cells may be genetically engineered to express the immunogen. The genetically engineered cells can be bacteria, yeast, parasites, insect cells, or mammalian cells. The mammalian cells can be autologous, allogeneic or xenogeneic relative to the subject. In an aspect, the immunogen can be a live, attenuated pathogen, e.g., virus or bacteria that is propagated in the encapsulated cells. Alternatively, the immunogen can be one or more specific proteins generated in the cells using standard recombinant DNA techniques. For example, the cDNA sequence corresponding to the immunogen can be generated using standard polymerase chain reaction (PCR) amplification and an appropriate cDNA library or reverse-transcribed mRNA with primers designed based on the known cDNA sequence of the immunogen from, e.g., the GenBank Database. Benson, et al., *Nucleic Acids Res.* 36:D25-30, 2008, which is incorporated herein by reference. In an aspect, site-directed mutations can be made to nucleotide sequence of codons within the immunogen coding sequence to align the sequence with mammalian codon usage to enable more efficient expression in mammalian cells. See, e.g., Garmory, et al., *Genetic Vaccines Ther.* 1:2, 2003, which is incorporated herein by reference. The cDNA encoding the immunogen is cloned into an expression vector, transfected into a cell line, and cloned cells expressing the immunogen biomolecule, which may or may not be modified by glycosylation and/or lipidation, are identified using standard methods. The cells can transiently or stably express the immunogen. The relative expression of the immunogen by the cells can be assessed using any of a number of assay systems. The expression of messenger RNA (mRNA) corresponding to the immunogen can be assessed by quantitative PCR, Northern analysis, in situ hybridization, or other methods designed to assess the presence and/or quantity of a specific mRNA in a cell. The expression of actual immunogen in the cells can be assessed by Western analysis, immunocytochemistry, or other methods designed to assess the presence and/or quantity of a specific protein in a cell. Secretion of the immunogen out of the genetically engineered cell can be assayed, for example, by analysis of in vitro culture medium using, e.g., an immunoassay system such as an enzyme-linked immunosorbent assay (ELISA) with immunoreagents specific for the immunogen. Secretion of the immunogen out of the genetically engineered cell can further be assayed, for example, by analysis in vivo for presence of the immunogen in serum or tissue of the subject. In an aspect, the genetically engineered cells expressing the immunogen are encapsulated in alginate or other physiologically compatible encapsulation medium prior to incorporation into the bone cage. See, e.g., Read, et al., *Nature Biotechnol.* 19:29-34, 2001; Orive, et al., *Nature Medicine.* 9:104-107, 2003; U.S. Patent Application Nos. 2004/0005302; 2007/0258901; 2008/0107686 which are incorporated herein by reference.

The immunogen can include one or more polypeptides, which may or may not be modified by glycosylation and/or lipidation. In some instances, the one or more polypeptides can represent one or more immunogenic portions of a protein associated with a pathogen. The immunogenic polypeptides can be predicted using computational modeling. See, e.g., Florea, et al., Proceedings 2003 IEEE Bioinformatics Conference, Aug. 11-14, 2003, p. 17-26; Toussaint, et al., *PLoS Comput. Biol.* 4:e1000246, 2008, which are incorporated herein by reference. Alternatively, the one or more peptides can be mimotopes that act as surrogate immunogens for biomolecules that are otherwise not very immunogenic such as, for example, the carbohydrates found on the surface of some pathogens. See, e.g., Monzavi-Karbassi, et al., *Trends Biotechnol.* 20:207-214, 2002, which is incorporated herein by reference. A mimotope is a macromolecule that mimics the structure of an epitope or that portion of the immunogen recognized by an antibody or other receptor, and is able to induce an antibody response identical to that elicited by the authentic epitope. Mimotopes can be synthetic compounds, e.g., shaped gels. Alternatively, mimotopes can be synthetic peptides screened from combinatorial solid-phase peptide phage libraries using an antibody or other receptor that normally binds to the immunogen of interest. For example, studies describe screening a peptide library with a neutralizing, protective antibody against respiratory syncytial virus (RSV) to identify peptides that mimic the epitope of the fusion (F) protein of the virus. Steward. *Biologicals* 29:215-219, 2001, which is incorporated herein by reference. Once identified, the one or more peptides can be generated using either recombinant DNA techniques or by chemical synthesis with a commercially available peptide synthesizer (e.g., ABI 433A Peptide Synthesizer from Applied Biosystems, Inc., Foster City, Calif.).

The device including one or more bone cages including an immunogen and an adjuvant can further include one or more circular plasmid DNAs that include genes encoding all or part of one or more target immunogens, or one or more enzyme required for modification or production thereof, e.g., protein glycosylation or production of lipopolysaccharide, under the transcriptional control of a promoter region active in host cells. Promoters include, but are not limited to, SV40 promoter, rous sarcoma virus (RSV) promoter, adenovirus promoter, cytomegalovirus (CMV) immediate early promoter. In an aspect, site-directed mutations can be made to codons within the sequence encoding the immunogen or enzyme to align the sequence with mammalian codon usage to enable more efficient in vivo expression from the plasmid DNA. See, e.g., Garmory, et al., *Genetic Vaccines Ther.* 1:2, 2003, which is incorporated herein by reference. The bone cage including the plasmid DNA encoding an immunogen and/or an adjuvant can be administered to a subject, taken up by the cells in proximity to the site of administration, and the host cells expressing the immunogen and/or the adjuvant in the subject produce the pathogen-related immunogen. The plasmid DNA can be incorporated as a hydrogel within the bone cage. One or more DNA vaccines can be used within the bone cage. For example, the HIV DNA vaccine pGA2/JS2 (from GeoVax, Atlanta, Ga.) expresses several HIV proteins including those encoded by the genes gag, pro, RT, env, tat, vpu, and rev. DNA based vaccines, e.g., for HIV, avian influenza H5N1, SARS, hepatitis C virus, West Nile virus, tuberculosis, and malaria, have been or are currently undergoing clinical trials and a DNA vaccine for West Nile virus has been approved for veterinary use.

Tumor Immunogens.

The device including one or more bone cages can be used to administer one or more immunogens and one or more adjuvants that constitute a vaccine to treat neoplastic disease, e.g., tumor cells or cancer cells. Cancer vaccines are designed to stimulate a subject's immune system to recognize and eliminate cancer cells. Cancer vaccine strategies can include, for example, whole cell vaccines, antigen therapy vaccines, antigen-presenting cell vaccines, and non-specific therapy and cytokine therapy. Cancer vaccines can be used against neoplastic diseases that include, but are not limited to, pancreatic cancer, prostate cancer, cervical cancer, breast cancer, ovarian cancer, bladder cancer, kidney cancer, multiple myeloma, non-small cell lung cancer, colorectal cancer, leukemia, melanoma, glioma, gastric cancer, esophageal cancer, head and neck cancer, hepatic cancer, renal cell carcinoma, testicular cancer, or uterine cancer.

The immunogen included in a device including one or more bone cages for use as a cancer vaccine can be all or part of a tumor cell. The immunogen can be a multivalent cell-culture of different tumor cells lines established ex vivo prior to use in the bone cage. The cell culture can include non-autologous immunogens and the use of multiple cell lines to help ensure that at least some of the antigens in the vaccine are shared by the subject's own tumor. Alternatively or in addition, the immunogen can include an autologous cell line prepared by harvesting tumor cells from the subject to be treated. See, e.g., Berger, et al., *J. Pharm. Pharmaceut. Sci.* 10:144-152, 2007, which is incorporated herein by reference. The autologous and/or non-autologous tumor cells can be killed prior to (re)introduction into the subject. An example of a tumor killing agent is dinitrophylate. Alternatively, the autologous tumor cells can be otherwise alive but inactivated by lethal irradiation. The autologous or non-autologous tumor cells can be genetically modified by recombinant DNA techniques to boost the immune response. For example, the autologous or non-autologous tumor cells can be genetically engineered to ectopically express IL-2, IL-12, IL-21, GM-CSF, or other cytokine. The device including one or more bone cages including tumor cells can be administered alone or in combination with autologous antigen presenting cells, e.g., dendritic cells.

The immunogen can be one or more tumor-associated antigens. A tumor-associated antigen can be, for example, a endogenous protein or other molecule, e.g., lipid, lipoprotein, polysaccharide or lipopolysaccharide, that is otherwise well sequestered from the immune system, that is normally produced in extremely small quantities, that is normally produced only in certain stages of development, that carries inappropriate modification such as glycosylation, or whose structure is modified due to one or more mutation, or a combination thereof. See, e.g., Hakomori S. *Proc Natl Acad Sci USA.* 99:10231-10233, 2002, which is incorporated herein by reference. Alternatively, the tumor-associated antigen can be a viral protein derived from a virally induced tumor. Examples of tumor associated antigens that might be used as immunogens include, but are not limited to, prostatic acid phosphatase (PAP), carcinoembryonic antigen (CEA), a feto-protein, prostate specific antigen (PSA), CA-125, $\beta$2-microglobulin, $\beta$-hCG, bombesin, CA 19-9, CA 15-3, chromogranin A, thyroglobulin, TA 90, MART-1/Melan-A, MART-2, tyrosinase, Gp100, MAGE-1, MAGE-3, BAGE, GAGE, URLC10, Her2/neu, GM2, MUC1, MUC2G, globo H, LAGE-1, TTK-567, neuron-specific enolase (NSE), prostate-specific membrane antigen (PSMA). An extensive list of tumor antigens is provided in Novellino, et al., Abstract, *Cancer Immunol. Immunother.* 54:187-207, 2005, which is incorporated herein by reference. All or part of a tumor antigen can be produced as recombinant protein using standard techniques. For example, cDNA encoding all or part of a tumor antigen, or one or more enzyme required for modification or production thereof, can be isolated using polymerase chain reaction (PCR) amplification in combination with primers based on DNA sequence available in the Genbank Database. Benson, et al., *Nucleic Acids Res.* 36:D25-30, 2008, which is incorporated herein by reference. Production or modification of an immunogen can include, e.g., cDNA encoding glycosylation enzymes for glycosylation of a protein, glycoprotein, or lipopolysaccharide. cDNA encoding glycosylation enzymes can be configured to correct aberrant glycosylation in protein, glycoprotein, or lipopolysaccharide associated with tumor cells. Alternatively, the cDNA encoding all or part of a tumor antigen can be from a commercial source (from, e.g., Origene, Rockville, Md.).

One or more immunogens in a device including one or more bone cages useful as a tumor antigen in a cancer vaccine can be identified using a number of analytical methods including, but not limited to, genomics (e.g., comparative genomic hybridization (CGH) array, spectral karyotyping (SKY)), transcriptomics (e.g., microarrays, representational difference analysis (RDA), serial analysis of gene expression (SAGE), suppression subtractive hybridization (SSH), cancer profiling array (CPA), quantitative real time PCR (QPCR), RNA-in situ hybridization), proteomics (2-dimensional gel electrophoresis, mass spectrometry, glycomics, immunohistochemistry (IHC), tissue arrays, fluorescence activated cell sorting (FACS), serological identification of antigens by expression cloning (SEREX)), antibody technologies (e.g., murine or human monoclonal hybridomas, phage display libraries), or combinations thereof. See, e.g., Carter, et al., *Endocrine-Related Cancer* 11:659-687, 2004, which is incorporated herein by reference.

One or more immunogens in a device including one or more bone cages for use as a cancer vaccine can be produced by cells encapsulated in the bone cage. The cells encapsulated in the bone cage can naturally express the immunogen. Alternatively, the cells can be genetically engineered to express the immunogen. The genetically engineered cells can be bacteria, yeast, parasites, insect cells, or mammalian cells. The mammalian cells can be autologous, allogeneic or xenogeneic relative to the subject. The immunogen can be one or more specific tumor antigens generated in the cells using standard recombinant DNA techniques as described herein. The cDNA encoding the immunogen, or one or more enzymes required for modification or production thereof, is cloned into an expression vector, transfected into a cell line, and cells expressing the immunogen biomolecule are identified using standard methods. The cells can transiently or stably express the immunogen. The relative expression of the immunogen by the cells can be assessed using any of a number of assay systems as described herein. In an aspect, the genetically engineered cells expressing the immunogen are encapsulated in alginate or other physiologically compatible encapsulation medium prior to incorporation into the bone cage. See, e.g., Read, et al., *Nat. Biotechnol.* 19:29-34, 2001; U.S. Patent Application Nos. 2008/0107686 and 2007/0258901 which are incorporated herein by reference.

One or more immunogens can be one or more peptide epitopes derived from a tumor antigen. See, e.g., Sangha & Butts, *Clin. Cancer Res.* 13:4652s-4654s, 2007, which is incorporated herein by reference. In an aspect, the one or more peptides can represent one or more immunogenic portions of a protein associated with a tumor. The immunogenic peptides can be predicted using computational modeling. See, e.g., Florea, et al., *Proceedings* 2003 *IEEE Bioinformatics Conference*, Aug. 11-14, 2003, p. 17-26; Toussaint, et al., *PLoS Comput. Biol.* 4:e1000246, 2008, which are incorporated herein by reference. The immunogen can be one or more peptide mimotopes that mimic epitopes associated with tumor-associated carbohydrate antigens or other tumor associated antigens. See, e.g., Bramswig, et al., *Clin. Cancer Res.* 13:6501-6508, 2007, which is incorporated herein by reference. Alternatively, the immunogen can be a synthetic peptide that combines a tumor associated carbohydrate antigen covalently linked to a T-cell epitope and a B-cell epitope, enabling the immunogen to elicit both a humoral response and a cellular immune response. U.S. Patent Application No. 20090041836, which is incorporated herein by reference. In another aspect, a melanoma vaccine can include a device including one or more bone cages including a peptide derived from the tumor antigen gp100 linked to the T-helper epitope from tetanus toxoid. Slinghuff, et al., *Clin. Cancer Res.* 7:3012-3024, 2001, which is incorporated herein by reference. The peptides for use as immunogens in the bone cage can be generated using chemical synthesis or can be incorporated into a plasmid DNA. See, e.g., Fest, et al., *Cancer Res.* 66:10567-10575, 2006, which is incorporated herein by reference.

One or more immunogens can be one or more circular plasmid DNAs that include genes encoding all or part of one or more target immunogens, or one or more enzyme required for modification or production thereof, under the transcriptional control of a promoter region active in host cells. Promoters include, but are not limited to, SV40 promoter, rous sarcoma virus (RSV) promoter, adenovirus promoter, cytomegalovirus (CMV) immediate early promoter. The bone cage including the plasmid DNA encoding an immunogen and/or an adjuvant can be administered to a subject, taken up by the cells in proximity to the site of administration, and the host cells in the subject produce the pathogen-related immunogen. The plasmid DNA can be incorporated as a hydrogel within the bone cage. One or more DNA vaccines can be used within the bone cage. DNA vaccines for a number of cancers are currently undergoing clinical evaluation and include e.g., vaccines for prostate cancer, breast cancer, kidney cancer, liver cancer, cervical cancer, lymphoma, and melanoma.

One or more immunogens can be an antigen presenting cell, for example, a dendritic cell that has been genetically modified to express one or more tumor antigens. Autologous dendritic cells can be isolated from a subject by leukopheresis, transfected with an expression vector that includes, for example, DNA sequence encoding all or part of one or more tumor antigens, and subsequently used for immunization of the subject. See, e.g., Nakamura, et al., *Clin. Cancer Res.* 8:2742-2749, 2002, which is incorporated herein by reference. Alternatively, the autologous dendritic cells can be stimulated or activated ex vivo in the presence of a tumor cell lysate or mixture of tumor antigens and subsequently used for immunization of a subject. See, e.g., Hirschowitz, et al., *J. Clin. Oncol.* 22:2808-2815, 2004, which is incorporated herein by reference.

Other Immunogens.

The device including one or more bone cages can be used to administer one or more immunogens and one or more adjuvants that constitute a vaccine to treat a pathological condition in the subject, e.g., an allergic response, wherein the immunogen can be an allergen. Examples of allergens include, but are not limited to, inhaled allergens (e.g., grass, weed, and tree pollens, mold spores, chemicals, cockroach calyx, dust mite excretions, animal dander, saliva), ingested allergens (e.g., food, food supplements, home remedies, medications), contact allergens (e.g., cosmetics, fragrances, plants, detergents, chemicals, metals, latex), and injected allergens (e.g., medications, insect venom). For example, a number of clinical trials are underway to develop a vaccine against peanut allergies. In this latter instance, the immunogen can be peanut powder or one or more isolated peanut proteins such as, for example, Ara h1, Ar2 hw, and Ara h3. See, e.g., Li, et al., *J Immunol.* 170:3289-3295, 2003, which is incorporated herein by reference.

The device including one or more bone cages includes one or more immunogens that can be one or more biomolecules associated with a pathogenic state in the subject including, but not limited to, neoplastic disease, atherosclerosis, hypertension, autoimmune disease, diabetes, or substance addiction. A method for treating a pathological condition in the subject includes a device including one or more bone cages and one or more immunogens and one or more adjuvants that constitute a vaccine to treat a condition in the subject, wherein the pathological conditions includes, but is not limited to, atherosclerosis (*Cardiol Rev.* 16: 288-300, 2008), hypertension (*Drugs*, Abstract; 68: 2557-2560, 2008), obesity (*PLoS ONE*, 3: e3163, 2008), autoimmune diseases including diabetes (*Immunol Cell Biol*, Abstract; 86: 139-145, 2008), drug or substance addiction (*Ann NY Acad Sci*, 1141: 257-269, 2008), which are incorporated herein by reference.

A method for treating atherosclerotic disease can include providing a device including one or more bone cages wherein oxidized LDL is an immunogen to treat atherosclerotic disease. A method for treating hypertension can include providing an immunogen to inhibit renin-angiotensin system (RAS), e.g., modified angiotensin I coupled to keyhole limpet haemocyanin, or a conjugate of angiotensin II linked to virus particles, as an immunogen to treat disease in the subject.

A method for treating a pathological condition includes treatment for drug or substance addiction. The device including one or more bone cages can include norcocaine with inactivated cholera toxin as an immunogen. A large protein molecule attaches to cocaine, which stimulates response from antibodies which destroy the molecule. This prevents the cocaine from crossing the blood-brain barrier negating the euphoric high and rewarding effect of cocaine caused from stimulation of dopamine release in the mesolimbic reward pathway. Martell et al., *Biol. Psychiatry* 58: 158-164, 2006; *Ann NY Acad Sci*, 1141: 257-269, 2008, which are incorporated herein by reference.

A method for treating obesity can includes providing a device including one or more bone cages wherein GIP (gastric inhibitory peptide; or glucose-dependent insulinotropic polypeptide) is an immunogen to treat disease in the subject. A method for treating autoimmune disease, e.g., type 1 diabetes, can include providing self-antigen as an immunogen to treat disease in the subject. A method for treating substance abuse can include providing an antibody to bind the drug in the bloodstream, thereby blocking entry and/or reducing the rate of entry of the drug into the central nervous system.

The one or more immunogens includes, for example, β-amyloid associated with Alzheimer's disease. See, e.g., Wilcock & Colton, *J. Alzheimers Dis.* 15:555-569, 2008, which is incorporated herein by reference.

In an aspect, the device including one or more bone cages can be used to administer one or more immunogens derived from drugs of abuse such as, for example, nicotine, cocaine, methamphetamine, phencyclidine, and morphine. See, e.g., Orson, et al., *Ann. N.Y. Acad. Sci.* 1141:257-269, 2008, which is incorporated herein by reference.

Adjuvants. The device including one or more bone cages include one or more immunogens in combination with one or more adjuvants. Adjuvants are used as immune potentiators or immunomodulators to improve the immune response to the vaccine immunogens. An adjuvant can be incorporated into a vaccine formulation to enhance, accelerate and/or prolong the specific immune response towards the desired response to vaccine immunogens. Adjuvants potentially enhance the immunogenicity of immunogens, modify the nature of the immune response, reduce the amount of immunogen needed for a successful immunization, reduce the frequency of booster immunizations needed and improve the immune response, for example in elderly and immunocompromised vaccinees. In addition, adjuvants can aid in presentation of the antigen, defined by the physical appearance of the antigen in the vaccine; antigen/adjuvant uptake; distribution (targeting to specific cells); immune potentiation/modulation that includes activities that regulate both quantitative and qualitative aspects of the ensuing immune responses; the protection of the antigen from degradation and elimination. Selectively, adjuvants can be used to optimize a desired immune response, e.g., with respect to immunoglobulin classes and induction of cytotoxic or helper T lymphocyte responses. In addition, certain adjuvants can be used to promote antibody responses at mucosal surfaces.

Adjuvants can be classified according to their source (natural, synthetic or endogenous), mechanism of action, or physical or chemical properties. The current most common described adjuvant classes include mineral salts, e.g., aluminum hydroxide and aluminum or calcium phosphate gels; oil emulsions and surfactant based formulations, e.g., MF59 (sorbitan trioleate, microfluidized detergent stabilized oil-in-water emulsion), QS21 (purified saponin), AS02 (SBAS2, oil-in-water emulsion, MPL, and QS-21), Montanide ISA-51, and ISA-720 (stabilized water-in-oil emulsion); particular adjuvants, e.g., virosomes (unilamellar liposome vehicles, e.g., those incorporating influenza hemagglutinin), AS04 ([SBAS4]A1 salt with MPL), ISCOMS (structured complex of saponins and lipids), polylactide co-glycolide (PLG), archaeosomes (liposomes comprised of glycerolipids of Archaea); microbial derivatives (natural and synthetic), e.g., monophosphoryl lipid A (MLP), Detox (MLP, *M. phlei* cell wall skeleton), AGP (RC-529, synthetic acylated monosaccharide), DC-Chol (self-assembling lipoidal immunostimulators), OM-174 (lipid A derivative), CpG oligonucleotides (synthetic oligonucleotides containing immunostimulatory CpG motifs), modified LT and CT (genetically modified bacterial toxins); endogenous human immunomodulators, e.g., GM-CSF, IL-2 (cytokines that can be administered either as protein or plasmid-encoded), TRICOM (B7-1, ICAM-1, and LFA-3), Immudaptin (C3d tandem arrays); inert vehicles, e.g., gold particles.

In general, adsorbents and particulate adjuvants aid in presentation of the antigen to the immune system, whereas microbial, synthetic and endogenous adjuvants can directly stimulate or modulate the immune system. Adjuvant emulsions can be used to present the immunogen to the immune system, promote slow immunogen release and protect the immunogen from rapid elimination. Mineral salt adjuvants can be used to induce an inflammatory response at the site of injection, promote synthesis of pro-inflammatory cytokines, and stimulate innate immunity important for the initial steps of the immune response.

In an aspect, the adjuvants are one or more immunomodulators, such as but not limited to, interleukin 2 (IL-2), IL-12, IL-21, GM-CSF, or other cytokines, alone or in combination, that are capable of vigorously driving immune responses stimulated by vaccines. As an example, a multivalent melanoma cell vaccine appears more effective when encapsulated into liposomes containing IL-2 or GM-CSF. See, e.g., van Slooten et al., *Int J Pharm*. 183: 33-36, 1999; Koppenhagen et al., *Clin Cancer Res*. 4: 1881-1886, 1998; van Slooten et al., *Pharm Res*. 17: 42-48, 2000; Ben-Yehuda et al., *Vaccine* 21: 3169-3178, 2003; Reynolds, et al., *Clin. Cancer Res*. 9: 657-662, 2003, which are incorporated herein by reference. Examples of other immunomodulatory adjuvants include, but are not limited to, interferons (IFN) IFN-α, IFN-β, and IFN-γ; other interleukins (IL) IL-1, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); erythropoietin (EPO); and thrombopoietin (TPO); any of a number of chemotactic cytokines (chemokines) including, but not limited to, CC chemokines CCL1 through CCL28 exemplified by RANTES (CCL5), MCP-1 (CCL2), LARC (CCL20), MIP-1 α (CCL3), and MDC (CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF; and other immunodulators anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-β- and VEGF; soluble receptors to tumor necrosis factor receptor (sTNFr); soluble interleukin receptors sIL-1r and sIL-2r; C-reactive protein; CD11b; histamine; serotonin; apolipoprotein A1; β2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins. See, e.g., Tomai, et al., *Expert Rev. Vaccines* 6:835-847, 2007, which is incorporated herein by reference.

In an aspect, the adjuvant can be a molecule, for example a pathogen-associated molecular patterns (PAMPs), that is recognized by a component of the innate immune system, called a pattern recognition receptor (PRRs). PRRs can, for example, include secreted molecules that circulate in blood and lymph and can trigger responses such as the complement cascade and subsequent accelerated phagocytosis; surface receptors on phagocytic cells like macrophages that bind the pathogen for engulfment, for example mannose-binding protein (MBP); and receptors that bind the pathogen initiating a signal leading to the release of effector molecules such as cytokines. In a further aspect, the adjuvant can be a molecule that binds to and/or induces a response in a PRR that is one or more Toll-like receptor (TLRs). TLRs, which can exist as heterodimers, play an important role in immune response by recognizing molecular patterns associated with pathogens. Ligands that are or mimic PAMPs and activate immune cells via TLRs can be used as vaccine adjuvants. See, e.g., Pulendran and Ahmed, *Cell*, 124:849-63, 2006; Kanzler et al., *Nat. Med.* 13: 552-559, 2007; Graham *PLoS Med.* 3:e57, 2006, Celis *Cancer Res.* 67: 7945-7947, 2007, Tomai, et al., *Expert Rev. Vaccines* 6:835-847, 2007, which are incorporated herein by reference. Molecules recognized by TLR2 include a wide array of microbial molecules representing broad groups of species such as gram-positive and gram-negative bacteria, as well as mycoplasma and yeast (e.g., Pam3CSK4; HKLM). TLR2 can be a heterodimer with TLR1 or TLR6. TLR3 ligands include double stranded RNA, a molecular pattern associated with viral infection. Polyinosine-polycytidylic acid (poly(I:C)), a synthetic analog of dsRNA, is the ligand of choice for TLR3. Molecules recognized by TLR4 include lipopolysaccharide (LPS) and lipid A. Low toxicity versions of LPS, monophosphoryl lipid A (MPL) and a chemical mimetic, RC529 are efficient adjuvants for CD4-positive T-cells. Thompson, et al., *J. Leukoc. Biol.* 78:1273-1280, 2005, which is incorporated herein by reference. One TLR5 ligand is flagellin, the major component of the bacterial flagellar filament. TLR7/TLR8 ligands include GU-rich short single-stranded RNA as well as small synthetic molecules such as imidazoquinolines and nucleoside analogues (e.g., Imiquimod, Resiquimod (R-848)). TLR9 ligands include specific unmethylated CpG oligodeoxynucleotides (CpG-ODN) sequences that distinguish microbial DNA from mammalian DNA, and synthetic CpG-ODN are used in vaccine therapies. See, e.g., Kanzler et al., *Nat. Med.* 13: 552-559, 2007, which is incorporated herein by reference. Additional natural and synthetic TLR agonists include, but are not limited to, IMO-2055, IMO-2125, QAX935, monophosphoryl lipid A, loxoribine, isatoribine, 3M-001, 3M-002, 3M-003, SD-101, and CPG 7909.

The adjuvant can be one or more biomolecules that stimulate activation, proliferation, and/or differentiation of T cell lymphocytes. Examples of T cell stimulators include, but are not limited to, enterotoxins, MHC-peptide complexes, CD80 (B7-1), B7-2, antibodies to CD2, CD28, CD3; phorbol esters, IL-2, protein kinase C activators such as phorbol myristate acetate, calcium ionophores such as inonmycin, agents that trigger T cell receptor (TCR/CD3) activation, CD86, tumor necrosis factor (ligand) superfamily member 14 (TNFSF14), CD5, and ICOS.

The adjuvant can be one or more biomolecules that stimulate activation, proliferation, and/or differentiation of B cell lymphocytes. Examples of B cell stimulators include, but are not limited to, antigen dependent lipopolysaccharide, CD98hc, phorbol esters, interleukin 4 (IL-4), interleukin 15 (IL-15), tumor necrosis factor (ligand) super family member 13b (TNFSF13B), TNFSF13C (B cell-activating factor; BAFF), TLR7 and TLR9 agonists (e.g., 852A, 3M-003, CpG2006), IFN-α or IFN-β.

In an aspect, the one or more adjuvants incorporated into the one or more bone cages can be a purified protein, for example, one or more cytokine immunomodulator. The adjuvant can be purified from a natural source such as plasma, cells or tissue. Alternatively, the adjuvant can be purified from a genetically engineered cell line in which the adjuvant has been expressed using standard recombinant DNA techniques.

The one or more adjuvants can be admixed with the one or more immunogens and loaded into the bone cage. Alternatively, the adjuvant and the immunogen can be placed in separate bone cages or in separate compartments within a bone cage.

The one or more adjuvants can be produced in cells encapsulated in the bone cage, wherein the encapsulated cells can naturally express the adjuvant. Alternatively, the encapsulated cells can be genetically engineered to express the adjuvant. The genetically engineered cells can be bacteria, yeast, insect cells or mammalian cells. The mammalian cells can be autologous, allogeneic, or xenogeneic. In an aspect, the adjuvant is a protein or peptide such as, for example, a cytokine immunomodulator, which may or may not be modified, for example by glycosylation or lipidation. A protein or peptide, and/or one or more enzymes required for modification or production thereof, can be expressed in a genetically engineered cell using standard recombinant DNA techniques. In an aspect, the cDNA corresponding to the adjuvant and the immunogen, or one or more enzymes required for modification or production thereof, can be incorporated into the same expression vector and transfected into a mammalian cell line. Alternatively, the cDNA corresponding to the adjuvant and the immunogen can be incorporated into distinct expression vectors. The two or more expression vectors can be transfected simultaneously into the same cells, creating a single genetically engineered cell line that expresses both the adjuvant and the immunogen. Alternatively, the two or more expression vectors can be transfected into separate cultures of the same or differing cells and the two genetically engineered cell lines incorporated into the bone cage. In an aspect, the genetically engineered cells expressing the adjuvant and/or the immunogen are encapsulated in alginate or other physiologically compatible encapsulation medium prior to incorporation into the bone cage.

The adjuvant can be administered as part of a plasmid DNA into which DNA sequence encoding all or part of the adjuvant has been incorporated. Methods for generating a plasmid DNA for this purpose have been described herein. In this instance, the plasmid DNA encoding the adjuvant is loaded into the bone cage and the adjuvant protein is expressed by the host cells following implantation of the bone cage. The plasmid DNA can also include DNA encoding one or more immunogen. Alternatively, the DNA encoding one or more immunogen and the one or more adjuvants can be incorporated into separate plasmid DNAs.

Temporal Release of Immunogen and Adjuvant from Bone Cage Device

The release of the one or more immunogen and the one or more adjuvant from a device including one or more bone cages can be temporally controlled. Temporal release can be controlled by the properties of the bone cage, the formulation of the immunogen and/or adjuvant placed in the bone cage, or a combination thereof. Temporally controlled release of the one or more immunogen and the one or more adjuvant from the bone cage is useful for primary immunization and secondary immunization to establish memory cells responsive to the pathogenic organism or pathogenic condition. For example, vaccines for diphtheria-tetanus-pertussis (DTaP) is recommended to be given in 5 doses between 2 months and 18 months and a final dose at 4-6 years, with a tetanus and diphtheria vaccine boosted every 10 years. As a further example, vaccination with Gardasil® human papillomavirus quadrivalent (types 6, 11, 16, 18) vaccine is recommended in three doses over approximately six months. The method for treating an infectious disease in a subject can include providing a device including one or more bone cages as a single administered dose to deliver the one or more immunogen and the one or more adjuvant over an extended period of time from 2 months up to 24 months.

The temporal release of immunogen and adjuvant from the device including one or more bone cages can be controlled based on the size of the pores in the bone cage relative to the size of the immunogen and/or adjuvant. The smaller the pores, the slower the release of immunogen and/or adjuvant from the bone cage. In addition, release of immunogen and adjuvant can be controlled by the number of pores. The fewer the pores, the slower the release of immunogen and adjuvant from the bone cage. The pores can range in size from about 1 nanometer to about 20 micrometers and can be dependent upon the size of the immunogen and adjuvant. For example, proteins and peptides range in size from sub-nanometer to greater than 16 nanometers (e.g., diameter of immunoglobulin molecule); plasmid DNA ranges in size from sub-nanometer to greater than 25 nanometer; live or killed whole viral particles range in size from about 10 nanometers to about 300 nanometers; live or killed bacteria range in size from 100 nanometers to 6 micrometers; and attenuated *Plasmodium falciparum* sporozoites are about 10 micrometers in length. The pores may be uniform in size or may vary in size. Different compartments of the bone cage can have pores of different sizes allowing for differential release rates from each of the compartments.

The temporal release of the one or more immunogens and/or one or more adjuvants from the device including one or more bone cages can be controlled by the formulation of the immunogen and adjuvant. The formulation can allow for immediate release, extended release, delayed release, or a combination thereof. An immediate release formulation can be a simple aqueous solution, e.g., saline, into which the immunogen and/or adjuvant have been dissolved. An extended or delayed release formulation can include a matrix through which the immunogen and/or adjuvant must diffuse to escape the bone cage. Examples of matrix material for use in extended and/or delayed release formulation include, but are not limited to, insoluble plastics (e.g., methyl acrylate-methylmethacrylate, polyvinyl chloride, and polyethylene), hydrophilic polymers (e.g., methylcellulose, hydroxypropylmethylcellulose, sodium carboxymethylcellulose, and carbopol 934), and fatty compounds (e.g., carnauba wax, glyceryl tristearate). In an aspect, the immunogen and/or adjuvant can be encapsulated in small particles surrounded by a membrane barrier coat through which the immunogen and/or adjuvant diffuse over time. Examples of material for use in generating a membrane barrier coat include, but are not limited to, hardened gelatin, methyl- or ethylcelluloses, polyhydroxymethacrylate, hydroxypropylcellulose, polyvinylactate, and various waxes. Alternatively, the immunogen and adjuvant can be formulated in a hydrogel material including natural polymers (e.g., chitosan, alginate, fibrin, collagen, gelatin, hyaluronic acid, and dextran), synthetic monomers (e.g., hydroxyethyl methacrylate, N-(2-hydroxypropyl) methacrylate, N-vinyl-2-pyrrolidone, N-isopropyl acrylamide, vinyl acetate, acrylic acid, methacrylic acid, polyethylene glycol acrylate/methacrylate, and polyethylene glycol diacrylate/dimethacrylate), or a combination thereof. See, e.g., Lin & Metters. *Adv. Drug Deliv. Rev.* 58:1379-1408, 2006, which is incorporated herein by reference. General information regarding formulation can be found in Remington: The Science and Practice of Pharmacy; $20^{th}$ Edition; Cover page (3 pgs.); printed on May 5, 2010; Lippincott Williams & Wilkins, Baltimore, Md. which is incorporated herein by reference. See also Heit, et al., *Eur. J. Immunol.* 37:2063-2074, 2007; U.S. Pat. No. 5,762,965; U.S. Pat. No. 5,820,873; U.S. Pat. Appl. No. 2007/0026005, which are incorporated herein by reference.

The device including one or more bone cages can be constructed utilizing cells cultured in vitro including, but not limited to, stem cells, fibroblasts, endothelial cells, osteoblasts and/or osteoclasts. The in vitro cultured cells can be configured to form the bone cage structure or configured to restructure the bone cage wall or inner compartment. Restructuring the device including one or more bone cages is useful to design compartments that can provide temporal release of the one or more immunogens and one or more adjuvants from the bone cage. Temporal release can depend upon the size of the bone cage compartment, the thickness of the bone cage wall, and the size and configuration of pores in the bone cage wall. As discussed in more detail herein, the bone cage wall can be slowly degraded to release one or more of the one or more immunogens and one or more adjuvants.

Triggered Release of Immunogen and/Adjuvant from Bone Cage Device

The release of one or more immunogens and/or one or more adjuvants from a device including one or more the bone cage can be controlled by a trigger, for example, a biomolecule, a specific analyte, a pathogen or tumor cell, or an externally-administered compound. The trigger can stimulate immediate or sustained release of the immunogen and/or adjuvant from the bone cage. Alternatively, the trigger can stimulate the synthesis of the immunogen and/or adjuvant by cells incorporated in the bone cage. The trigger can be a biomolecule. Examples of biomolecules include, but are not limited to, pathogen associated biomolecules (e.g., toxins, polysaccharides, double stranded RNA, CpG polynucleotides), tumor-associated biomolecules (e.g., tumor antigens, tumor markers), other disease-associated biomolecules (e.g., β-amyloid), allergens (e.g., food allergen), or other biomolecules (e.g., drugs of abuse). Alternatively, the trigger can be a physiological change induced by the pathogen, tumor, disease, or allergic response. Examples of a physiological change include, but are not limited to, changes in pH, temperature, osmolarity, hypoxia, ion concentrations, and endogenous biomolecule concentrations (e.g., cytokines).

The immunogen and the adjuvant can be incorporated into a stimuli-responsive gel that is further incorporated into the bone cage. The stimuli-responsive gel, for example, may undergo swelling and deswelling in response to environmental conditions. The swelling and deswelling of the gel alters the ability of the immunogen and/or the adjuvant to diffuse out of the bone cage. Examples of stimuli-responsive gels include pH/electro-responsive gels (e.g., hyaluronic acid, chondroitin sulphate, agarose, carbomer, xanthan gum, calcium alginate, acrylate and methacrylate derivatives such as partially hydrolyzed polyacrylamide, polydimethylaminopropyl acrylamide, and poly(methacrylic acid) PMAA, polyethyloxazoline), thermo-responsive gels (e.g., poly(N-isopropylacrylamide), poly(N-vinylcaprolactam), polyethylene glycol, poly(propylene oxide) and combinations thereof), and magnetically responsive gels (e.g., incorporation of magnetic carriers such as magnetite, iron, nickel and/or cobalt into the polymer matrix). See, e.g., *Anal. Rec. Pat. Endo. Metab. Immune Drug Dis.* 1:83-90, 2007; Liu, et al., *Nano Today* 4:52-65, 2009 which are incorporated herein by reference.

The stimuli-responsive gel can be constructed such that it releases the one or more immunogens and/or the one or more adjuvants in response to a specific analyte. For example, Yang et al. describe a hydrogel system that incorporates two or more overlapping aptamers that serve as recognition elements for an analyte. Yang, et al., *J. Am. Chem. Soc.* 130:6320-6321, 2008, which is incorporated herein by reference. The two or more partially overlapping aptamers are copolymerized into a polyacrylamide-based hydrogel. At least one of the aptamers is a recognition element that binds to an analyte. The interaction of the analyte with the aptamer recognition element causes the two partially overlapping aptamers to separate from one another and to change the properties of the hydrogel, releasing the contents of the hydrogel. The one or more aptamers can interact with an analyte that is all or part of a pathogen or tumor associated biomolecule. In response to interacting with the analyte, the hydrogel can release one or more immunogens and/or adjuvants incorporated in the hydrogel.

The synthesis of the one or more immunogens and/or one or more adjuvants by genetically engineered cells incorporated into the device including one or more bone cages can be controlled by a trigger, for example, one derived from a pathogen or tumor. The cells can be genetically engineered to include a receptor that is responsive to the trigger and is linked to the expression of the immunogen and/or adjuvant. Examples of expression systems that are linked to receptor activation by a trigger include those linked to signaling through the Toll-like receptors (TRL) such as, for example, a TLR-signaling reporter plasmid. See, e.g., pNIFTY from InvivoGen, San Diego, Calif.; Roger, et al., *Biochem. J.* 387: 355-365, 2005, which are incorporated herein by reference. TLRs are activated by pathogen-associated molecular patterns (PAMPs) such as, for example, bacterial lipopolysaccharide (LPS), flagellin, and lipoteichoic acid and viral peptidoglycan, double-stranded RNA, and unmethylated CpG motifs.

Alternatively, the synthesis of the immunogen and/or adjuvant by genetically engineered cells incorporated into the device including one or more bone cages can be controlled by an external trigger administered to the subject. For example, cells can be engineered to switch on genes in response to administration of the dietary supplement vitamin H (biotin; Weber, et al., *Metabolic Eng.* 11:117-124, 2009, which is incorporated herein by reference). The expression system can include an inducible promoter that is activated in the presence of an inducing agent. Examples of expression systems with inducible promoters include, but are not limited to, lactose-inducible expression systems, tetracycline-inducible expression systems, doxycycline-inducible expression system, cumate-inducible expression system, metal (e.g., zinc)-inducible expression system, ethanol-inducible expression system, rapamycin-inducible expression system, and ecdysone-inducible expression system.

The synthesis of the immunogen and/or adjuvant by cells incorporated into the bone cage can be controlled by a trigger that is a physiological trigger. For example, studies describe an inducible expression system that is activated by a hypoxic environment. Lee, et al., Abstract, *J Control Release* 115:113-119, 2006, which is incorporated herein by reference. Other examples might include expression systems that incorporate a heat shock protein promoter.

Figure 1B:
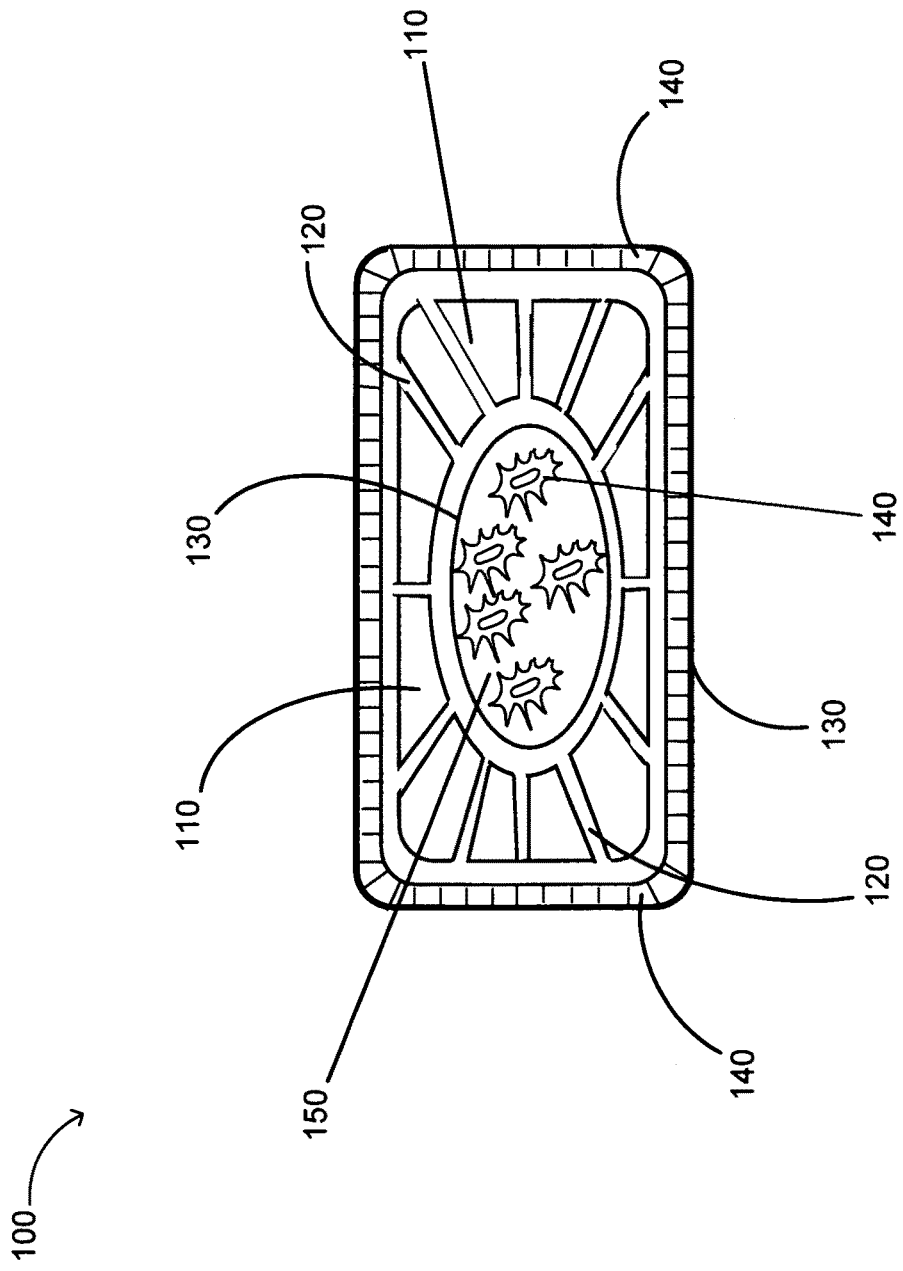

Configuration and Structure of Bone Cage Device Including One or More Immunogens and One or More Adjuvants The device including one or more bone cages can partially surround or can completely surround the one or more immunogens and one or more adjuvants, optionally in combination with one or more cells or tissues that produce the one or more immunogen and/or the one or more adjuvant. Examples of bone cages that completely surround the one or more immunogens and one or more adjuvants, optionally in combination with one or more cells or tissues are shown in FIG. 1. In FIG. 1A, a rectangular cage 100 is depicted, showing the bone wall 110 with pores 120 partially surrounded by a semi-permeable component 130 optionally comprised of cells 140 (e.g., at least one altered microorganism). FIG. 1B shows a cross-section of the rectangular cage 100, showing the optional exterior semi-permeable component 130 optionally comprised of cells 140, and the optional interior semi-permeable component 130, as well as the bone structure 110 with pores 120, and the internal cavity 150 with optional living cells 140.

The device including one or more bone cages partially surrounds the one or more immunogens and one or more adjuvants, optionally in combination with one or more cells or tissues that produce the one or more immunogen and/or the one or more adjuvant. "Partially surrounds" refers to the external wall of the bone cage surrounding less than 100% of the one or more immunogens and one or more adjuvants optionally in combination with one or more cells or tissues in the internal cavity. "Less than 100%" includes any integer percentage from 1% to 99%, for example, 10%, 25%, 50%, 75%, and 95%.

Examples of devices including one or more bone cages with external walls that partially surround the internal cavity include, but are not limited to, those where the external wall is a lattice, and/or where there are openings in the wall that are larger than the pore size of the bone. Examples of lattice work external walls include, but are not limited to, those patterned after buckeyballs.

Examples of external walls with openings include, but are not limited to, those with openings designed to facilitate the placement of the semi-permeable membrane, and the one or more immunogens and one or more adjuvants optionally in combination with the one or more cells or tissues, for example, within the internal cavity. In an aspect, the width of the one or more openings in the external wall can be any integer μm from approximately 1 to approximately 1,000 including, but not limited to, approximately 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm and 1,000 μm. In an aspect, the width can be approximately 1 μm to 1,000 μm, 2 μm to 800 μm, 5 μM to 750 μm, 10 to 500 μM, 20 μl, to 250 μm, 10 μm to 100 μm, 5 μm to 50 μm, 1 μm to 10 μm, 2 μm to 20 μm, 1 μm to 50 μm, 50 μm to 500 μm, or 250 μm to 1,000 μm in width, and the length is the width of the external wall as described above.

Examples of devices including one or more bone cages that partially surround the one or more immunogens and one or more adjuvants, optionally in combination with one or more cells or tissues that produce the one or more immunogen and/or the one or more adjuvant is shown in FIG. 2. FIG. 2A shows a buckeyball shaped cage 201 in which the pentagonal and hexagonal shapes are comprised of bone 210. FIG. 2B shows a barrel-like shape 202, in which the vertical and horizontal members are comprised of bone 210 with pores in between 220. FIG. 2C shows a rectangular structure 203, comprised of a bone wall 210 containing large openings as pores 220.

In an aspect, the external wall has one or more openings, and the openings are closable. Closable refers to the opening configured to be completely or partially filled, such that the opening can be made no longer larger than the pore size of the bone. The closure has a width sufficiently greater than the width of the opening to allow attachment to the external wall completely surrounding the opening, and can be secured by any method known in the art. In an aspect, the closure spans the entire width of the opening, and/or the entire length. The plug or closure can be comprised of bone, including, but not limited to, anorganic, artificial, demineralized, cultured in vitro, autologous, allogeneic or xenogeneic bone, or any combination thereof.

Figure 3B:
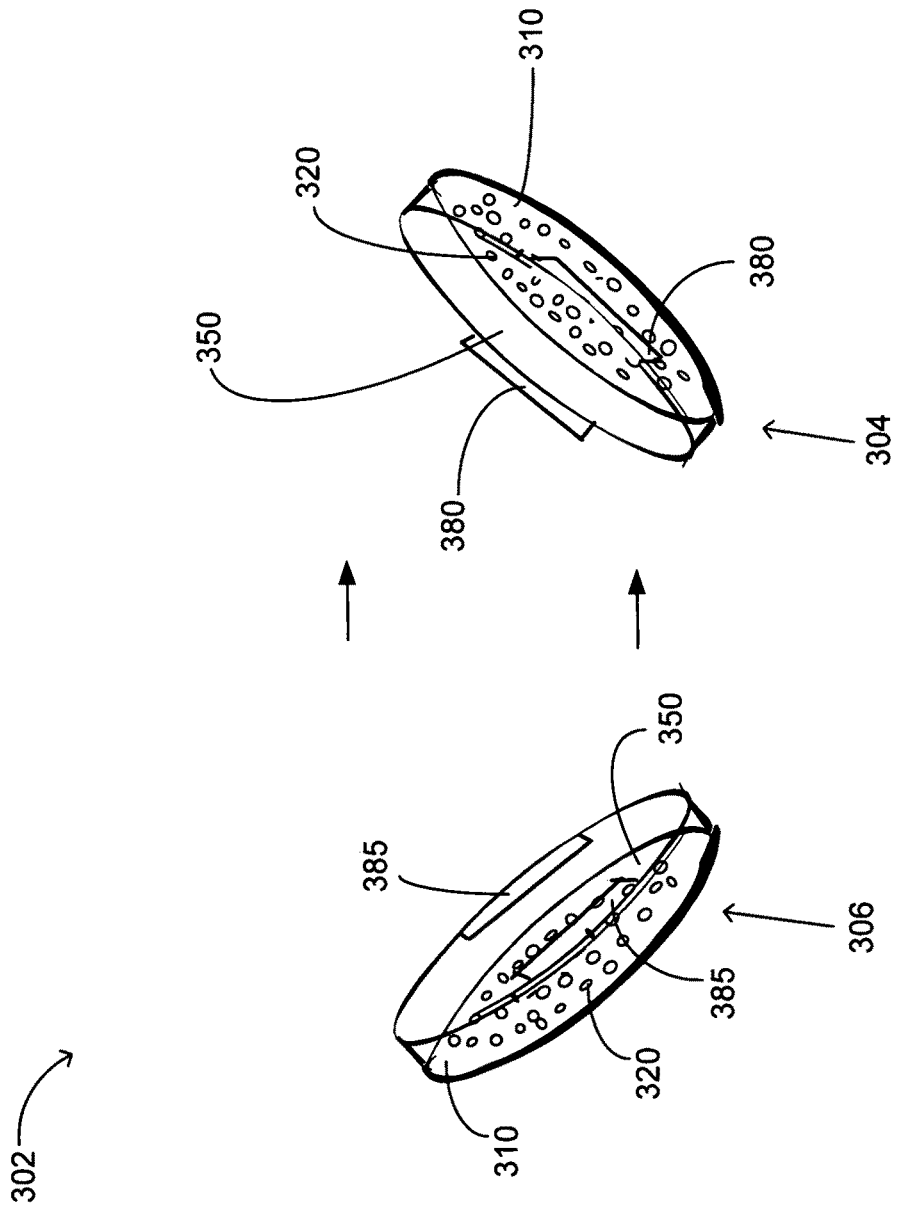

Aspects of a device including one or more bone cages with closable openings are shown in FIG. 3. FIG. 3A shows a rectangular cage 301 comprised of bone 310 containing pores 320 containing an opening 360 that connects with the internal cavity 350. The opening 360 is closable by the insertion of a plug 370 made of bone 310 of a size to approximately entirely fill the opening. FIG. 3B shows the two open halves of a petri dish-shaped cage 302 made of bone 310 containing pores 320 in which one half 304 has a uniformly slightly smaller diameter than the other half 306 so that the sides of 306 overlap the sides of 304 on closure such that an internal cavity 350 remains. The two halves are optionally secured by sliding a partially internally protruding edge 385 under a partially externally protruding edge 380. On closing, 304 and 306 are positioned such that 380 and 385 can slide past each other. Once 385 is past 380, 304 and 306 are twisted such that 380 and 385 align. FIG. 3C shows the two open halves of an egg shell-shaped structure 303 made of bone 310 comprising pores 320, where the edges 390 and 395 of the two halves 305 and 307, respectively, optionally mate to allow a screw-type seal, forming an internal cavity 350.

In an embodiment, as shown in FIG. 4, a blood brain barrier device includes one or more cells. FIG. 4A shows a cross-section of one orientation of an ovoid blood brain barrier endothelium device 401 comprised of endothelial cells 410 optionally containing interendothelial tight junctions 420, P glycoprotein efflux pump 430 at interior plasma membrane surfaces 490, ion transporters 440 and glucose receptor 450 at exterior plasma membrane surfaces 495, pinocytic vesicles 460, mitochondria 470, and nuclei 480. FIG. 4B shows a cross-section of another orientation of an ovoid blood brain barrier endothelium device 402 comprised of endothelial cells 410 optionally containing interendothelial tight junctions 420, the P glycoprotein efflux pump 430 at exterior plasma membrane surfaces 495, ion transporters 440 and glucose receptor 450 at interior plasma membrane surfaces 490, pinocytic vesicles 460, mitochondria 470, and nuclei 480.

Figure 5:
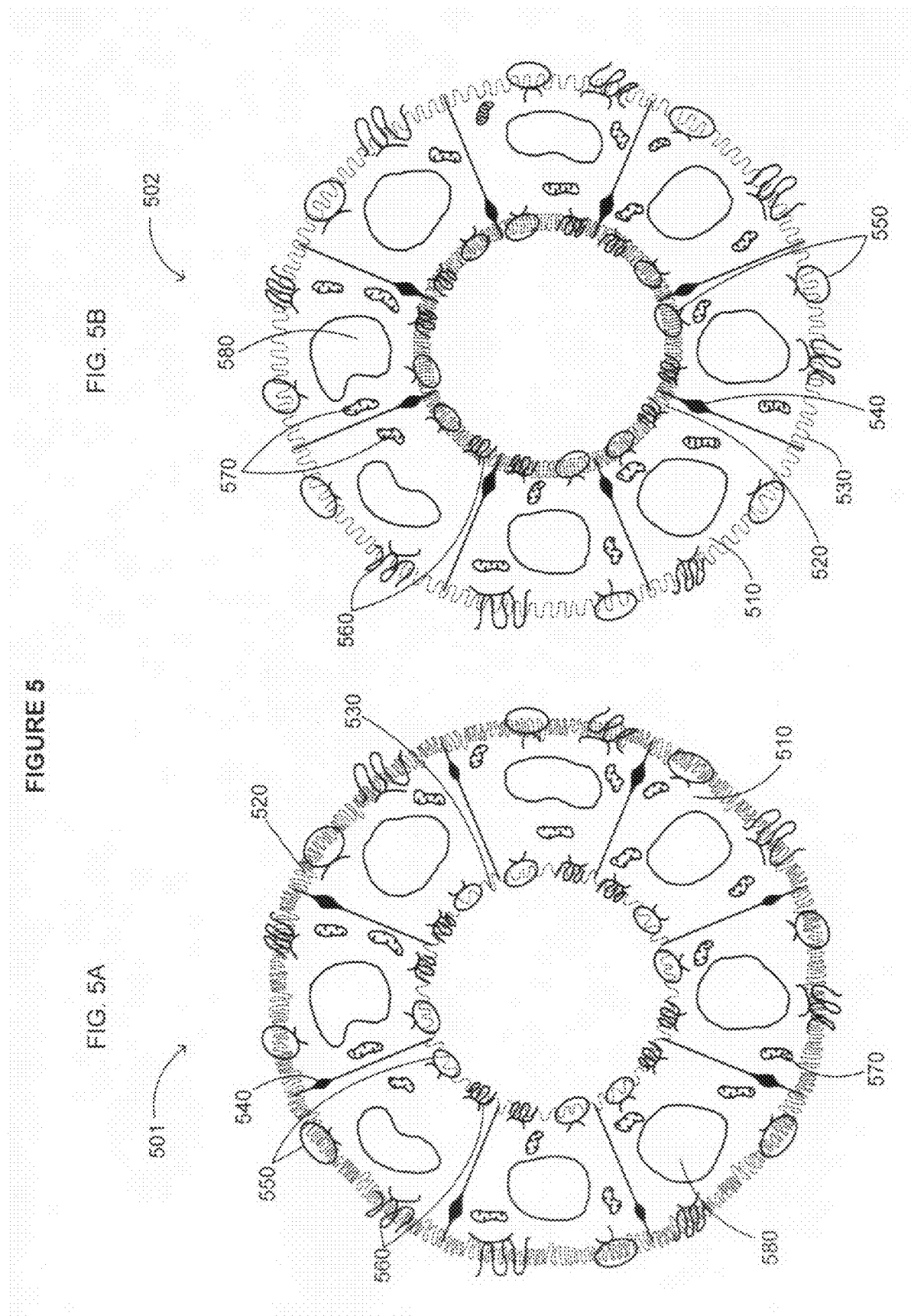
FIGS. 5A and 5B depict a diagrammatic view of an aspect of an embodiment of a device.
Figure 6A:
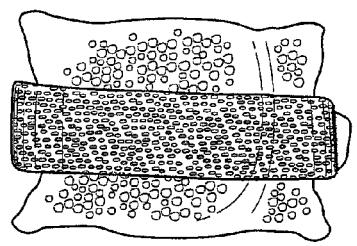
FIGS. 6A, 6B, 6C, and 6D show scanning electron micrographs of centric and pinnate diatoms.
Figure 6C:
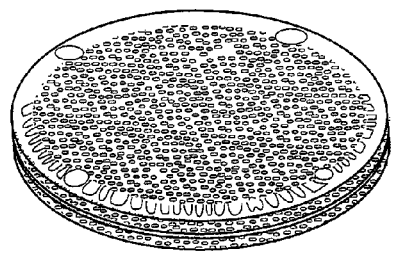
Figure 6B:
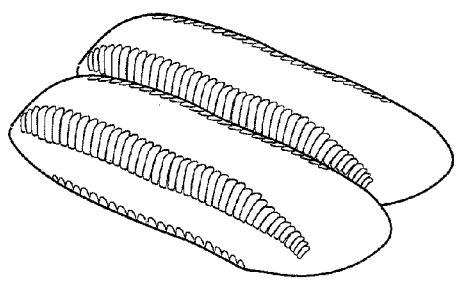
Figure 6D:
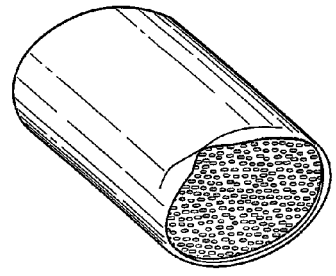
Figure 7A:
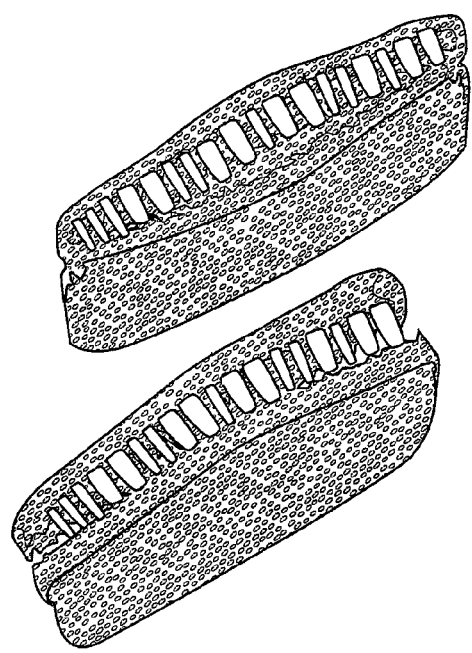
FIGS. 7A and 7B show scanning electron micrographs of diatoms with interlocking fingerlike protuberances at the closure of the frustules.
Figure 7B:
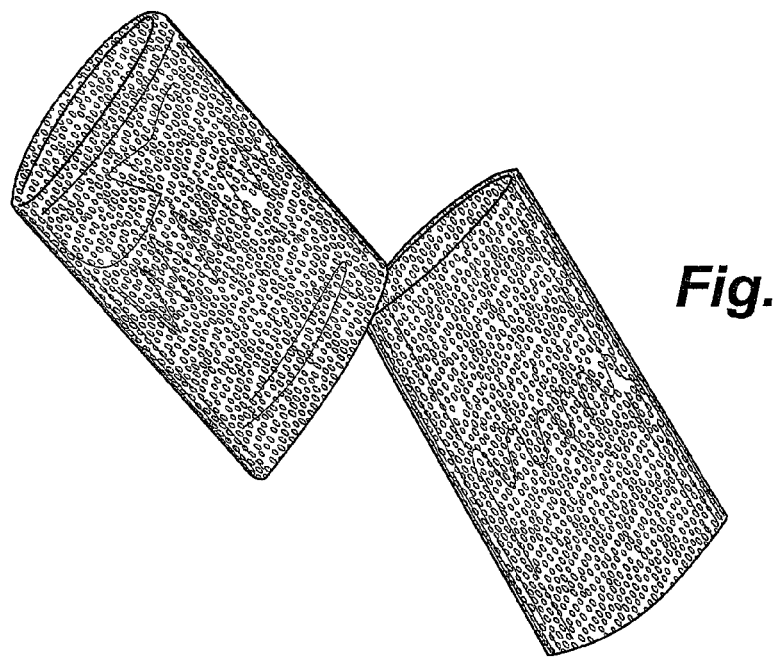

In an embodiment, as shown in FIG. 5, a blood cerebrospinal fluid barrier device is described. FIG. 5A shows a cross-section of one orientation of an ovoid choroid plexus epithelium device 501 comprised of epithelial cells 510 optionally containing exterior plasma membrane microvilli 520, interior plasma membrane interdigitations 530, interepithelial tight junctions 540 near the external surface, ion transport systems 550 on interior and exterior plasma membranes, organic transport systems on interior and exterior plasma membranes 560, mitochondria 570 and nuclei 580. FIG. 5B shows a cross-section of another orientation of an ovoid choroid plexus epithelium device 502 comprised of epithelial cells 510 optionally containing interior plasma membrane microvilli 520, exterior plasma membrane interdigitations 530, interepithelial tight junctions 540 near the internal surface, ion transport systems 550 on interior and exterior plasma membranes, organic transport systems 560 on interior and exterior plasma membranes, mitochondria 570 and nuclei 580.

Referring to FIG. 12, a logic flowchart is depicted for a method 1101 for modulating a pathological condition in a subject. The method 1101 includes providing 1102 a device comprising one or more bone cages including one or more immunogens and one or more adjuvants. In an aspect 1103, the one or more bone cages is configured to be non-weight-bearing when implanted into a soft tissue of a subject. In a further aspect 1104, the pathological condition in the subject includes infectious disease, neoplastic disease, atherosclerosis, hypertension, autoimmune disease, diabetes, or substance addiction. The method further includes providing 1105 one or more cells or tissues encapsulated in the bone cage and configured to produce the one or more immunogens. The method further includes providing 1106 one or more cells or tissues encapsulated in the bone cage and configured to produce the one or more adjuvants. In an aspect 1107, the one or more adjuvants includes a biologically derived agent. In an aspect 1108, the one or more adjuvants includes a synthetically derived agent. In an aspect 1109, the one or more immunogens include a microbial antigen, viral antigen, parasite antigen, plant antigen, animal antigen, endogenous antigen, or synthetic antigen. In an aspect 1110, the one or more immunogens include protein, lipid, lipoprotein, glycolipid, glycoprotein, proteoglycan, polysaccharide, or lipopolysaccharide.

Bone encompasses all types of bone, including, but not limited to, organic, anorganic, demineralized, freeze-dried, and artificial bone. The bone can be cultured in vitro, and/or genetically engineered. The bone can be living or dead. The bone can be autologous, allogeneic, or xenogeneic with respect to a subject within whom the bone is implanted. The bone can be a combination of one or more of the types of bone described above.

As depicted in FIG. 13, a system 1300 comprises 1310 at least one computing device; at least one treatment device including at least one semi-permeable barrier substantially enclosing at least one auxotrophic microorganism, the at least one auxotrophic microorganism including at least one nucleic acid construct encoding at least one therapeutic agent, the barrier defining an interior region and exterior region; wherein the device includes at least one metabolite required by the at least one auxotrophic microorganism; the treatment device further comprising at least one pump for dispensing at least one therapeutic agent, the pump including electronic circuitry configured to send or receive signals from the computing device; and one or more instructions on a recordable medium that when executed on the computing device cause the computing device to regulate dispensing of the at least one therapeutic agent from the at least one treatment device.

In an embodiment 1320, the at least one computing device includes one or more of a desktop computer, phone, personal digital assistant, remote controller, workstation computer, or computing system. In an embodiment 1330, the at least one computing system includes one or more of a cluster of processors, a networked computer, a tablet personal computer, a laptop computer, a mobile device, a mobile telephone, or a personal digital assistant computer.

In an embodiment 1340, the system further comprises one or more instructions on a recordable medium that when executed on the at least one computing device cause the at least one computing device to generate at least one output to a user readable display.

As depicted in FIG. 14, in an embodiment 1400, the at least one output includes at least one graphical illustration of the at least one auxotrophic microorganism, at least one component thereof, or at least one product thereof; at least one property of the treatment device; or at least one property of dispensing the at least one therapeutic agent from the treatment device. In an embodiment 1410, the at least one output includes at least one protocol for administering the at least one treatment device to at least one biological tissue. In an embodiment 1420, the user includes at least one entity. In an embodiment 1430, the entity includes at least one person, or computer. In an embodiment 1440, the user readable display includes a human readable display. In an embodiment 1450, the user readable display includes one or more active displays. In an embodiment 1460, the user readable display includes one or more passive displays. In an embodiment 1470, the user readable display includes one or more of a numeric format, graphical format, or audio format. In an embodiment 1480, the system further comprises one or more instructions on a recordable medium that when executed on the computing device cause the computing device to evaluate the at least one biological tissue for one or more indicators prior to, during, or subsequent to administering the at least one treatment device to the at least one biological tissue.

As depicted in FIG. 15, in an embodiment 1500, to evaluate at least one biological tissue for one or more indicators includes to evaluate at least one of an assay, image, or gross assessment of the at least one biological tissue prior to, during, or subsequent to administering the at least one treatment device to the at least one biological tissue. In an embodiment 1510, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In an embodiment 1520, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation. In an embodiment 1530, the system further comprises one or more instructions on a recordable medium that when executed on the computing device cause the computing device to alter at least one microorganism isolated from at least one biological tissue.

As depicted in FIG. 16, the system 1600 further comprises one or more instructions on a recordable medium that when executed on the computing device cause the computing device to amplify the at least one microorganism isolated from the at least one biological tissue. In an embodiment 1610, the system further comprises one or more instructions on a recordable medium that when executed on the computing device cause the computing device to reinstate the at least one microorganism to the biological tissue from which it was isolated subsequent to alteration. In an embodiment 1620, the system further comprises one or more instructions on a recordable medium that when executed on the computing device cause the computing device to predetermine at least one microorganism strain or type for altering in order to produce at least one therapeutic agent based on at least one feature of at least one biological tissue. In an embodiment 1630, the at least one feature of the at least one biological tissue includes at least one property of one or more microorganism populations associated with the at least one biological tissue. In an embodiment 1640, the system further comprises one or more instructions for delivering at least one agent sufficient to induce death in the at least one auxotrophic microorganism. In an embodiment 1650, the one or more instructions for delivering at least one agent sufficient to induce death in the at least one auxotrophic microorganism includes one or more instructions for delivering the at least one agent at least one of locally or systemically.

As depicted in FIG. 17, in an embodiment 1700, the system further comprises a cryptographic logic component. In an embodiment 1710, the cryptographic logic component is configured to implement at least one cryptographic process or cryptographic logic. In an embodiment 1720, the cryptographic logic component is configured to implement one or more processes associated with at least one of a cryptographic protocol, decryption protocol, or encryption protocol. In an embodiment 1730, the cryptographic logic component is configured to implement one or more processes associated with at least one of a regulatory compliance protocol, regulatory protocol, or authentication protocol. In an embodiment 1740, the cryptographic logic component is configured to implement one or more processes associated with at least one of an authorization protocol, activation protocol, or treatment regimen protocol. In an embodiment 1750, the cryptographic logic component includes one or more of a crypto-algorithm, signal-bearing media, crypto controller, or cryptographic module.

As depicted in FIG. 18, in an embodiment 1800 the cryptographic logic component is configured to generate information associated with at least one of an authentication protocol, authorization protocol, anti-microbial agent reservoir delivery protocol, activation protocol, encryption protocol, decryption protocol authorization instruction, prescription dosing instruction, or prescribed regimen instruction. In an embodiment 1810, the cryptographic logic component is configured to generate information associated with at least one of an activation code, error code, command code, or authorization code. In an embodiment 1820, the cryptographic logic component is configured to generate information associated with at least one of a cryptographic protocol, decryption protocol, encryption protocol, regulatory compliance protocol, or regulatory use protocol.

As depicted in FIG. 19, a system 1900 comprises 1910 at least one computing device; one or more instructions on a recordable medium that when executed on the at least one computing device cause the at least one computing device to receive a first input associated with a first possible dataset, the first possible dataset including data representative of at least one parameter for making or administering at least one treatment device to at least one biological tissue, wherein the at least one treatment device includes at least one semi-permeable barrier structured to substantially enclose at least one auxotrophic microorganism; wherein the at least one auxotrophic microorganism includes at least one nucleic acid construct encoding at least one therapeutic agent; and one or more instructions on a recordable medium that when executed on the at least one computing device cause the computing device to generate an output to a user readable display. In an embodiment 1915, the system further comprises one or more instructions on a recordable medium that when executed on the at least one computing device cause the at least one computing device to compare a value associated with the first possible dataset with a second dataset including values of at least one predictive parameter. In an embodiment 1920, the first input includes one or more values derived from at least one property of the at least one treatment device.

As depicted in FIG. 20, in an embodiment 2000, the first input includes at least one parameter for generating the at least one auxotrophic microorganism. In an embodiment 2010, the first input includes at least one parameter for making the at least one treatment device. In an embodiment 2020, the at least one parameter for making the at least one treatment device includes one or more of constitution of the at least one treatment device, configuration of the at least one treatment device, formulation of the at least one therapeutic agent, type of auxotrophic microorganism, strain of auxotrophic microorganism, configuration of the at least one inducible genetic element of the auxotrophic microorganism, or alteration of the at least one auxotrophic microorganism.

In an embodiment 2030, the second input includes one or more values related to the at least one parameter for administering at least one treatment device to the at least one biological tissue. In an embodiment 2040, the at least one parameter for administering the at least one treatment device includes one or more of: biological tissue type; biological tissue function; biological tissue size; biological tissue constitution; biological tissue architecture; biological tissue durability; biological tissue temperature; temperature of administration conditions; depth of administration of the at least one treatment device; biological tissue source; one or more temporal coordinates; one or more spatial coordinates; angle of administration of the at least one treatment device; force of administration of the at least one treatment device; velocity of administration of the at least one treatment device; quantity of treatment devices administered; rate of administration of more than one treatment device; method of administration of the at least one treatment device; timing of administration of the at least one treatment device; rate of production of the at least one therapeutic agent of the at least one treatment device, or rate of dispensing of the at least one therapeutic agent from the at least one treatment device.

As depicted in FIG. 21, the system 2100 further comprises one or more instructions on a recordable medium that when executed on the at least one computing device cause the at least one computing device to determine a graphical illustration of the second possible dataset. In an embodiment 2120, the system further comprises one or more instructions on a recordable medium that when executed on the at least one computing device cause the at least one computing device to determine from the comparison at least one parameter for making or administering the at least one treatment device. In an embodiment 2130, the system further comprises one or more instructions on a recordable medium that when executed on the at least one computing device cause the at least one computing device to access the first possible dataset in response to the first input. In an embodiment 2140, the system further comprises one or more instructions on a recordable medium that when executed on the at least one computing device cause the at least one computing device to generate the first possible dataset in response to the first input. In an embodiment 2150, the system further comprises one or more instructions on a recordable medium that when executed on the at least one computing device cause the at least one computing device to determine a graphical illustration of the first possible dataset. In an embodiment 2160, the at least one computing device includes one or more of a desktop computer, workstation computer, phone, personal digital assistant, remote controller, or computing system. In an embodiment 2170, the at least one computing system includes one or more of a cluster of processors, a networked computer, a tablet personal computer, a laptop computer, a mobile device, a mobile telephone, or a personal digital assistant computer.

As depicted in FIG. 22, in an embodiment 2200, the output includes at least one graphical description of the at least one treatment device, at least one component thereof; or at least one cell or substance associated with at least one biological tissue. In an embodiment 2210, the user includes at least one entity. In an embodiment 2220, the entity includes at least one person, or computer. In an embodiment 2230, the user readable display includes a human readable display. In an embodiment 2240, the user readable display includes one or more active displays. In an embodiment 2250, the user readable display includes one or more passive displays. In an embodiment 2260, the user readable display includes one or more of a numeric format, graphical format, or audio format. In an embodiment 2270, the system further comprises one or more instructions for receiving a third input associated with at least one feature of at least one subject. In an embodiment 2280, the at least one feature of the at least one subject includes one or more of a physiological condition; genotype; phenotype; genetic profile; proteomic profile; lipidomic profile; glycomic profile; system biology profile; circulatory condition; respiratory condition; lymph condition; anatomic, genetic or proteomic characteristic; response to previous treatment; weight; height; medical diagnosis; familial background; results of one or more medical tests; ethnic background; body mass index; age; presence or absence of at least one disease or condition; species; ethnicity; race; allergies; gender; presence or absence of at least one biological, chemical, or therapeutic agent in the subject; pregnancy status; lactation status; medical history; or blood condition.

As depicted in FIG. 23, in an embodiment 2300, the user readable display includes one or more of a display of one or more differences in the comparison of at least one value related to the first input and at least one value related to at least one property of the at least one treatment device. In an embodiment 2310, the user readable display includes one or more of a display of one or more differences in the comparison of at least one value related to the second input and at least one value related to at least one parameter for administration of the at least one treatment device to the at least one biological tissue. In an embodiment 2320, the system further comprises means for transmitting one or more signals that include information related to the processing of the first input and the second input. In an embodiment 2330, the means for transmitting one or more signals includes means for transmitting one or more signals associated with selection of at least one parameter for making the at least one treatment device. In an embodiment 2340, the means for transmitting one or more signals includes means for transmitting one or more signals associated with selection of at least one parameter for administering the at least one treatment device to the at least one biological tissue. In an embodiment 2350, the means for transmitting one or more signals includes means for transmitting one or more signals associated with comparing the information related to the processing of the first input and the second input. In an embodiment 2360, the system further comprises means for generating the at least one auxotrophic microorganism. In an embodiment 2370, the system further comprises means for administering the at least one treatment device to at least one biological tissue.

In an embodiment 2400, the system further comprises means for evaluating the at least one biological tissue for one or more indicators prior to, during, or subsequent to administering the at least one treatment device to at least one biological tissue. In an embodiment 2410, the one or more indicators include at least one of an assay, image, or gross assessment of the at least one biological tissue prior to, during, or subsequent to at least one administration of the at least one treatment device. In an embodiment 2420, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In an embodiment 2430, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation. In an embodiment 2440, the system further comprises one or more instructions on a recordable medium that when executed on the computing device cause the computing device to evaluate the at least one biological tissue for one or more indicators relating to one or more of: administering the at least one device, at least one component thereof, or at least one product thereof; cell or tissue formation; cell or tissue growth; cell or tissue apoptosis; cell or tissue necrosis; cell division; cellular cytoskeletal rearrangement; cell or tissue secretion; cell or tissue differentiation; status of the at least one auxotrophic microorganism of the at least one treatment device; status of the at least one treatment device; or status of the at least one therapeutic agent.

As depicted in FIG. 25, in an embodiment 2500, the system further comprises means for transmitting one or more signals that include information relating to the accepting a first input or a second input and information related to the evaluating the at least one biological tissue. In an embodiment 2510, the means for transmitting one or more signals includes means for transmitting one or more signals associated with selection of at least one parameter for making the at least one treatment device. In an embodiment 2520, the means for transmitting one or more signals includes means for transmitting one or more signals associated with selection of at least one parameter for administering the at least one treatment device. In an embodiment 2530, the system further comprises means for obtaining genetic sequence information from at least one microorganism isolated from at least one biological tissue. In an embodiment 2540, the system further comprises means for altering the at least one microorganism isolated from the at least one biological tissue. In an embodiment 2550, the system further comprises means for amplifying the at least one microorganism isolated from the at least one biological tissue. In an embodiment 2560, the system further comprises means for reinstating the at least one microorganism isolated from the at least one biological tissue subsequent to alteration. In an embodiment 2570, the system further comprises means for predetermining at least one microorganism strain or type for altering to produce at least one therapeutic agent based on at least one feature of at least one biological tissue. In an embodiment 2580, the at least one feature of the at least one biological tissue includes at least one property of one or more microorganism populations associated with the at least one biological tissue.

As depicted in FIG. 26, a computer-implemented method 2600 comprises 2610 executing one or more instructions located on a recordable medium for regulating dispensing of at least one treatment device including at least one semipermeable barrier substantially enclosing at least one auxotrophic microorganism, the at least one auxotrophic microorganism including at least one nucleic acid construct encoding at least one therapeutic agent, the barrier defining an interior region and exterior region; wherein the device includes at least one metabolite required by the at least one auxotrophic miroorganism. In an embodiment 2620, the computer-implemented method further comprises generating at least one output to a user readable display. In an embodiment 2630, the generating the at least one output includes generating at least one graphical illustration of one or more of the at least one auxotrophic microorganism, at least one component thereof, or at least one product thereof; at least one property of the at least one treatment device; or at least one property of dispensing the at least one treatment device. In an embodiment 2640, the generating the at least one output includes generating at least one protocol for generating the at least one auxotrophic microorganism. In an embodiment 2650, the at least one output includes at least one protocol for administering the at least one treatment device to at least one biological tissue. In an embodiment 2660, the user includes at least one entity. In an embodiment 2670, the entity includes at least one person, or computer. In an embodiment 2680, the user readable display includes a human readable display.

As depicted in FIG. 27, in an embodiment 2700, the user readable display includes one or more active displays. In an embodiment 2710, the user readable display includes one or more passive displays. In an embodiment 2720, the user readable display includes one or more of a numeric format, graphical format, or audio format. In an embodiment 2730, the computer-implemented method further comprises executing one or more instructions for evaluating at least one biological tissue for one or more indicators prior to, during, or subsequent to administering the at least one treatment device to the at least one biological tissue. In an embodiment 2740, the evaluating at least one biological tissue for one or more indicators includes evaluating at least one of an assay, image, or gross assessment of the at least one biological tissue prior to, during, or subsequent to administering the at least one treatment device to the at least one biological tissue. In an embodiment 2750, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In an embodiment 2760, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation.

As depicted in FIG. 28, in an embodiment 2800, the computer-implemented method further comprises executing one or more instructions for evaluating the at least one biological tissue for one or more indicators relating to one or more of: administering the at least one treatment device, at least one component thereof, or at least one product thereof; cell or tissue formation; cell or tissue growth; cell or tissue apoptosis; cell or tissue necrosis; cell division; cellular cytoskeletal rearrangement; cell or tissue secretion; cell or tissue differentiation; status of the at least one auxotrophic microorganism of the at least one treatment device; status of the at least one treatment device; or status of the at least one therapeutic agent. In an embodiment 2810, the computer-implemented method further comprises executing one or more instructions for obtaining genetic sequence information from at least one microorganism isolated from at least one biological tissue. In an embodiment 2820, the computer-implemented method further comprises executing one or more instructions for altering the at least one microorganism isolated from the at least one biological tissue. In an embodiment 2830, the computer-implemented method further comprises executing one or more instructions for amplifying the at least one microorganism isolated from the at least one biological tissue. In an embodiment 2840, the computer-implemented method further comprises executing instructions for replacing the at least one microorganism isolated from the at least one biological tissue subsequent to alteration. In an embodiment 2850, the computer-implemented method further comprises executing one or more instructions for predetermining at least one microorganism strain or type for altering to produce at least one therapeutic agent based on at least one feature of at least one biological tissue. In an embodiment 2860, the at least one feature of the at least one biological tissue includes at least one property of one or more microorganism populations associated with the at least one biological tissue.

As depicted in FIG. 29, a computer program product 2900, in an embodiment 2910 comprises a recordable medium bearing one or more instructions for regulating dispensing of at least one treatment device including an semi-permeable barrier structured to substantially enclose at least one auxotrophic microorganism, and wherein the at least one auxotrophic microorganism includes at least one nucleic acid construct encoding at least one therapeutic agent. In an embodiment 2920, the recordable medium includes a computer-readable medium. In an embodiment 2930, the recordable medium includes a communications medium. In an embodiment 2940, the computer program product further comprises one or more instructions for evaluating the at least one biological tissue for one or more indicators prior to, during, or subsequent to administering the at least one treatment device. In an embodiment 2950, the computer program product further comprises one or more instructions for evaluating the at least one biological tissue for one or more indicators relating to one or more of: administering the at least one treatment device, at least one component thereof, or at least one product thereof; cell or tissue formation; cell or tissue growth; cell or tissue apoptosis; cell or tissue necrosis; cell division; cellular cytoskeletal rearrangement; cell or tissue secretion; cell or tissue differentiation; status of the at least one auxotrophic microorganism of the at least one treatment device; status of the at least one treatment device; or status of the at least one therapeutic agent. In an embodiment 2960, the first input includes at least one parameter for generating the at least one auxotrophic microorganism. In an embodiment 2970, the second input includes at least one parameter for administering the at least one treatment device to at least one biological tissue.

As depicted in FIG. 30, in an embodiment 3000, the output includes at least one protocol for generating the at least one auxotrophic microorganism. In an embodiment 3010, the output includes at least one protocol for administering the at least one treatment device to the at least one biological tissue. In an embodiment 3020 the at least one output includes at least one graphical illustration of one or more of the at least one auxotrophic microorganism, at least one component thereof, or at least one product thereof; at least one property of the at least one treatment device; or at least one property of dispensing the at least one treatment device. In an embodiment 3030, the user includes at least one entity. In an embodiment 3040, the entity includes at least one person, or computer. In an embodiment 3050, the user readable display includes a human readable display. In an embodiment 3060, the user readable display includes one or more active displays. In an embodiment 3070, the user readable display includes one or more passive displays. In an embodiment 3080, the user readable display includes one or more of a numeric format, graphical format, or audio format. In an embodiment 3090, the computer program product further comprises one or more instructions for obtaining genetic sequence information from at least one microorganism isolated from the at least one biological tissue.

In an embodiment 3100, the computer program product further comprises one or more instructions for altering the at least one microorganism isolated from the at least one biological tissue. In an embodiment 3110, the computer program product further comprises one or more instructions for amplifying the at least one microorganism isolated from the at least one biological tissue. In an embodiment 3120, the computer program product further comprises one or more instructions for reinstating the at least one microorganism isolated from the at least one biological tissue subsequent to modification. In an embodiment 3130, the computer program product further comprises one or more instructions for predetermining at least one microorganism type for altering to produce at least one therapeutic agent based on at least one feature of the at least one biological tissue. In an embodiment 3140, the at least one feature of the at least one biological tissue includes at least one property of one or more microorganism populations associated with the at least one biological tissue.

As one of skill in the art would appreciate, a computing device as described herein includes any instrument containing a processor to execute instructions, for example a phone, personal digital assistant, remote-controller, desktop computer, workstation computer, or computing system.

PROPHETIC EXAMPLE 1

Device Including Bone Cage Formed from Cortical Bone and/or Cancellous Bone

A device including one or more bone cages configured to include one or more immunogens and one or more adjuvants is delivered into a soft tissue of a subject for use as a vaccine against a pathogen, cancer, or tumor in the subject. The device includes a bone cage formed from autologous, allogeneic, or xenogeneic cortical bone and/or cancellous bone. The one or more immunogens is delivered as a live attenuated or an inactivated viral particle. The one or more adjuvants include complete Freund's adjuvant.

The device including one or more bone cages utilizes bone obtained from the subject (autologous) or from a donor subject (allogeneic) by biopsy, surgery, or autopsy. Alternatively, bone is obtained from a non-human subject (xenogeneic), for example, from bovine or porcine subjects. Autologous bone is obtained from the calvarial, rib and/or iliac bone of the subject. To obtain autologous bone from the iliac crest, a small incision (4-5 cm) is made just below the anterior iliac wing and a 2×2 centimeter area of bone is exposed on top of the crest. A rongeur, osteotome or chisel is used to remove a portion of cortical and/or cancellous bone from the top of the crest. Alternatively, the sample of bone is excised from the subject using a microsaw (e.g., FRIOS® MicroSaw, FRIADENT GmbH, Mannhein, Germany). The excised bone is optionally cleaned of any associated tissue; fat, and/or blood components.

The autologous bone used to form the one or more bone cages is further cut with a bone saw into smaller pieces (e.g., 5×5×5 millimeter) or to even smaller pieces using a saw microtome, e.g., Leica SP2600 (Leica Microsystems Nussloch GmbH, Postfach 1120, Heidelberger Strasse 17-19, D-69226 Nussloch, Germany). The bone is optionally ground to the desired dimensions using a grinding table and a series of graded abrasive sand papers (from, e.g., Buehler, Ldt., Lake Bluff, Ill.) or using an automated grinding instrument (e.g., Exakt Apparatebau GMBH, Norderstedt, Germany). Calipers are used to assess thickness (e.g., Mitutoyo digital, Kanagawa, Japan). The shape is rectangular, or smoothed to an oblong, although other shapes may be implemented. An interior cavity is hollowed into a bone cage using a micromachining laser. For example, a Nd:YAG laser rod is used to cut the interior of the bone leaving an approximately 10 micrometer thick bone wall. The bone wall is further perforated with multiple pores 1 to 2 micrometer in diameter using the laser. A second piece of bone is micromachined and shaped to form a bone cap or plug.

Alternatively, the bone cage is manufactured from bone powder derived from autologous, allogeneic, or xenogeneic bone obtained by biopsy, surgery, autopsy, or necropsy. For example, an allogeneic bone sample is obtained from a donor undergoing hip replacement. In this instance, the head of the femur is removed, substantially cleaned of associated tissue, fat, and blood components and cut into smaller pieces (e.g., 1×1×1 centimeter) using a bone saw. Any residual blood components are removed from the bone pieces by soaking in purified water for 12 to 24 hours. Fat and protein material are substantially removed from the bone pieces by boiling in purified water for 12 to 72 hours. The bone pieces are pulverized into a powder using a bone mill (from, e.g., Aesculap Inc. USA, Center Valley, Pa.; Medtronic, Minneapolis, Minn.). Residual fatty material is removed from the bone powder by extracting the powder in an organic solvent mixture, e.g., chloroform and methanol (1:1 v/v), for 24 hours with or without agitation. The bone powder is rinsed repeatedly with purified water to remove the organic solvent. The washed bone powder is dried in an oven at 60° C. Residual protein material is removed by soaking the bone powder in a 4% (w/v) solution of sodium hypochlorite for 12 to 72 hours with or without agitation. The bone powder is rinsed repeatedly with purified water to remove the sodium hypochlorite and dried in an oven at 60° C. The bone powder is further milled to generate a finer bone powder. The bone powder is sieved through a series of sieves of various mesh size openings, e.g., 10-200 micrometers, 200-425 micrometers, 425-1000 micrometers, 1000-2000 micrometers, etc. The bone powder is heated at 600° C. for 3-5 hours to remove any residual organic material and to sterilize the powder. A similar process is used to generate milled bone from a xenogeneic donor.

The bone powder is compressed using compression molding techniques into appropriate building blocks for forming the bone cages. Alternatively, the bone powder is admixed with a biocompatible substance to form a paste that is molded into appropriate cage forms. Examples of appropriate biocompatible substances for this purpose include fibrinogen, MATRIGELT™ basement membrane matrix, gelatin, alginate, polyglycolide, polylactide, glycolide-lactide copolymer, etc. In some instances, heating the formed cages polymerizes the biocompatible material and forms a rigid cage-like structure.

The bone cage is molded to include pores sufficiently large enough for passive diffusion of live/attenuated or inactivated viral particles including the one or more immunogens and/or the one or more adjuvants, e.g., complete Freund's adjuvant. In general, viral particles range in size from 10 to 300 nanometers. The complete Freund's adjuvant is bound ionically or covalently to the surface of the bone cage structure.

The live/attenuated or inactivated viral particles including the immunogen and adjuvant, e.g., complete Freund's adjuvant, are injected into the one or more cavities of the bone cage. The one or more cavities include micro-holes large enough to allow diffusion of the viral particles. The number of viral particles added to each bone cage is dependent upon the size of the one or more bone cage cavities, the number of bone cages to be used for immunization, and the expression efficiency of the genetically engineered cells. For example, a bone cage with an internal cavity measuring 1×1×0.3 centimeters accommodates a volume of 300 microliters of viral particles. Assuming a maximum packing density of 0.524 and a particle diameter of 300 nanometers, as many as $4 \times 10^9$ densely packed viral particles are incorporated into the bone cage cavity. The viral particles are suspended within a hydrogel at this density or at a lower density and incorporated into the bone cage cavity. The cavity is plugged with an additional bone fragment or with another material to immunoisolate the viral particles. One or more of the bone cages are implanted into a subject. The viral particles diffuse out of the bone cage and into the surrounding tissue of the subject.

PROPHETIC EXAMPLE 2

Device Including Bone Cage Formed by Growing Bone on a Scaffold

A device including one or more bone cages configured to include one or more immunogens and one or more adjuvants is delivered into a soft tissue of a subject for use as a vaccine against a pathogen, cancer, or tumor in the subject. The device includes a bone cage formed from growing bone progenitor cells on an appropriate scaffold. Bone is formed by growing bone progenitor cells on a scaffold in the presence of appropriate growth conditions. Bone progenitor cells are differentiated into osteoblasts for formation of bone and osteoclasts for resorption of bone.

Bone-forming osteoblasts are differentiated from preosteoblastic cells such as, for example, MC3T3 cell line, primary cells isolated from bone, mesenchymal stem cells isolated from bone marrow, adipose tissue, placenta, cartilage, and other tissues. Duplomb, et al., *Stem Cell* 25:544-552, 2007, which is incorporated herein by reference. Mesenchymal stem cells, for example, are isolated from bone marrow by Percoll density gradient centrifugation and differentiated into osteoblasts using a basal culture medium supplemented with fetal bovine serum (FBS), L-glutamine, penicillin/streptomycin, dexamethasone, ascorbate, and β-glycerophosphate. Ogura, et al., *J. Oral Sci.* 46:207-213, 2004, which is incorporated herein by reference. Alternatively, mesenchymal stem cells are derived from embryonic stem cells and differentiated into osteoblast-like cells using medium supplemented with dexamethasone, ascorbate, and β-glycerophosphate as described by Barberi, et al., *PLoS Med.* 2:e161, 2005, which is incorporated herein by reference. Various assays are used to assess osteoblast differentiation, e.g., expression of collagen, osteopontin, osteonectin, osteocalcin, and bone sialoprotein, alkaline phosphatase assay, and mineralization assay.

Scaffolds for use in bone tissue engineering to form one or more bone cages include synthetic polymers (e.g., polylactic acid and polyglycolic acid and copolymers, thereof, polycaprolactone, polyanhydrides, and polypohsphazenes; polymethylmethacrylate, polytetrafluoroethylene, polyhydroxyethylmethacrylate); ceramics (e.g., alumina, hydroxyapatite); native polymers (e.g., Type I collagen); and composites thereof. Growth conditions include nutrients, growth factors, appropriate temperature, and oxygenation.

Bone tissue configured to form one or more bone cages is engineered using bone marrow-derived stem cells grown in three-dimensional superporous poly (ethylene glycol) diacrylate (PEGDA) hydrogels. See, e.g., Keskar, et al., Abstract, *Tissue Eng. Part A* 15, 1695-707 (2009), which is incorporated herein by reference. PEGDA is combined with a foam stabilizer and initiators N,N,N',N'-tetramethylethylene-diamine and ammonium persulfate and the pH adjusted to pH 3.7 with citric acid. The mixture is heated at 37° C. for 2 minutes. Sodium bicarbonate is added to the mixture with constant stirring to evenly distribute the salt and evolving gas. Polymerization is allowed to proceed for 30 minutes. Residual monomers are removed with rinsing in distilled water. The hydrated hydrogel is cut into appropriate sized pieces (e.g., 5×3 millimeter) and seeded with mesencymal cells derived from bone marrow aspirates. The cells seeded on the hydrogel are grown in an osteogenic medium containing Dulbecco's modified Eagle's medium (DMEM), fetal bovine serum, penicillin/streptomycin, dexamethasone, β-glycerophosphate, and ascorbic acid 2-phosphate. After 3-7 weeks in culture, gross calcification is observed in the form of a white deposit on and within the hydrogel cell culture system. The bone-like material is further processed using machining techniques as described above to form a cage-like structure. In a further aspect, the hydrated hydrogel is shaped into a cage-like structure and seeded with mesenchymal cells to form the one or more bone cages.

Alternatively, the bone cage is derived from bone tissue generated in the absence of an underlying exogenous scaffold. Bone marrow cells are collected from the pelvic bone from the subject or from an allogeneic donor using standard medical procedures. The collected cells are grown in Dulbecco's modified eagle medium (DMEM) supplemented with 20% fetal bovine serum, basic fibroblast growth factor (bFGF), dexamethasone, and antibiotics/antimycotics. After 48 hours, non-adherent cells are removed. The cells are transferred to dishes containing SYLGARD® polymer coated with laminin and grown in the supplemented medium described above. After the cells reach confluence, two pins are placed in the SYLGARD® polymer about 1.5 centimeters apart and ascorbic acid and organic phosphate are added to the medium. Over the course of 6 weeks, cells lay down extracellular matrix, differentiate and begin to form a tube-like solid structure that exhibits bone-like qualities including calcification and increased stiffness, see e.g., Syed-Picard, et al., *Tissue Eng. Part A* 15:187-195, 2009, which is incorporated herein by reference. Bone-like structures formed in this manner are further processed as described above to form one or more bone cages.

PROPHETIC EXAMPLE 3

Genetically Engineered Cells Generating Immunogen/Adjuvant for Device Including Bone Cage A device including one or more bone cages and configured to include one or more immunogens and one or more adjuvants is delivered into a soft tissue of a subject for use as a vaccine against cancer or a tumor in the subject. The device includes genetically engineered cells expressing one or more immunogens and/or one or more adjuvants for use as a vaccine against a cancer or tumor. The device includes a bone cage formed from synthetic or artificial materials, from excised bone, or from in vitro tissue engineering. In this instance, the genetically engineered cells are encapsulated by the bone cage. The bone cage itself has pores that allow passage of the immunogen and the adjuvant produced by the encapsulated cells, but the pores are small enough to prevent passage of the genetically engineered cells.

The immunogen and the adjuvant include any of a number of tumor specific antigens. For example, the tumor is colorectal carcinoma. The device including one or more bone cages includes the immunogen, carcinoembryonic antigen (CEA) or polypeptide epitopes thereof, and the adjuvant, the immunomodulator interleukin 2 (IL-2), or interleukin 21 (IL-21). Shievely, et al., *Crit. Rev Oncol Hematol.* 2: 355-399, 1985; Frederiksen et al., *Cancer Immunol. Immunother.* 57: 1439-1449, 2008; Parrish-Novak et al., *Journal of Leukocyte Biology;* 72: 856-863, 2002; Lamprecht et al., *Blood* 112: 3339-3347, 2008, which are incorporated herein by reference. In a further example, the cancer is metastatic melanoma. The device including one or more bone cages includes the immunogen, one or more of the tumor antigens or polypeptide epitopes thereof: Melan-A/MART-1, MAGE-3, Gp100/pmel17, Tyrosinase, TRP-1/-2, P. polypeptide, MC1R, β-catenin, or MART-2. Kawakami, et al., *J Exp Med* 180: 347-52, 1994; Bakker, et al., *J Exp Med* 179: 1005-9, 1994;

Brichard, et al., *J Exp Med* 178: 489-95, 1993; Kawakami, et al., *J Immunother* 21: 237-46, 1998; Wang, et al., *J Exp Med* 184: 2207-16, 1996; Touloukian, et al., *Cancer Res* 61: 8100-4, 2001; Salazar-Onfray, et al., *Cancer Res* 57: 4348-55, 1997; Alexander, et al., Abstract, *Urology* 51: 150-7, 1998; Robbins, et al., *J Exp Med* 183: 1185-92, 1996, which are incorporated herein by reference. The adjuvant in combination with the melanoma tumor antigen is the immunomodulator interleukin 21 (IL-21), interleukin 12 (IL-12), or incomplete Freund's adjuvant. Frederiksen et al., *Cancer Immunol. Immunother.* 57: 1439-1449, 2008; Gajewski, et al., *Clin Cancer Res.* 7(3 Suppl): 895s-901s, 2001, which are incorporated herein by reference Immunization with CEA and IL-2 is used to induce an immune response against CEA-expressing colorectal carcinoma cells. Immunization with metastatic melanoma tumor antigen and IL-21 is used to induce an immune response against metastatic melanoma cells. Standard molecular biology techniques are used to express the CEA and IL-2 in a mammalian cell line. The cDNA sequences corresponding to CEA and IL-2 are generated using standard polymerase chain reaction (PCR) amplification and an appropriate cDNA library or reverse-transcribed mRNA with primers designed based on the known cDNA sequence of CEA and IL-2 from, e.g., the GenBank Database. Benson, et al., *Nucleic Acids Res.* 36:D25-30, 2008, which is incorporated herein by reference. All or a portion of the cDNA sequences corresponding to CEA and IL-2 are cloned into expression vectors containing the cytomegalovirus (CMV) promoter (see, e.g., Sigma-Aldrich, St. Louis, Mo.). Alternatively, a vector using an adenovirus expression system or other promoter or viral expression systems is used (see, e.g., Promega, Madison, Wis.; Clontech Laboratories, Inc., Mountain View, Calif.; Invitrogen, Carlsbad, Calif.). Alternatively, the cDNA for CEA and/or IL-2 is obtained from a commercial source, in a mammalian expression vector expressed under control of a CMV promoter (see, e.g., Origene, Rockville, Md.).

In some instances, the cDNA corresponding to CEA and to IL-2 are incorporated into the same expression vector and transfected into the mammalian cell line. Alternatively, the cDNA corresponding to CEA and to IL-2 are incorporated into distinct expression vectors. The two expression vectors are transfected simultaneously into the same cells. In this instance, a single genetically engineered cell line is generated that expresses both CEA and IL-2. Alternatively, the two expression vectors are transfected into separate cultures of the same or differing mammalian cells. For example, the CEA expression vector is transfected into one culture of Chinese hamster ovary (CHO) cells while the IL-2 expression vector is transfected into another culture of CHO cells, creating two distinct genetically engineered cell lines.

Prior to incorporating the genetically engineered cells into the bone cages, the relative expression of CEA and IL-2 by the cells is assessed using any of a number of assay systems. The expression of messenger RNA (mRNA) corresponding to CEA and IL-2 is assessed by quantitative PCR, Northern analysis, in situ hybridization, or other methods designed to assess the presence and/or quantity of a specific mRNA in a cell. The expression of CEA and IL-2 in the cells is assessed by Western analysis, immunocytochemistry, or other methods designed to assess the presence and/or quantity of a specific protein in a cell. The secretion of CEA and IL-2 out of the genetically engineered cell and into the culture medium is assayed using an immunoassay system with immunoreagents specific for CEA and IL-2. In an example assay, the supernatant from the genetically engineered mammalian cells is collected and subjected to analysis by enzyme-linked immunosorbent assays (ELISAs) specific for CEA and IL-2 (from, e.g., Signosis, Inc., Sunnyvale, Calif.).

The genetically engineered cells expressing the CEA immunogen and IL-2, or the metastatic melanoma immunogen and IL-21, are injected into the one or more cavities of the bone cage. The one or more cavities include micro-holes large enough to allow diffusion of the immunogen and adjuvant but small enough to prevent release of the genetically engineered cells. The number of cells added to each bone cage is dependent upon the size of the one or more bone cage cavities, the number of bone cages to be used for immunization, and the expression efficiency of the genetically engineered cells. For example, a bone cage with an internal cavity measuring 1×1× 0.3 centimeters accommodates a volume of 300 microliters of cells. Assuming a maximum packing density of 0.524 and a cell diameter of 15 micrometers, as many as 80 million densely packed cells are incorporated into the bone cage cavity. The cavity is plugged with an additional bone fragment or with another material to immunoisolate the genetically engineered cells. One or more of the bone cages are implanted into a subject. The genetically engineered cells are retained within the confines of the implanted bone cage, while the expressed CEA and IL-2 are secreted from the genetically engineered cells and diffuse out of the bone cage and into the surrounding tissue of the subject.

PROPHETIC EXAMPLE 4

Immunogen and Adjuvant Attached to the Bone Cage Structure

A device including a bone cage configured to include an immunogen and an adjuvant is delivered into a soft tissue of a subject for use as a vaccine against a pathogen in the subject. The device includes a bone cage formed from synthetic or artificial materials, from excised bone, or from in vitro tissue engineering. The device includes one or more immunogens and/or adjuvants that are bound to one or more surfaces of the bone cage. The immunogen and/or adjuvant are attached either by adsorption or by chemical crosslinking, e.g., by covalent or ionic bonding to the surface of the bone cage. The immunogen and/or adjuvant are released over time from the surface of the bone cage and induce an immune response in the subject.

The immunogen is any of a number of pathogen specific antigens. For the purposes of this example, the immunogen is one or more peptide mimotopes directed against the HBs antigen associated with hepatitis B virus and the surface antigen lipooligosaccharide (LOS) associated with infectious bacteria such as *Haemophilus influenzae*. The adjuvant includes one or more of aluminum hydroxide, aluminum phosphate, or potassium aluminum sulfate. The peptide mimotopes are generated by screening an LOS-specific antibody and/or an HBs antigen-specific antibody against a phage-display peptide library expressing random peptides. See, e.g., Hou & Gu. *J. Immunol.* 170: 4373-4379, 2003, which is incorporated herein by reference. An antibody that specifically recognizes the *Haemophilus influenzae* LOS is generated using standard methods. The antibody is used to coat the surface of 96-well plates and a commercially available phage-display peptide library (from, e.g., New England Biolabs, Beverly, Mass.) is added to the wells. The plates are washed with buffered saline and phage adhering to the antibody-coated plates are eluted, amplified, and subjected to additional rounds of screening against the LOS antibody. The subsequent rounds of screening continue until phage displaying peptides of sufficient affinity are identified. Once identified, the one or more high affinity peptides are synthesized using a commercially available peptide synthesizer (e.g., ABI 433A Peptide Synthesizer from Applied Biosystems, Inc., Foster City; CA).

The peptide mimotope immunogens generated as described are attached to one or more surfaces of the bone cage. The immunogen and an adjuvant are crosslinked to the bone cage using a bisphosphonate linkage. In general, bisphosphonates bind to the mineral component of bone and are used as anti-resorptive therapy for the treatment of osteoporosis. Aminomethylene bisphosphonic acid (aminobisphosphonate) is modified with ligands and used to attach biomolecules to the surface of natural bone or hydroxyapatite. See, e.g., Ehrick et al., *Bioconjug. Chem.* 19:315-321, 2008, which is incorporated herein by reference. Aminobiphosphonate is synthesized by combining dibenzylamine, diethyl phosphate, and triethyl orthoformate to form N,A-dibenzylamine-bisphosphonate. The latter intermediate is treated with Pd/C and hexane to deprotect the amine. The ester groups are hydrogenated with aqueous hydrochloric acid to generate the final product. The aminobisphosphonate is functionalized with succinimidyl 4-hydrazinonicotinate acetone hydrazone that converts primary amines to hydrazinopyridine moieties (from, e.g., Thermo Fisher Scientific Inc., Rockford, Ill.). The peptide mimotope immunogens are functionalized with succinimidyl 4-formylbenzoate that converts primary amines to benzaldehyde moieties (from, e.g., Thermo Fisher Scientific Inc., Rockford, Ill.). Conjugation is completed by combining the functionalized aminobisphosphonate and the functionalized peptides in buffered solution (pH 4.7-7.2) for 1-3 hours. Bisphosphonate is also be functionalized using azide-alkyne click chemistry as described by Skarpos, et al., *Org. Biomol. Chem.* 5:2361-2367, 2007 which is incorporated herein by reference.

The peptide-bisphosphonate conjugate in phosphate buffered saline is incubated with one or more bone cages for 1 to 24 hours. Longer incubation times are used to ensure efficient binding of the peptide-bisphosphonate conjugate to the bone cage. The adjuvant, one or more of aluminum hydroxide, aluminum phosphate, or potassium aluminum sulfate, is optionally linked to the surface of the bone structure using a similar protocol or is incorporated into one or more cavities in the bone cage.

PROPHETIC EXAMPLE 5

Temporal Release of Immunogen/Adjuvant from Device Including Bone Cage

A device including one or more bone cages configured to include one or more immunogens and one or more adjuvants is delivered to a subject to treat pathological condition in the subject. The device is delivered to a subject for use as a vaccine against a pathogen, cancer, or tumor in the subject. The device is implanted into a soft tissue, e.g., subcutaneously or intramuscularly, in the subject. The device including the bone cage is formed from synthetic or artificial materials, from extracted autologous, allogeneic, or xenogeneic bone, or from bone progenitor cells cultured on an appropriate matrix.

The device including the bone cage is generated from biocompatible and/or implantable artificial bone substitutes containing metals, ceramics and/or polymers. The bone cage is generated using hydroxyapatite, a calcium/phosphate ceramic, either alone or in combination with other agents.

Temporal release of the one or more immunogens and the one or more adjuvants from the bone cage is controlled by using a biodegradable hydrogel. Depending upon the composition of the hydrogel containing the immunogen and the adjuvant, the device including one or more bone cages will release the composition of immunogen and adjuvant over a period of time from 2 to 24 hours up to as long as 18 to 24 months. In an aspect, an immunogen derived from an infectious pathogen is formulated with poly(DL-lactide-co-glycolide) (PLGA) to generate microspheres with slow release properties. See, e.g., O'Brien, et al., *J. Dairy Sci.* 79:1954-1959, 1996, which is incorporated herein by reference. An immunogen, such as, for example, a lysate of bacterial cell wall components is emulsified with copolymer PLGA (from, e.g., Sigma-Aldrich, St. Louis, Mo.) dissolved in dichloromethane using a homogenizer. The emulsion is either further emulsified with polyvinyl alcohol solution to produce small microspheres (<10 microns) or poured drop-wise into a polyvinyl alcohol solution to produce larger microspheres (>20 microns). The solvent is evaporated overnight at room temperature and the microspheres are washed in water and lyophilized. Release of the immunogen from the microspheres is optionally assessed prior to insertion into the bone cage by placing the microspheres in phosphate buffered saline at 37° C. and performing weekly measurements on supernatant samples for the presence of the immunogen. An adjuvant, e.g., complete Freund's adjuvant (CFA), is similarly encapsulated in PLGA, either in combination with the immunogen or in separate particles.

The microspheres are loaded into the one or more cavities of the bone cage. The number and/or volume of microspheres loaded is dependent upon the internal size of the bone cage. For example, a bone cage with internal dimensions of 1×1×1 millimeter accommodates a 1 microliter volume of microspheres. Assuming a microsphere diameter of 10 micron and a maximal packing density of 0.524, the 1 microliter internal volume of a bone cage could accommodate as many as 1 million microspheres containing the immunogen and/or adjuvant.

PROPHETIC EXAMPLE 6

Triggered Release of Immunogen/Adjuvant from Device Including Bone Cage

The release of one or more immunogens and one or more adjuvants from a device including one or more bone cages is triggered in response to changes in the immediate environment of the implanted device. The trigger is a general change in the environment such as a change in pH, temperature or osmolality. Alternatively, the trigger is one or more specific biomolecules associated with a pathogen, cancer cell, or tumor cell. Examples of a physiological change further include, but are not limited to, increases in concentrations of endogenous compounds in the subject such as radical oxygen species, cytokines, nitric oxide (NO), anti-microbial peptides, or pro-inflammatory molecules. Controlled release of the immunogen and/or adjuvant in response to the trigger is mediated through a stimulus-responsive gel associated with the bone cage. Alternatively, controlled release of the immunogen and/or adjuvant is mediated by a genetically engineered stimulus-responsive cell line incorporated into the bone cage.

Triggered release of the immunogen is controlled using stimuli-responsive cells in which a pathogen, cancer cell, or tumor cell or parts thereof interact with a receptor on the surface of a genetically modified cell and trigger synthesis of an immunogen through a receptor-mediated signaling event linked to an expression vector encoding the immunogen.

The cells incorporated into the bone cage are genetically engineered to include a receptor that is responsive to the trigger and is linked to the expression of the immunogen and/or adjuvant. Examples of expression systems that are linked to receptor activation by a trigger include those linked to signaling through interferon regulatory factors activatingan interferon promoter, e.g., IFNα4. See, e.g., pNiFty2 inducible promoters from InvivoGen, San Diego, Calif.; Roger, et al., Biochem. J. 387:355-365, 2005, which are incorporated herein by reference. The cells include a plasmid expressing the immunogen and/or adjuvant includes the mouse IFNβ minimal promoter, which comprises several positive regulatory domains (PRDs) that bind different cooperating transcription factors such as NF-κB, and interferon regulatory factor IRF3 and IRF7. Expression of IFNβ-SEAP coexpressing the immunogen and/or adjuvant with constitutively activated interferon regulatory factors IRF3 (saIRF3) or IRF7 (saIRF7) in transfected cells leads to a strong increase in immunogen and/or adjuvant expression in the cells. Braganca J. et al., J Biol. Chem. 272: 22154-22162, 1997; Morin P, et al., J Mol Biol. 316: 1009-1022, 2002, which are incorporated herein by reference.

PROPHETIC EXAMPLE 7

Device Including Altered Microorganisms for the Delivery of a Therapeutic Agent

Microorganisms are modified to produce at least one therapeutic agent (which may include an agent used as a responsive therapy, or prophylactic therapy, etc.). The altered microorganisms are retained in vivo by limited supply of at least one essential nutrient.

In an embodiment, the arabinose promoter ($P_{BAD}$) can be fused to heterologous genes encoding therapeutic proteins, or other therapeutic agents. Coexpression of araC, an arabinose operon regulatory protein, and provision of L-arabinose regulates expression of genes fused to the $P_{imp}$ promoter. See, for example, U.S. Pat. No. 7,341,860, Ibid. The regulatory proteins can be provided to the subject (e.g., oral dosage), or can be supplied by the device (either initially implanted with at least one storage component containing the regulatory proteins or by way of a shunt or other device connecting component.

In an embodiment, gene constructs employ a constitutive promoter including, for example, promoter sequences derived from the bacterial thymidine synthase gene which continuously express at least one therapeutic agent, such as a cytokine. See, for example, Steidler et al, Nature Biotechnology vol. 21, pp. 785-789 (2003), which is incorporated herein by reference. For example, gene constructs directing expression of at least one therapeutic agent (e.g. antigenic, microbicidal or tolerogenic protein, etc.) can be incorporated into expression plasmids with drug-resistance selectable markers (e.g. ampicillin resistance marker, β-lactamase, or chloramphenicol resistance marker) and transfected or electroporated into bacteria, or other microbes. See, for example, Sambrook et al, Molecular Cloning, A Laboratory Manual, second ed., Cold Spring Harbor Laboratory Press (1989), which is incorporated by reference herein.

In an embodiment, a propionate inducible expression system is utilized, in order to provide a relatively homogenous expression in individual microorganism cells, and allow for highly regulatable expression. See, for example, Lee and Keasling, App. Env. Microbiol. vol. 71, no. 11, pp. 6856-6862 (2005), which is incorporated herein by reference. For example, expression vector pPro, described by Lee and Keasling, is capable of being regulated at the single cell level over a wide range of inducer concentrations in a dose-dependent manner. Id. Furthermore, since bacterial cells are permeable to the inducer proprionate (which is metabolized by 2-MC by native chromosomal expression), regulatable and consistent induction in all cells of the culture is attainable.

In certain instances, repression is equally important as induction (for example, in instances where the gene product is particularly toxic or difficult to maintain in the host microorganism). Since protein synthesis depends on translational efficiency as well as promoter strength, background expression may be reduced by using a weaker ribosome binding site sequence, or by decreasing the strength of the promoter by introducing nucleotide changes in the consensus promoter sequence (or by variations in the spacer sequence).

In an embodiment, gene constructs that direct protein expression can be integrated into bacterial or other microbial chromosomal DNA by homologous recombination using methods described in Steidler et al, Ibid.

In an embodiment, the altered microorganism is engineered or selected for by utilizing specific nutrient or metabolite requirements (e.g., auxotrophic). For example deletion of the thymidine synthase gene in Lactococcus lactis (L. Lactis) by homologous recombination using recombinant DNA plasmids results in L. lactis clones that require thymidine for growth. See, for example, Steidler et al, Ibid. Since thymidine is present only at low levels in human colon, L. lactis thymidine auxotrophs survive less than two days following oral administration to human volunteers. See, for example, Braat et al, Ibid. However, thymidine auxotrophs can survive longer than 200 hours in vitro when thymidine (10 μM) is provided in the media. Thus, one can control the growth and survival of thymidine auxotrophs in vivo by dosing and scheduling administration of thymidine prior to, during, or subsequent to administration of the altered microorganism composition. For example, in an embodiment, bacterial (or other microbial) auxotrophs are derived from standard bacterial strains (or other microbial strain) by deleting or mutating genes encoding enzymes or other proteins essential for bacterial (or other microbial) metabolism and growth. Methods for creating mutations, insertions and deletions (such as homologous recombination, recombinant DNA techniques, insertional mutagenesis, targeted gene deletion, etc.) in essential genes are described at, for example, U.S. Pat. No. 5,643,771, and Biswas et al, J. Bacteriology, vol. 175, pp. 3628-3635 (1993); each of which is incorporated herein by reference. For example, mutation or deletion of the β-aspartate semialdehyde dehydrogenase gene (Asd) in bacteria or other microbe precludes synthesis of diaminopimelic acid (DAP), an essential cell wall constituent that is not present in animal tissues. Without exogenous DAP, bacteria or other microbe that have a mutated or deleted Asd gene will undergo cell death and lysis (See, for example, U.S. Pat. No. 7,341,860, Ibid.), but providing DAP by oral administration allows Asd mutants to grow, colonize and survive on mucosal surfaces in vivo.

Measurement of altered microorganisms present in vivo can be done using the quantitative polymerase chain reaction (PCR) and primers specific for the microbial strain and the gene expression construct. For example, in an embodiment, stool samples from subjects given L. Lactis, engineered to express human IL-10, is assayed with PCR primers specific for the 16s ribosomal RNA of L. lactis and the human IL-10 expression construct (See, for example, Braat et al, Ibid.).

Similarly, in an embodiment, an optical density meter is configured to measure the optical density of the microorganism population(s) present in the interior of the semi-permeable barrier. In an embodiment, the optical density reading is provided to the subject or another entity (e.g., computer, physician, etc.). In an embodiment, the optical density reading is utilized to correlate the population number of microorganisms present in the measured area.

In an embodiment, the number of colony forming units (CFU) of L. Lactis is assessed by culturing stool samples on microbiological plates containing selective media. For example, fecal samples are suspended in minimal media and then selected on plates coated with antibodies specific for L. Lactis. Next, media containing essential nutrients is overlaid and the bacterial colonies arising are counted to determine the CFU present in the fecal sample (See, for example, Steidler et al, Ibid.). In an embodiment, PCR is conducted with colonies and primers specific for the bacteria or other microorganism, and gene expression construct (e.g. 16s ribosomal RNA and IL-10) to verify the identity of the colonies (See, for example, Braat et al, Ibid.).

PROPHETIC EXAMPLE 8

Devices Including Altered Microorganisms for the Delivery of Therapeutic Agents

In an embodiment, bacteria or other microorganisms are modified to deliver at least one therapeutic agent, while requiring an essential metabolite not usually present in biological tissues of the subject (or present at low concentrations). In vivo provision of essential nutrients or metabolites required by the bacteria, or other microorganisms allows for control of the survival and colonization of the bacterial or other microbial delivery, and allows for regulation of the schedule or dose of the at least one therapeutic agent. For example, thymidine synthase mutants of L. lactis (ThyA⁻ L. Lactis) are dependent on exogenous thymidine for growth in vitro and in vivo.

In an embodiment, in vitro, no viable ThyA⁻ L. Lactis are present after culture 72 hours in rich media devoid of thymidine, but in cultures containing 10 µM thymidine, the microbes survive beyond 200 hours. In vivo, only 4% of ThyA⁻ L. Lactis auxotrophs survive after 4 hours in the mammalian intestine with only endogenous thymidine present (thymidine concentration is less than 0.075 µM in human ileal lavage; See, for example, Steidler et al, Ibid.). In one embodiment, the implantable device is seeded with at least one altered microorganism prior to, during, or subsequent to implanting into the subject.

In certain instances, the device is merely seeded with at least one altered microorganism, then conditions are established in the device that are sufficient (e.g., increase the microorganism population wherein the device acts as a bioreactor and there is a lag time) to produce the at least one therapeutic agent and transfer at least a portion to the exterior of the at least one semi-permeable barrier. In certain instances, the device is fully stocked with ample microorganism populations such that therapeutic agent production occurs almost immediately upon implantation into a biological tissue or organ.

In an embodiment, production of at least one therapeutic agent, for example, IL-10, by bacterial or other microbial auxotrophs are controlled by a constitutive promoter, such as the thymidine synthase promoter. Production of IL-10 depends in part on the growth and survival of the bacterial or other microbial auxotroph.

In an embodiment, an inducible promoter such as the $P_{BAD}$/araC promoter/regulator system (see, for example, U.S. Pat. No. 7,341,860, Ibid.), is used in conjunction with arabinose to regulate the production of IL-10. In an embodiment, production and delivery in situ is regulated by dosing and scheduling of arabinose administration, and by controlling bacterial or other microbe survival and growth through dosing and scheduling of thymidine administration. In an embodiment, the amount of protein delivered can be monitored by immunoassay of fecal samples. For example, human IL-10 derived from feces samples can be measured by enzyme linked immunosorbent assay (ELISA; Steidler et al, Ibid.). ELISA reagents and protocols for numerous cytokines including IL-10 are available, for example, from Invitrogen Corp., Carlsbad, Calif.

In an embodiment the production of a therapeutic agent, such as IL-10 and a suicide factor, such as Rel F, are controlled by a synthetic gene network engineered into a microorganism. For example, oral administration of an inducer molecule controls expression of IL-10. A synthetic gene network responsive to pulses of a metabolite (e.g., arabinose), is utilized, as described in Friedland et al., Science, vol. 324, pp. 1199-1202 (2009), which is incorporated herein by reference. In an embodiment, a gene network is constructed by combining transcriptional and translational regulatory elements. For example in an embodiment, the $P_{BAD}$ promoter, a transactivating noncoding RNA, a cis repressor sequence RNA, and a T7 RNA polymerase gene may be combined in a synthetic gene network to control the expression of multiple proteins as shown by Friedland et al., Ibid. In an embodiment, the regulatory elements cause one particular product to be produced with a first induction event (e.g., exposure to arabinose); a second particular product to be produced with a second induction event; a third particular product to be produced with a third induction event, etc. In this manner, the synthetic system allows for exhibiting the number of induction events that have occurred, or "counting" induction events. Id.

In an embodiment, a therapeutic agent (e.g., IL-10) may be delivered to a patient's intestine by ingestion of modified E. coli containing a plasmid encoding a synthetic gene network that responds to multiple pulses of an inducer molecule (e.g., arabinose) by the production of IL-10. The gene network may also contain suicide genes (e.g. rel F) that will cause cell death when they are expressed. See, for example, U.S. Pat. No. 6,610,529, which is incorporated herein by reference. The frequency and duration of arabinose pulsing determines the expression of genes (and their corresponding proteins) in the gene network, while the dose and schedule of oral arabinose administration determines the timing and duration of expression of the therapeutic agent and suicide gene, IL-10 and rel F, respectively. In an embodiment, synthetic gene networks with optimal pulse intervals of approximately 10-40 minutes and optimal pulse lengths of approximately 20-30 minutes are utilized. In an embodiment, gene networks with optimal pulse intervals and pulse lengths of approximately 2-12 hours are also utilized (see Friedland et al., Ibid.). For example, gene networks encoding IL-10 might require approximately two 10-minute pulses of arabinose separated by an interval of 20 minutes to optimally induce IL-10 expression, but rel F expression and cell death would only ensue following two 2-hour pulses with arabinose separated by 2 hours. In an embodiment, gene networks incorporate multiple inducers (e.g., arabinose, anhydrotetracycline and IPTG), and the expression of multiple genes in the network depends, for example, on the order, length and interval of pulsing with each of the inducers. See, Friedland et al., Ibid.

PROPHETIC EXAMPLE 9

Compositions Including Altered Microorganisms for the Delivery of a Therapeutic Agent In an embodiment, microorganisms are modified to include at least one lethal or suicide gene to regulate population growth. For example, in an embodiment, the relF gene is controlled by a regulated promoter such as pLac that is repressed by a regulator protein, LacIq, unless isopropyl β-D-thiogalactoside (IPTG) is provided. To control growth of a modified microbial strain in vivo one can administer IPTG to induce relF expression and cause cell death. Alternatively the rel F gene can be controlled by the arabinose promoter/repressor. In this example expression of relF is regulated by the C2 repressor which, in turn, is regulated by the presence of arabinose. Thus, when arabinose levels are reduced C2 repressor levels decline and relF is expressed leading to bacterial cell death (see, for example, U.S. Pat. No. 6,610,529, which is incorporated herein by reference).

In an embodiment, mutually dependent strains of bacteria that signal via small molecules such as acyl-homoserine lactones (acyl-HSL), are modified to express heterologous target genes only when sufficient numbers of both bacterial strains (and acyl-HSL) are present. See, for example, Brenner et al, PNAS, vol. 104, pp. 17300-17304 (2007), which is incorporated herein by reference. For example, in an embodiment, two E. coli strains, modified to produce specific acyl-HSL, control the expression of target genes for each another.

In an embodiment, target gene expression is controlled by provision of exogenous acyl-homoserine lactone to the individual microbial strains. For example, administration of 3-oxododecanoyl-HSL (3OC12HSL) and butanoyl-HSL (C4HSL) in vivo can be used to control target protein production of E. coli strains engineered to be responsive to specific acyl-HSL molecules (see, for example, Brenner et al, Ibid.). In addition, survival of the engineered bacterial strains can be controlled by acyl-HSL-regulated expression of toxin (ccd B) and antitoxin (ccd A) genes, which cause cell death, or allow survival, respectively. See, for example, Balagadde et al, Mol. Sys. Biol., vol. 4, pp. 1-8 (2008), which is incorporated herein by reference. In an embodiment, the toxin-antitoxin includes at least one of masEF, chpBIK, relBE, yefM-yoeB, dinJ-yaf!, or ecnA-ecnB. See, Engleberg-Kulka, et al., PLOS Genetics, vol. 2, no. 10, 1518-1526 (2006), which is incorporated herein by reference.

Coadministration in the device of multiple bacterial strains that express different target genes can be used to co-deliver multiple therapeutic agents. For example, localized co-expression of IL-10 and transforming growth factor beta by two bacterial strains can provide localized immunoregulatory therapy for inflammatory bowel disease.

In an embodiment, a bacterial strain that expresses an antigen derived from a viral pathogen, for example, E7 antigen from human papilloma virus type 16, is coadministered with a second bacterial strain that produces interleukin-12 (IL-12) to promote immunization. In an embodiment, the two bacterial strains are auxotrophs that are mutually dependent on each other for essential metabolites, such as amino acids or DAP.

In an embodiment, one or both auxotrophic strains are sustained in vivo by administering exogenous metabolites (e.g. histidine, arabinose, DAP, acyl-HSL, thymidine) to the host organism. In an embodiment, expression of the E7 gene and IL-12 is directed by the same or a different promoter. The promoter may be constitutive or inducible. For example, in an embodiment, E7 and IL-12 are fused to the lac operon promoter ($P_{lac}$), which is inducible with IPTG or lactose.

In an embodiment, bacterial or other microbial survival and target protein expression is regulated by administration of the same metabolite. For example, in an lac promoter is used to regulate expression of a polycistronic transcript (see, for example, Brenner et al, Ibid.) that encodes a target protein and a survival factor. Providing lactose (or IPTG) to a subject hosting the bacterial or other microbial strain will not only sustain survival of the strain but also induce expression of the target protein.

PROPHETIC EXAMPLE 10

Compositions Including Altered Microorganisms for the Delivery of a Therapeutic Agent Engineered or altered microorganisms, such as fungi, derived from generally regarded as safe (GRAS) species can be auxotrophic for essential metabolites and express protein encoding genes under the control of regulated promoters. For example, in an embodiment, Saccharomyces cerevesiae (S. cerevesiae) and Saccharomyces boulardii (S. boulardii) are GRAS organisms that are mutated and selected (See Aborsereh et al, Res. J. Agric. Biol. Sci., vol. 2, pp. 478-482 (2006) which is incorporated by reference herein) to obtain clones that require amino acids (e.g., leucine, tryptophan, lysine, arginine), purines, or pyrimidines (e.g., adenine, thymidine). Growth and survival of yeast auxotrophs in vitro and in vivo is dependent on an essential metabolite (e.g., adenine), and if adenine is not present (or present at low levels) in the device or a subject hosting the strain, then growth of the yeast auxotroph can be regulated by administering adenine to the device or subject. For example, the dose and schedule of adenine administration can control the proliferation and survival of the yeast adenine auxotrophs. In certain instances, the adenine is present in a storage component in the device prior to implantation into a biological tissue or organ.

In an embodiment, yeast or other microbial strains are modified to express at least one therapeutic agent (e.g., protein). In an embodiment, yeast cloning vectors used for protein expression include but are not limited to yeast integrative plasmids, yeast episomal plasmids, and yeast centromeric plasmids that contain selectable markers based on metabolite requirements. In an embodiment, genes used as selectable markers include but are not limited to LEU2, URA3, and HIS3, which encode enzymes needed to biosynthesize leucine, uracil and histidine (for example, yeast vectors for protein expression are described in Glazer et al, Microbial Biotechnology: Fundamentals of Applied Microbiology, $2^{nd}$ edition, Cambridge University Press (2007), which is incorporated herein by reference. In an embodiment, transcription of heterologous genes is directed by a constitutive promoter (e.g., ADH1, TDH3) or a regulated promoter (e.g., GAL1, ADH2, PHO5, CUP-1, etc.).

In an embodiment, an engineered or modified yeast strain that requires two metabolites, for example, leucine and histidine, a selectable marker (e.g. LEU2) provides plasmid stability, while the metabolite (e.g., histidine or leucine) regulates growth and survival of the yeast strain. For example, in an embodiment, engineered S. boulardii is used for vaccination, wherein the strain requires leucine and histidine, and produces a heterologous protein. In an embodiment, the heterologous protein includes but is not limited to, hepatitis B surface antigen encoded on a yeast episomal plasmid containing LEU2, and under the control of the ADH1 constitutive promoter. In an embodiment, dosing and scheduling of histidine administration regulates the growth and survival of the engineered S. boulardi and, in turn, the production and delivery of hepatitis B surface antigen. In an embodiment, yeast or other microbial strains are engineered to express at least one suicide gene. For example, yeast or other microbe strain transformed with a recombinant plasmid encoding a nuclease (e.g. Serratia marcescens nuclease A) under the control of the S. cerevesiae ADH2 promoter, undergoes cell death when the nuclease A gene is expressed. Ordinarily, the ADH2 promoter is repressed by glucose, and when glucose levels are depleted, the ADH2 promoter/nuclease A gene is expressed, resulting in cell death. See, for example, Balan et al, Yeast, vol. 22, pp. 203-212 (2005) which is incorporated herein by reference. Thus, in a glucose poor environment (e.g. feces, intestine, soil, etc.) death of the modified yeast or other microorganism strain is induced.

In an embodiment, at least two strains of modified auxotrophic microbes are supplied in the device, for example, in order to provide essential nutrients to each other. For example, in an embodiment, two yeast (*Saccharomyces cerevesiae*) auxotrophs, one that requires lysine, and a second that requires adenine, are modified or engineered to overproduce adenine and lysine, respectively. Conventional methods, such as mutation, selection and genetic crosses, can be employed to generate the mutants. See, for example, Shou et al, PNAS, vol. 104, pp. 1877-1882 (2007), which is incorporated herein by reference.

In an embodiment, growth of each of the yeast strains is dependent on the other strain to supply an essential metabolite (i.e., adenine or lysine). Providing in the device live yeast strains that are mutually dependent on each other for survival allows prolonged survival and colonization of both strains on mucosal surfaces (e.g. intestinal, vaginal, nasal, oral, bronchial, etc.). In an embodiment, the yeast strains are modified to express enzymes essential for overproduction of adenine and lysine under the control of regulated promoters such as the CUP-1 promoter derived from the metallothionein gene. (See, for example, Glazer et al, Ibid.) In an embodiment, transcription of genes fused to CUP-1 is induced by providing metal ions such as $Cu^{2+}$ and $Zn^{2+}$. For example, $ZnCl_2$ can be given orally to induce expression of $ADE4^{op}$ and $LYS21^{op}$, enzymes that mediate over-production of adenine and lysine, respectively, by modified yeast residing, for example, in the colon (see, for example, Shou et al, Ibid.). Withdrawal of $ZnCl_2$ from the diet lowers $Zn^{2+}$ levels, reduces expression of $ADE4^{op}$ and $LYS21^{op}$, and reduces production of adenine and lysine which, in turn, will lead to death of the engineered yeast strains.

Each recited range includes all combinations and sub-combinations of ranges, as well as specific numerals contained therein. Further, all references to specific numerals are meant to be approximate, and not limiting. For example, a phrase such as "approximately 1 nm to 100 nm, 200 nm, 300 nm or 400 nm" is intended to mean approximately 1 nm to approximately 100 nm, approximately 200 nm, approximately 300 nm or approximately 400 nm. The words "approximately" and "about" are used interchangeably herein.

All publications and patent applications cited in this specification are herein incorporated by reference to the extent not inconsistent with the description herein and for all purposes as if each individual publication or patent application were specifically and individually indicated to be incorporated by reference for all purposes.

All range values included herein are intended to be approximate and inclusive, such that "approximately 1 to 5," is read to mean "approximately 1 to approximately 5."

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an surgeon determines that speed and accuracy are paramount, the surgeon may opt for a mainly hardware and/or firmware vehicle; alternatively, if flexibility is paramount, the surgeon may opt for a mainly software implementation; or, yet again alternatively, the surgeon may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the surgeon, any of which may vary. Those skilled in the art will recognize that optical aspects of implementations will typically employ optically-oriented hardware, software, and or firmware.

In a general sense, the various aspects described herein can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art after reading the above description. The various aspects and embodiments disclosed herein are for purposes of illustration and are not intended to be limiting, with the true scope and spirit being indicated by the following claims.

What is claimed is:

1. An implantable device, comprising:
at least one semi-permeable barrier of a polymer film or thermoplastic hollow fibers substantially enclosing at least one first auxotrophic microorganism and at least one second auxotrophic microorganism, the at least one first auxotrophic microorganism including at least one nucleic acid construct encoding at least one first vaccine therapeutic agent and located in a first compartment, the barrier defining an interior region and exterior region; and a peristaltic pump for dispensing the at least one first vaccine therapeutic agent; wherein the device includes at least one metabolite required by at least one auxotrophic microorganism; and the at least one second auxotrophic microorganism including at least one nucleic acid construct encoding at least one second vaccine and located in a second compartment; wherein the first and second compartments are configured to release the first vaccine prior to the second vaccine.

2. The device of claim 1, wherein the at least one metabolite required by at least one auxotrophic microorganism resides on the surface of the semi-permeable barrier.

3. The device of claim 1, wherein the at least one metabolite required by at least one auxotrophic microorganism is located in a compartment configured to dispense the at least one metabolite to the interior region of the at least one semi-permeable barrier.

4. The device of claim 1, wherein the at least one metabolite required by at least one auxotrophic microorganism is embedded in the at least one semi-permeable barrier.

5. The device of claim 1, wherein the at least one metabolite required by at least one auxotrophic microorganism is released as at least a portion of the at least one semi-permeable barrier degrades.

6. The device of claim 1, wherein the metabolite includes at least one energy source, nutrient, or other metabolic pathway requirement.

7. The device of claim 1, wherein the at least one semi-permeable barrier is structured to facilitate egress of the at least one therapeutic agent.

8. The device of claim 1, further including at least one tissue-anchoring component.

9. The device of claim 8, wherein the at least one tissue-anchoring component includes at least one latch, hook or tether.

10. The device of claim 1, wherein the at least one auxotrophic microorganism includes at least one population of auxotrophic microorganisms.

11. The device of claim 1, wherein the semi-permeable barrier includes a bone cage.

12. The device of claim 1, wherein the semi-permeable barrier includes a diatom cage.

13. The device of claim 1, wherein the semi-permeable barrier includes at least one component configured to selectively limit access between the interior and the exterior of the barrier.

14. The device of claim 1, further including at least one sensor.

15. The device of claim 14, wherein the at least one sensor is configured to sense at least one biological cell or material.

16. The device of claim 14, wherein the at least one sensor is located in the interior of the semi-permeable barrier.

17. The device of claim 14, wherein the at least one sensor is located exterior to the semi-permeable barrier.

18. The device of claim 14, wherein the at least one sensor includes an optical density sensor.

19. The device of claim 1, wherein the semi-permeable barrier is configured to actively or passively transfer at least a portion of the at least one therapeutic agent to the exterior of the barrier.

20. The device of claim 19, wherein the semi-permeable barrier is configured to actively or passively transfer at least a portion of the at least one therapeutic agent based on at least one chemical gradient.

21. The device of claim 1, wherein the at least one semi-permeable barrier includes at least one of an emulsion, lipid, dispersion, or micelle.

22. The device of claim 1, wherein the at least one semi-permeable barrier includes one or more cells.

23. The device of claim 1, wherein the at least one semi-permeable barrier includes one or more cell junctions.

24. The device of claim 1, wherein the semi-permeable barrier is at least one of expandable, compressible, rigid, or pliable.

25. The device of claim 1, further including at least one detection material.

26. The device of claim 25, wherein the at least one detection material includes at least one of a contrast agent, or electronic identification device.

27. The device of claim 26, wherein the at least one electronic identification device includes at least one radio frequency identification device.

28. The device of claim 1, further including at least one transmitter.

29. The device of claim 1, further including at least one receiver.

30. The device of claim 1, further including at least one circuit.

31. The device of claim 1, wherein at least one auxotrophic microorganism includes at least one inducible genetic element configured to initiate death of at least one auxotrophic microorganism.

32. The device of claim 31, wherein the at least one inducible genetic element includes at least one of a nuclease gene or lysise gene E.

33. The device of claim 31, wherein the at least one inducible genetic element includes at least one of extracellular death factor, mazF, or mazEF.

34. The device of claim 1, wherein at least one auxotrophic microorganism includes at least one of a prokaryote or eukaryote.

35. The device of claim 1, wherein at least one auxotrophic microorganism includes at least one of bacteria, fungi, or protozoa.

36. The device of claim 1, wherein the implantable device is configured to be implanted into at least one biological tissue or organ of a subject.

37. The device of claim 36, wherein the subject includes at least one of a vertebrate or invertebrate.

38. The device of claim 36, wherein the subject includes at least one of a mammal, bird, fish, reptile, or amphibian.

39. The device of claim 36, wherein the subject includes a human.

40. The device of claim 36, wherein the subject includes a plant.

41. The device of claim 1, wherein the implantable device is configured to be implanted in at least one body cavity of a subject.

42. The device of claim 41, wherein the at least one body cavity includes at least one of an otic cavity, oral cavity, vaginal cavity, anal cavity, nasal cavity, esophagus, or eyelid.

43. The device of claim 41, wherein the at least one body cavity includes the gastrointestinal tract of a subject.

44. The device of claim 1, wherein the at least one nucleic acid construct includes at least one regulatory element.

45. The device of claim 44, wherein the at least one regulatory element includes at least one of a promoter, enhancer, or repressor.

46. The device of claim 44, wherein the at least one regulatory element is regulated by at least one inducer.

47. The device of claim 46, wherein the at least one inducer includes at least one quorum-sensing molecule.

48. The device of claim 1, further including one or more micro-gears operably coupled to the peristaltic pump.

49. The device of claim 1, further including at least two semi-permeable barriers, wherein the at least two semi-permeable barriers include different pore sizes.

* * * * *